United States Patent
Henikoff et al.

(10) Patent No.: US 11,885,814 B2
(45) Date of Patent: Jan. 30, 2024

(54) HIGH EFFICIENCY TARGETED IN SITU GENOME-WIDE PROFILING

(71) Applicant: Fred Hutchinson Cancer Research Center, Seattle, WA (US)

(72) Inventors: Steven Henikoff, Seattle, WA (US); Hatice Seda Kaya Okur, Redmond, WA (US); Terri Dawn Bryson, Lynnwood, WA (US); Peter James Skene, Issaquah, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

(21) Appl. No.: 17/585,465

(22) Filed: Jan. 26, 2022

(65) Prior Publication Data
US 2022/0228203 A1  Jul. 21, 2022

Related U.S. Application Data

(63) Continuation of application No. 16/650,179, filed as application No. PCT/US2018/052707 on Sep. 25, 2018, now Pat. No. 11,733,248.

(60) Provisional application No. 62/562,918, filed on Sep. 25, 2017.

(51) Int. Cl.
| | | |
|---|---|---|
| G01N 33/68 | (2006.01) | |
| C12Q 1/6804 | (2018.01) | |
| C12N 15/10 | (2006.01) | |
| C12Q 1/6841 | (2018.01) | |

(52) U.S. Cl.
CPC ..... *G01N 33/6872* (2013.01); *C12N 15/1065* (2013.01); *C12Q 1/6804* (2013.01); *C12Q 1/6841* (2013.01); *C12Q 2522/10* (2013.01)

(58) Field of Classification Search
None
See application file for complete search history.

(56) References Cited

U.S. PATENT DOCUMENTS 7,790,379 B2 * 9/2010 Laemmli .............. C12Q 1/6827
435/7.1

FOREIGN PATENT DOCUMENTS

| | | |
|---|---|---|
| JP | 2016-518860 A | 6/2016 |
| WO | 01/68807 A2 | 9/2001 |
| WO | 2013/078470 A2 | 5/2013 |
| WO | 2014/190214 A1 | 11/2014 |
| WO | 2014/205296 A1 | 12/2014 |
| WO | 2014/189957 A2 | 1/2015 |
| WO | 2015/160895 A1 | 10/2015 |
| WO | 2015/179706 A1 | 11/2015 |
| WO | 2016/130704 A2 | 8/2016 |
| WO | 2017/025594 A1 | 2/2017 |
| WO | 2017/156336 A1 | 9/2017 |

OTHER PUBLICATIONS

Extended European Search Report dated Jul. 26, 2022, issued in EP 22163030.4, filed Sep. 25, 2018, 7 pages.
International Preliminary Report on Patentability dated Mar. 31, 2020, issued in International Application No. PCT/US2018/052707, filed Sep. 25, 2018, 10 pages.
"U.S. Appl. No. 16/650,179; office action dated Feb. 1, 2023".
Notice of Reasons for Rejection dated Jun. 17, 2022, issued in JP Application No. 2020-517134, filed Sep. 26, 2018, 10 pages.
Extended European Search Report dated Apr. 29, 2021, in corresponding European Patent Application No. 18858858.6, 8 pages.
International Search Report and Written Opinion dated Nov. 30, 2018, issued in corresponding International Application No. PCT/US2018/052707, filed Sep. 25, 2018, 13 pages.
Skene, P.J., "An efficient targeted nuclease strategy for high-resolution mapping of DNA binding sites," eLife, 6:e21856, Jan. 16, 2017.

* cited by examiner

*Primary Examiner* — Nancy J Leith
*Assistant Examiner* — Jessica D Parisi
(74) *Attorney, Agent, or Firm* — Myers Bigel, P.A.

(57) ABSTRACT

A method for detecting the binding of a chromatin-associated factor of interest to a sequence of chromatin DNA in a cell, including: contacting a permeabilized cell or nucleus with a specific binding agent that specifically recognizes the chromatin-associated factor of interest, wherein the specific binding agent is linked to a nuclease that is inactive or an activatable transposome; activating the nuclease or transposase, thereby excising the sequence of chromatin DNA bound to the chromatin-associated factor of interest; isolating the excised DNA; and determining the sequence of the excised DNA, thereby detecting binding of a chromatin-associated factor of interest to a sequence of chromatin DNA in the cell.

32 Claims, 105 Drawing Sheets
Specification includes a Sequence Listing.

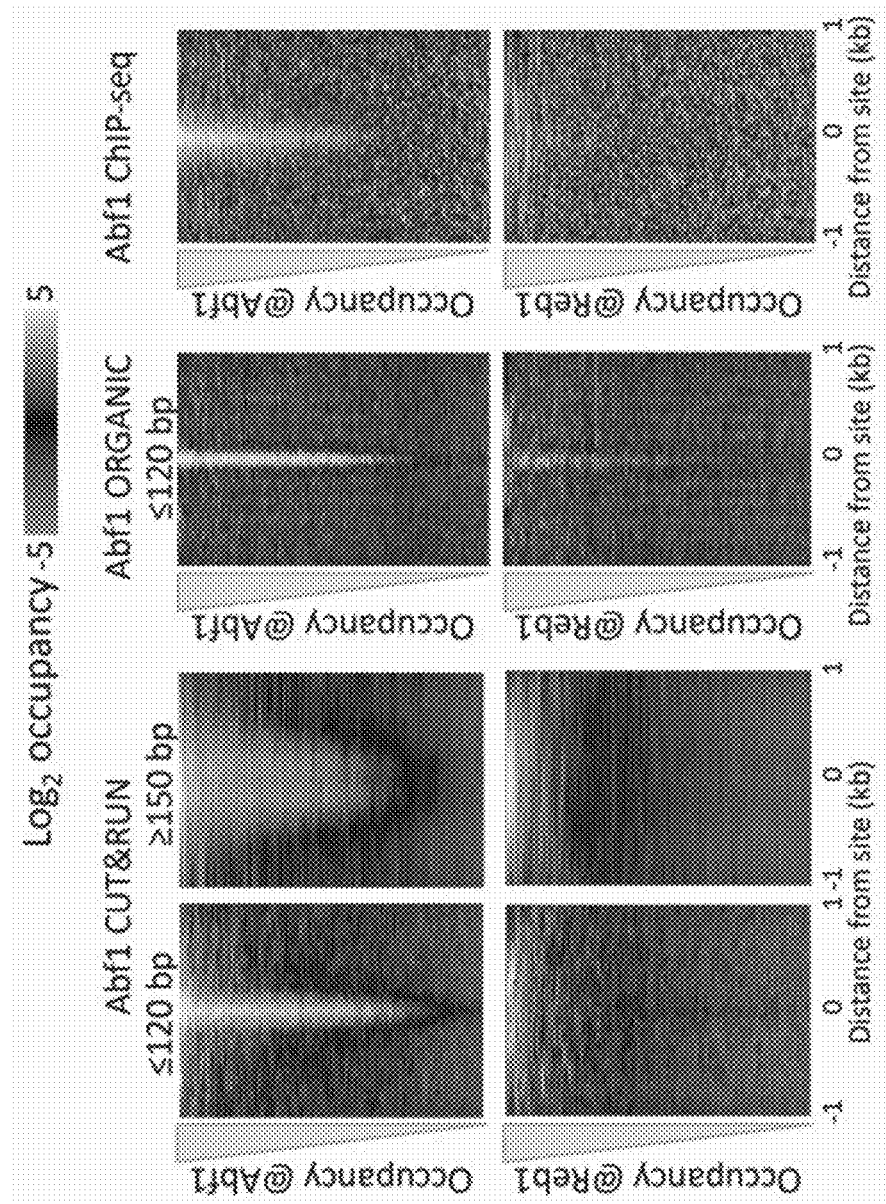
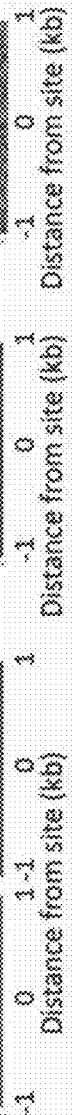
FIG. 2A-1   FIG. 2A-2   FIG. 2A-3

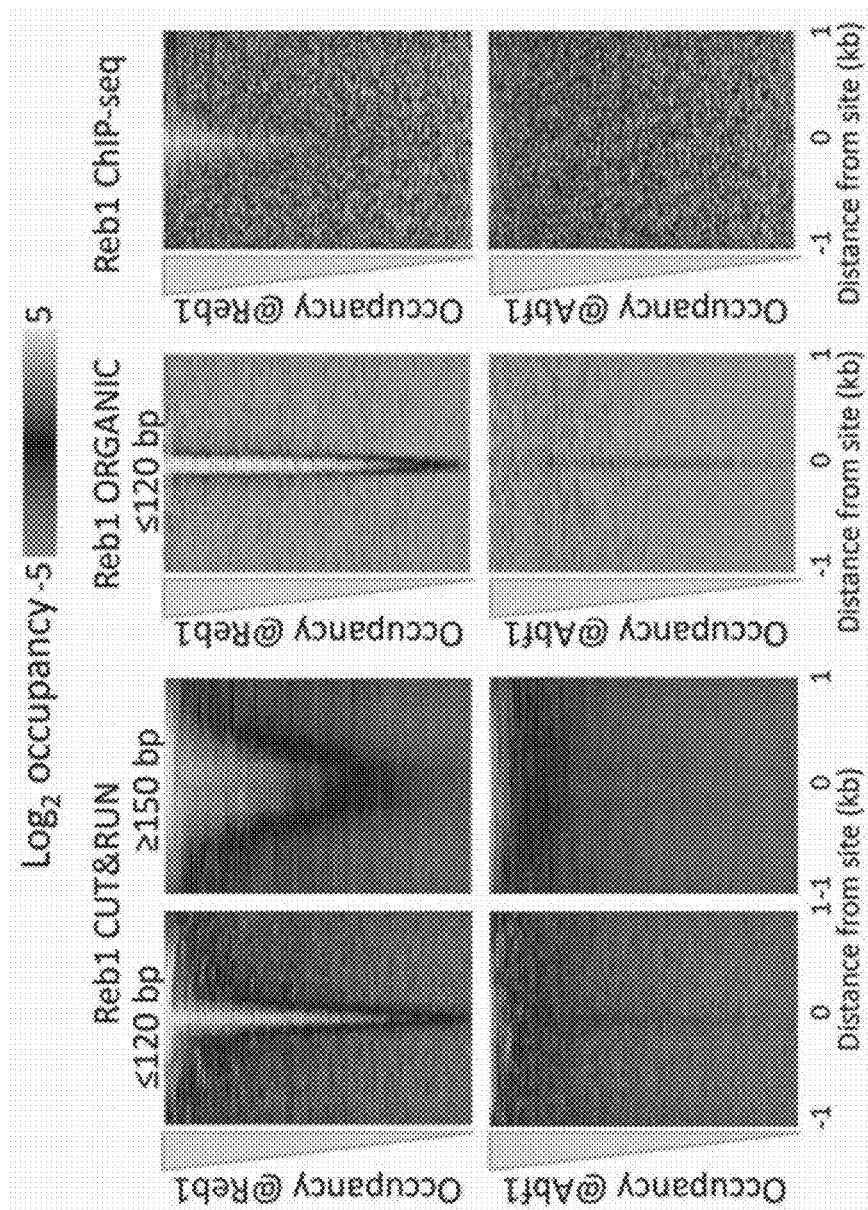

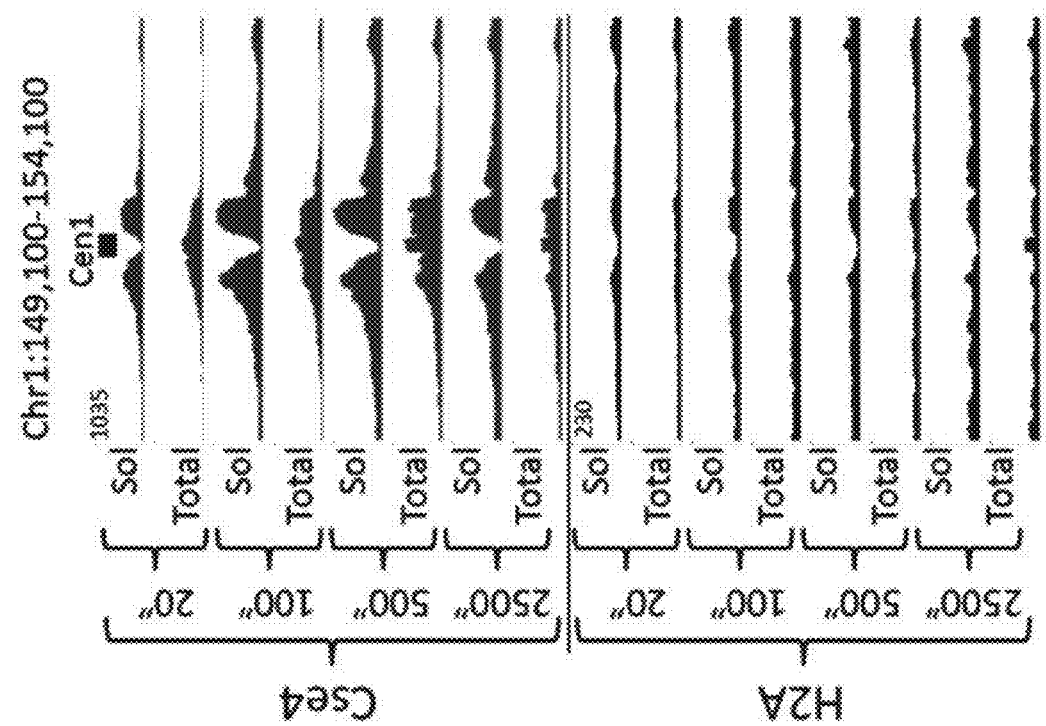
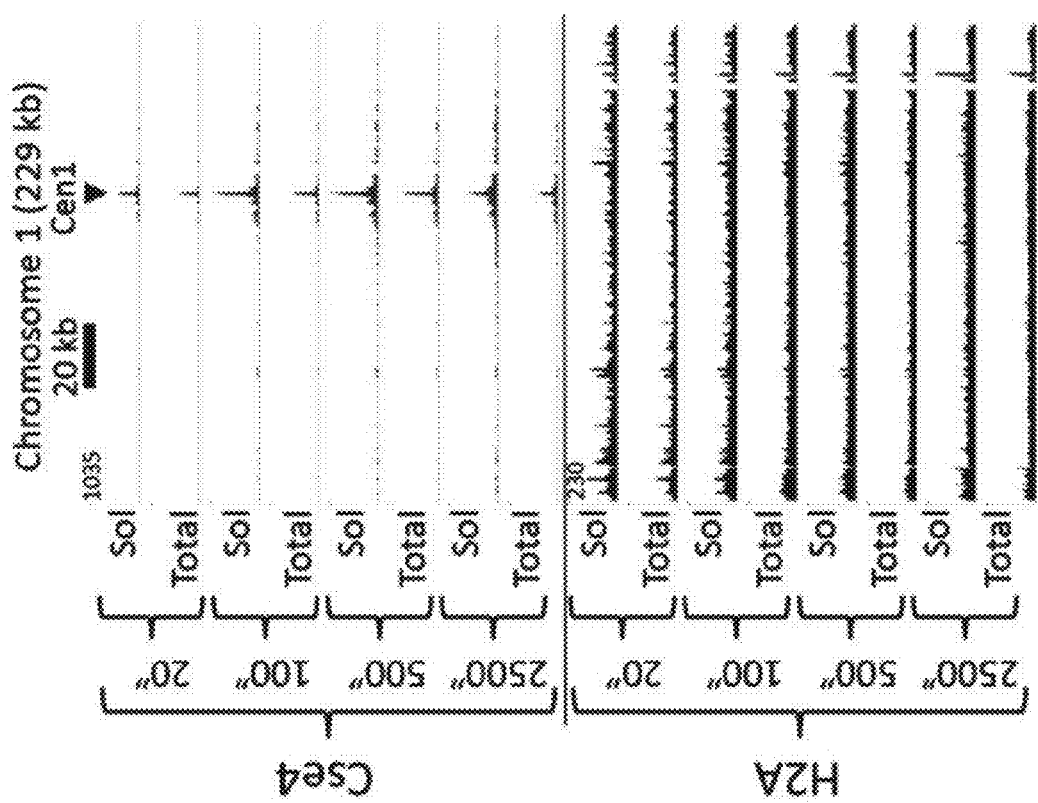
FIG. 5A
FIG. 5B

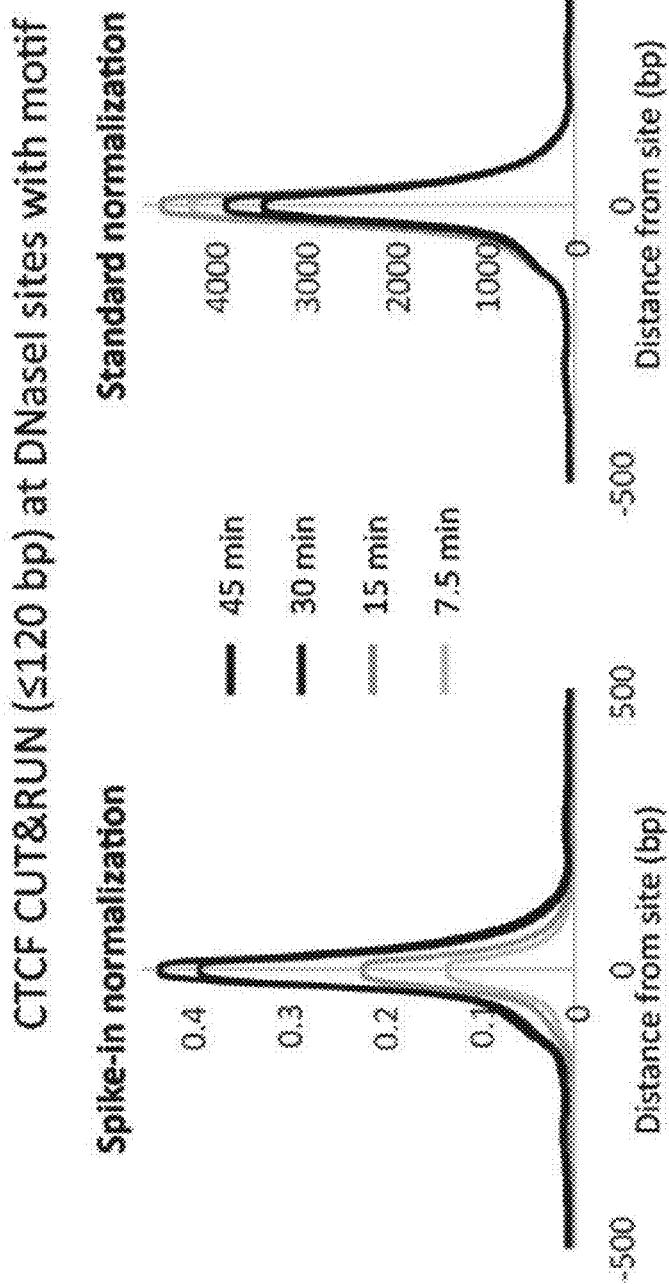

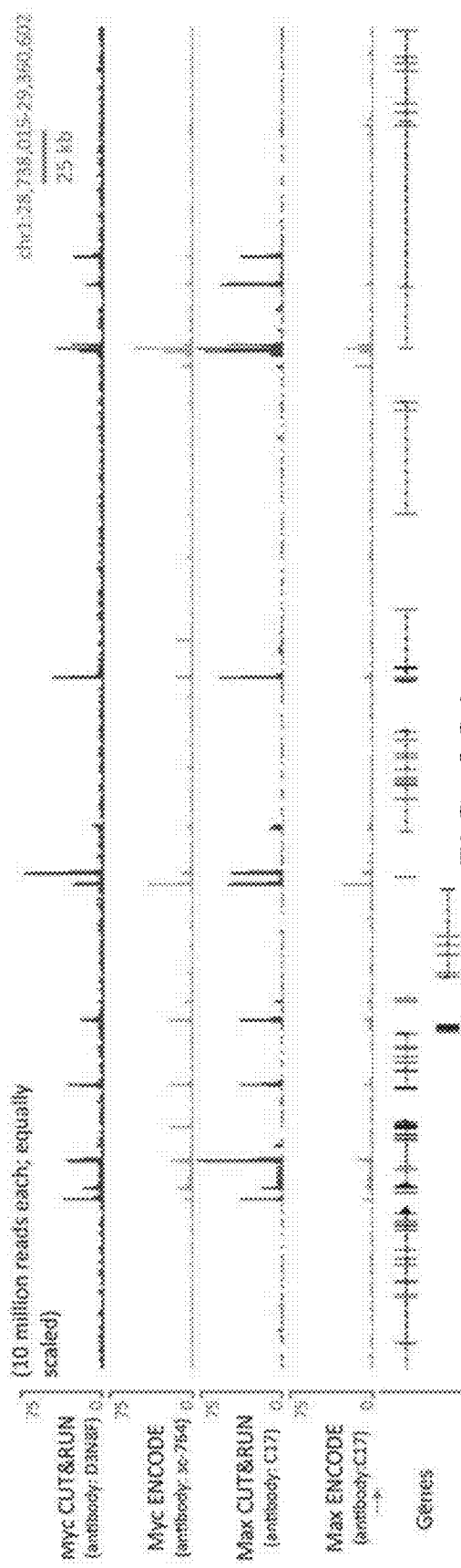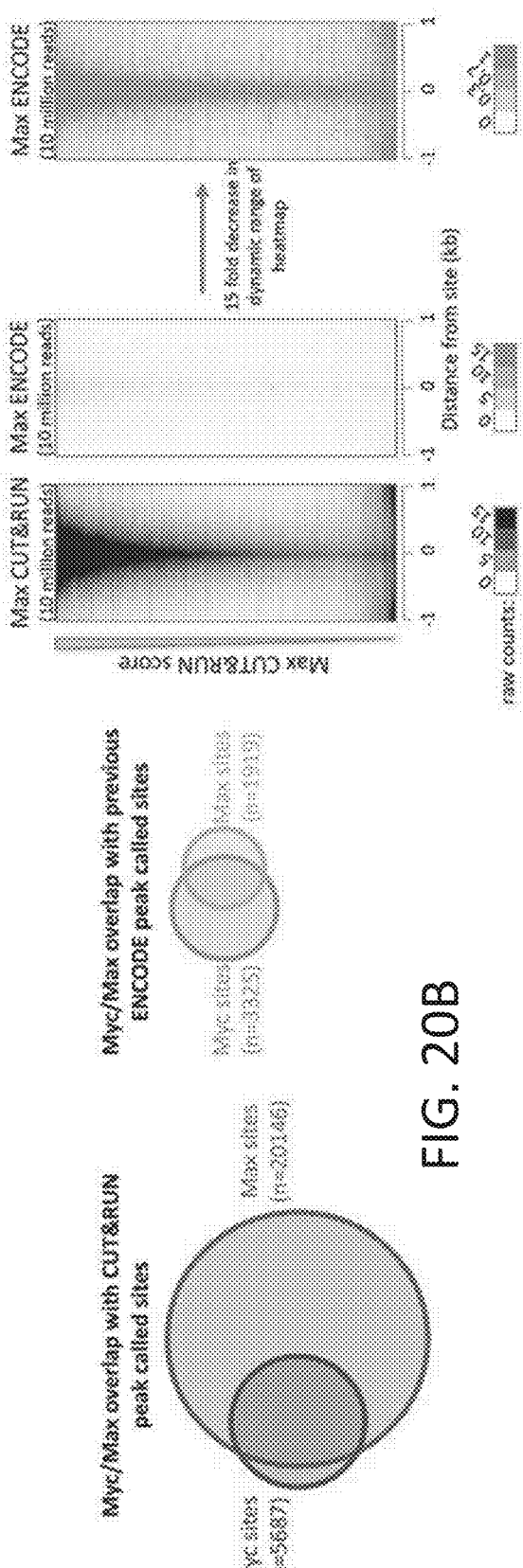
FIG. 20A
FIG. 20B
FIG. 20C pA-MN-6His

CUT&RUN.Proteomics

FIG. 41A
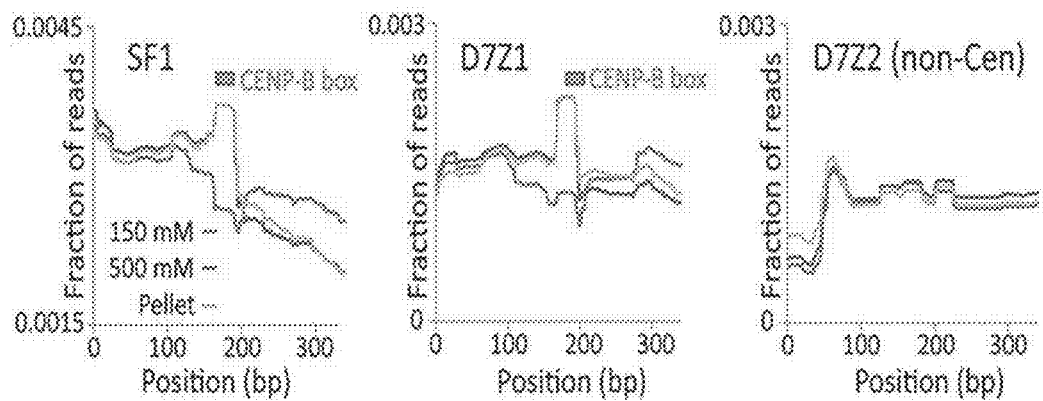
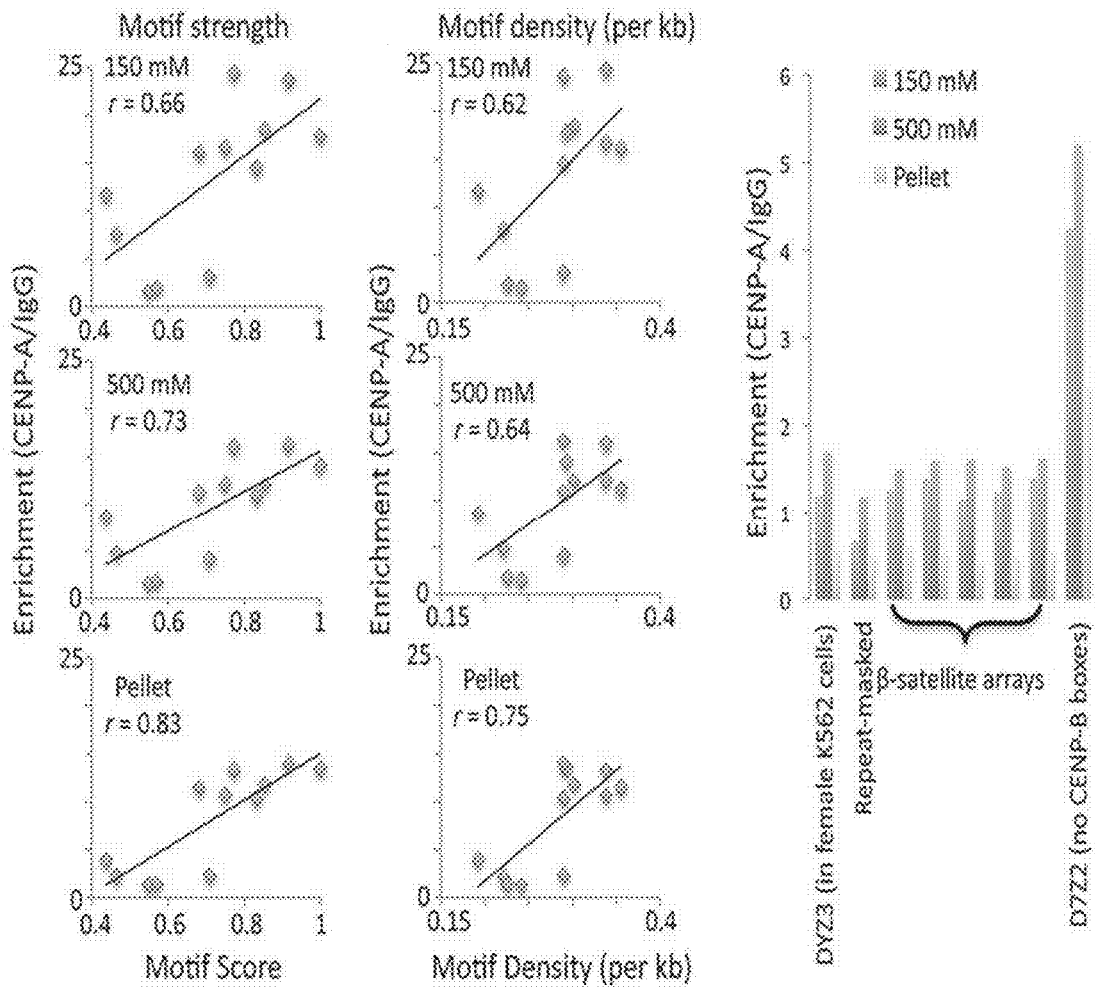
FIG. 41C  FIG. 41B  FIG. 41D

FIG. 45A
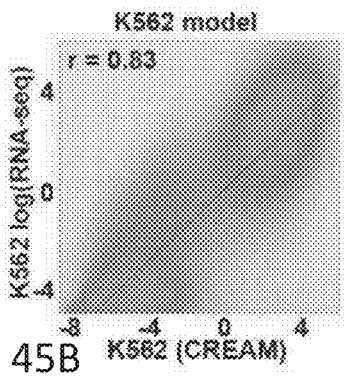
FIG. 45B
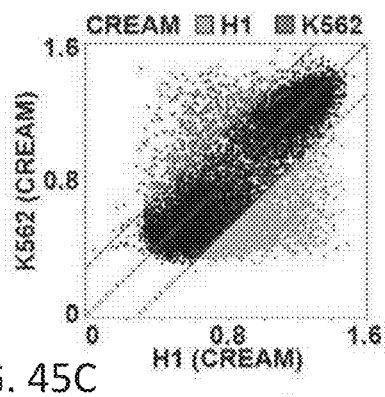
FIG. 45C
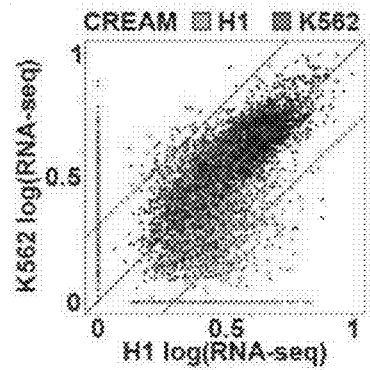
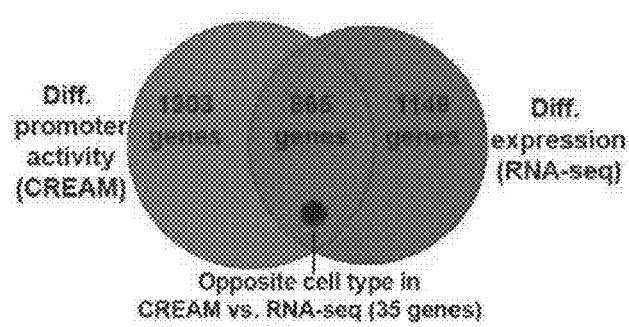
FIG. 45D
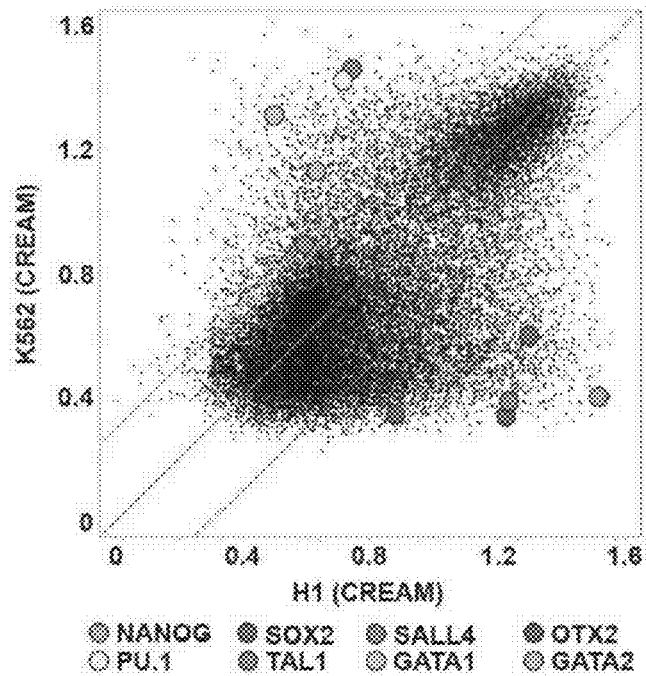
FIG. 45E

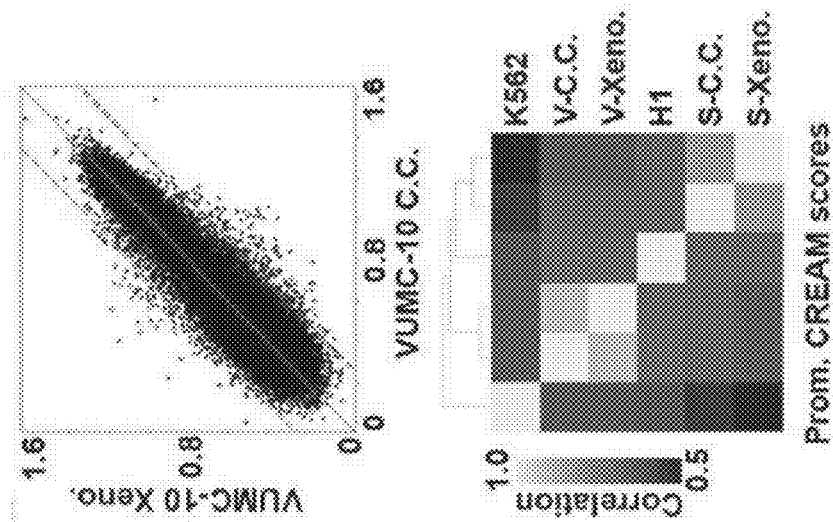
FIG. 47B
FIG. 47C
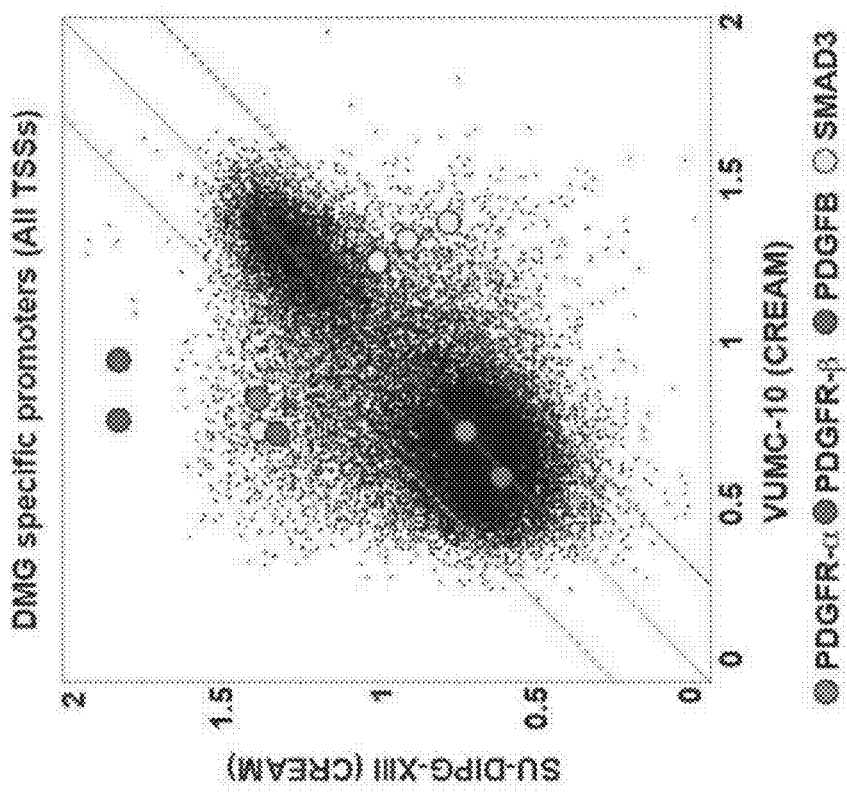
FIG. 47A

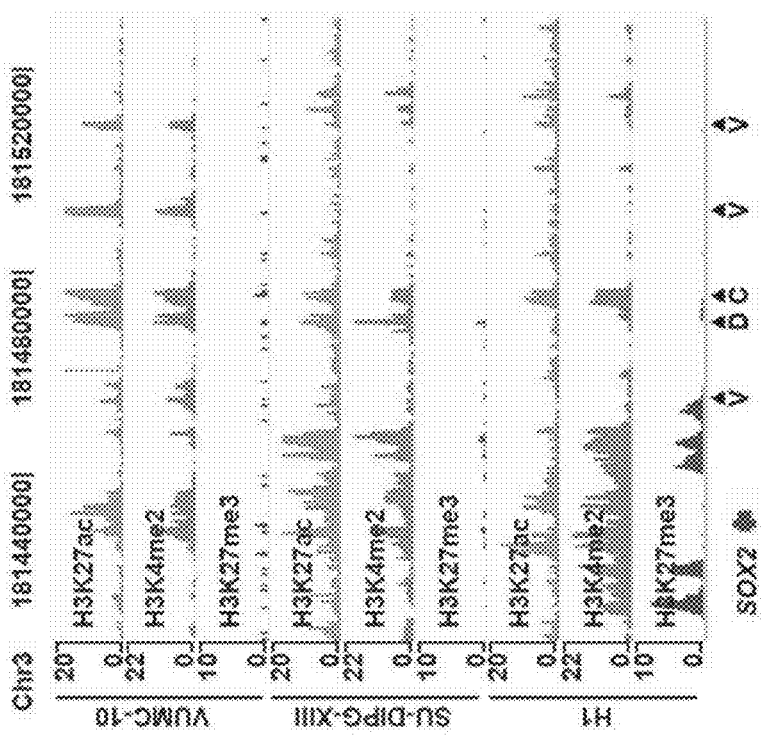
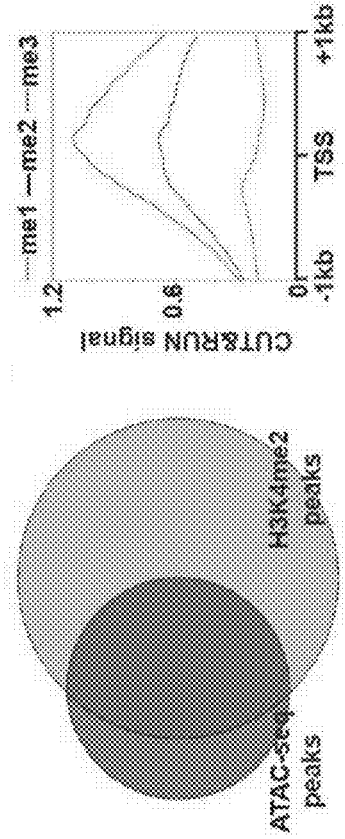
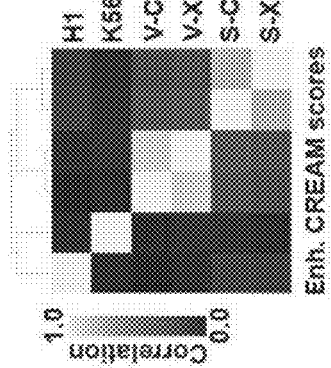
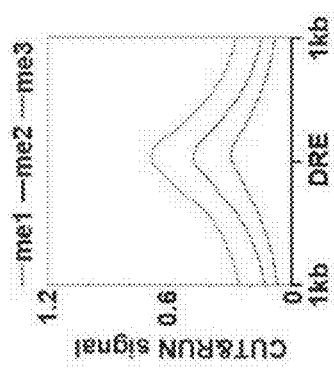
FIG. 48A  FIG. 48B  FIG. 48C  FIG. 48D  FIG. 48E

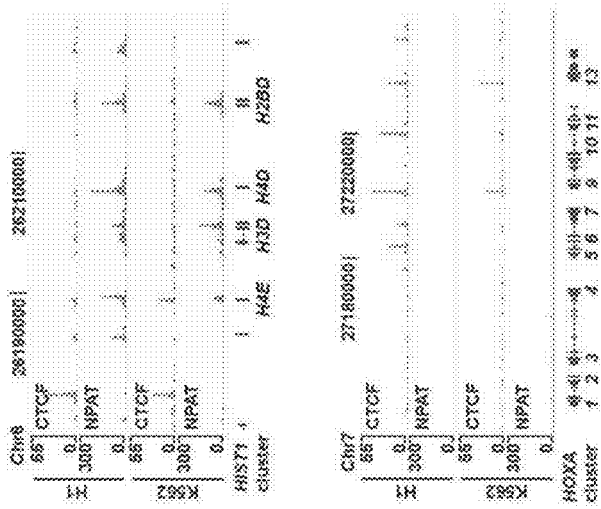
FIG. 49A
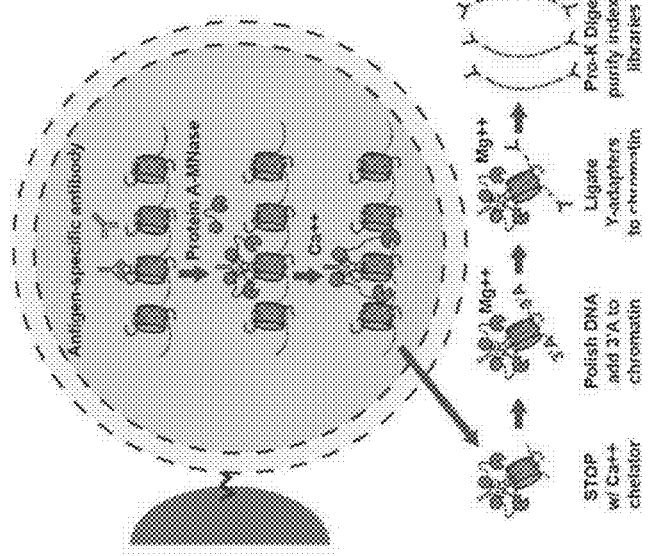
FIG. 49B
FIG. 49C
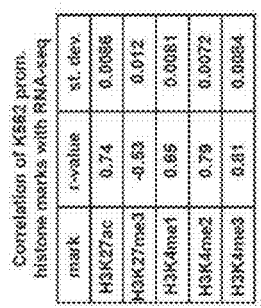
FIG. 49D
FIG. 49E

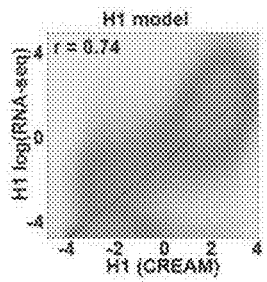
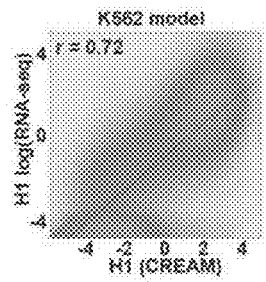
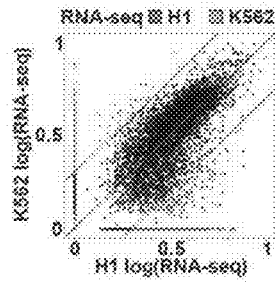
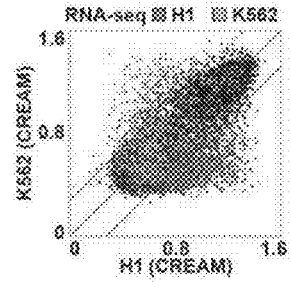
FIG. 50A  FIG. 50B  FIG. 50C  FIG. 50D
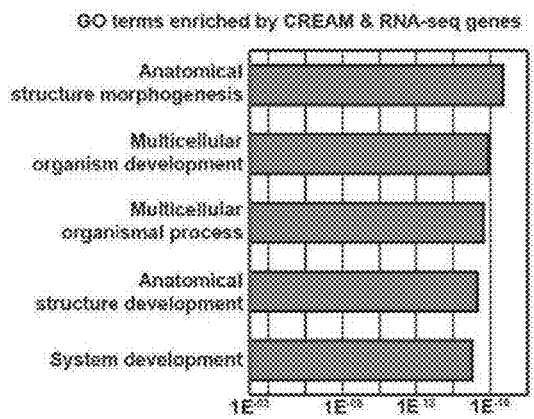
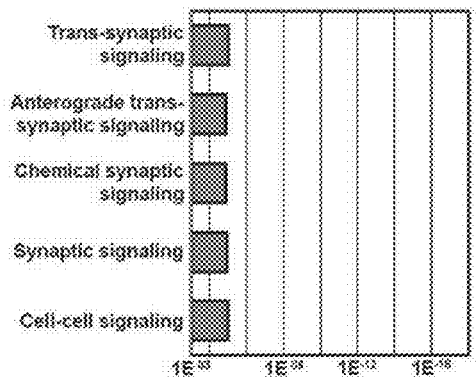
FIG. 50E
FIG. 50F
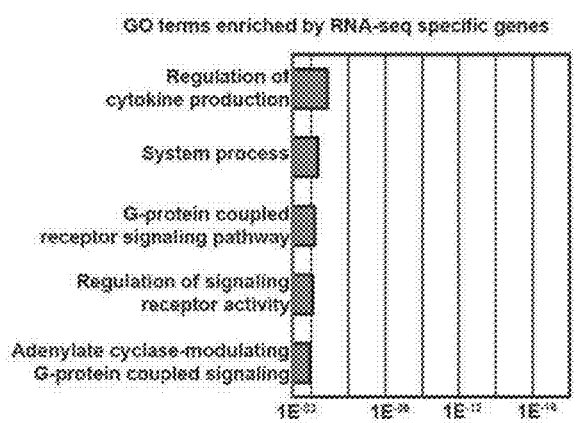
FIG. 50G

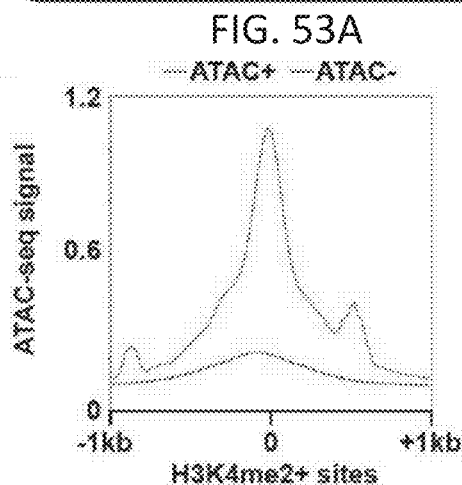
FIG. 53A
FIG. 53B
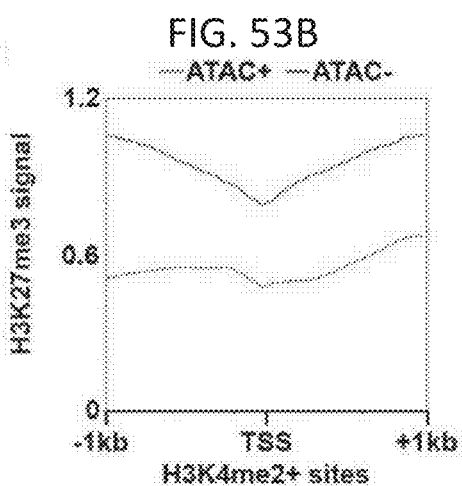
FIG. 53C
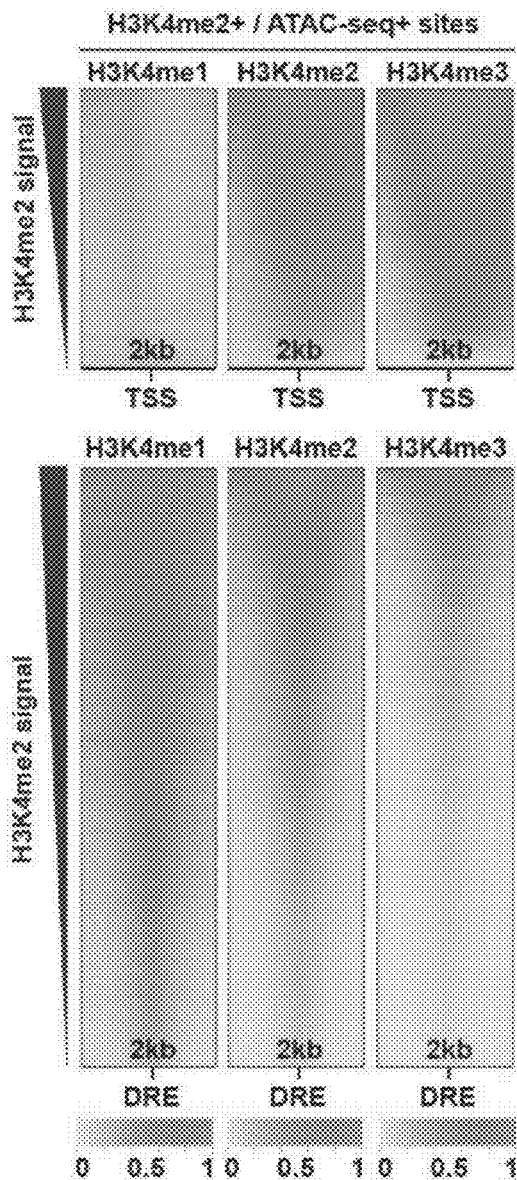
FIG. 53D

FIG. 59A
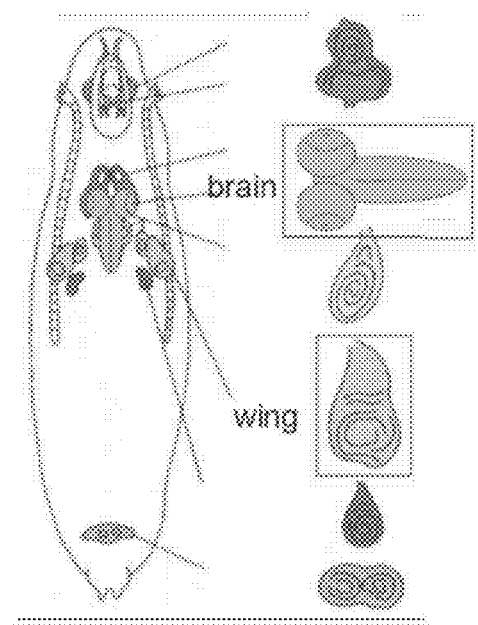
FIG. 59B
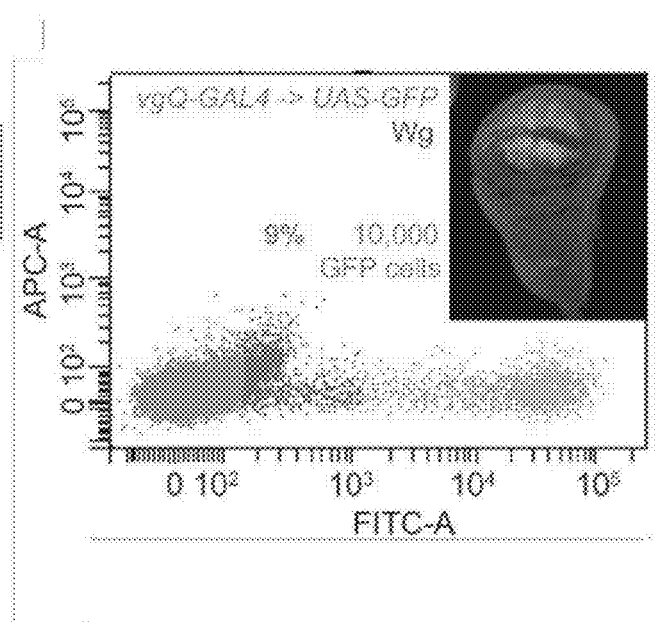
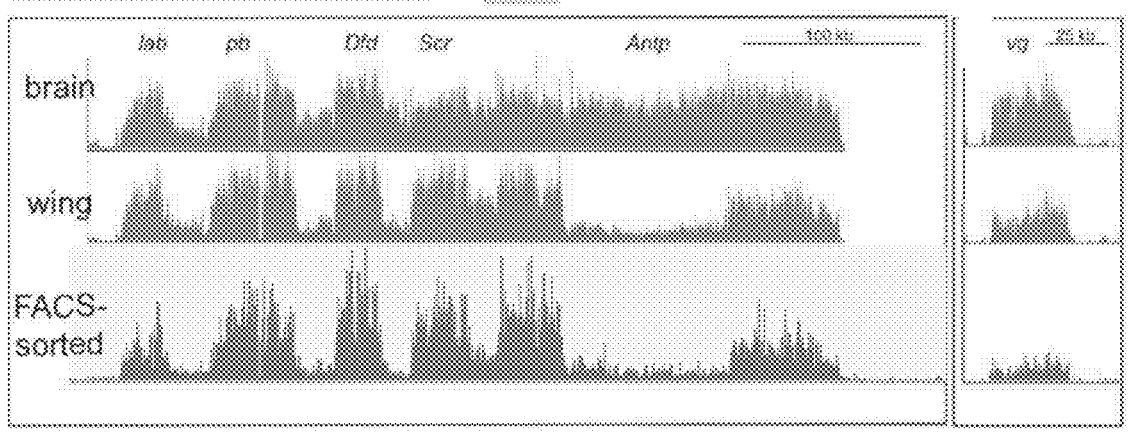
FIG. 59C
FIG. 59D

SEQUENCE LISTING

<160> NUMBER OF SEQ ID NOS: 4

<210> SEQ ID NO 1
<211> LENGTH: 26
<212> TYPE: PRT
<213> ORGANISM: Artificial sequence
<220> FEATURE:
<223> OTHER INFORMATION: polypeptide linker

<400> SEQUENCE: 1

Asp Asp Asp Lys Glu Phe Gly Gly Gly Ser Gly Gly Gly Gly Ser
1               5                   10                  15

Gly Gly Gly Gly Ser Gly Gly Gly Gly Ser
            20                  25

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
ctgtctctta tacacatct                                           19

<210> SEQ ID NO 3
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 3
tcgtcggcag cgtcagatgt gtataagaga cag                           33

<210> SEQ ID NO 4
<211> LENGTH: 34
<212> TYPE: DNA
<213> ORGANISM: Artificial sequence
<220> FEATURE:

```
<223> OTHER INFORMATION: Synthetic oligonucleotide

<400> SEQUENCE: 4
gtctcgtggg ctcggagatg tgtataagag acag                                    34
```

HIGH EFFICIENCY TARGETED IN SITU GENOME-WIDE PROFILING

CROSS REFERENCE TO RELATED APPLICATIONS

This application claims the benefit of U.S. Provisional Application No. 62/562,918, filed Sep. 25, 2017, which is specifically incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 18-010-PCT_ST25.txt, 1,220 bytes in size, generated on Oct. 13, 2018 and filed via EFS-Web, is provided in lieu of a paper copy. This Sequence Listing is hereby incorporated by reference into the specification for its disclosures.

TECHNICAL FIELD

This disclosure relates to methods of chromatin profiling. Specifically, this disclosure relates to methods for profiling DNA binding proteins, such as transcription factors and nucleosomes, in which antibody-targeted controlled cleavage by an enzyme, such as a transposase or nuclease, releases bound DNA for DNA sequencing.

BACKGROUND

The action of transcription factors (TFs) at their binding sites on DNA drives gene expression patterns, and so genome-wide TF mapping has become a central goal both for individual researchers and large-scale infrastructural projects. TF profiling is most commonly carried out using chromatin immunoprecipitation (ChIP), a protocol that has changed little since it was first introduced over 30 years ago (Solomon and Varshavsky, 1985). Cells are crosslinked with formaldehyde, chromatin is fragmented and solubilized, an antibody is added, and the antibody-bound chromatin is recovered for DNA extraction. Successive advances in DNA mapping technologies have revolutionized the use of X-ChIP (formaldehyde crosslinking ChIP), and with ChIP-seq, base-pair resolution mapping of TFs became feasible (Rhee and Pugh, 2011; Skene and Henikoff, 2015; He et al., 2015).

Specific DNA sites in direct physical interaction with transcription factors and other proteins can be isolated by chromatin immuneprecipitation to produce a library of target DNA sites bound to a protein of interest in vivo. With the advent of massively parallel sequencing, the libraries can be rapidly analyzed, and mapped to whole-genome sequence databases to determine the interaction pattern of any protein with DNA, or the pattern of any epigenetic chromatin modifications. This can be applied to the set of ChIP-able proteins and modifications, such as transcription factors, polymerases and transcriptional machinery, structural proteins, protein modifications, and DNA modifications. ChIP sequencing (ChIP-seq) can be used to determine how proteins interact with DNA, for example to regulate gene expression. ChIP-seq technology is currently seen primarily as an alternative to ChIP-chip which requires a hybridization array. This necessarily introduces some bias, as an array is restricted to a fixed number of probes. Improvements to ChIP-seq retain the crosslinking step to preserve the in vivo pattern while the entire genome is fragmented to create a soluble extract for immunoprecipitation. However, crosslinking can promote epitope masking and can generate false positive binding sites (Teytelman et al., 2013; Park et al., 2013; Jain et al., 2015; Baranello et al., 2016; Meyer and Liu, 2014). ChIP can also be performed without crosslinking, using ionic conditions that do not disrupt electrostatic contacts (Kasinathan et al., 2014). 'Native' ChIP provides a map of direct protein-DNA interactions with sensitivity and specificity trade-offs that compare favorably with X-ChIP methods. Native ChIP also minimizes problems with epitope masking and improves efficiency relative to X-ChIP, making it more amenable to low starting numbers of cells (O'Neill et al., 2006; Brind'Amour et al., 2015). But problems remain with incomplete extraction efficiency of protein-DNA complexes and the potential loss of binding. Also, solubilization exposes all chromatin to the antibody, resulting in non-specific background that limits signal-to-noise and requires extra sequencing to discern specific chromatin features. Because of these biases and inefficiencies, ChIP require large numbers of cells making it unsuitable for example where there are limited numbers of primary cells or small amounts of tissues. New and better non-ChIP based methods are thus needed. This disclosure meets those needs.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 1A-1 to 1D show that the CUT&RUN methods disclosed herein produce limit digests of TF-DNA complexes. FIG. 1A-1, 1A-2: Schematic diagram of the CUT&RUN strategy. Nuclei attached to magnetic beads can be treated successively with an antibody (or optionally with a primary and secondary antibody) and Protein A-MNase (pA-MN), which diffuse in through the nuclear pores. After Ca++ addition to activate MNase cleavage, fragments are released and diffuse out of the nucleus. DNA extracted from the supernatant is used to prepare libraries for paired-end sequencing. FIG. 1C-1, 1C-2, 1C-3; Size distributions of mapped paired-end reads from sequencing of indicated TF samples. An H2A size distribution is included for comparison. Data are normalized such that the sum of all points at each length step in base pairs equals 1. FIG. 1D; Time-course profiles for Abf1 and Reb1 samples (~2-3 million mapped paired-end reads per track) showing less than 120 bp and greater than 150 bp fragment length classes, compared to ORGANIC ChIP-seq (~20-30 million mapped paired-end reads) and standard ChIP-seq (Paul et al., 2015) (~5 million Abf1 and ~126 million Reb1 mapped single-end 50 bp reads). A negative control track shows the result of leaving out the primary antibody (No 1° Ab). Within each TF and fragment size group, the Y-axis scale is autoscaled by IGV showing normalized counts and the fragment size classes are superimposed. Ticks mark the location of significant Abf1 (upper) and Reb1 (lower) motifs. This region was chosen as having the largest cluster of Abf1 motifs on Chromosome 3.

FIGS. 2A-1 to 2B-3 show that CUT&RUN accuracy and robustness compares favorably with ChIP-seq. Abf1 (FIG. 2A-1, 2A-2, 2A-3) and Reb1 (FIG. 2B-1, 2B-2, 2B-3) heat maps of CUT&RUN datasets from a single experiment (20160630), pooling 1" to 32" time-course samples, and separating into less than 120 bp and greater than 150 bp size classes (FIGS. 2A-1 and 2B-1). Also shown is the ORGANIC ChIP-seq less than 120 bp size class (FIGS. 2A-2 and 2B-2) and standard ChIP-seq datasets (FIGS. 2A-3 and 2B-3). Abf1 has two DNA-binding domains spaced ~10 bp apart (Cho et al., 1995), whereas Reb1 has a single Myb-like DNA-binding domain (Morrow et al., 1990). Solubilization of Abf1 chromatin after MNase digestion required 600 mM NaCl to obtain the best trade-off between specificity and sensitivity, whereas for Reb1, 80 mM gave the best results (Kasinathan et al., 2014), and these are the datasets used for comparison. As in the previous comparison of ORGANIC to ChIP-exo and ChIP-chip (Kasinathan et al., 2014), the set of all statistically significant Abf1 and Reb1 motifs is considered as the 'gold standard' for judging sensitivity (occupancy of sites by the correct TF) and specificity (exclusion from sites of an incorrect TF). Aligned profiling data were centered and oriented over the motif for the same TF (top) and for the other TF (bottom) for display (removing 81 sites where Abf1 and Reb1 sites were within 50 bp of one another) and were ordered by average pixel density over the −1 kb to +1 kb span of the less than 120 bp datasets using Java Treeview with $\log^2$ scaling and contrast=5. Ordering was performed independently for CUT&RUN (based on less than 120 bp fragments) and ChIP-seq, in which case the approximate fraction of sites occupied relative to flanking regions becomes evident, and comparison of the top panel (correct TF) to the bottom panel (incorrect TF) reflects the sensitivity/specificity tradeoff for a dataset. Sites were determined by MAST searching of the S. cerevisiae genome using the position-specific scoring matrices (PSSMs) based on ChIP-seq data but similar results were obtained using MAST with PSSMs based on CUT&RUN data.

FIG. 3A; Mapping of fragment ends reveals a deep 'hole' and steep 'walls' for Abf1 and Reb1 CUT&RUN datasets averaged at their oriented and aligned motifs genome-wide, plotting all normalized base-pair counts from combined 1"-32" datasets (see FIG. 3.2A-1 to 2B-3). Saw tooth patterns with an apparent ~10 bp periodicity on the upstream and downstream 'slopes' are confirmed by FIG. 3B autocorrelation analysis of the difference between the 1 bp resolution profile shown in FIG. 3A and the same profile smoothed with an 11 bp sliding window, which also shows that there is no corresponding periodicity in average G+C content (thin lines). FIG. 3C is the same as FIG. 3A, but subject to smoothing with an 11 bp sliding window and displayed at larger scale. The fact that the slopes around Reb1 show depressions at +150 and −150 likely reflects the presence of phased nucleosomes, shown below (Nucls, Y-axis arbitrary) based on the greater than 150 bp size class from ORGANIC input data (Kasinathan et al., 2014).

FIGS. 4A-4C show that CUT&RUN precisely maps large mobile chromatin complexes. FIG. 4A; representative tracks showing a Mot1 CUT&RUN time-course experiment (average ~3 million paired-end reads per sample), including a no primary antibody (No 1° Ab) negative control, aligned with Mot1 ORGANIC data for two MNase digestion time points (2.5' and 10', average 22 million reads per sample) (Zentner and Henikoff, 2013). TBP sites shown as dotted lines reveal that Mot1 peaks are just upstream of TBP peak maxima. FIG. 4B-1, 4B-2: occupancy profiles for Sth1 CUT&RUN digestion over a 120-fold range, spike-in normalized, showing absolute quantitation. FIG. 4C: Sth1 ORGANIC profiles (~15 million reads) show concordance with the CUT&RUN 5 s sample (~2 million reads). Note that the same CUT&RUN 5 s less than 120 bp profile is shown in both panels (FIG. 4B-4B-2) and (FIG. 4C), but at different scales.

FIGS. 5A to 5D-2 show that CUT&RUN maps the rare highly insoluble S. cerevisiae kinetochore complex. FIG. 5A; after stopping digestion for the indicated times, samples were split in half and both the soluble fraction and total DNA were extracted. Large fragments were removed from total DNA with AMPure beads before library preparation. Normalized counts are shown for S. cerevisiae Centromere 1, where Cse4 and H2A tracks are on the same Y-axis scale. Similar maxima over centromeres was also seen genome-wide. FIG. 5B is the same as FIG. 5A but zoomed in over the 5 kb interval at the centromere. FIG. 5C-1, 5C-2: occupancies of insoluble Cse4 and H2A, where it is defined that $\log 2$ (Insoluble)=$\log 2$ (Total)−$\log 2$ (Soluble)=$\log 2$ (Total/Soluble) for the medians of all 16 S. cerevisiae centromeres aligned around their midpoints. A published X-ChIP-seq profile (Pekgoz Altunkaya et al., 2016) is shown on the same scale for comparison (FIG. 5C-1). Asterisk: $\log_2$ (ChIP/Input) averaged over two replicates. FIG. 5D-1, 5D-2; normalized count profile of Cse4 and H2A CUT&RUN applied to formaldehyde crosslinked cells digested for the indicated times.

FIG. 6A; representative signal over a genomic locus for 10 million randomly sampled reads from ENCODE CTCF ChIP (GSM749690), CTCF ChIP-exo, and CUT&RUN. In the top panel, the y-axis is the same for all datasets indicating the higher dynamic range for CUT&RUN. In the bottom panel, the y-axis is individually set. FIG. 6B; heat maps of CUT&RUN pooled datasets (7.5 min to 45 min) separated into less than 120 bp (including fragment ends) and greater than 150 bp size classes and of ENCODE X-ChIP-seq and high resolution X-ChIP-seq (Skene and Henikoff, 2015) for CTCF in human K562 cells. Sites were determined by an unbiased approach in which the data were centered and oriented on CTCF motifs that were found within DNaseI hypersensitive sites and ordered by genomic location. Asymmetric release of the upstream and downstream nucleosome likely comes from epitope location controlling access to nucleosomes either side of the motif. FIG. 6C; mean plots of end positions from less than 120 bp fragments resulting from a CUT&RUN digestion time-course centered over sites as above. Data are represented as a percentage of the maximum signal within the ±1 kb flanking region.

FIG. 7A; chromatin was fragmented and solubilized under native conditions and either directly sequenced as native input or CTCF bound chromatin was immunoprecipitated and sequenced. ENCODE X-ChIP-seq was analyzed for comparative purposes. Peaks of CTCF binding under native conditions were identified and centered on the best match to the CTCF motif (JASPAR database MA0139.1, jaspar.genereg.net/). Data were plotted over these sites (−1 to +1 kb) as heat maps for native ChIP DNA fragments (20-75 bp) and CUT&RUN (less than 120 bp) and ordered by native CTCF ChIP occupancy (sum over the center region (−30 to +30 bp) minus the sum over the flanks (−1000 to −700 and +700 to +1000 bp). The graph below shows the cumulative percent of sequencing counts for the different techniques over peak-called sites (−30 to +30 bp) and ranked by similarity to the CTCF motif. This shows the high concordance between the chromatin profiling techniques at native ChIP peaks. Note that the dynamic range scales for Native ChIP and CUT&RUN are ~30-40 fold higher than those for Native Input and ENCODE X-ChIP, which was needed to show the input and ENCODE patterns. FIG. 7B; data plotted over CUT&RUN peak-called sites, with processing as per FIG. 7A. The cumulative distribution shows the shift to lower motif scores for CUT&RUN sites (see the separation between CUT&RUN and native ChIP).

FIG. 8A; typical genomic region displaying CUT&RUN (less than 120 bp), native ChIP (20-75 bp) data for CTCF and CTCF ChIA-PET fragments (GSM1872886; score greater than 15). ChIA-PET fragments were ascribed as a direct interaction (overlapping a native ChIP peak) or an indirect interaction (overlapping a CUT&RUN peak only). FIG. 8B; peak called sites were separated into either direct (present in native ChIP) or indirect (only present in CUT&RUN). Hi-C fragments that intersect with direct sites or an equal number of random genomic locations were identified. The Hi-C interacting fragment was then intersected with the indirect sites and the CUT&RUN signal compared to Hi-C raw signal. Data were ranked by CUT&RUN score and plotted as a moving average with a window size of 1500. FIG. 8C; ChIA-PET fragments that contained a direct site were identified and the interacting fragment intersected with direct peaks, indirect peaks or random locations as above. Interacting fragments that did not overlap with these sites were classed as uncategorized. Boxplots indicate the CUT&RUN score for the observed contacts at the interacting fragment.

FIGS. 9A-1 to 9B-4 show that CUT&RUN allows simple quantification of protein-DNA interactions. FIG. 9A-1, 9A-2; digestion time course of CUT& RUN was performed for CTCF in K562 cells. To allow quantification of released fragments, 1 ng of Drosophila DNA was added after the cleavage reaction. Mean plots of less than 120 bp sequenced fragments were centered over CTCF motifs found within DNaseI sites. Data were normalized either to the number of fly reads (Spike-in normalization) or to the total number of human reads (Standard normalization). FIG. 9B-1, 9B-2, 9B-3, 9B-4; titration of starting material was used to map CTCF binding genome-wide. Heat maps and mean plots were generated for the less than 120 bp sequenced fragments using Spike-in or Standard normalization. Data were centered over CTCF motifs found within DNaseI sites.

FIG. 11A; Electrophoresis on a 1% agarose gel of DNA from the pellet fractions (10 µL per sample) over a 1-128 s digestion time series at 0° C. for the two yeast TFs described in this study. As these sites are on average ~10 kb apart in the yeast genome a gradual decrease in fragment size can be observed with time of digestion from 1 s to 128 s for both Abf1 and Reb1. The average distance between CTCF sites in the human genome is too large to observe cleavages using a conventional gel assay. FIG. 11B; Percent release of DNA based on Picogreen fluorescence measurements: [Supn]/([Supn]+[Pellet])*100. Total yield ~500 ng/sample.

FIG. 12A; A comparison of Abf1 and Reb1 profiles of CUT&RUN data from a single experiment as described herein, except comparing the supernatant fraction (Soluble) to Total DNA after removal of large fragments on AMPure beads. FIG. 12B; Expanded region of high TF occupancy in FIG. 12A. FIG. 12C; Heat map alignments of CUT&RUN ≤120 bp digestion data to motifs and ordering by TF occupancy was performed as described herein, except with log scaling and Contrast=5, centered on 2.

FIG. 13E; Percentage of peak calls with motifs. For each ≤120 bp dataset, peaks were called using thresholds set to recover similar numbers of peaks (stringent ~650 and relaxed ~1100).

FIG. 15A; Heat maps of two CUT&RUN and two ORGANIC time points aligned around TBP sites and ordered by increasing Mot1 occupancy over the 2 kb region surrounding each site. FIG. 15B; Occupancy profiles for Mot1 CUT&RUN digestion over a 120-fold range, spike-in normalized, showing absolute quantitation.

FIG. 16A; Length distributions of Sth1 CUT&RUN AMPure-bead filtered total DNA fragments normalized such that there is equal areas under the curves. Uniform digestion and release is observed over the time-course. Data are combined from two biological replicates. No anti-FLAG primary antibody (No Ab). FIG. 16B; Tracks of the Gal1-Gal4 region (ChrII: 276,000-281,000) showing concordance with the mapping of RSC to the Gal4 UAS (UASg, Floer et al., 2010).

FIG. 17A; After antibody and pA-MN addition, samples were split in half, pA-MN was activated with calcium, and the reaction stopped with either the standard 100 mM NaCl buffer (−) or a buffer containing 2 M NaCl (+). Tracks are displayed for Chromosome one using spike-in normalization to reflect absolute recovery. FIG. 17B; Close-up views of Cse4 and log-ratios of Cse4 and H2A high-salt versus low-salt extracted fragments. FIG. 17C; Log-ratios of high-salt versus low-salt extracted fragments for the medians of all 16 S. cerevisiae centromeres aligned around their midpoints.

FIG. 19A; Initially 37° C. was used for MNase reactions. Careful analysis of the data, however, showed that despite clearly mapping CTCF at its true sites with a low density genome-wide background, we also had a specific background at random DNase1 sites. It was rationalized that specific background arose from the liberated chromatin complexes that are still bound by Protein A-MNase diffusing around the nucleus and cutting accessible regions of chromatin. FIG. 19B; To test this hypothesis, after the CTCF antibody and Protein A-MNase had bound in situ, the nuclear envelope was disrupted with limited sonication to release the chromatin into the large reaction volume. When CUT&RUN was performed under disrupted conditions, this specific background was no longer observed. FIG. 19C; the diffusion of these chromatin complexes was limited by performing the cleavage reaction at room temperature. The signal-to-noise ratio started low, but increased over time and by 8 min the noise was indistinguishable from the signal. FIG. 19D; However, by keeping the reaction on ice the signal-to-noise ratio was high and independent of time. Therefore, by controlling the temperature for the cleavage reaction, a low background can be robustly maintain.

FIGS. 20A-20C show that the high signal-to-noise ratio of CUT&RUN allows robust identification of DNA binding sites not possible with X-ChIP-seq. CUT&RUN was performed for Myc and Max in K562 cells and compared to ENCODE X-ChIP-seq datasets (GSM935410; GSM935539). For each dataset 10 million reads were randomly selected and (FIG. 20A) a typical genomic region is shown. Note for Myc different antibodies were used and therefore quantitative comparison is not possible. FIG. 20B; Proportional Venn diagrams displaying the overlap between Myc and Max peak called sites identified by CUT&RUN or previously by ENCODE. FIG. 20C; Heat maps showing CUT&RUN and ENCODE X-ChIP-seq signal plotted at peak called sites identified by Max CUT&RUN (n=20146). Sites were ranked by Max CUT&RUN score, note the change in the dynamic range of the heat maps.

FIG. 22A; Western blotting to test the extraction efficiency of RNA polymerase II (RNAPII) and CTCF under native conditions with varying SDS and sonication conditions. FIG. 22B; To test for potential redistribution of CTCF under native conditions, extracts were incubated with 95 bp DNA probes with a high scoring motif (positive), or a shuffled sequence (negative), or the 601 nucleosome positioning sequence at 1000 copies per cell. Following the ChIP and DNA extraction, quantitative PCR was used to test for CTCF binding to a native peak in the genome (genomic) or to the DNA probes.

FIG. 31A; ChIP applied to CUT&RUN supernatants. By using a 3×FLAG tag on the targeted protein and an anti-FLAG antibody (followed by a rabbit anti-mouse secondary antibody, not illustrated), the pA-MN/antibody complex recovered in the CUT&RUN supernatant is competed off the DNA-protein complex by addition of FLAG peptide. A second antibody is then added and the immunoprecipitate is captured on Protein A magnetic beads. FIG. 31B; CUT&RUN.ChIP applied to S. cerevisiae nucleosomes; a representative example of region spanning 11 genes is shown. 1. CUT&RUN was first performed using either 3×FLAG-H2A.Z (green) or 3×FLAG-H2B (blue). 2. The inputs and supernatants were then subjected to ChIP-seq using various histone modification and control (IgG) antibodies as indicated. Profiles are autoscaled to illustrate the landscape pattern. Analysis of the profiles (not shown) indicates that the H2A.Z histone variant is enriched over promoters of active genes and is enriched for histone H4 acetylation and H3K4me3, but depleted for H3K36me3, consistent with previous studies.

FIG. 32A; A map of pA-MN-6His. FIG. 32B; Strategy for protein purification and proteomic analysis of particles released by CUT&RUN.

FIG. 33A; Schematic of protocol for Cleavage Under Targets and Release Using Nuclease (CUT&RUN). FIG. 33B; IGV representation of CUT&RUN data with H3K27M antibody in the different DMG cell lines, top panel is group-autoscaled relative to highest signal and bottom panel is individually autoscaled. FIG. 33C; Average (top) and heat map (below) profiles of H3K27M CUT&RUN signal residing in H3K27me3 and H3K27ac domains in the H3 mutant DMG cell lines. FIG. 33D Top: Western blotting for H3K27M and H3K27me3 in protein extracts from CUT&RUN reaction supernatants in the H3 mutant DMG cell lines performed with H3K27me3, H3K27M and IgG antibodies.

FIG. 34A; Representative IGV tracks for the labeled genes. FIG. 34B; Correlation matrices for H3K27me3 CUT&RUN in DMG cell lines using normalization-insensitive Pearson's correlation and normalization-sensitive Lin's correlation. FIG. 34C; Heat maps of H3K27me3 CUT&RUN residing in H3K27me3 domains using hierarchical clustering to classify domains based on differences between DMG cell lines, with relevant clusters numbered 1-6. In relation to FIG. 34A, WNT6 is found in cluster 3, WT1 in cluster 5 and PRDM1 in cluster 6.

FIG. 35A; Average profiles (top) and heat maps (below) of H3K27me3 CUT&RUN from all cell lines used in this report, residing in clusters of differential H3K27me3 domains identified in FIG. 34. FIG. 35B; Correlation matrix comparing genome-wide H3K27me3 CUT&RUN in histone wildtype (VUMC), neural stem cells (CB660 and U5), ES cells (H1) and the two H3 mutant DMG cell lines using Lin's correlation. FIG. 35C Bar graph displaying the number of H3K27me3 domains specific to or shared by the cell lines specified, the number of those domains that overlap with Cluster 6, and the number that overlap with Cluster 6 after randomly shuffling genome coordinates. P-values derived by Chi-square between experimental and randomized overlaps.

FIG. 36A; Correlation matrix comparing genome-wide CUT&RUN for H3K27ac in histone wildtype (VUMC), neural stem cells (CB660 and U5), ES cells (H1) and the two H3 mutant DMG cell lines, and H3K27M in the histone mutant DMG lines, using Pearson's correlation. FIG. 36B; Representative IGV tracks of CUT&RUN signal for H3K27M in H3.3K27M and H3K27ac in H3.3K27M, H1, CB660 and U5 at loci at which H3K27ac is specific to hESCs (top left), is shared in hESCs and NSCs (bottom left), is specific to NSCs (bottom right), or is only found in H3.3K27M (top right).

FIG. 37A; IGV representation of CUT&RUN data from reactions with H3K27me3, H3K27M, SUZ12 and MTF2 antibodies performed in the H3.3K27M cell line. FIG. 37B; Average profiles showing enrichment of H3K27me3, H3K27M, SUZ12, and MTF2 CUT&RUN in H3K27me3 or H3K27M enriched regions in H3.3K27M-DMGs. FIG. 37C; Average profiles showing enrichment of SUZ12 and MTF2 in H3K27me3- and H3K27M-enriched regions in the H3.1K27M-DMG cell line.

FIG. 39A; Schematic showing cooperativity between cell-of-origin, secondary mutations and H3K27M in gliomagenesis. FIG. 39B; Model for contribution of H3K27M to PRC2 landscapes. Nucleosomes containing either wildtype H3.1 and H3.3, H3.1K27M (w/asterisk) or H3.3K27M (w/asterisk) are shown. H3.1K27M promotes derepression of many stemness and pro-proliferation genes but low-level residual PRC2 activity can still silence a subset of genes. H3.3K27M prevents silencing of stemness genes despite repressive signals occurring but allows robust silencing of PRC2 domains containing wildtype H3.1.

FIG. 40A; Fragment length analysis of merged pairs mapped to D7Z1 (left) and DXZ1 (right) in CENP-A, CENP-B, and CENP-C CUT&RUN.Salt fractions. FIG. 40B; Mapping of CENP-A, CENP-B, and CENP-C CUT&RUN.Salt 250-bp×250-bp merged pairs to D5Z2, D7Z1, and DXZ1 arrays. A region spanning two tandem dimers from these contigs is presented. Filled boxes represent CENP-B boxes.

FIGS. 41A-41D. CENP-B stabilizes CENP-A/B/C. CUT&RUN was performed using permeabilized cells (Skene and Henikoff 2017a). FIG. 41A; Mapping of CENP-B CUT&RUN. Salt to SF1, D7Z1, and D7Z2 sequences. To avoid edge effects, paired-end 25-bp×25-bp reads were mapped to a tandemly triplicated 340-bp dimer consensus sequence representing each contig. The average occupancy over the middle dimer is shown. FIG. 41B; Correlation between CENP-B box motif score (where 1 indicates identity to the central 15 bp of the CENP-B box, and 0 indicates more than three mismatches) and CENP-A/ IgG fold enrichment values in CUT&RUN.Salt fractions. The average of two experiments (10-min and 30-min digestion times) is shown. FIG. 41C; Same as B for motif density per kilobase. FIG. 41D; CENP-A CUT&RUN. Salt fold enrichments are shown for a Y-chromosome α satellite (DYZ3) that is absent from the female K562 cells used in this experiment, the repeat masked Hg19 genome, annotated β satellites, and α satellites from a homogeneous array (D7Z2) that lacks CENP-B boxes. Data are from 250-bp× 250-bp mapped merged pairs.

FIG. 43A; AutoCUT&RUN workflow. (1) Cells or tissue are bound to Concanavalin A-coated beads, permeabilized with digitonin, and incubated with an antibody targeting a chromatin protein. (2) Samples are arrayed in a 96-well plate and (3) processed on a Biomek robot fitted with a 96-well magnetic plate for magnetic separation during washes (α), and an aluminum chiller block (β) routed to a circulating water bath (γ) for temperature control. (4) AutoCUT&RUN produces up to 96 libraries in 2 days that are ready to be pooled and sequenced. FIG. 43B; Hierarchically clustered correlation matrix of AutoCUT&RUN profiles of histone-H3 modifications that mark active (pink) and repressed (blue) chromatin in H1 (orange) and K562 (purple) cells. Pearson correlations were calculated using the log 2 transformed values of read counts split into 500 bp bins across the genome.

FIG. 44A; Scaled Venn diagrams showing the relative amount of the genome that falls within H3K27me3, H3K4me2, and H3K27ac domains in H1 cells and K562 cells. FIG. 44B; Genome browser tracks showing the overlap of H3K4me2 and H3K27me3 in H1 cells, as well as the expansion of H3K27me3 domains and loss of overlap with H3K4me2 in K562 cells at a representative locus (NODAL). FIG. 44C; Heat maps showing the distribution of AutoCUT&RUN profiles of histone modifications in H1 cells centered on the TSSs of genes with a single promoter, oriented left-to-right according to the 5'-to-3' direction of transcription and rank ordering according to RNA-seq values (FPKM). FIG. 44D; Heat maps showing the distribution of AutoCUT&RUN histone modification profiles on transcriptionally active and repressed promoters in K562 cells.

FIGS. 45A-45E show a linear regression model accurately predicts cell-type specific promoter activity. FIG. 45A; Density scatterplot comparing RNA-seq values for single-promoter genes to K562 promoter CREAM scores predicted by the model trained on K562 data. FIG. 45B; Scatterplot of CREAM scores for single-promoter genes in H1 and K562 cells. Colored dots indicate the CREAM scores are ≥2-fold enriched in either H1 cells or K562 cells. FIG. 45C; Scatterplot of promoter CREAM scores that are ≥2-fold enriched in either H1 cells or K562 cells mapped onto their corresponding RNA-seq values. Blue dotted lines indicated the 2-fold difference cut-off. FIG. 45D; Scaled Venn diagram showing the overlap between genes called as cell-type specific according to their promoter CREAM scores, or according to their RNA-expression values. Genes predicted to have opposite cell-type specificities according to CREAM vs RNA-seq are indicated (scaled black circle). FIG. 45E; Scatterplot comparing the H1 and K562 CREAM scores of all promoters separated by ≥2 kb. Master regulators of H1 and K562 cell identities are indicated as colored circles. Both OTX2 and TAL1 have two promoters that can be distinguished.

FIG. 46A; DMG experimental set up. Two DMG cell lines derived from a similar region of the brainstem were grown as xenografts in the brains of immuno-compromised mice and upon forming tumors were resected and frozen. Xenografts were thawed and process by AutoCUT&RUN in parallel with control DMG samples harvested directly from cell culture. FIG. 46B; Hierarchically clustered correlation matrix of Auto CUT&RUN profiles of histone-H3 modifications that mark active and repressed chromatin in VUMC-10 and SU-DIPG-XIII cells grown in cell culture (C.C.) or as xenografts (Xeno.). As a quality control H3K27ac was also profiled manually in these cell lines using a different antibody (*). Pearson correlations were calculated using the log 2 transformed values of reads counts split into 500 bp bins across the genome.

FIGS. 47A-47C show promoter CREAM scores distinguish gene activities in DMG samples. FIG. 47A; Scatterplot comparing the promoter CREAM scores of VUMC-10 and SU-DIPG-XIII cell culture samples. Locations of the promoters of several cell-signaling components implicated in tumor growth are indicated as colored circles. FIG. 47B; Scatterplot comparing the promoter CREAM scores of VUMC-10 cell culture (C.C.) and xenograft (Xeno.) samples. Only 388 promoters have a ≥2-fold difference in CREAM scores between these samples. FIG. 47C; Hierarchically clustered matrix of Spearman correlations of promoter CREAM scores between VUMC-10 (V) and SU-DIPG-XIII (S) cells grown in cell culture (C.C.) or as xenografts (Xeno.), as well as H1 and K562 cells.

FIGS. 48A-48E show auto CUT&RUN identifies cell-type specific enhancer elements. FIG. 48A; Scaled venn diagram showing the overlap of accessible chromatin sites (ATAC-seq peaks) and peaks called on H3K4me2 AutoCUT&RUN profiles in H1 cells. FIG. 48B; Mean enrichment of H3K4me1 H3K4me2 and H3K4me3 over all H3K4me2+/ATAC+ TSSs. FIG. 48C; Mean enrichment of H3K4me1 H3K4me2 and H3K4me3 over all H3K4me2+/ ATAC+ distal regulatory elements (DREs). FIG. 48D; Hierarchically clustered matrix of Spearman correlations of enhancer CREAM scores in VUMC-10 (V) and SU-DIPG-XIII (S) cells grown in cell culture (C.C.) or as xenografts (Xeno.), as well as H1 and K562 cells. FIG. 48E; Genome browser tracks showing the location of putative enhancer elements (arrow heads) that are specific to VUMC-10 cells (V), both DMG cell lines (D), or common to DMG cells and H1 cells (C) at a representative locus (SOX2).

FIGS. 49A-49E show auto CUT&RUN accurately maps NPAT and CTCF as well as histone marks. FIG. 49A; A modified CUT&RUN protocol allows for automation. ConA bead-bound samples are incubated with a chromatin protein-specific antibody, and arrayed on the Biomek for successive washes, tethering of a proteinA-MNase fusion protein, and cleavage of DNA by adding $Ca^{2+}$. To avoid having to purify the digested DNA prior to library prep, the reaction is stopped with and EGTA only STOP buffer which specifically chelates $Ca^{2+}$, but leaves adequate $Mg^{2+}$ to allow End-polishing and Ligation of Illumina Y-adapters to the chromatin fragments. Chromatin protein is then digest with Proteinase-K and the indexed CUT&RUN libraries are purified on the Biomek using Ampure Magnetic Beads. FIG. 49B; Genome browser tracks of NPAT and CTCF AutoCUT&RUN showing NPAT is enrichment at promoters of the HIST1 gene cluster in both H1 and K562 cells. FIG. 49C; Genome browser tracks confirming CTCF is bound to insulator regions in the HOXA locus. FIG. 49D; Table of the Pearson correlations between AutoCUT&RUN profiles of the indicated histone marks around the TSSs of genes with a single-promoter and their corresponding RNA-seq value in H1 cells. FIG. 49E; Table of the Pearson correlations between AutoCUT&RUN profiles of the indicated histone marks around the TSSs of genes with a single-promoter and their corresponding RNA-seq value in H1 cells.

FIGS. 50A-50G show a developing a linear regression model to predict the activity of cis-regulatory elements. FIG. 50A; Density scatterplot comparing H1 RNA-seq values for single-promoter genes to H1 promoter CREAM scores predicted by the model trained on H1 data. FIG. 50B; Density scatterplot comparing H1 RNA-seq values for single-promoter genes to H1 promoter CREAM scores predicted by the model trained on K562 data. FIG. 50C; Scatterplot of RNA-seq values for single-promoter genes in H1 and K562 cells. Dots indicate the RNA expression levels are ≥2-fold enriched in either H1 cells or K562 cells. FIG. 50D; Scatterplot showing the distribution of genes with RNA-seq values that are ≥2-fold enriched in either H1 cells or K562 cells mapped onto their corresponding promoter CREAM scores. Dotted lines indicated the 2-fold difference cut-off. FIG. 50E; Gene Ontology (GO) terms overrepresented in the collection of cell-type specific, single-promoter genes identified by both CREAM scores as well as RNA-seq. FIG. 50F; GO terms overrepresented in the collection of single-promoter genes uniquely identified as cell-type specific according to promoter CREAM scores but not RNA-seq (see venn diagram in FIG. 45D). FIG. 50G; GO terms overrepresented in the collection of single-promoter genes uniquely identified as cell-type specific according to RNA-seq but not promoter CREAM scores.

FIG. 52A; GO terms that are overrepresented in the collection of promoters that are ≥2-fold enriched in VUMC-10 cells according to CREAM analysis. FIG. 52B; GO terms that are overrepresented in the collection of promoters that are ≥2-fold enriched in SU-DIPG-XIII cells according to CREAM analysis. FIG. 52C; Scatterplot comparing the promoter CREAM scores of SU-DIPG-XIII cell culture (C.C.) and xenograft (Xeno.) samples. 1,619 promoters have a ≥2-fold difference in CREAM scores between these samples.

FIGS. 53A-53D show autoCUT&RUN is a sensitive method to distinguish proximal and distal cis-regulatory elements. FIG. 53A; Table of the overlap of accessible chromatin sites (ATAC-seq peaks) and peaks called on various Auto CUT&RUN profiles of histone marks in H1 cells. FIG. 53B; Mean enrichment of ATAC signal at H3K4me2 peaks that were either called as ATAC+ or ATAC−. FIG. 53C; Mean enrichment of H3K27me3 signal at H3K4me2+ TSSs that were either called as ATAC+ or ATAC−. FIG. 53D; Heat maps showing the distribution of normalized H3K4me1, H3K4me2 and H3K4me3 profiles over all H3K4me2+/ATAC+ TSS and distal regulatory elements (DREs).

FIG. 58A; A representative 20 Mb region is shown. FIG. 58B; Heat map of fragment counts±1 kb over 74,906 H3K27ac peaks rank-ordered by MACS2 score.

FIGS. 59A-59D show CUT&RUN profiling of intact tissues and FACS-isolated cells. FIG. 59A; Brains and wing imaginal discs are dissected from 10 larvae, the intact unfixed material is lightly permeabilized with digitonin, and soaked in antibody and pAMNase solutions for CUT&RUN. FIG. 59B; GFP was produced in cells expressing the vestigial (vg) gene using the vg-Q enhancer, discs were dissociated, and 10,000 GFP-positive cells were isolated by FACS. FIG. 59C; CUT&RUN profiles of H3K27me3 from intact tissues and FACS-isolated cells across the Polycomb-repressed ANTPComplex. The Antennapedia (Antp) gene is repressed and methylated in brains, but is expressed and unmethylated in wing imaginal discs. Derepression of Antp is also clear in FACS-isolated cells, with high signal over background ratios. FIG. 59D; H3K27me3 profiles across the vg gene in brains (where it is repressed), in wing imaginal discs (where ~20% of cells express vg and the rest don't) and in FACS-isolated vg expressing cells.

FIG. 60A; Methodology for summit detection. CUT&RUN fragments contained within regions of enrichment are mapped on a fragment offset vs. fragment length scatterplot, a LOESS curve is derived from the data, and the single base pair positions at which local minima in the curve occur are reported as summits. FIG. 60B; Single base-pair CTCF peak summits were partitioned by predicted fragment size using a two-component Gaussian mixture model, and motifs enriched in a 20 bp window surrounding the summits for each of the two cohorts were detected using MEME.

FIG. 63A; When loaded with free 19-mer Tn5 end DNA duplexes to form a pA-Tn5 transposome, pA-Tn5 can be used for tagmentation in the same way as pA-MN can be used for ChIC (Chromatin Immunocleavage) and CUT&RUN. In tagmentation, a non-sequence-specific transposase loaded with two end-duplex DNAs corresponding to the transposon's mosaic end sequence and adapter overhangs compatible with the sequencing platform used, performs a cut-and-paste reaction, thus capping both ends of the cut site with transposon end sequences and adapter overhangs. Unlike CUT&RUN, there is no release of the particle, but rather following tagmentation the DNA is extracted and subjected to PCR using primers with sequences complementary to the mosaic end at the 3' end and sequencing adapters to the 5' side. FIG. 63B; An example of the Tapestation readout from a variable-cell number experiment.

FIG. 69A; The number of mapped fragments is indicated in millions. Ov is CUT&RUN followed by in situ ligation of adapters using the NuGen Ovation library preparation kit. The relative magnitude of hypersensitive site detection to targeted signal can be estimated from H3K27me3 tracks by comparing to CUT&RUN, where there is little if any hypersensitive site detection. Hypersensitivity is seen to be reduced by raising the salt concentration of wash steps. This confirms that hypersensitivity results from untethered Tn5, but can be reduced or eliminated by adjusting the conditions. FIG. 69B; Two distinct size classes are seen using different anti-RNAPII antibodies with binding and tagmentation done in 150 mM NaCl (top panel), whereas in 300 mM NaCl the smaller size class is sharply diminished.

DETAILED DESCRIPTION OF SEVERAL EMBODIMENTS

A. Terms and Definitions

Figures 1, 1A, 2:
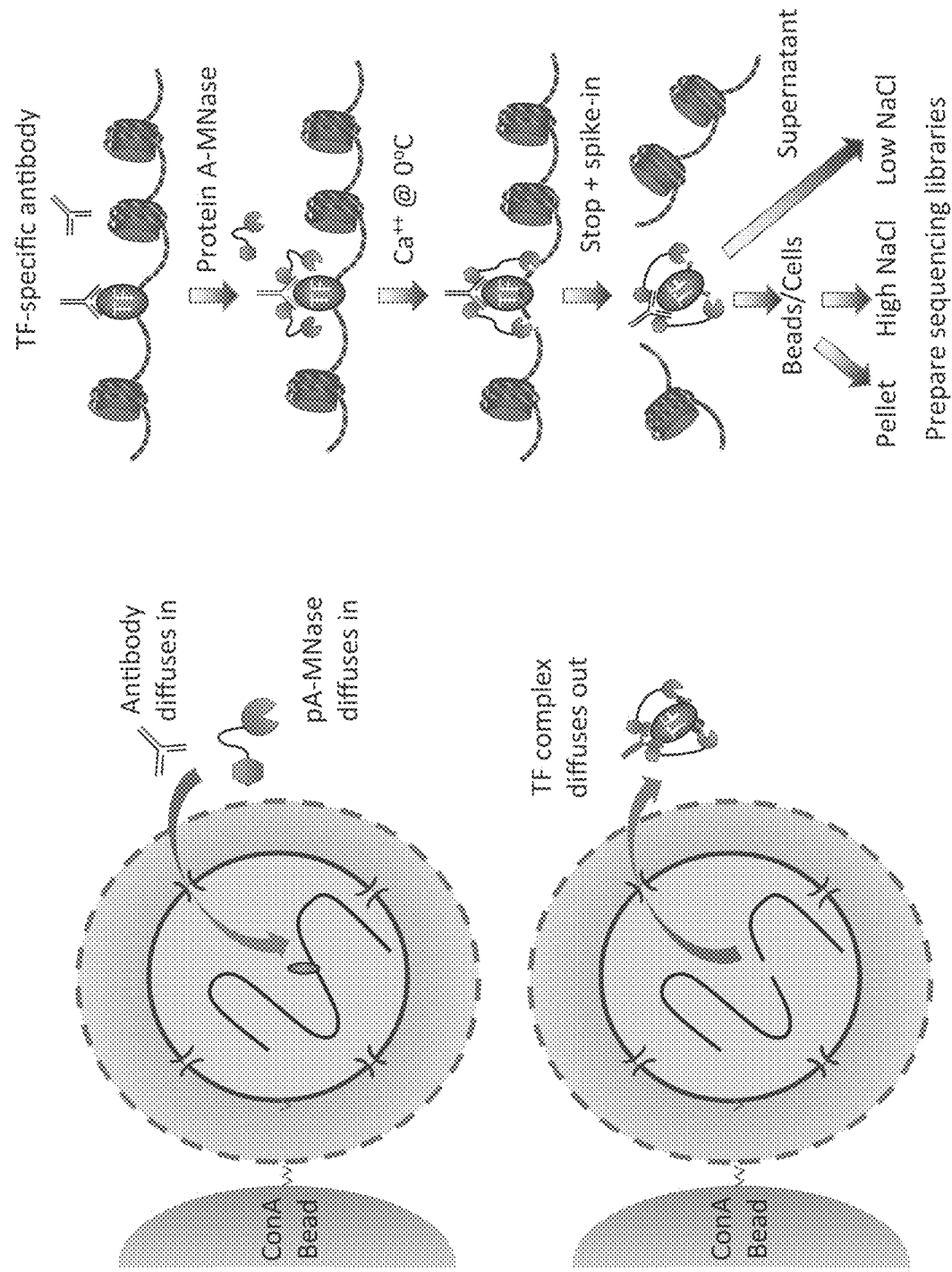

In the following detailed description, reference is made to the accompanying drawings which form apart hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references. In case of conflict, the terms in the specification will control.

To facilitate review of the various embodiments of this disclosure, the following explanations of specific terms are provided.

Antibody: A polypeptide ligand that includes at least a light chain or heavy chain immunoglobulin variable region and specifically binds an epitope of an antigen, such as an epitope on a protein associated with chromatin DNA. Antibodies can include monoclonal antibodies, polyclonal antibodies, or fragments of antibodies.

The term "specifically binds" refers to, with respect to an antigen, the preferential association of an antibody or other ligand, in whole or part, with a specific polypeptide, such as a specific protein bound to chromatin DNA, for example a transcription factor. A specific binding agent binds substantially only to a defined target, such as a specific chromatin associated factor. It is recognized that a minor degree of non-specific interaction may occur between a molecule, such as a specific binding agent, and a non-target polypeptide. Nevertheless, specific binding can be distinguished as mediated through specific recognition of the antigen.

Although selectively reactive antibodies bind antigen, they can do so with low affinity. Specific binding typically results in greater than 2-fold, such as greater than 5-fold, greater than 10-fold, or greater than 100-fold increase in amount of bound antibody or other ligand (per unit time) to a target polypeptide, such as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

Antibodies can be composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv") diabodies and all other variations. The term also includes recombinant forms such as chimeric antibodies (for example, humanized murine antibodies), heteroconjugate antibodies (such as bispecific antibodies). See also, Pierce Catalog and Handbook, 1994-1995 (Pierce Chemical Co., Rockford, 111); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Amplification: To increase the number of copies of a nucleic acid molecule, such as nucleic acids identified and/or obtained by the methods described herein. The resulting amplification products are called "amplicons." Amplification of a nucleic acid molecule (such as a DNA or RNA molecule) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative realtime PCR; reverse transcriptase PCR (RT-PCR); real-time PCR (rt PCR); real-time reverse transcriptase PCR (it RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Binding or stable binding: An association between two substances or molecules, such as the hybridization of one nucleic acid molecule to another or itself, the association of an antibody with a peptide, or the association of a protein with another protein (for example the binding of a transcription factor to a cofactor) or nucleic acid molecule (for example the binding of a transcription factor to a nucleic acid, such as chromatin DNA).

Binding site: A region on a protein, DNA, or RNA to which other molecules stably bind. In one example, a binding site is the site on a DNA molecule, such as chromatin DNA, that a chromatin associated factor, such as a transcription factor, binds (referred to as a transcription factor binding site).

Contacting: Placement in direct physical association, for example both in solid form and/or in liquid form. Contacting can occur in situ with isolated cells, for example permeabilized cells, or in vivo by administering to a subject.

Control: A reference standard. A control can be a known value or range of values indicative of basal levels or amounts or present in a tissue or a cell or populations thereof. A control can also be a cellular or tissue control, for example a tissue from a non-diseased state. A difference between a test sample and a control can be an increase or conversely a decrease. The difference can be a qualitative difference or a quantitative difference, for example a statistically significant difference. In some embodiments a control is added DNA, such as spike in DNA and/or contaminating DNA.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A; is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Covalently linked: Refers to a covalent linkage between atoms by the formation of a covalent bond characterized by the sharing of pairs of electrons between atoms. In one example, a covalent link is a bond between an oxygen and a phosphorous, such as phosphodiester bonds in the backbone of a nucleic acid strand. In another example, a covalent link is one between a nucleic acid and a protein and/or two or more proteins or fragments thereof, such as an antibody and an enzyme, for example an antibody to a transposase, or an antibody to a nuclease.

Cross-linking agent: A chemical agent or even light, that facilitates the attachment of one molecule to another molecule. Cross-linking agents can be protein-nucleic acid cross-linking agents, nucleic acid-nucleic acid cross-linking agents, and/or protein-protein cross-linking agents. Examples of such agents are known in the art. In some embodiments, a cross-linking agent is a reversible cross-linking agent. In some embodiments, a cross-linking agent is a non-reversible cross-linking agent.

Detectable label: A compound or composition that is conjugated directly or indirectly to another molecule to facilitate detection of that molecule. Specific, non-limiting examples of labels include fluorescent tags, enzymatic linkages, and radioactive isotopes. In some examples, a label is attached to an antibody or nucleic acid to facilitate detection of the molecule antibody or nucleic acid specifically binds.

DNA sequencing: The process of determining the nucleotide order of a given DNA molecule. Generally, the sequencing can be performed using automated Sanger sequencing (AB 13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®) other next generation sequencing techniques for use with the disclosed methods include, Massively parallel signature sequencing (MPSS), Polony sequencing, Ion Torrent semiconductor sequencing, DNA nanoball sequencing, Heliscope single molecule sequencing, Single molecule real time (SMRT) sequencing, and Nanopore DNA sequencing.

High throughput technique: Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog) and the DNA, or RNA. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component has been substantially separated or purified away from other biological components in the cell of the organism in which the component naturally occurs, for example, extra-chromatin DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Mass spectrometry: A method wherein a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample can be subjected to one or more dimensions of chromatographic separation, for example, one or more dimensions of liquid or size exclusion chromatography.

Nucleic acid (molecule or sequence): A deoxyribonucleotide or ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein. The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxy acetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others. Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Peptide/Protein/Polypeptide: All of these terms refer to a polymer of amino acids and/or amino acid analogs that are joined by peptide bonds or peptide bond mimetics. The twenty naturally occurring amino acids and their single-letter and three-letter designations known in the art.

Sample: A sample, such as a biological sample, that includes biological materials (such as nucleic acids) obtained from an organism or a part thereof, such as a plant, or animal, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated). For example, a biological sample can be bone marrow, tissue biopsies, whole blood, serum, plasma, blood cells, endothelial cells, circulating tumor cells, lymphatic fluid, ascites fluid, interstitial fluid (also known as "extracellular fluid" and encompasses the fluid found in spaces between cells, including, inter alia, gingival crevicular fluid), cerebrospinal fluid (CSF), saliva, mucous, sputum, sweat, urine, or any other secretion, excretion, or other bodily fluids.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5: 151-3, 1989; Corpet et al, Nuc. Acids Res. 16: 10881-90, 1988; Huang et al. Computer Appls. in the Biosciences 8, 155-65, 1992; and Pearson et al, Meth. Mol. Bio. 24:307-31, 1994. Altschul et al, J. Mol. Biol. 215:403-10, 1990, presents a detailed consideration of sequence alignment methods and homology calculations.

The NCBI Basic Local Alignment Search Tool (BLAST) (Altschul et al, J. Mol. Biol. 215:403-10, 1990) is available from several sources, including the National Center for Biological Information (NCBI, National Library of Medicine, Building 38 A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15±20*100=75).

One indication that two nucleic acid molecules are closely related is that the two molecules hybridize to each other under stringent conditions. Stringent conditions are sequence-dependent and are different under different environmental parameters.

Specific Binding Agent: An agent that binds substantially or preferentially only to a defined target such as a protein, enzyme, polysaccharide, oligonucleotide, DNA, RNA, recombinant vector or a small molecule. A nucleic acid-specific binding agent binds substantially only to the defined nucleic acid, such as DNA, or to a specific region within the nucleic acid. In some embodiments, a specific binding agent is a probe or primer, that specifically binds to a target nucleic acid of interest. In some embodiments, a specific binding agent is a transcription factor, that specifically binds to a target nucleic acid of interest, such as chromatin DNA. A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999). In some embodiments, a specific binding agent is an antibody.

Transcription factor: A protein that regulates transcription. In particular, transcription factors regulate the binding of RNA polymerase and the initiation of transcription. A transcription factor binds upstream or downstream to either enhance or repress transcription of a gene by assisting or blocking RNA polymerase binding. The term transcription factor includes both inactive and activated transcription factors.

Transcription factors are typically modular proteins that affect regulation of gene expression. Exemplary transcription factors include but are not limited to AAF, ab1, ADA2, ADA-NF1, AF-1, AFP1, AhR, AIIN3, ALL-1, alpha-CBF, alpha-CP 1, alpha-CP2a, alpha-CP2b, alphaHo, alphaH2-alphaH3, Alx-4, aMEF-2, AML1, AML1a, AML1b, AML1c, AML1DeltaN, AML2, AML3, AML3a, AML3b, AMY-1L, A-Myb, ANF, AP-1, AP-2alphaA, AP-2alphaB, AP-2beta, AP-2gamma, AP-3 (1), AP-3 (2), AP-4, AP-5, APC, AR, AREB6, Art, Arnt (774 M form), ARP-1, ATBF1-A, ATBF1-B, ATF, ATF-1, ATF-2, ATF-3, ATF-3deltaZIP, ATF-a, ATF-adelta, ATPFI, Barhl1, Barhl2, Barx1, Barx2, Bcl-3, BCL-6, BD73, beta-catenin, Bin1, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CACCbinding factor, Cart-1, CBF (4), CBF (5), CBP, CCAAT-binding factor, CCMT-binding factor, CCF, CCG1, CCK-1a, CCK-1b, CD28RC, cdk2, cdk9, Cdx-1, CDX2, Cdx-4, CFF, ChxlO, CLIMI, CLIM2, CNBP, CoS, COUP, CP1, CPIA, CPIC, CP2, CPBP, CPE binding protein, CREB, CREB-2, CRE-BP1, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin T1, cyclin T2, cyclin T2a, cyclin T2b, DAP, DAX1, DB1, DBF4, DBP, DbpA, DbpAv, DbpB, DDB, DDB-1, DDB-2, DEF, deltaCREB, deltaMax, DF-1, DF-2, DF-3, Dlx-1, Dlx-2, Dlx-3, Dlx4 (long isoform), Dlx-4 (short isoform, Dlx-5, Dlx-6, DP-1, DP-2, DSIF, DSIF-p14, DSIF-p160, DTF, DUX1, DUX2, DUX3, DUX4, E, E1 2, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EIIaE-A, EIIaE-B, EIIaE-Calpha, EIIaE-Cbeta, EivF, Eff-1, Elk-1, Emx-1, Emx-2, Emx-2, En-1, En-2, ENH-bind. prot, ENKTF-1, EPAS1, epsilonF1, ER, Erg-1, Erg-2, ERR1, ERR2, ETF, Ets-1, Ets-1 deltaVil, Ets-2, Evx-1, F2F, factor 2, Factor name, FBP, f-EBP, FKBP59, FKHL18, FKHRLIP2, Fli-1, Fos, FOXB1, FOXC1, FOXC2, FOXD1, FOXD2, FOXD3, FOXD4, FOXE1, FOXE3, FOXF1, FOXF2, FOXG1a, FOXG1b, FOXG1c, FOXH1, FOXI1, FOXJ1a, FOXJ1b, FOXJ2 (long isoform), FOXJ2 (short isoform), FOXJ3, FOXK1a, FOXK1b, FOXK1c, FOXL1, FOXM1a, FOXM1b, FOXM1c, FOXN1, FOXN2, FOXN3, FOXO1a, FOXO1b, FOX02, FOX03a, FOX03b, FOX04, FOXP1, FOXP3, Fra-1, Fra-2, FTF, FTS, G factor, G6 factor, GABP, GABP-alpha, GABP-beta1, GABP-beta2, GADD 153, GAF, gammaCMT, gammaCAC1, gammaCAC2, GATA-1, GATA-2, GATA-3, GATA-4, GATA-5, GATA-6, Gbx-1, Gbx-2, GCF, GCMa, GCNS, GF1, GLI, GLI3, GR alpha, GRbeta, GRF-1, Gsc, Gscl, GT-IC, GT-IIA, GT-IIBalpha, GT-IIBbeta, HITF1, HITF2, H2RIIBP, H4TF-1, H4TF-2, HAND1, HAND2, HB9, HDAC1, HDAC2, HDAC3, hDaxx, heat-induced factor, HEB, HEB1-p67, HEB1-p94, HEF-1 B, HEF-1T, HEF-4C, HEN1, HEN2, Hesxl, Hex, HIF-1, HIF-1alpha, HIF-1beta, HiNF-A, HiNF-B, HINF-C, HINF-D, HiNF-D3, HINF-E, HiNF-P, HIP1, HIV-EP2, Hlf, HLTF, HLTF (Met123), HLX, HMBP, HMG I, HMG I(Y), HMG Y, HMGI-C, HNF-IA, HNF-IB, HNF-IC, HNF-3, HNF-3alpha, HNF-3beta, HNF-3gamma, HNF4, HNF-4alpha, HNF4alpha1, HNF-4alpha2, HNF-4alpha3, HNF-4alpha4, HNF4gamma, HNF-6alpha, hnRNP K, HOX11, HOXA1, HOXAIO, HOXAIO PL2, HOXA11, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXB5, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Id1, Id1 H', Id2, Id3, Id3/Heir-1, IF1, IgPE-1, IgPE-2, IgPE-3, IkappaB, IkappaB-alpha, IkappaB-beta, IkappaBR, II-1 RF, IL-6 RE-BP, 11-6 RF, INSAF, IPF1, IRF-1, IRF-2, B, IRX2a, Irx-3, Irx-4, ISGF-1, ISGF-3, ISGF3alpha, ISGF-3gamma, 1st-1, ITF, ITF-1, ITF-2, JRF, Jun, JunB, JunD, kappay factor, KBP-1, KER-1, KER-1, Kox1, KRF-1, Ku autoantigen, KUP, LBP-1, LBP-1a, LBX1, LCR-F1, LEF-1, LEF-IB, LF-A1, LHX1, LHX2, LHX3a, LHX3b, LHXS, LHX6.1a, LHX6.1b, LIT-1, Lmo1, Lmo2, LMX1A, LMX1B, L-My1 (long form), L-My1 (short form), L-My2, LSF, LXRalpha, LyF-1, Lyl-1, M factor, Mad1, MASH-1, Max1, Max2, MAZ, MAZ1, MB67, MBF1, MBF2, MBF3, MBP-1 (1), MBP-1 (2), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2D0B, MEF-2DA0, MEF-2DA0, MEF-2DAB, MEF-2DA'B, Meis-1, Meis-2a, Meis-2b, Meis-2c, Meis-2d, Meis-2e, Meis3, Meox1, Meox1a, Meox2, MHox (K-2), Mi, MIF-1, Miz-1, MM-1, MOP3, MR, Msx-1, Msx-2, MTB-Zf, MTF-1, mtTF1, Mxil, Myb, Myc, Myc 1, Myf-3, Myf-4, Myf-5, Myf-6, MyoD, MZF-1, NCI, NC2, NCX, NELF, NER1, Net, NF Ill-a, NF NF-1, NF-IA, NF-1B, NF-1X, NF-4FA, NF-4FB, NF-4FC, NF-A, NF-AB, NFAT-1, NF-AT3, NF-Atc, NF-Atp, NF-Atx, Nf etaA, NF-CLEOa, NF-CLEOb, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaB1, NF-kappaB 1, precursor, NF-kappaB2, NF-kappaB2 (p49), NF-kappaB2 precursor, NF-kappaE1, NF-kappaE2, NF-kappaE3, NF-MHCIIA, NF-MHCIIB, NF-muE1, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3Av1, NKX3Av2, NKX3Av3, NKX3Av4, NKX3B, NKX6A, Nmi, N-Myc, N-Oct-2alpha, N-Oct-2beta, N-Oct-3, N-Oct-4, N-Oct-5a, N-Oct-5b, NP-TCII, NR2E3, NR4A2, Nrfl, Nrf-1, Nrf2, NRF-2beta1, NRF-2gamma1, NRL, NRSF form 1, NRSF form 2, NTF, 02, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otx1, Otx2, OZF, p107, p130, p28 modulator, p300, p38erg, p45, p49erg,-p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8b, Pax-8c, Pax-8d, Pax-8e, Pax-8f, Pax-9, Pbx-1a, Pbx-1b, Pbx-2, Pbx-3a, Pbx-3b, PC2, PC4, PC5, PEA3, PEBP2alpha, PEBP2beta, Pit-1, PITX1, PITX2, PITX3, PKNOX1, PLZF, PO-B, Pontin52, PPARalpha, PPARbeta, PPARgamma1, PPARgamma2, PPUR, PR, PR A, pRb, PRD1-BF1, PRDI-BFc, Prop-1, PSE1, P-TEFb, PTF, PTFalpha, PTFbeta, PTFdelta, PTFgamma, Pu box binding factor, Pu box binding factor (B JA-B), PU.1, PuF, Pur factor, R1, R2, RAR-alpha1, RAR-beta, RAR-beta2, RAR-gamma, RAR-gamma1, RBP60, RBP-Jkappa, Re1, Re1A, Re1B, RFX, RFX1, RFX2, RFX3, RFXS, RF-Y, RORalpha1, RORalpha2, RORalpha3, RORbeta, RORgamma, Rox, RPF1, RPGalpha, RREB-1, RSRFC4, RSRFC9, RVF, RXR-alpha, RXR-beta, SAP-1a, SAP1b, SF-1, SHOX2a, SHOX2b, SHOXa, SHOXb, SHP, SIII-p1 lO, SIII-p15, SIII-p18, SIM', Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, Sp1, Sp2, Sp3, Sp4, Sph factor, Spi-B, SPIN, SRCAP, SREBP-1a, SREBP-1b, SREBP-1c, SREBP-2, SRE-ZBP, SRF, SRY, SRP1, Staf-50, STAT1alpha, STAT1beta, STAT2, STAT3, STAT4, STAT6, T3R, T3R-alpha1, T3R-alpha2, T3R-beta, TAF(I)110, TAF(I)48, TAF(I)63, TAF(II)100, TAF(II)125, TAF(II)135, TAF(II)170, TAF(II)18, TAF(II)20, TAF(II) 250, TAF(II)250Delta, TAF(II)28, TAF(II)30, TAF(II)31, TAF(II)55, TAF(11)70-alpha, TAF(11)70-beta, TAF(II)70-gamma, TAF-I, TAF-II, TAF-L, Tal-1, Tal-1beta, Tal-2, TAR factor, TBP, TBX1A, TBX1B, TBX2, TBX4, TBXS (long isoform), TBXS (short isoform), TCF, TCF-1, TCF-1A, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbeta1, TEF-1, TEF-2, tel, TFE3, TFEB, TFIIA, TFIIA-alpha/beta precursor, TFIIA-alpha/beta precursor, TFIIA-gamma, TFIIB, TFIID, TFIIE, TFIIE-alpha, TFIIE-beta, TFIIF, TFIIF-alpha, TFIIF-beta, TFIIH, TFIIH*, TFIIH-CAK, TFIIH-cyclin H, TFIIH-ERCC2/CAK, TFIIH-MAT1, TFIIH-M015, TFIIH-p34, TFIIH-p44, TFIIH-p62, TFIIH-p80, TFIIH-p90, TFII-I, Tf-LF1, Tf-LF2, TGIF, TGIF2, TGT3, THRA1, TIF2, TLE1, TLX3, TMF, TR2, TR2-11, TR2-9, TR3, TR4, TRAP, TREB-1, TREB-2, TREB-3, TREF1, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-1A, vHNF-1B, vHNF-1C, VITF, WSTF, WT1, WT1I, WT1 I-KTS, WT1 I-del2, WT1-KTS, WT1-del2, X2BP, XBP-1, XW-V, XX, YAF2, YB-1, YEBP, YY1, ZEB, ZF1, ZF2, ZFX, ZHX1, ZIC2, ZID, ZNF 174, amongst others.

An activated transcription factor is a transcription factor that has been activated by a stimulus resulting in a measurable change in the state of the transcription factor, for example a post-translational modification, such as phosphorylation, methylation, and the like. Activation of a transcription factor can result in a change in the affinity for a particular DNA sequence or of a particular protein, such as another transcription factor and/or cofactor.

Transposome: A transposase-transposon complexes. A conventional way for transposon mutagenesis usually place the transposase on the plasmid. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation".

Under conditions that permit binding: A phrase used to describe any environment that permits the desired activity, for example, conditions under which two or more molecules, such as nucleic acid molecules and/or protein molecules, can bind. Such conditions can include specific concentrations of salts and/or other chemicals that facilitate the binding of molecules.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999. In addition, the materials, methods, and examples are illustrative only and not intended to be limiting.

B. Introduction

The uncertainties caused by systematic biases and artifacts in ChIP emphasize the need for methods based on different principles. A class of non-ChIP mapping methods involves tethering of an enzyme to a DNA-binding protein by a chimeric fusion and action of the enzyme on DNA in the local vicinity. For example, in DamID (van Steensel et al., 2001) and related methods (Southall et al., 2013; Hass et al., 2015), Escherichia coli Dam methyltransferase is tethered to the TF and catalyzes N6-methylation of adenine at GATC sites in vivo. Sites can be mapped genome-wide using an N6-methyl-directed restriction enzyme. However, as the resolution of DamID is limited by the distribution of GATC sites, DamID cannot obtain the high resolution that is potentially attainable using a sequencing read-out (Aughey and Southall, 2016). An alternative enzyme tethering method, chromatin endogenous cleavage (ChEC) tethers the endo-exonuclease Micrococcal Nuclease (MNase) to the TF (Schmid et al., 2004). In ChEC, MNase is activated by permeabilizing cells and adding calcium for controlled cleavage. An Illumina sequencing read-out was recently applied to ChEC (ChEC-seq), achieving near base-pair resolution (Zentner et al., 2015). Enzyme tethering methods fundamentally differ from ChIP because they are carried out in vivo (DamID) or in situ (ChEC), with extraction of DNA directly from live or permeabilized cells, thus eliminating the need to solubilize and recover chromatin. Both DamID and ChEC require that a different chimeric fusion construct be produced for each TF to be mapped, limiting their transferability, for example to animal models, patient biopsies and post-translational modifications. In the original chromatin immunocleavage (ChIC) method, crude nuclei from crosslinked cells are first treated with a TF-specific antibody, followed by addition of a chimeric fusion between Protein A and MNase (pA-MN) and activation by calcium (Schmid et al., 2004). Protein A binds specifically to Immunoglobulin G, which obviates the need for a fusion protein.

C. Description of Exemplary Embodiments

Disclosed herein is a major development of ChIC that retains the advantages of enzyme tethering methods, while extending its applicability and ease-of-use to a point that it replaces other existing methodologies. A unique feature of the disclosed method is that in the absence of crosslinking, seconds after induced cleavage, such as calcium-induced MNase cleavage, on both sides of the TF, the TF-DNA complex is released into solution, allowing for recovery of pure TF-bound DNA fragments for sequencing simply by centrifugation and DNA extraction. Furthermore, in some examples, by carrying out the procedure on magnetic beads, the disclosed 'Cleavage Under Targets and Release Using Nuclease' (CUT&RUN) method is simpler than ChIP-seq while retaining the advantages of in situ methods. Targeted digestion by CUT&RUN greatly reduces background relative to complete genomic fragmentation for ChIP, requiring only ~1/10th the sequencing depth of standard ChIP methods. Furthermore, simple spike-in controls allow accurate quantification of protein binding not possible by other methods. The disclosed method allows low starting cell numbers, and robotic automation is possible by performing the reaction on magnetic beads.

Cleavage Under Targets and Release Using Nuclease (CUT&RUN) is an epigenomic profiling strategy in which antibody-targeted controlled cleavage, for example by micrococcal nuclease, releases specific protein-DNA complexes into the supernatant for paired-end DNA sequencing. As only the targeted fragments enter into solution, and the vast majority of DNA is left behind, CUT&RUN has exceptionally low background levels as compared to other techniques for probing chromatin binding. CUT&RUN outperforms the most widely used Chromatin Immunoprecipitation (ChIP) protocols in resolution, signal-to-noise, and depth of sequencing required. In contrast to ChIP, CUT&RUN is free of solubility and DNA accessibility artifacts and can be used to profile insoluble chromatin and to detect long-range 3D contacts without cross-linking. Further, disclosed herein is an improved CUT&RUN protocol that does not require isolation of nuclei and provides high-quality data starting with as little as only 1 or 2 cells for a histone modification and 1000 cells for a transcription factor mapping. From cells to purified DNA CUT&RUN requires less than a day at the lab bench.

Disclosed herein is a method for detecting the binding of a chromatin-associated factor of interest to a sequence of DNA in a cell (or a population of cells). In certain embodiments, the disclosed methods include contacting an uncrosslinked permeabilized cell at a temperature less than about 4° C. with a specific binding agent that specifically recognizes the chromatin-associated factor of interest, wherein the specific binding agent is linked to a nuclease that is inactive and activatable or a transposome, that includes a transposase that is optionally inactive and activatable, for example by addition of an ion such as a cation. In certain embodiments, the cell and/or the nucleus of the cell is permeabilized by contacting the cell with an agent that permeabilizers the cells, such as with a detergent, for example Triton and/or NP-40 or another agent, such as digitonin. By using intact cells or nuclei the disclosed methods have the advantage over ChIP methods of looking at native chromatin structure, which otherwise might be altered by fragmentation and other processing steps. In embodiments, the nuclease or transposase is activated, for example using an exogenous activator. Once activated the nuclease or transposase is able to excise the sequence of DNA bound to the chromatin-associated factor of interest. In certain embodiments, the reaction is allowed to proceed for a time period sufficient to excise the DNA bound to the chromatin-associated factor of interest but sufficiently short such that the nuclease or transposase does not diffuse away and cut the accessible DNA non-specifically. In certain embodiments, this time period is between about 1 second and about 4 hours.

When using a nuclease, the time period can be selected for the specific chromatin-associated factor of interest. For example, for a very abundant protein, even 10 minutes can be too long because over time the protein gets released and chews up accessible DNA in the genome, an unwanted side-effect that, without being bound is likely linear with concentration. After inactivating the nuclease, the excised DNA bound to the chromatin-associated factor of interest to is recovered. This excised chromatin can be isolated and interrogated to determine the sequence of the excised DNA, thereby detecting binding of a chromatin-associated factor of interest to a sequence of DNA in the cell (or population of cells).

The above limitations would not apply with the use of a transposase. When a transposase is used, the fragments stay bound. This is not an issue with a transposase, as it does not release during tagmentation, which is a major advantage of the method. In fact, when Tn5 inserts its payload it is incapable of causing damage elsewhere, "one and done". Therefore, with these methods time variation in not an important parameter but just tagment to completion (about 1 hr at 37° C.) for all factors. This is a major advantage. Thus, further disclosed herein is a refinement of CUT&RUN termed ImmunoTethered Insertion Sequencing (ITIS or IT-seq). Although standard CUT&RUN can be applied to 100-1000 cells without significant loss of data quality, high-throughput single-cell applications are complicated by the need to separate the supernatant containing the targeted fragments from the cells containing the rest of the genome. Furthermore, the easy workflow afforded by immobilizing cells on paramagnetic beads must be followed by DNA sequencing library preparation, greatly increasing the time, cost and effort of the overall procedure. As disclosed in the Examples below, the inventors have expanded the power of CUT&RUN by fusing a transposase, such as the hyperactive Tn5 transposase, to Protein A and substituting addition of pA-MN by Protein A/Tn5 complex loaded with sequencing platform-compatible Mosaic End oligonucleotides. Activation of Tn5 with $Mg^{++}$ results in antibody-targeted tagmentation, ready for PCR amplification for both bulk and single-cell applications. The ITIS method disclosed herein provides amplified sequence-ready libraries from live cells in a single day which is an attractive feature of the method.

In certain embodiments, the DNA is chromatin DNA. In certain embodiments, the cells and/or nuclei may be subjected to crosslinking. In other embodiments, the cells are not subjected to crosslinking.

ChIC, ChEC and ChEC-seq are based on targeting cleavages and mapping these cleavages close to the targeted sites. In contrast, the disclosed methods use pairs of cleavages close enough together that the DNA-protein complexes are released into the supernatant. In the disclosed methods, DNA from the released DNA-protein complexes are purified and subjected to library preparation and sequencing. In other embodiments of the disclosed methods the supernatant is not extracted, but rather is subjected to further analytical methodologies, for example: 1) Salt fractionation (CUT&RUN.Salt); 2) ChIP-seq using the supernatant from CUT&RUN as input (CUT&RUN.ChIP); 3) Characterizing the protein complement of particles in the supernatant. Because all three of these extensions of CUT&RUN require release of the DNA-protein complexes into the supernatant, they represent unique innovations of CUT&RUN. In embodiments, the methods include subjecting the excised DNA diffused out of the cell to salt fractionation. In embodiments, the methods include subjecting the supernatant to ChIP-seq. In embodiments, the methods include determining an identity of one or more proteins associated with of the chromatin-associated factor of interest. In embodiments, the determining the identity of the protein comprises the use of an antibody. In embodiments, the determining identity of the protein comprises mass spectrometry.

In certain embodiments, the chromatin DNA is cleaved using a nuclease, which is linked and/or tethered to the specific binding agent, such as an antibody. Thus, in embodiments, the disclosed methods include contacting an uncrosslinked permeabilized cell with a specific binding agent that specifically recognizes the chromatin-associated factor of interest, wherein the specific binding agent is linked to at least one artificial transposome, under conditions that permit integration of a transposon into chromatin DNA. In certain embodiments, the nuclease, is an endo-deoxyribonuclease, such as Micrococcal nuclease (MNase). By activatable, it is meant that the nuclease can be switched from an inactive state to an active state. This switch can be initiated by the addition of an effector or by changing the conditions. In certain embodiments, the effector is a small molecule or atom, such as a $Ca^{2+}$ or $Mg^{++}$ ion. The nuclease which can be used is any protein capable of inducing cleavage sites into DNA, either single or preferably double-stranded cleavage sites, provided this activity can be activated. The nucleases used in the disclosed methods are capable of breaking the DNA in a largely sequence-independent manner, generally at nucleosomal linker regions and at nuclease hypersensitive sites. Many nucleases however cleave the DNA in a sequence-specific manner, i.e. cleavage occurs mainly at recognition sequences of a few nucleotides. By inactive state, it is meant that the activity of the nuclease is too low to be monitored, or is less than 10% of its maximal rate when active, preferably, less than 4% or less than 1%. The transition from an inactive state to an active state may be triggered by the addition of a chemical compound or by switching the temperature for example. A particularly useful nuclease is the micrococcal nuclease (MN), whose activity stringently depends on $Ca^{2+}$ ions. This enzyme introduces DNA double stranded breaks in chromatin at nucleosomal linker regions and at nuclease hypersensitive (HS) sites. An example of a particularly useful MNase is the sequence encoding the mature chain of Nuclease A (amino acids 83 to 231 of Genbank P00644 (which is hereby incorporated by reference as available on Sep. 25, 2017). Variants that retain the activity are also contemplated, such as those having a sequence identity of at least 70% 80%, 90%, 95% or even 99% identity to amino acids 83 to 231 of Genbank P00644.

The enzyme, e.g., nuclease, of the disclosure is tethered to a chromatin protein binding the chromatin at defined sites, which are preferably sequence-specific sites. By tethering the enzyme to this chromatin protein of interest, the previously non-specific enzyme (e.g. nuclease) is recruited to a specific sequence defined by the tethered chromatin protein.

In a preferred embodiment of the present disclosure, the nuclease (or other enzymatic activity) is tagged. The tag used may be any type of tag, for example a His-Tag in order to ease the purification of the protein, or an epitope like the hemagglutinin (HA) epitope, or avidin, streptavidin or biotin.

According to preferred embodiments, the nuclease is part of a fusion protein X-nuclease or nuclease-X, wherein X is a peptidic domain. X may be an epitope or an antibody, X may also be an affinity domain for e.g. biotin. In the context of the application, by antibody, it is meant either a complete antibody or part of an antibody sufficient to direct an interaction. Such part is preferably the variable region Fab of an antibody.

In some embodiments, the antibody is indirectly coupled to the at least one transposome. In some embodiments, the transposase is linked to a specific binding agent that specifically binds the antibody. In some embodiments, the specific binding agent comprises protein A, protein G or a second antibody that specifically binds the antibody. In some embodiments, the antibody is a first antibody and the method further comprises: contacting the cell with a second antibody that specifically binds the first antibody, and wherein the transposase is linked to a specific binding agent that specifically binds the second antibody. In some embodiments, the specific binding agent comprises protein A or protein G or an a third antibody that specifically binds the second antibody. In some embodiments, the binding of the chromatin-associated factor of interest to the sequence of chromatin DNA is direct.

The nuclease and/or transposase may also be fused to all or part of the staphylococcal protein A (pA) or to all or part of staphylococcal protein G (pG) or to both pA and pG (pAG). These proteins have indeed different affinities for rabbit and mouse IgG. The nuclease may also be fused to any other protein or protein moiety, for example derivatives of pA or pG, which has an affinity for antibodies. A preferred embodiment of the disclosure is the fusion protein pAG-MN, detailed in the examples. In this case, the pA moiety contains 2 IgG binding domains of staphylococcal protein A, i.e. amino acids 186 to 327 of Genbank AAA26676 (which is hereby incorporated by reference as available on Sep. 25, 2017). Variants that retain the activity are also contemplated, such as those having a sequence identity of at least 70% 80%, 90%, 95% or even 99% identity to amino acids 186 to 327 of Genbank AAA26676. The disclosure is however not limited to this specific fusion protein. Alternatively, the enzyme, e.g. nuclease, may be linked chemically to the X domain by a bound other than a peptidic bond.

The time of nuclease activation is greatly dependent on the temperature at which the reaction takes place. When the enzymatic reaction is to be carried out on ice, at zero degree, the time of activation is adapted accordingly, that is lengthened with respect to the same enzymatic reaction carried out at a temperature below about 10° C., such as below about 10° C., about 9° C., about 8° C., about 7° C., about 6° C., about 5° C., about 4° C., about 3° C., about 2° C., about 1° C., or about 0° C., yet above about −4° C.

Methods of linking and/or tethering enzymes, such as nucleases or transposases is conventional and can be found for example in U.S. Pat. No. 7,790,379, which is hereby incorporated herein by reference in its entirety. In certain embodiments, the nuclease or the transposase is part of a fusion protein. In certain embodiments, the fusion protein comprises staphylococcal protein A (pA), staphylococcal protein G (pG) a fusion between pA and pG (pAG), or an antibody.

In certain embodiments, the specific binding agent comprises an antibody or an specific binding fragment thereof. A chromatin associated factor, or a fragment or conservative variant thereof can be used to produce antibodies which are immunoreactive or bind to an epitope of the receptor polypeptide. Polyclonal or monoclonal antibodies and fragments of monoclonal antibodies such as Fab, F(ab')2 and Fv fragments, as well as any other agent capable of specifically binding to a peptide derived from a chromatin associated factor may be produced. Optimally, antibodies raised against a chromatin associated factor would specifically bind the chromatin associated factor of interest. That is, such antibodies would recognize and bind the protein and would not substantially recognize or bind to other proteins. The determination that an antibody specifically binds the target or internalizing receptor polypeptide of interest is made by any one of a number of standard immunoassay methods; for instance, the Western blotting technique (Sambrook et al., 1989, Molecular Cloning: A Laboratory Manual, Cold Spring Harbor Laboratory, Cold Spring Harbor, N.Y.).

A substantially pure target or internalizing receptor polypeptide suitable for use as an immunogen is isolated by purification or recombinant expression. Alternatively, antibodies may be raised against a synthetic target.

The preparation of polyclonal antibodies is known to those skilled in the art. See, for example, Green et al., "*Production of Polyclonal Antisera*," in Immunochemical Protocols pages 1-5, Manson, ed., *Humana Press* 1992; Coligan et al., "*Production of Polyclonal Antisera in Rabbits, Rats, Mice and Hamsters*," in: Current Protocols in Immunology, section 2.4.1, 1992. The preparation of monoclonal antibodies likewise is conventional. See, for example, Kohler & Milstein, *Nature* 256:495, 1975; Coligan et al., sections 2.5.1-2.6.7; and Harlow et al., in: *Antibodies: a Laboratory Manual*, page 726, Cold Spring Harbor Pub., 1988. Monoclonal antibody to epitopes of the target or internalizing receptor polypeptide identified and isolated as described can be prepared from murine hybridomas according to the classical method of Kohler and Milstein (*Nature*

256:495, 1975) or derivative methods thereof. Specific antibodies can also be derived from subhuman primate antibody. General techniques for raising therapeutically useful antibodies in baboons can be found, for example, in WO 91/11465, 1991 and Losman et al., *Int. J. Cancer* 46:310, 1990. Alternatively, an antibody that specifically binds chromatin associated factor can be derived from a humanized monoclonal antibody. Humanized monoclonal antibodies are produced by transferring mouse complementarity determining regions from heavy and light variable chains of the mouse immunoglobulin into a human variable domain and then substituting human residues in the framework regions of the murine counterparts. Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE® Cloning Systems (La Jolla, Calif.). Antibodies include intact molecules as well as fragments thereof, such as Fab, F(ab')$_2$ and Fv which are capable of binding the epitopic determinant. Methods of making these fragments are known in the art. (See for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

Molecules, such as enzymes, for example nucleases and transposases can be linked together using any number of means known to those of skill in the art. The linker can be any molecule used to join a molecule to another molecule. Depending on such factors as the molecules to be linked and the conditions in which the method of detection is performed, the linker can vary in length and composition for optimizing such properties as flexibility, stability and resistance to certain chemical and/or temperature parameters. A linker should be of sufficient length that the linked molecule is capable of binding a chromatin associated factor and allow the enzyme to cleave the chromatin DNA.

In certain embodiments, the binding of the chromatin-associated factor of interest to the sequence of chromatin DNA is direct. In other words, the chromatin-associated factor of interest makes direct contacts with the chromatin DNA, for example is in direct physical contact with the chromatin DNA, as would be the case with DNA binding transcription factors. Thus, in some embodiments, the chromatin-associated factor of interest is a transcription factor. In other embodiments, the binding of the chromatin-associated factor of interest to the sequence of chromatin DNA is indirect. In other words, the contact may be indirect, such as through members of a complex. In this way longer range interactions can be elucidated.

In certain embodiments, proteins that interact with a chromatin binding agent can also be detected and their identity determined. Such proteins may be detected by mass spectrometry assays coupled to immunoaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE) (Kiernan et al., Anal. Biochem., 301: 49-56, 2002; Poutanen et al., Mass Spectrom., 15: 1685-1692, 2001), electrospray ionization (ESI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample can be subjected to one or more dimensions of chromatographic separation, for example, one or more dimensions of liquid or size exclusion chromatography.

Mass spectroscopic methods, such as SELDI, can be used to analyze and identify proteins in a sample. In one example, surface-enhanced laser desorption-ionization time-of-flight (SELDI-TOF) mass spectrometry is used to detect protein expression, for example by using the ProteinChip™ (Ciphergen Biosystems, Palo Alto, CA). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

In some embodiments, the cell, or the population thereof, is immobilized on a solid surface, for example a bead or the wall of a microtiter plate. Methods of coupling cells to such solid surfaces are known in the art, for example in the context of high throughput techniques.

In embodiments, a tag, such a DNA tag, can be added to the excised chromatin DNA, for example at one or both ends of the excised chromatin DNA. A variety of tag sequences can be added covalently to the excised chromatin DNA in the process of the disclosed method. As used herein, the term "tag" means a nucleotide sequence that is attached to another nucleic acid to provide the nucleic acid with some functionality. Examples of tags include barcodes, primer sites, affinity tags, and reporter moieties or any combination thereof.

In some embodiments, the tag is a nucleic acid tag. In some embodiments, the nucleic acid tag includes a barcode. These nucleic acid barcodes can be used to tag the excised chromatin DNA, for example by sample, organism, or the like, for example so that multiple samples can be analyzed simultaneously while preserving information about the sample origin. Generally, a barcode can include one or more nucleotide sequences that can be used to identify one or more particular nucleic acids. The barcode can be an artificial sequence, or can be a naturally occurring sequence. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 4, 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated, for example using spit-pool methodology. It will be understood that in some embodiments, the vast number of available barcodes permits each tagged excised chromatin DNA molecule to comprise a unique identification. Unique identification of each molecule in a mixture of template nucleic acids can be used in several applications to identify individual nucleic acid molecules, in samples having multiple chromosomes, genomes, cells, cell types, cell disease states, and species, for example in haplotype sequencing, parental allele discrimination, metagenomic sequencing, and sample sequencing of a genome.

In some embodiments, the nucleic acid tag includes a sequencing adaptor. The sequencing adaptors may be the same or different on each end of the excised chromatin DNA. The inclusion of a sequence adaptor facilitates the sequencing of the fragmented DNA produced, for example using next generation sequencing, such as paired end, and/or array-based sequencing.

In some embodiments, the nucleic acid tag includes a universal priming site. The inclusion of a universal priming site facilitates the amplification of the fragmented DNA produced, for example using PCR based amplification. In one embodiment, the primer sequence can be complementary to a primer used for amplification. In another embodiment, the primer sequence is complementary to a primer used for sequencing. In certain embodiments, the chromatin DNA is tagged and cleaved simultaneously, for example using a transposase. Thus, in embodiments, the disclosed methods include contacting an uncrosslinked permeabilized cell with a specific binding agent that specifically recognizes the chromatin-associated factor of interest, wherein the specific binding agent is linked to at least one artificial transposome, under conditions that permit integration of a transposon into chromatin DNA.

In some embodiments the method is an in situ method for determining the binding site of a chromatin-associated factor of interest to DNA sequences in a cell. In some embodiments the method includes contacting a permeabilized cell with a first antibody that specifically binds the chromatin-associated factor interest wherein the first antibody is coupled to a plurality of transposomes, such as 2, 3, 4, 5, 6, 7, 8, or even more, for example 2-4, Or even 2-10 and anywhere in between. In embodiments, each of the plurality of transposomes includes at least one transposase, and a transposon including a first DNA molecule comprising a first transposase recognition site, and a second DNA molecule comprising a second transposase recognition site. In embodiments, the method includes activating the transposase, for example with a divalent cation, such as Mg2+, thereby excising and tagging the sequence of DNA bound to the chromatin-associated factor of interest with the DNA tag, wherein the at least one transposase integrates the first and second DNA molecules into chromatin DNA, thereby cleaving and tagging chromatin DNA with the first and second DNA molecules. In embodiments, the method includes isolating the excised DNA. In embodiments, the method includes determining the sequence of the excised DNA, thereby mapping binding of a chromatin-associated factor of interest to one or more sequences of DNA in the cell. In embodiments, the antibody is indirectly coupled to the at least one transposase. In embodiments, the transposase is linked to a specific binding agent that specifically binds the first antibody. In embodiments, the method further includes contacting the cell with a second antibody that specifically binds the first antibody, and wherein the transposase is linked to a specific binding agent that specifically binds the second antibody. In embodiments, the method further includes contacting the cell with a second antibody that specifically binds the first antibody; contacting the cell with a third antibody that specifically binds the second antibody, and wherein the transposase is linked to a specific binding agent that specifically binds the third antibody.

In certain embodiments, the methods include contacting an uncrosslinked permeabilized cell with an antibody that specifically binds the chromatin-associated factor interest, wherein the antibody is coupled to at least one transposome. In certain embodiments, the at least one transposome comprising: at least one transposase; and a transposon comprising: a first DNA molecule comprising a first transposase recognition site; and a second DNA molecule comprising a second transposase recognition site. In certain embodiments the methods includes activating the transposase, for example with the addition of a divalent cation, thereby excising and tagging the sequence of DNA bound to the chromatin-associated factor of interest with the DNA tag wherein the at least one transposase integrates the first and second DNA molecules into chromatin DNA. In embodiments, the method may include isolating the excised DNA; and determining the sequence of the excised DNA, thereby mapping binding of a chromatin-associated factor of interest to one or more sequences of DNA in the cell. The artificial transposome includes at least one transposase and a transposon. The transposon includes a first DNA molecule comprising a first transposase recognition site and a second DNA molecule comprising a second transposase recognition site. Integration of the transposon (or really the two parts of the broken transposon) yields a cleaved (or fragmented) DNA with the first and second DNA molecules integrated on either side of the fragmentation site. In this way, the chromatin DNA is both fragmented and tagged at the fragmentation site. In some examples, the transposase recognition sites have the same sequence, while in other examples, the transposase recognition sites have different sequences. With multiple insertions throughout the chromatin DNA, the DNA is effectively fragmented into small fragments amenable to analysis by next generation sequencing methods. In some embodiments, the chromatin DNA is contacted with at least two different transposomes, and wherein the different transposomes comprise different DNA sequences. Thus, the tagged chromatin DNA can be tagged at the 5' and 3' end with different transposon sequences.

The first and second DNA molecules of the transposon can further include a variety of tag sequences, which can be added covalently to the fragments in the process of the disclosed method. As used herein, the term "tag" means a nucleotide sequence that is attached to another nucleic acid to provide the nucleic acid with some functionality. Examples of tags include barcodes, primer sites, affinity tags, and reporter moieties or any combination thereof, such as those described above.

The disclosed methods can use any transposase. Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al, EMBO J., 14: 4893, 1995). An exemplary transposase recognition site that forms a complex with a hyperactive Tn5 transposase (e.g., EZ-Tn5™ Transposase). More examples of transposition systems that can be used with certain embodiments provided herein include *Staphylococcus aureus* Tn552 (Colegio et al, J. Bacteriol, 183: 2384-8, 2001; Kirby C et al, Mol. Microbiol, 43: 173-86, 2002), Tyl (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol, 204:27-48, 1996), Tn/O and IS 10 (Kleckner N, et al, Curr Top Microbiol Immunol, 204:49-82, 1996), Mariner transposase (Lampe D J, et al, EMBO J., 15: 5470-9, 1996), Te1 (Plasterk R H, Curr. Topics Microbiol. Immunol, 204: 125-43, 1996), P Element (Gloor, G B, Methods Mol. Biol, 260: 97-114, 2004), Tn3 (Ichikawa & Ohtsubo, J Biol. Chem. 265: 18829-32, 1990), bacterial insertion sequences (Ohtsubo & Sekine, Curr. Top. Microbiol. Immunol. 204: 1-26, 1996), retroviruses (Brown, et al, Proc Natl Acad Sci USA, 86:2525-9, 1989), and retrotransposon of yeast (Boeke & Corces, Annu Rev Microbiol. 43: 403-34, 1989). More examples include IS5, Tn1O, Tn903, IS91 1, and engineered versions of transposase family enzymes (Zhang et al, (2009) PLoS Genet. 5:e1000689. Epub 2009 Oct 16; Wilson C. et al (2007) J. Microbiol. Methods 71: 332-5) and those described in U.S. Pat. Nos. 5,925,545; 5,965,443; 6,437,109; 6,159,736; 6,406,896; 7,083,980; 7,316,903; 7,608,434; 6,294,385; 7,067,644, 7,527,966; and International Patent Publication No. WO2012103545, all of which are specifically incorporated herein by reference in their entirety. In some embodiments, the transposase is a Tn5 transposase or a hyperactive mutant thereof. In some embodiments, the transposase is a Mu transposon.

In certain embodiments, the excised chromatin DNA fragments are purified by immobilizing the fragments on a substrate, such as a bead, membrane, or surface (e.g, a well or tube) that is coated with an affinity molecule suitable for immobilizing the excised chromatin DNA. In certain embodiments, the affinity molecule is silica or carboxyl-coated magnetic beads (SPRI beads). In certain embodiments, a library (e.g., for next generation sequencing applications, such as Illumina® sequencing (Illumina® Inc., San Diego, CA)) is constructed on magnetic particles. The same DNA absorbing magnetic beads can then be used to purify the resulting library. In some embodiments, a further advantage of providing an affinity surface in a well or as a bead, e.g., magnetic beads, is that the disclosed methods may be adapted for parallel processing of multiple samples, such as in a 96-well format or microfluidic platform, from starting chromatin material to the end of a sequencing library construction and purification. In certain embodiments, the excised chromatin DNA are purified after they have been released from the specific chromatin-associated factor and/or antibody with which or to which the nucleic acid fragments were bound.

In some embodiments, the identity of an excised chromatin DNA is determined by DNA sequencing, such as massively parallel sequencing. Some technologies may use cluster amplification of adapter-ligated excised chromatin DNA on a solid flow cell substrate. The resulting high density array of template clusters on the flow cell surface may then be submitted to sequencing-by-synthesis in parallel using for example fluorescently labeled reversible terminator nucleotides.

Templates can be sequenced base-by-base during each read. In certain embodiments, the resulting data may be analyzed using data collection and analysis software that aligns sample sequences to a known genomic sequence. Sensitivity of this technology may depend on factors such as the depth of the sequencing run (e.g., the number of mapped sequence tags), the size of the genome, and the distribution of the target factor. By integrating a large number of short reads, highly precise binding site localization may be obtained. In certain embodiments, the data can be used to locate the binding site within few tens of base pairs of the actual protein binding site, and tag densities at the binding sites may allow quantification and comparison of binding affinities of a protein to different DNA sites.

Generally, the sequencing can be performed using automated Sanger sequencing (AB 13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®). Other next generation sequencing techniques for use with the disclosed methods include, Massively parallel signature sequencing (MPSS), Polony sequencing, Ion Torrent semiconductor sequencing, DNA nanoball sequencing, Heliscope single molecule sequencing, Single molecule real time (SMRT) sequencing, and Nanopore DNA sequencing. In some embodiments, the excised chromatin DNA is analyzed, for example by determining the nucleotide sequence. In some examples, the nucleotide sequence is determined using sequencing or hybridization techniques with or without amplification.

In certain embodiments, the methods can be carried out easily and data can be obtained reproducibly. In certain embodiments, these methods are used to screen large numbers of DNA binding proteins and/or chromatin modifiers. In certain embodiments, the methods provided are used to screen 5, 10, 50, 100, 200, 500, 750, or 1000, or more DNA binding proteins and/or chromatin regulators (CRs) and modified forms thereof. Modified forms include, but are not limited to, mutants and post-translationally modified DNA binding proteins and/or chromatin modifiers.

In certain embodiments, the methods provided are used to screen one or more of the following DNA binding proteins and/or chromatin modifiers and modified forms thereof: AAF, ab1, ADA2, ADA-NF1, AF-1, AFP1, AhR, AIIN3, ALL-1, alpha-CBF, alpha-CP 1, alpha-CP2a, alpha-CP2b, alphaHo, alphaH2-alphaFB, Alx-4, aMEF-2, AML1, AML1a, AML1b, AML1c, AML1DeltaN, AML2, AML3, AML3a, AML3b, AMY-1L, A-Myb, ANF, AP-1, AP-2alphaA, AP-2alphaB, AP-2beta, AP-2gamma, AP-3 (1), AP-3 (2), AP-4, AP-5, APC, AR, AREB6, Art, Arnt (774 M form), ARP-1, ATBF1-A, ATBF1-B, ATF, ATF-1, ATF-2, ATF-3, ATF-3 deltaZIP, ATF-a, ATF-adelta, ATPFI, Barhl1, Barhl2, Barx1, Barx2, Bcl-3, BCL-6, BD73, beta-catenin, Bin1, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CACCbinding factor, Cart-1, CBF (4), CBF (5), CBP, CCAAT-binding factor, CCMT-binding factor, CCF, CCG1, CCK-1a, CCK-1b, CD28RC, cdk2, cdk9, Cdx-1, CDX2, Cdx-4, CFF, ChxlO, CLIM1, CLIM2, CNBP, CoS, COUP, CP1, CPIA, CPIC, CP2, CPBP, CPE binding protein, CREB, CREB-2, CRE-BP1, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin T1, cyclin T2, cyclin T2a, cyclin T2b, DAP, DAX1, DB1, DBF4, DBP, DbpA, DbpAv, DbpB, DDB, DDB-1, DDB-2, DEF, deltaCREB, deltaMax, DF-1, DF-2, DF-3, Dlx-1, Dlx-2, Dlx-3, DIx4 (long isoform), Dlx-4 (short isoform, Dlx-5, Dlx-6, DP-1, DP-2, DSIF, DSIF-p14, DSIF-p160, DTF, DUX1, DUX2, DUX3, DUX4, E, E12, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EIIaE-A, EIIaE-B, EIIaE-Calpha, EIIaE-Cbeta, EivF, Elf-1, Elk-1, Emx-1, Emx-2, Emx-2, En-1, En-2, ENH-bind. prot., ENKTF-1, EPAS 1, epsilonF 1, ER, Erg-1, Erg-2, ERR1, ERR2, ETF, Ets-1, Ets-1 deltaVil, Ets-2, Evx-1, F2F, factor 2, Factor name, FBP, f-EBP, FKBP59, FKHL18, FKHRL1P2, Fli-1, Fos, FOXB1, FOXC1, FOXC2, FOXD1, FOXD2, FOXD3, FOXD4, FOXE1, FOXE3, FOXF1, FOXF2, FOXG1a, FOXG1b, FOXG1c, FOXH1, FOXI1, FOXJ1a, FOXJ1b, FOXJ2 (long isoform), FOXJ2 (short isoform), FOXJ3, FOXK1a, FOXK1b, FOXK1c, FOXL1, FOXM1a, FOXM1b, FOXM1c, FOXN1, FOXN2, FOXN3, FOXO1a, FOXO1b, FOX02, FOX03a, FOX03b, FOX04, FOXP1, FOXP3, Fra-1, Fra-2, FTF, FTS, G factor, G6 factor, GABP, GABP-alpha, GABP-beta1, GABP-beta2, GADD 153, GAF, gammaCMT, gammaCAC1, gammaCAC2, GATA-1, GATA-2, GATA-3, GATA-4, GATA-5, GATA-6, Gbx-1, Gbx-2, GCF, GCMa, GCNS, GF1, GLI, GLI3, GR alpha, GRbeta, GRF-1, Gsc, Gscl, GT-IC, GT-IIA, GT-IIBalpha, GT-IIBbeta, H1TF1, H1TF2, H2RIIBP, H4TF-1, H4TF-2, HAND 1, HAND2, HB9, HDAC1, HDAC2, HDAC3, hDaxx, heat-induced factor, HEB, HEB1-p67, HEB1-p94, HEF-1 B, HEF-1T, HEF-4C, HEN1, HEN2, Hesxl, Hex, HIF-1, HIF-1alpha, HIF-1beta, HiNF-A, HINF-B, HINF-C, HINF-D, HiNF-D3, HiNF-E, HiNF-P, HIP1, HIV-EP2, Hlf, HLTF, HLTF (Met123), HLX, HMBP, HMG I, HMG I(Y), HMG Y, HMGI-C, HNF-IA, HNF-IB, HNF-1C, HNF-3, HNF-3alpha, HNF-3beta, HNF-3gamma, HNF4, HNF-4alpha, HNF-4alpha1, HNF-4alpha2, HNF-4alpha3, HNF-4alpha4, HNF4gamma, HNF-6alpha, hnRNP K, HOX11, HOXA1, HOXA10, HOXA10 PL2, HOXA11, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXB5, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Id1, Id1 H', Id2, Id3, Id3/Heir-1, IF1, IgPE-1, IgPE-2, IgPE-3, IkappaB, IkappaB-alpha, IkappaB-beta, IkappaBR, II-1 RF, IL-6 RE-BP, 11-6 RF, INSAF, IPF1, IRF-1, IRF-2, B, IRX2a, Irx-3, Irx-4, ISGF-1, ISGF-3, ISGF3alpha, ISGF-3gamma, 1st-1, ITF, ITF-1, ITF-2, JRF, Jun, JunB, JunD, kappay factor, KBP-1, KER1, KER-1, Kox1, KRF-1, Ku autoantigen, KUP, LBP-1, LBP-1a, LBX1, LCR-F1, LEF-1, LEF-1B, LF-A1, LHX1, LHX2, LHX3a, LHX3b, LHXS, LHX6.1a, LHX6.1b, LIT-1, Lmo1, Lmo2, LMX1A, LMX1B, L-My1 (long form), L-My1 (short form), L-My2, LSF, LXRalpha, LyF-1, Lyl-1, M factor, Mad1, MASH-1, Max1, Max2, MAZ, MAZ1, M1B67, M1BF1, MBF2, MBF3, MBP-1 (1), MBP-1 (2), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2DOB, MEF-2DA0, MEF-2DAO, MEF-2DAB, MEF-2DA'B, Meis-1, Meis-2a, Meis-2b, Meis-2c, Meis-2d, Meis-2e, Meis3, Meox1, Meox1a, Meox2, MHox (K-2), Mi, MIF-1, Miz-1, MM-1, MOP3, MR, Msx-1, Msx-2, MTB-Zf, MTF-1, mtTF1, Mxil, Myb, Myc, Myc 1, Myf-3, Myf-4, Myf-5, Myf-6, MyoD, MZF-1, NCI, NC2, NCX, NELF, NER1, Net, NF Ill-a, NF NF-1, NF-IA, NF-1B, NF-1X, NF-4FA, NF-4FB, NF-4FC, NF-A, NF-AB, NFAT-1, NF-AT3, NF-Atc, NF-Atp, NF-Atx, NfbetaA, NF-CLEOa, NF-CLEOb, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaB1, NF-kappaB1, precursor, NF-kappaB2, NF-kappaB2 (p49), NF-kappaB2 precursor, NF-kappaE1, NF-kappaE2, NF-kappaE3, NF-MHCIIA, NF-MHCIIB, NF-muE1, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3A v1, NKX3A v2, NKX3A v3, NKX3A v4, NKX3B, NKX6A, Nmi, N-Myc, N-Oct-2alpha, N-Oct-2beta, N-Oct-3, N-Oct-4, N-Oct-5a, N-Oct-5b, NP-TCII, NR2E3, NR4A2, Nrfl, Nrf-1, Nrf2, NRF-2beta1, NRF-2gamma1, NRL, NRSF form 1, NRSF form 2, NTF, 02, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otx1, Otx2, OZF, p107, p130, p28 modulator, p300, p38erg, p45, p49erg,-p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8b, Pax-8c, Pax-8d, Pax-8e, Pax-8f, Pax-9, Pbx-1a, Pbx-1b, Pbx-2, Pbx-3a, Pbx-3b, PC2, PC4, PC5, PEA3, PEBP2alpha, PEBP2beta, Pit-1, PITX1, PITX2, PITX3, PKNOX1, PLZF, PO-B, Pontin52, PPARalpha, PPARbeta, PPARgamma1, PPARgamma2, PPUR, PR, PR A, pRb, PRD1-BF1, PRDI-BFc, Prop-1, PSE1, P-TEFb, PTF, PTF alpha, PTFbeta, PTFdelta, PTFgamma, Pu box binding factor, Pu box binding factor (BJA-B), PU. 1, PuF, Pur factor, R1, R2, RAR-alpha1, RAR-beta, RAR-beta2, RAR-gamma, RAR-gamma1, RBP60, RBP-Jkappa, Re1, Re1A, Re1B, RFX, RFX1, RFX2, RFX3, RFXS, RF-Y, RORalpha1, RORalpha2, RORalpha3, RORbeta, ROR-gamma, Rox, RPF1, RPGalpha, RREB-1, RSRFC4, RSRFC9, RVF, RXR-alpha, RXR-beta, SAP-1a, SAP 1b, SF-1, SHOX2a, SHOX2b, SHOXa, SHOXb, SHP, SIII-p1 lO, SIII-p15, SIII-p18, SIM', Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, Sp1, Sp2, Sp3, Sp4, Sph factor, Spi-B, SPIN, SRCAP, SREBP-1a, SREBP-1b, SREBP-1c, SREBP-2, SRE-ZBP, SRF, SRY, SRP1, Staf-50, STAT1alpha, STAT1beta, STAT2, STAT3, STAT4, STAT6, T3R, T3R-alpha1, T3R-alpha2, T3R-beta, TAF(I)110, TAF(I)48, TAF(I)63, TAF(II)100, TAF(II)125, TAF(II)135, TAF(II)170, TAF(II)18, TAF(II)20, TAF(II) 250, TAF(II)250Delta, TAF(II)28, TAF(II)30, TAF(II)31, TAF(II)55, TAF(II)70-alpha, TAF(II)70-beta, TAF(II)70-gamma, TAF-I, TAF-II, TAF-L, Tal-1, Tal-1beta, Tal-2, TAR factor, TBP, TBXIA, TBXIB, TBX2, TBX4, TBXS (long isoform), TBXS (short isoform), TCF, TCF-1, TCF-IA, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbeta1, TEF-1, TEF-2, tel, TFE3, TFEB, TFIIA, TFIIA-alpl^eta precursor, TFIIA-alpha/beta precursor, TFIIA-gamma, TFIIB, TFIID, TFIIE, TFIIE-alpha, TFIIE-beta, TFIIF, TFIIF-alpha, TFIIF-beta, TFIIH, TFIIH*, TFIIH-CAK, TFIIH-cyclin H, TFIIH-ERCC2/CAK, TFIIH-MAT1, TFIIH-M015, TFIIH-p34, TFIIH-p44, TFIIH-p62, TFIIH-p80, TFIIH-p90, TFII-I, Tf-LF1, Tf-LF2, TGIF, TGIF2, TGT3, THRA1, TIF2, TLE1, TLX3, TMF, TR2, TR2-11, TR2-9, TR3, TR4, TRAP, TREB-1, TREB-2, TREB-3, TREF1, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-1A, vHNF-1B, vHNF-1C, VITF, WSTF, WT1, WT1I, WT1 I-KTS, WT1 I-del2, WT1-KTS, WT1-del2, X2BP, XBP-1, XW-V, XX, YAF2, YB-1, YEBP, YY1, ZEB, ZF1, ZF2, ZFX, ZHX1, ZIC2, ZID, ZNF174, ASH1L, ASH2, ATF2, ASXL1, BAP1, bllO, Bmil, BRGI, CARMI, KAT3A/CBP, CDC73, CHD1, CHD2, CTCF, DNMT1, DOTL1, EHMT1, ESET, EZH1, EZH2, FBXL10, FRP(Plu-1), HD AC 1, HDAC2, HMGA1, hnRNPA1, HP1 gamma, Hsetlb, Jarid1A, Jarid1C, KIAA1718 JHDMID, KAT5, KMT4, LSD1, NFKB P100, NSD2, MBD2, MBD3, MLL2, MLL4, P300, pRB, RbAP46/48, RBP1, RbBP5, RING IB, RNApolII P S2, RNApolII P S5, ROCI, sap30, setDB 1, Sf3b1, SIRT1, Sirt6, SMYD1, SP1, SUV39H1, SUZ12, TCF4, TET1, TRRAP, TRX2, WDR5, WDR77, and/or YY1. Antibodies for these DNA binding proteins and/or chromatin modifiers are commercially available.

Chromatin-associated factors, as used herein, are factors that can be found at one or more sites on the chromatin and/or that may associate with chromatin in a transient manner. Examples of low abundance chromatin-associated factors include, but are not limited to, transcription factors (e.g., tumor suppressors, oncogenes, cell cycle regulators, development and/or differentiation factors, general transcription factors (TFs)), ATP-dependent chromatin remodelers (e.g., (P)BAF, MOT1, ISWI, INO80, CHD1), activator (e.g., histone acetyl transferase (HAT)) complexes, repressor (e.g., histone deacetylase (HDAC)) complexes, co-activators, co-repressors, other chromatin-remodelers, e.g., histone (de-) methylases, DNA methylases, replication factors and the like. Such factors may interact with the chromatin (DNA, histones) at particular phases of the cell cycle (e.g., G1, S, G2, M-phase), upon certain environmental cues (e.g., growth and other stimulating signals, DNA damage signals, cell death signals) upon transfection and transient or stable expression (e.g., recombinant factors) or upon infection (e.g., viral factors).

Abundant factors are constituents of the chromatin, e.g., histones and their variants. Histones may be modified at histone tails through posttranslational modifications which alter their interaction with DNA and nuclear proteins and influence for example gene regulation, DNA repair and chromosome condensation. The H3 and H4 histones have long tails protruding from the nucleosome which can be covalently modified, for example by methylation, acetylation, phosphorylation, ubiquitination, sumoylation, citrullination and ADP-ribosylation. The core of the histones H2A and H2B can also be modified.

In certain embodiments, the disclosed methods are provided that allow sample processing in a high-throughput manner. For example, 10, 50, 100, 200, 500, 750, 1000, or more chromatin-associated factors and/or chromatin modifications may be immuno-precipitated and/or analyzed in parallel. In one embodiment, up to 96 samples may be processed at once, using e.g., a 96-well plate. In other embodiments, fewer or more samples may be processed, using e.g., 6-well, 12-well, 32-well, 384-well or 1536-well plates. In some embodiments, the methods provided can be carried out in tubes, such as, for example, common 0.5 ml, 1.5 ml or 2.0 ml size tubes. These tubes may be arrayed in tube racks, floats or other holding devices.

In particular embodiments, a sample may comprise about 1 cell, about 2 cells, about 3 cells, about 5 cells, about 10 cells, about 25, about 50 cells, about 100 cells, about 150 cells, about 200 cells, about 300 cells, about 400 cells, about 500 cells, about 1000 cells, about 2000 cells, about 3000 cells, about 4000 cells, about 5000 cells, about 10,000 cells, about 20,000 cells, about 30,000 cells, about 40,000 cells, about 50,000 cells, about 100,000 cells, about 200,000 cells, about 300,000 cells, about 400,000 cells, about 500,000 cells, or about 1,000,000 cells. In some embodiments, a sample may comprise about 1 cell to about 10,000 cells, or about 10,000 cells to about 100,000 cells, or more.

Specific DNA sites that are in direct physical interaction with transcription factors and other proteins, such as histones, may be isolated by, which produces a library of target DNA sites bound by a protein in vivo. In some embodiments, massively parallel sequence analyses may be used in conjunction with whole-genome sequence databases to analyze the interaction pattern of a protein of interest (e.g., transcription factors, polymerases or transcriptional machinery) with DNA or to analyze the pattern of an epigenetic chromatin modification of interest (e.g., histone modifications or DNA modifications).

The disclosed methods are also particularly suited to monitoring disease states, such as disease state in an organism, for example a plant or an animal subject, such as a mammalian subject, for example a human subject. Certain disease states may be caused and/or characterized differential binding or proteins and/or nucleic acids to chromatin DNA in vivo. For example, certain interactions may occur in a diseased cell but not in a normal cell. In other examples, certain interactions may occur in a normal cell but not in diseased cell. Thus, using the disclosed methods a profile of the interaction between a in vivo, can be correlated with a disease state.

Accordingly, aspects of the disclosed methods relate to correlating the interactions of a target nucleic acid with proteins and/or nucleic acid with a disease state, for example cancer, or an infection, such as a viral or bacterial infection. It is understood that a correlation to a disease state could be made for any organism, including without limitation plants, and animals, such as humans.

The interaction profile correlated with a disease can be used as a "fingerprint" to identify and/or diagnose a disease in a cell, by virtue of having a similar "fingerprint." The profile of chromatin associated factors and chromatin DNA can be used to identify binding proteins and/or nucleic acids that are relevant in a disease state such as cancer, for example to identify particular proteins and/or nucleic acids as potential diagnostic and/or therapeutic targets. In addition, the profile can be used to monitor a disease state, for example to monitor the response to a therapy, disease progression and/or make treatment decisions for subjects.

The ability to obtain an interaction profile allows for the diagnosis of a disease state, for example by comparison of the profile present in a sample with the correlated with a specific disease state, wherein a similarity in profile indicates a particular disease state.

Accordingly, aspects of the disclosed methods relate to diagnosing a disease state based on interaction profile correlated with a disease state, for example cancer, or an infection, such as a viral or bacterial infection. It is understood that a diagnosis of a disease state could be made for any organism, including without limitation plants, and animals, such as humans.

Aspects of the present disclosure relate to the correlation of an environmental stress or state with an interaction profile, for example a whole organism, or a sample, such as a sample of cells, for example a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value.

In some embodiments, the disclosed methods can be used to screen chemical libraries for agents that modulate interaction profiles, for example that alter the interaction profile from an abnormal one, for example correlated to a disease state to one indicative of a disease free state. By exposing cells, tissues, or even whole animals, to different members of the chemical libraries, and performing the methods described herein, different members of a chemical library can be screened for their effect on interaction profiles simultaneously in a relatively short amount of time, for example using a high throughput method.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Libraries can include a varying number of compositions (members), such as up to about 100 members, such as up to about 1,000 members, such as up to about 5,000 members, such as up to about 10,000 members, such as up to about 100,000 members, such as up to about 500,000 members, or even more than 500,000 members. In one example, the methods can involve providing a combinatorial chemical or peptide library containing a large number of potential therapeutic compounds. Such combinatorial libraries are then screened by the methods disclosed herein to identify those library members (particularly chemical species or subclasses) that display a desired characteristic activity.

The compounds identified using the methods disclosed herein can serve as conventional "lead compounds" or can themselves be used as potential or actual therapeutics. In some instances, pools of candidate agents can be identified and further screened to determine which individual or subpools of agents in the collective have a desired activity.

Control reactions can be performed in combination with the libraries. Such optional control reactions are appropriate and can increase the reliability of the screening. Accordingly, disclosed methods can include such a control reaction. The control reaction may be a negative control reaction that measures the transcription factor activity independent of a transcription modulator. The control reaction may also be a positive control reaction that measures transcription factor activity in view of a known transcription modulator.

Compounds identified by the disclosed methods can be used as therapeutics or lead compounds for drug development for a variety of conditions. Because gene expression is fundamental in all biological processes, including cell division, growth, replication, differentiation, repair, infection of cells, etc., the ability to monitor transcription factor activity and identify compounds which modulator their activity can be used to identify drug leads for a variety of conditions, including neoplasia, inflammation, allergic hypersensitivity, metabolic disease, genetic disease, viral infection, bacterial infection, fungal infection, or the like. In addition, compounds identified that specifically target transcription factors in undesired organisms, such as viruses, fungi, agricultural pests, or the like, can serve as fungicides, bactericides, herbicides, insecticides, and the like. Thus, the range of conditions that are related to transcription factor activity includes conditions in humans and other animals, and in plants, such as agricultural applications.

Appropriate samples for use in the methods disclosed herein include any conventional biological sample obtained from an organism or a part thereof, such as a plant, animal, bacteria, and the like, (such as plants or animals, including samples from a healthy or apparently healthy human subject or a human patient affected by a condition or disease to be diagnosed or investigated, such as cancer). A sample can also be a sample obtained from any organ or tissue (including a biopsy or autopsy specimen, such as a tumor biopsy) or can include a cell (whether a primary cell or cultured cell), tissue or organ. Exemplary samples include, without limitation, cells, tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner.

The following examples are provided to illustrate certain particular features and/or embodiments. This example should not be construed to limit the invention to the particular features or embodiments described.

EXAMPLES

Example 1

Chromatin Immuno-Cleavage (ChIC) has the advantage of using TF-specific antibodies to tether MNase and cleave only at binding sites. To adapt ChIC for deep sequencing, the disclosed methods were developed to reduce the representation of background breaks in DNA that otherwise dominate deep sequencing libraries. It was observed that light MNase treatment of nuclei liberates mononucleosomes and TF-DNA complexes, leaving behind oligonucleosomes. Targeted cleavage on both sides of a TF would further release the TF-DNA complex into the supernatant, leaving the remainder of the genome in the pelleted nuclei. By performing brief digestion reactions on ice, it was discovered that TF-DNA complexes could be recovered from the supernatant before TF-bound MNase diffused around the genome and cleaved accessible chromatin. Based on this rationale, an initial CUT&RUN protocol (FIG. 1A) was developed and refined.

In one example, the protocol includes the following steps:
(1) unfixed nuclei are immobilized on lectin-coated magnetic beads;
(2) successively incubated with antibodies and protein A-MNase (pA-MN) followed by minimal washing steps:

(3) mixed with $Ca^{++}$ on ice to initiate the cleavage reaction then stopped seconds-to-minutes later by chelation; and (4) centrifuged to recover the supernatant containing the released TF-DNA complexes. DNA is then extracted from the supernatant and used directly for sequencing library preparation.

CUT&RUN Produces Limited Digestion of Chromatin Complexes.

Figure 1B:
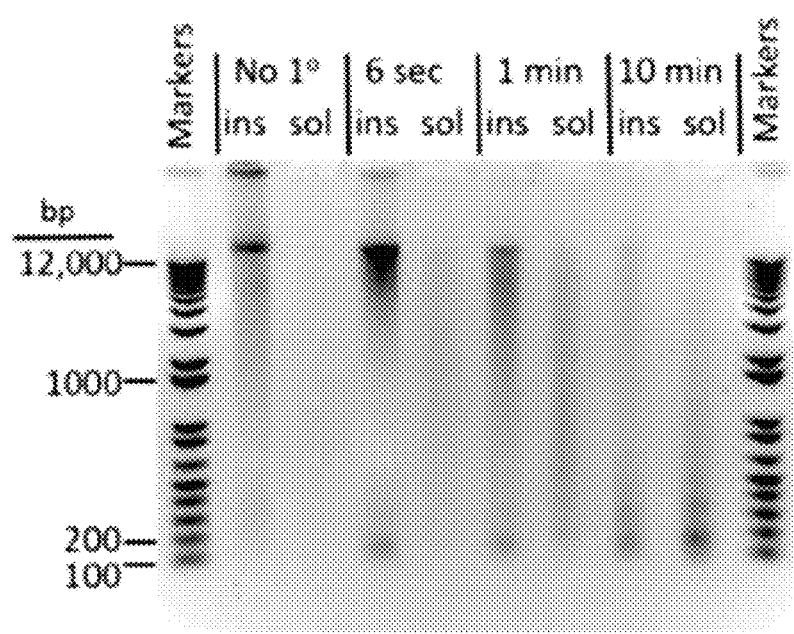
FIG. 1B; CUT&RUN cleaves and releases chromatin particles into the S. cerevisiae nuclei in which the endogenous H2A genes were replaced with H2A-3×FLAG, subjected to CUT&RUN and incubated at 0° C. in $Ca^{++}$ for the indicated times. DNA extracted from both the insoluble (ins) and soluble (sol) fractions was electrophoresed on a 1% agarose gel. The No 1° Ab control was digested for 10 min in parallel but without having added the primary mouse anti-FLAG antibody.
Figures 1, 1C:
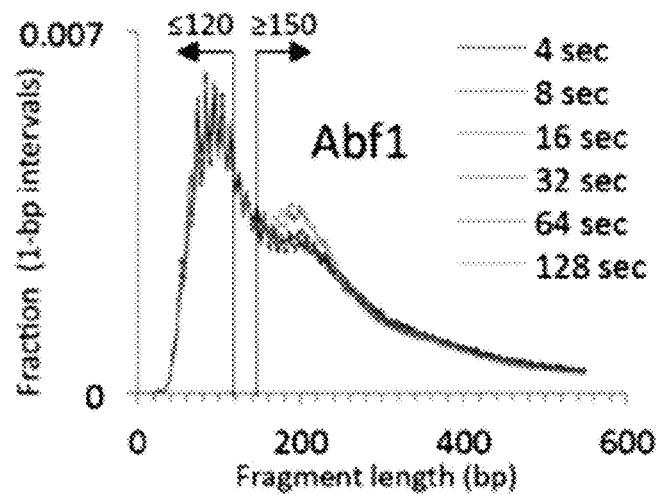
Figures 1, 1C, 2:
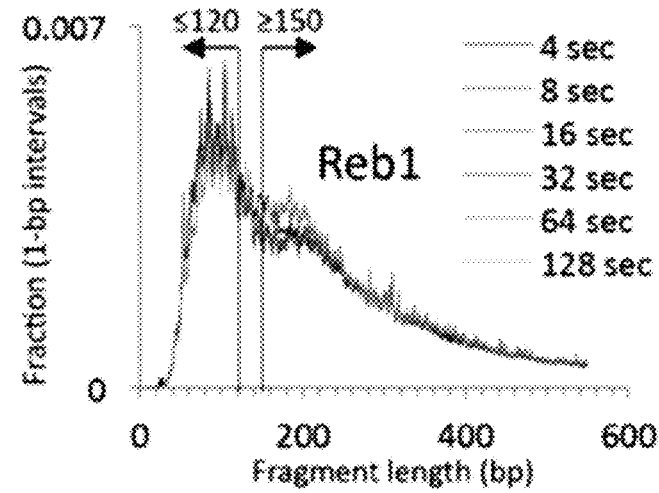
Figures 1, 1C, 2, 3:
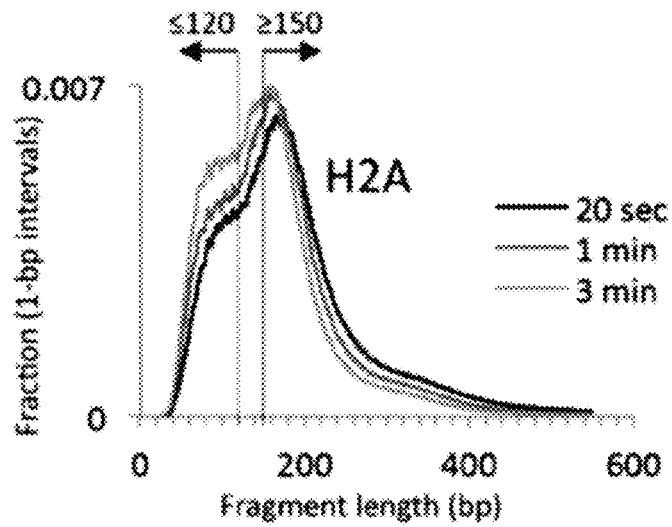

The CUT&RUN protocol was initially performed using crude yeast nuclei. To rigorously compare CUT&RUN and ChIP-seq, the same FLAG-tagged TF strains, the same nuclear preparation protocol, the same mouse anti-FLAG monoclonal antibody and the same procedure for Illumina library preparation and paired-end sequencing were used (Kasinathan et al., 2014). As mouse Protein A binds only weakly to mouse IgG, a rabbit anti-mouse secondary antibody was used for CUT&RUN. To test the efficiency of CUT&RUN, a *Saccharomyces cerevisiae* strain expressing 3×FLAG-tagged histone H2A was use, which would be expected to release nucleosomal fragments genome wide. Indeed, over a 100-fold digestion time course at 0° C., gradual cleavage was observed and release of fragments down to mononucleosomal size was completely dependent on the presence of the primary antibody (FIG. 1B).

CUT&RUN was then applied to two structurally distinct *S. cerevisiae* TFs, ARS binding factor 1 (Abf1), and rDNA enhancer binding protein 1 (Reb1), obtaining ~2-3 million mapped paired-end reads per sample. It was found that the size distributions of mapped fragments were virtually superimposable below ~150 bp for time points between 4 s and 128 s (FIG. 1C-1, 1C-2, 1C-3). This close concordance between time points over a 32-fold range suggests that limit digestion of TF-bound fragments occurs rapidly upon addition of $Ca^{++}$, and demonstrates that digestion time is not a critical parameter.

Figure 1D:
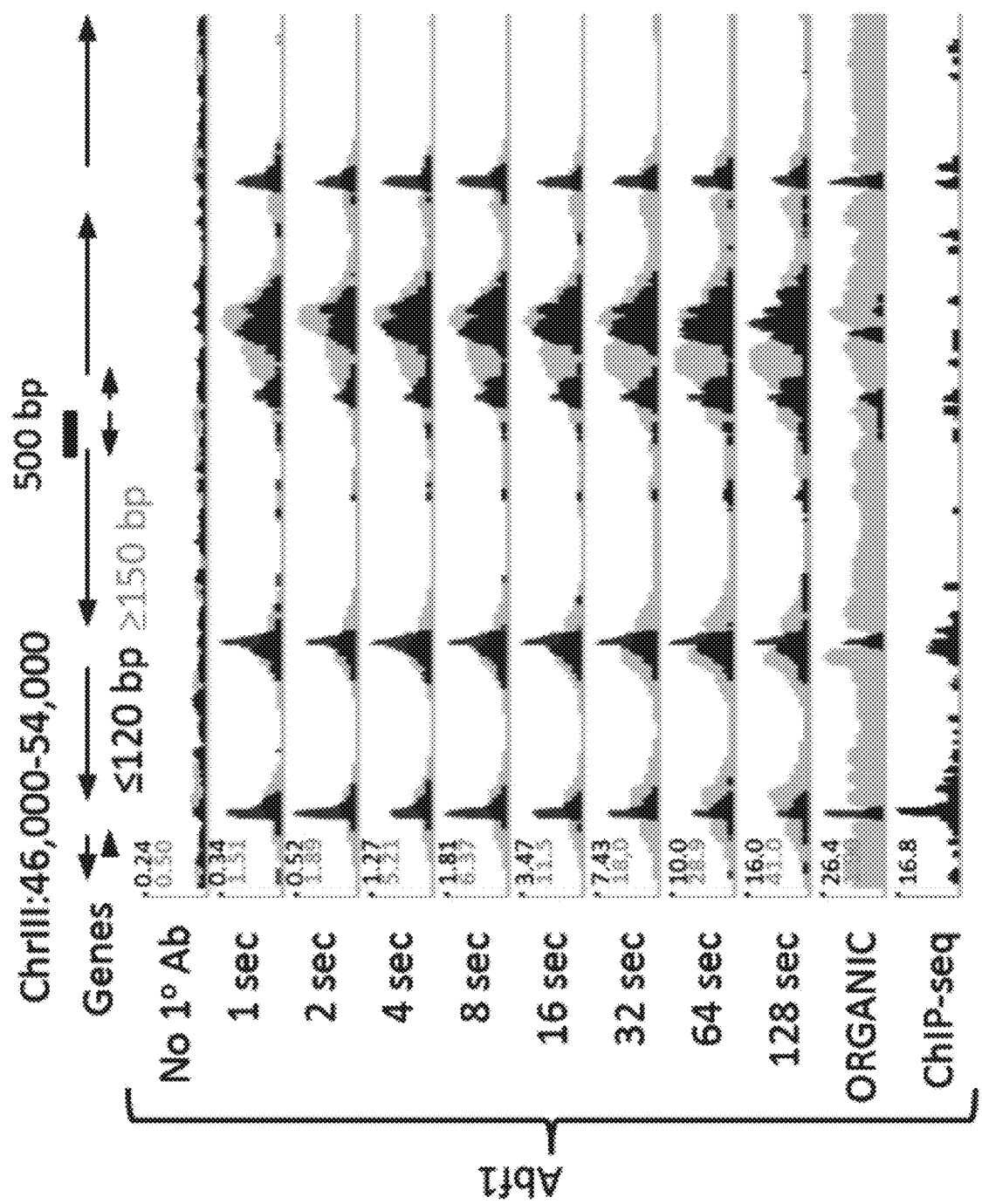
Figure 1D:
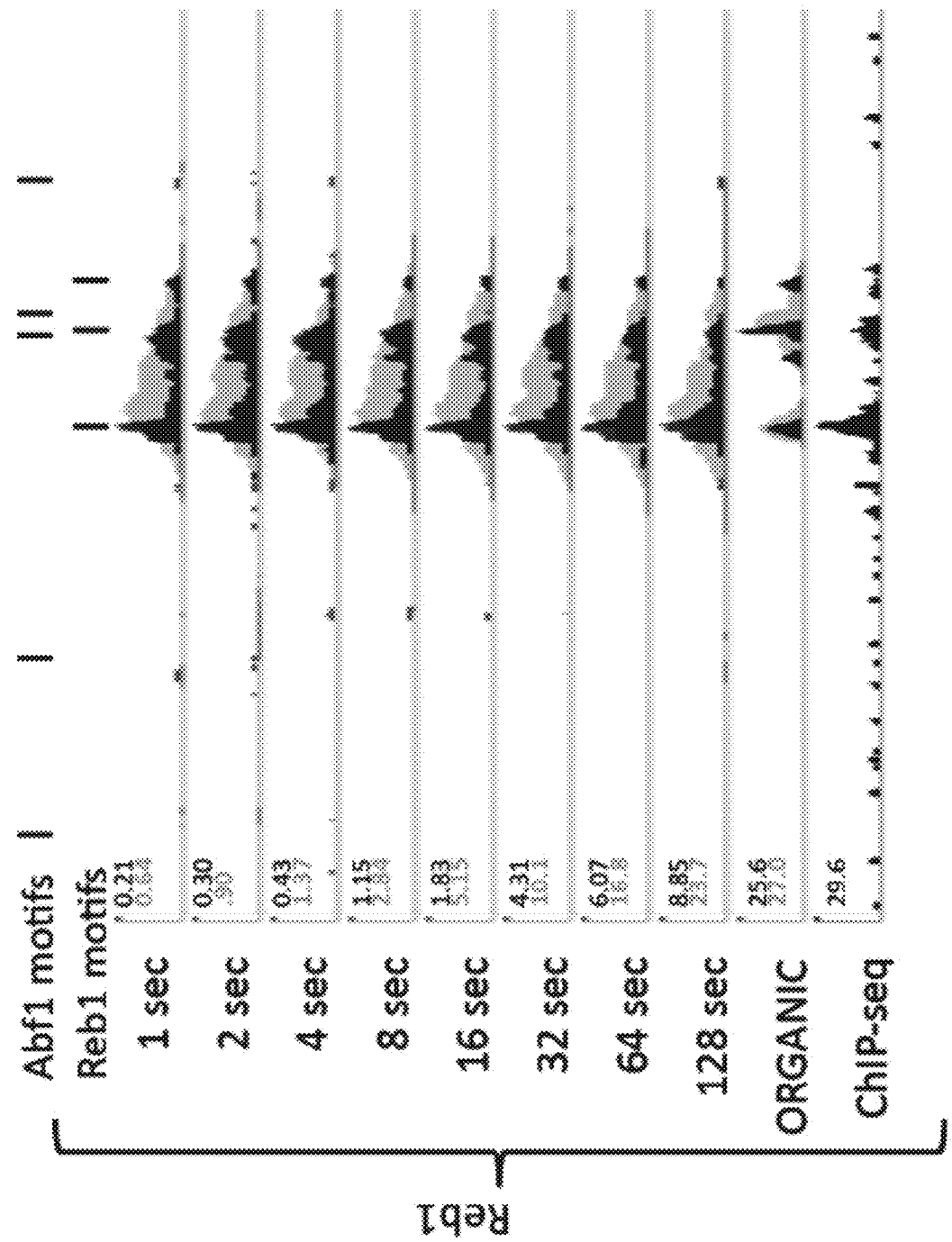
Figure 10:
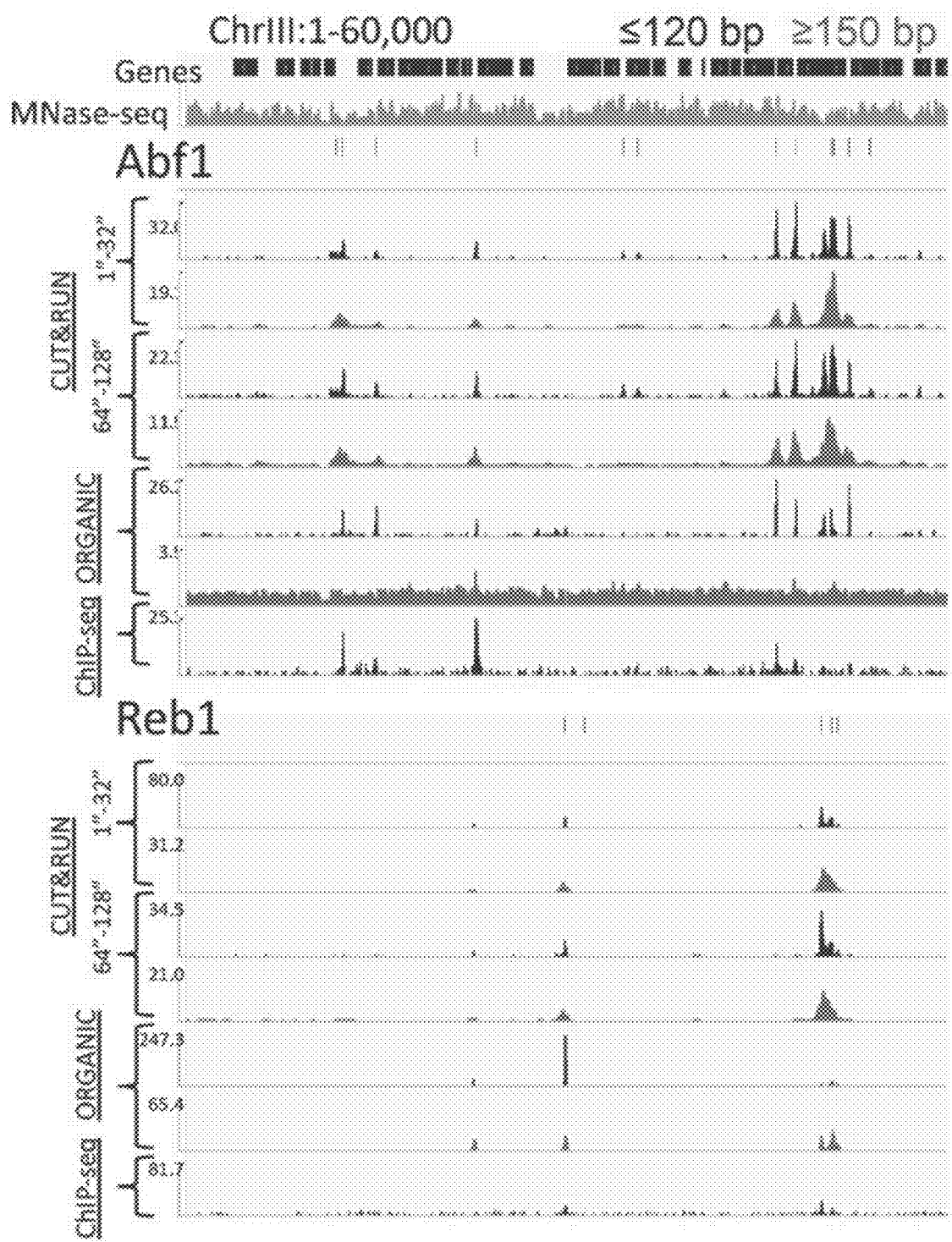
FIG. 10 shows that CUT&RUN and ORGANIC ChIP produce qualitatively similar TF occupancy profiles. Representative examples of Abf1 and Reb1 profiles for CUT&RUN data pooled from the 1" to 32" and the 64" and 128" time-course samples and ORGANIC for ≤120 bp and ≥150 bp fragment lengths, and standard ChIP-seq. An MNase-seq profile is shown in grey. Ticks mark the location of significant Abf1 (upper) and Reb1 (lower) motifs. The Y-axis was autoscaled within each region by IGV.
Figure 10:
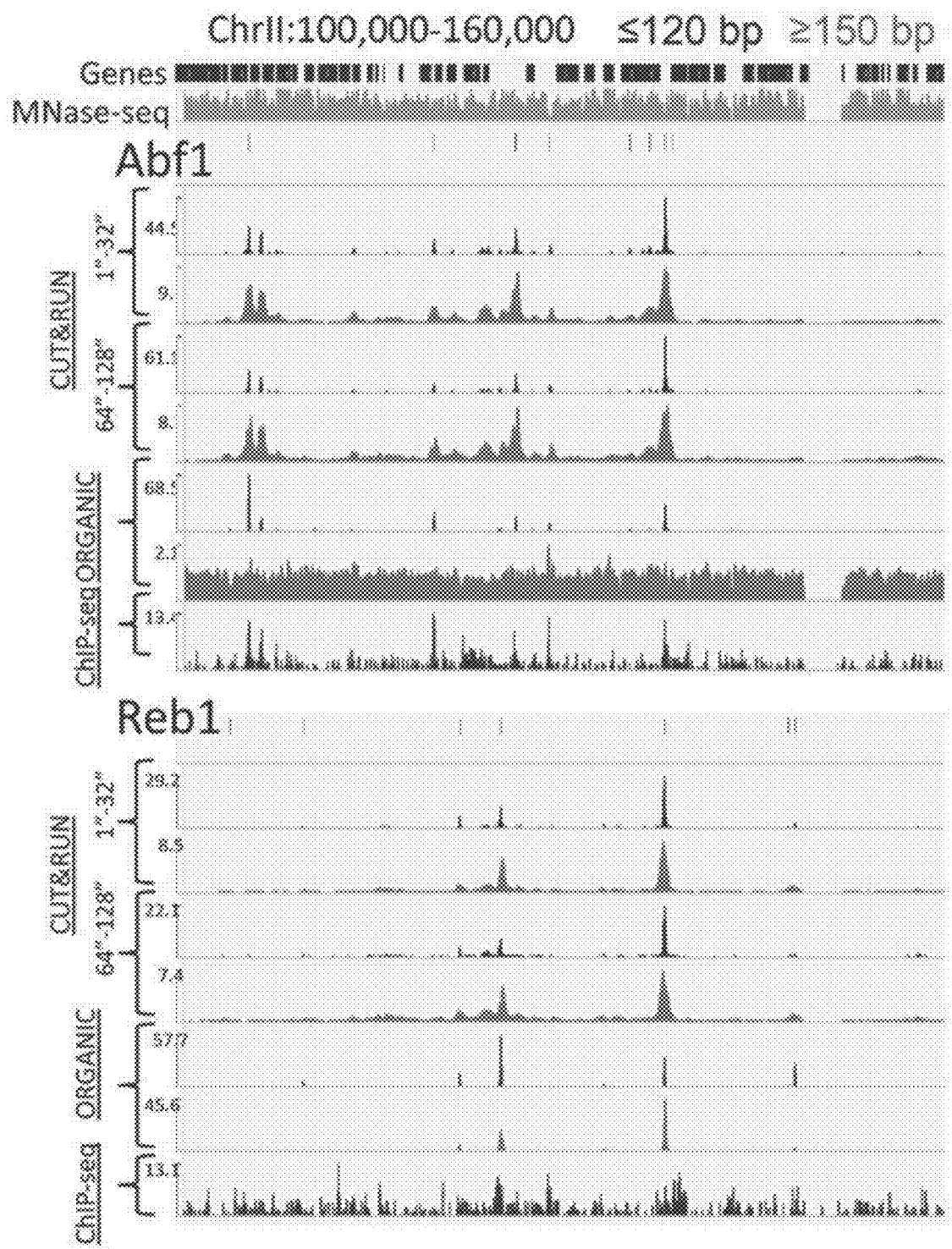
Figure 11B:
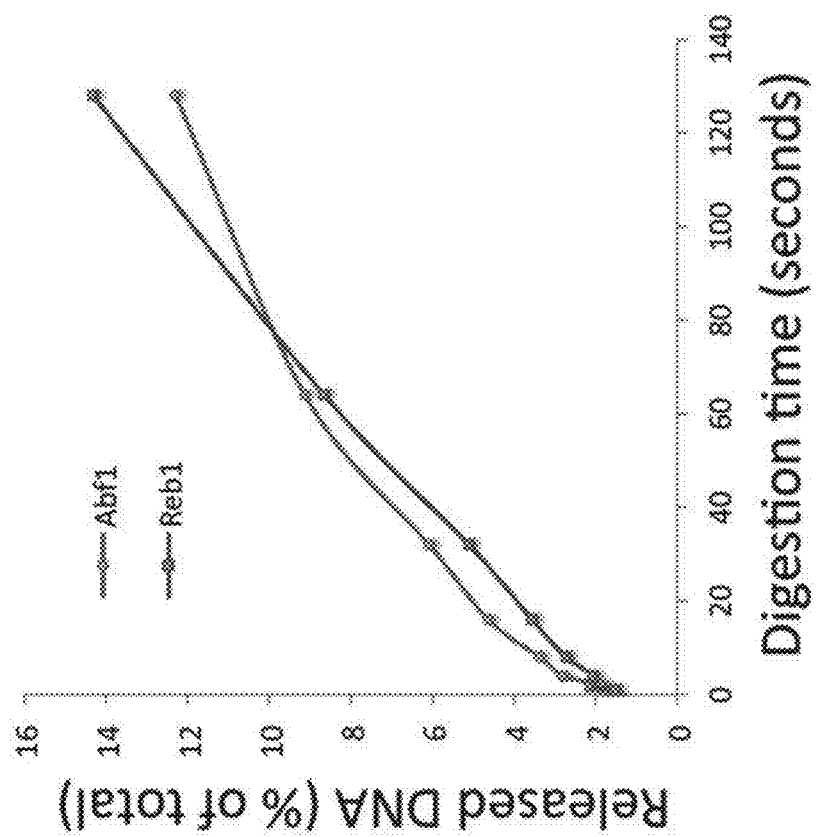
FIGS. 11A and 11B show the kinetics of CUT&RUN DNA release.
Figure 11A:
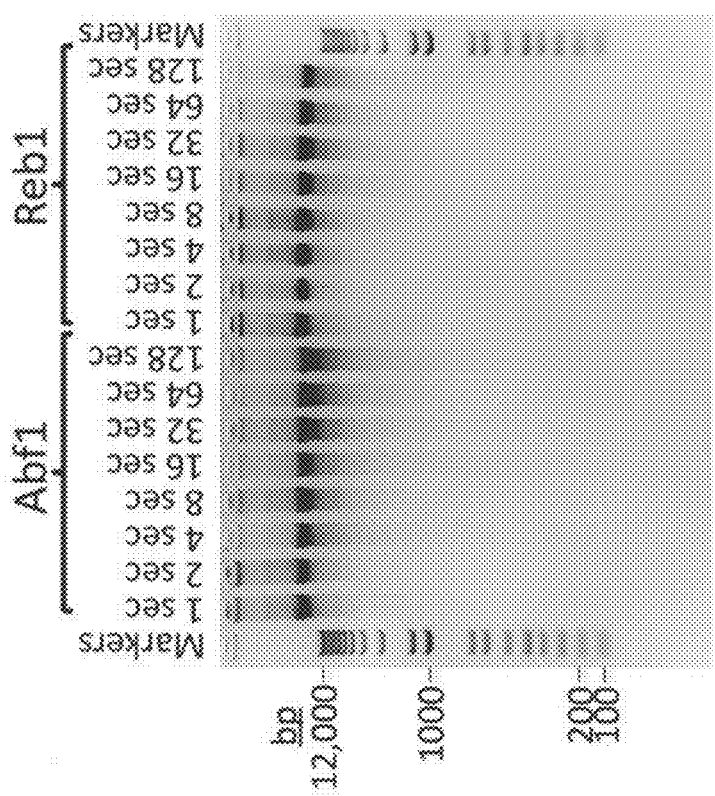
Figure 12A:
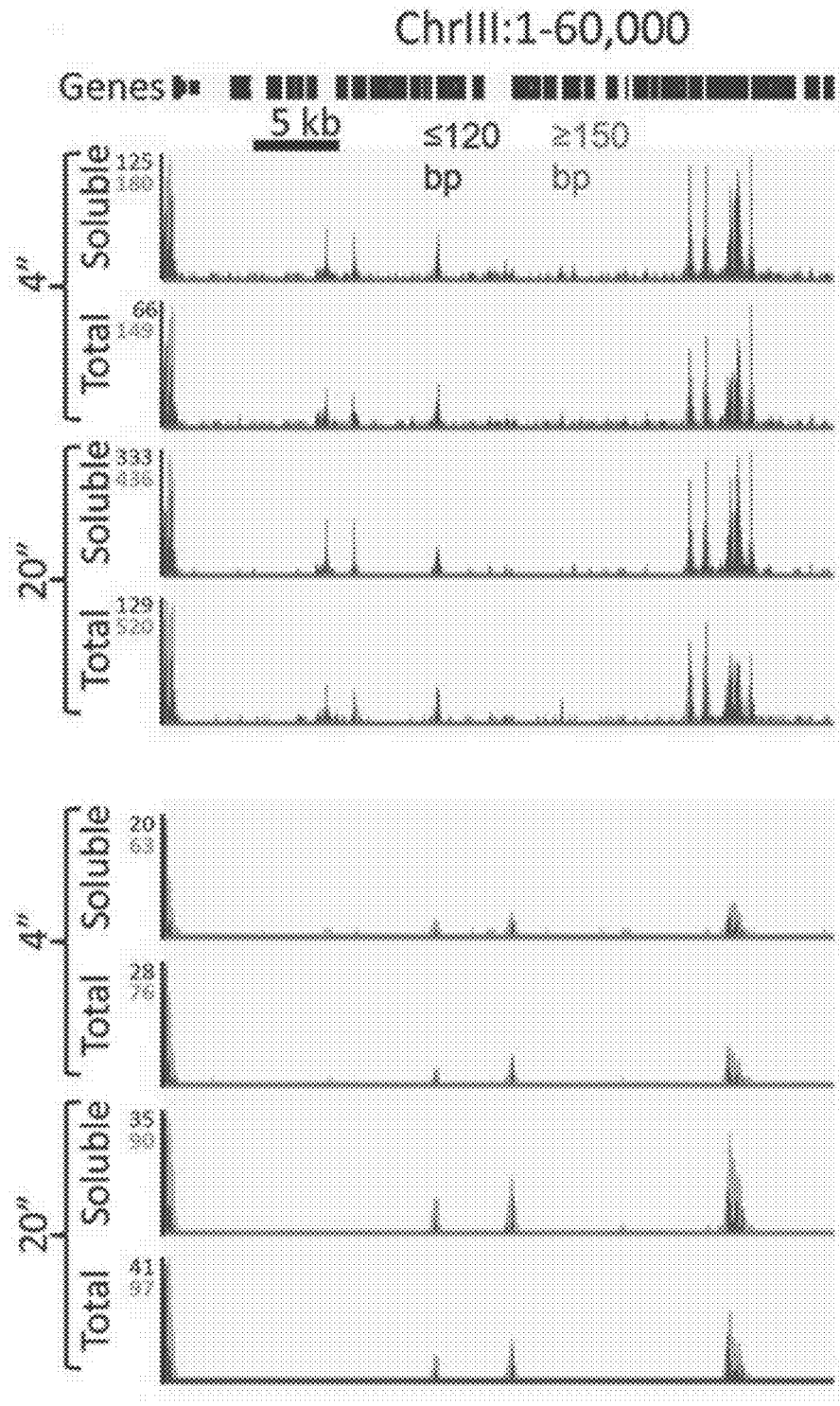
FIGS. 12A-12C show the quantitative recovery of bound TFs in supernatants.
Figure 12B:
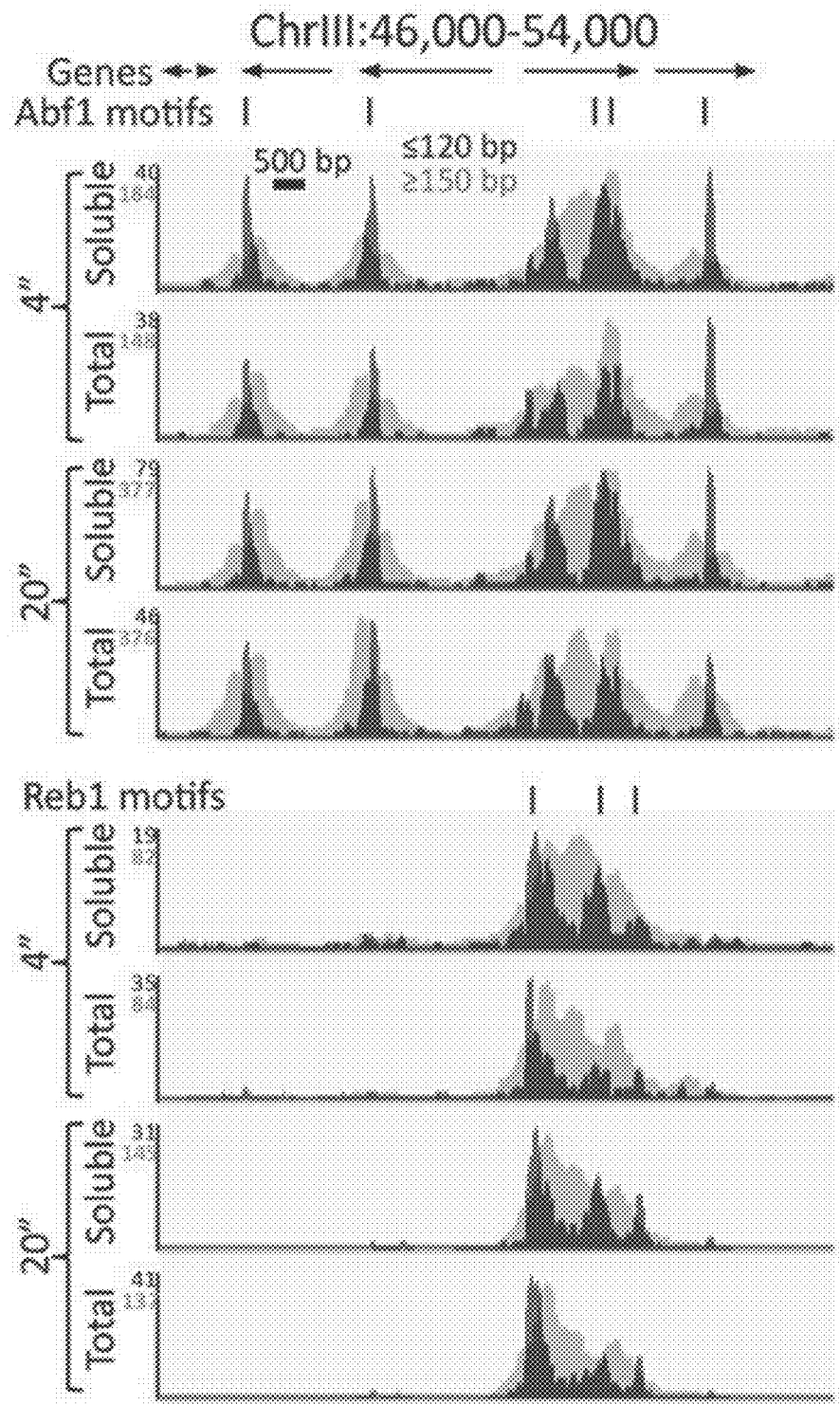
Figure 12C:
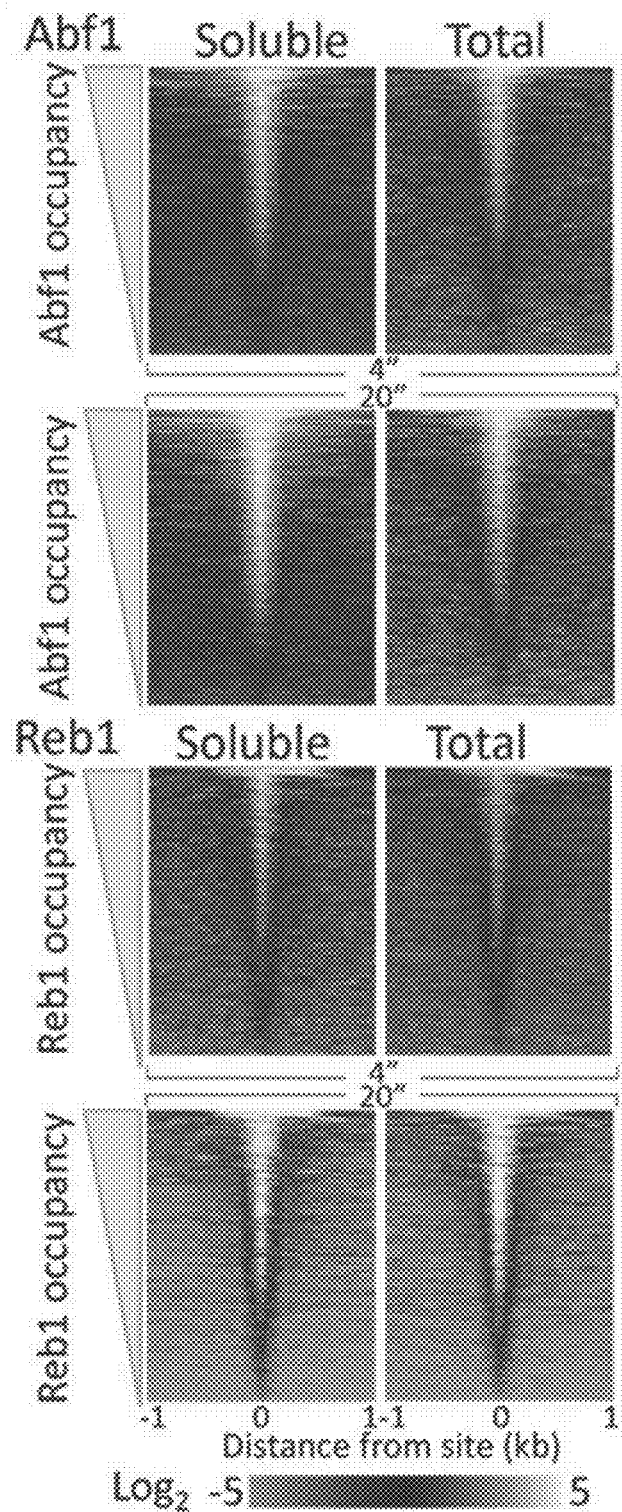

Mapped TF fragment sizes peaked at ~100 bp, in contrast to H2A fragments, which peaked at ~150 bp. It was expected that TF complexes would be smaller than ~100 bp, and nucleosomes would be ~150 bp, therefore less than 120 bp and greater than 150 bp fragments were mapped separately. Time-point profiles show crisp CUT&RUN peaks within the less than 120 bp size class for each TF motif in each region (FIG. 1D and FIG. 10). Except for a slow monotonic increase in peak occupancy when normalized to the spike-in control (FIGS. 11A-11B), no consistent differences between time points were observed within the 1 s to 128 s interval, confirming that gradual release of TF-DNA complexes yields limit digestion reactions. Total DNA extraction and purification of small fragments produced nearly identical results (FIGS. 12A-12C), which demonstrates that extraction of DNA from the supernatant quantitatively recovers TF-bound fragments.

CUT&RUN Robustly Maps Yeast TF Binding Sites In Situ at High Resolution

Figure 13A:
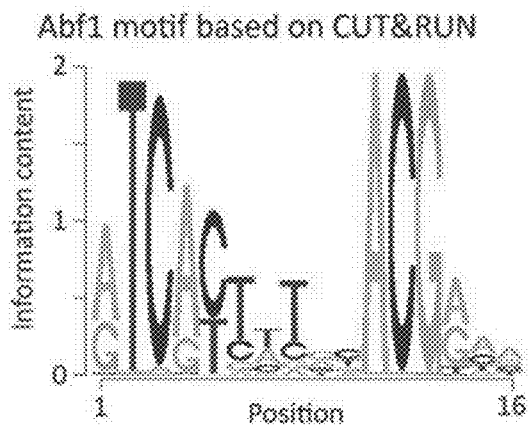
FIGS. 13A-13E show that Abf1 and Reb1 motifs based on CUT&RUN and ORGANIC ChIP-seq are similar. The MEME motif-finding program was applied to FIGS. 13A-B 1"-32" pooled CUT&RUN ≤120 bp data and (FIG. 13C) 600 mM Abf1 and (FIG. 13D) 80 mM Reb1 ORGANIC data, and log-odds sequence logos are shown. Note the close correspondence between motifs determined using CUT&RUN and ORGANIC.
Figure 13B:
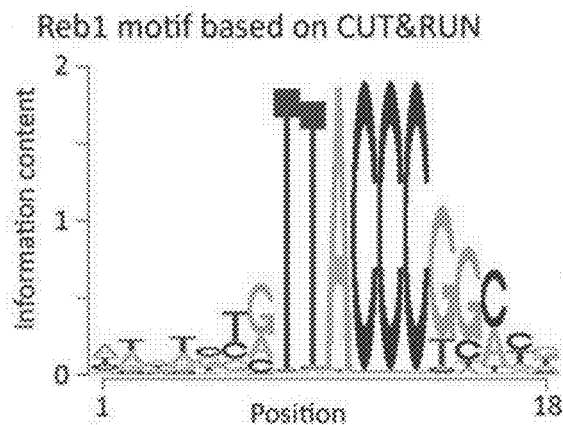
Figure 13C:
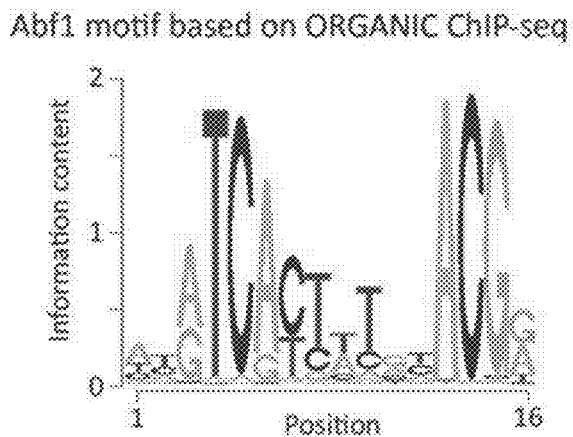
Figure 13D:
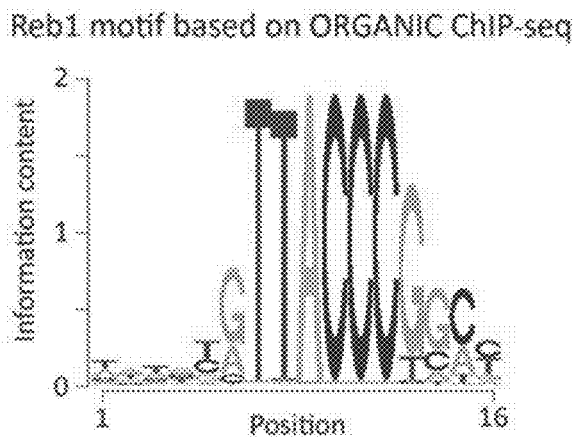
Figure 13E:
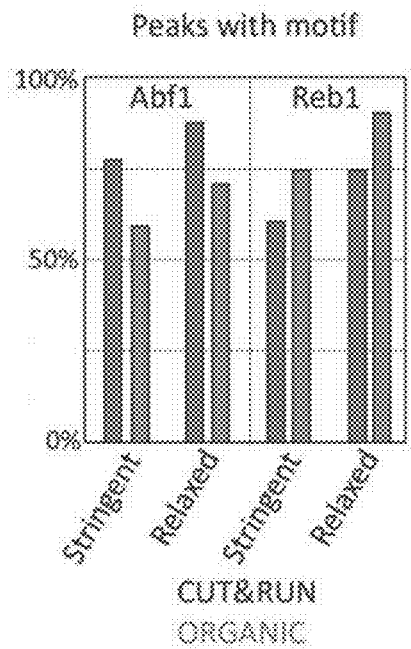

To verify that the less than 120 bp fragments represent cleavages around TF binding sites, all significant Abf1 and Reb1 motifs were identified in the genome and it was found that motifs based on CUT&RUN data and motifs based on ORGANIC data were nearly identical (FIGS. 13A-13D). ORGANIC-derived motifs were used to scan the yeast genome, which provided us with a comprehensive list of 1899 Abf1 and 1413 Reb1 motifs determined completely independently of CUT&RUN. It was confirmed that the majority of peak calls overlapped the motif for each dataset, with somewhat better performance for CUT&RUN than ORGANIC for Abf1 and vice versa for Reb1 (FIG. 13E).

Figure 14:
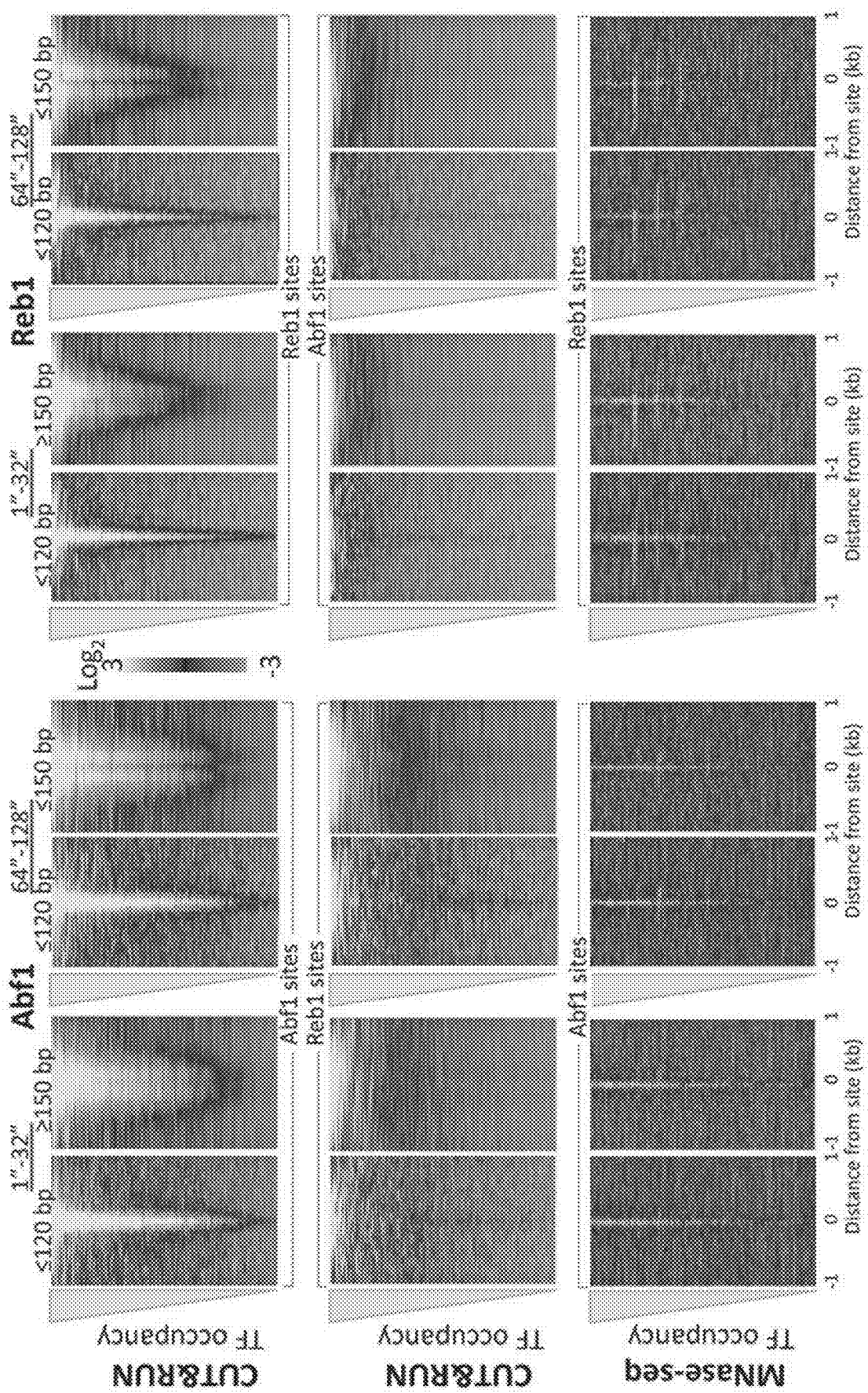
FIG. 14 shows that CUT&RUN reveals cleavage kinetics in situ. A comparison of Abf1 (left) and Reb1 (right) heat maps of CUT&RUN data from a single experiment (20160630), pooling the 1" to 32" and the 64" and 128" time-course samples, and separated into ≤120 bp (left) and ≥150 bp (right) size classes. Alignments to motifs and ordering by TF occupancy was performed as previously described, except that Treeview was used with log scaling and contrast=3. Note that with increased digestion time, more of the TFs are released, deepening the 'hole' of ≥150 bp fragments without any noticeable change in dynamic range. CUT&RUN shows a much higher dynamic range than MNase-seq for particle detection (compare top panels with bottom panels).

The ≤120 bp and ≥150 bp profiles were centered over these motifs and heat maps were constructed. When rank-ordered by occupancy over the 2 kb interval centered over each Abf1 and Reb1 motif, it was observed that >90% of the TF sites were occupied by fragments over the corresponding motif relative to flanking regions (FIGS. 2A-2B and FIG. 14 upper panels), representing likely true positives. CUT&RUN occupancies over Abf1 and Reb1 motifs showed high dynamic range relative to nuclease accessibility (FIG. 14, lower panels), seen in heat maps as higher contrast above background for CUT&RUN. In contrast, Abf1 fragments showed negligible occupancy at non-overlapping Reb1 sites and vice-versa for Reb1 fragments at non-overlapping Abf1 sites (FIGS. 2A-2B and FIG. 14, middle panels). The almost complete correspondence between the presence of a TF motif and occupancy of the TF, and the general absence at sites of a different TF, imply that CUT&RUN is both highly sensitive and specific for TF binding.

To directly compare CUT&RUN to high-resolution ChIP-seq, 'ORGANIC' ChIP-seq data was similarly lined up over Abf1 and Reb1 motifs. As previously reported (Kasinathan et al., 2014), ORGANIC ChIP-seq detected the large majority of Abf1 true positive motifs and nearly all Reb1 motifs throughout the genome (FIGS. 2A-2B, upper middle panels). The best Reb1 data were obtained with 80 mM NaCl extraction, and the best Abf1 data were obtained with 600 mM NaCl, although the dynamic range for Reb1 was always better than that for Abf1 with frequent false positive occupancy (FIGS. 2A-2B, lower middle panels). In contrast, CUT&RUN showed the same dynamic range for both TFs over the same range of digestion time points with ~10 fold fewer paired-end reads, demonstrating that CUT&RUN is more robust than ORGANIC ChIP-seq. Relative to these high-resolution methods (Kasinathan et al., 2014), standard ChIP-seq using crosslinking and sonication showed inferior sensitivity and specificity (FIGS. 2A-2B, right panels). Thus, CUT&RUN provides robust TF occupancy maps with improved sensitivity/specificity trade-offs relative to ChIP-seq.

Figure 3A:
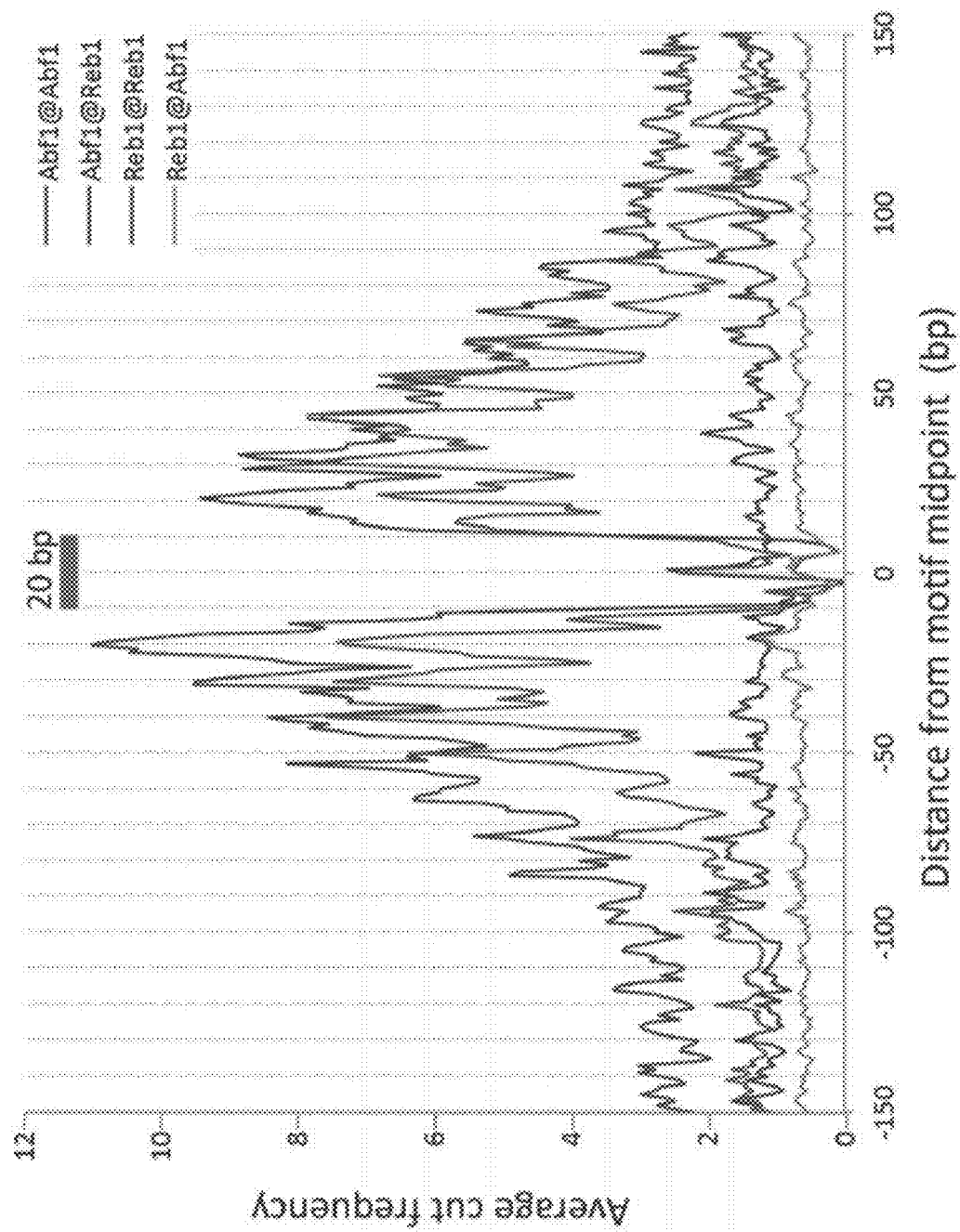
FIGS. 3A-3C show that CUT&RUN maps TF binding sites at high resolution.
Figure 3C:
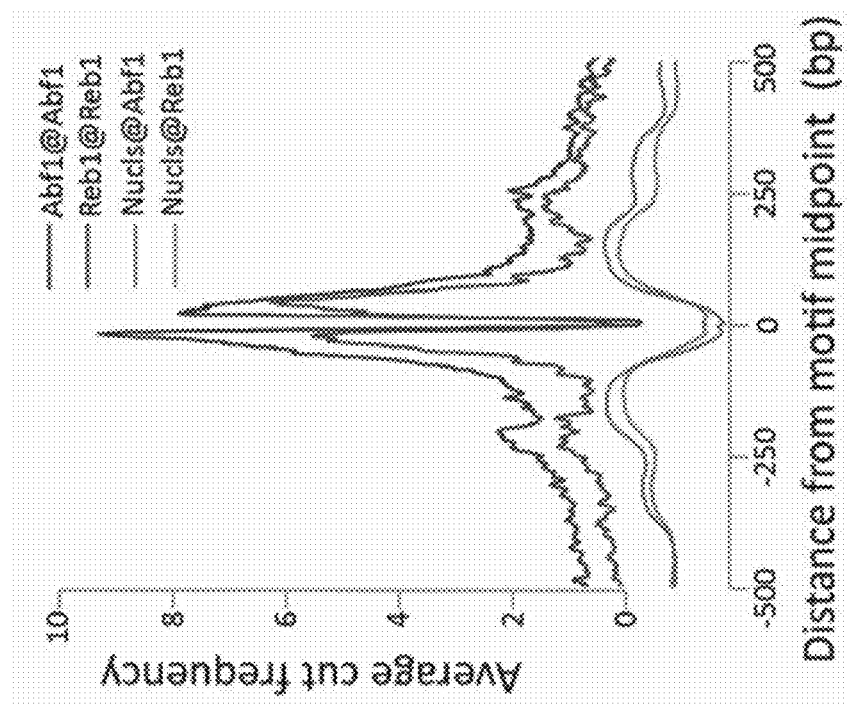
Figure 3B:
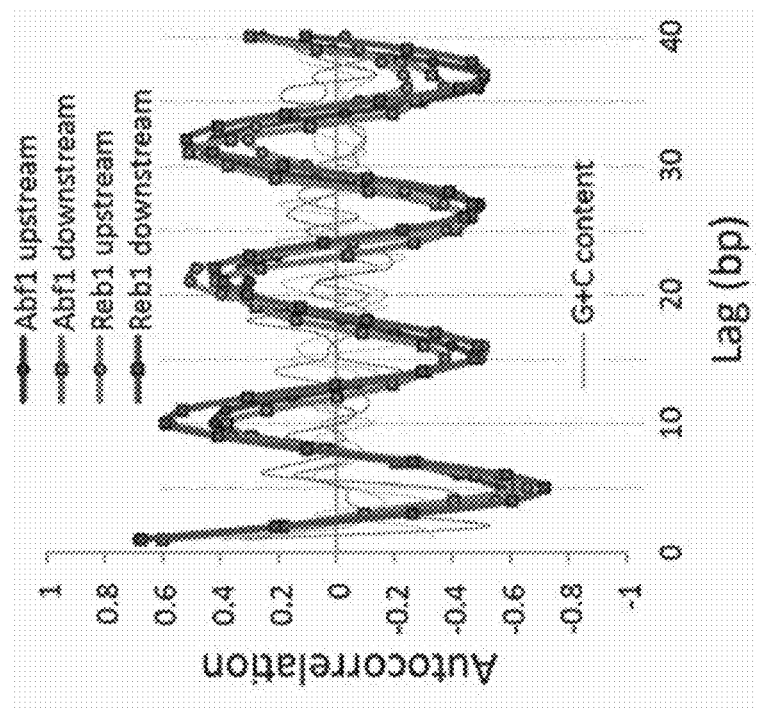

To estimate the resolution of CUT&RUN, the 'footprint' of each TF as the average density of fragment ends was plotted around the motif midpoint. For both Abf1 and Reb1, sharp 20 bp wide footprints were observed, indicating that these transcription factors protect ~20 bp centered over the motif with near base-pair resolution (FIG. 3A). Interestingly, upstream and downstream 'slopes' in the cleavage maps show a saw tooth pattern on either side of both Abf1 and Reb1 motifs, with distances between 'teeth' ~10 bp apart over >100 bp, and confirmed by autocorrelation analysis to be independent of base composition (FIG. 3B). Such 10 bp periodic cleavage preferences match the 10 bp/turn periodicity of B-form DNA, which suggests that the DNA on either side of these bound TFs is spatially oriented such that tethered MNase has preferential access to one face of the DNA double helix. Tethering of MNase to a TF constrains it to cleave nearby DNA even on the surface of a nucleosome, suggesting flexibility of the chromatin fiber (FIG. 3C). Thus, the very rapid kinetics observed at 0° C. are due to immobilized MNase poised for cleavage near the tethering site.

CUT&RUN Precisely Maps Chromatin-Associated Complexes

Figure 4A:
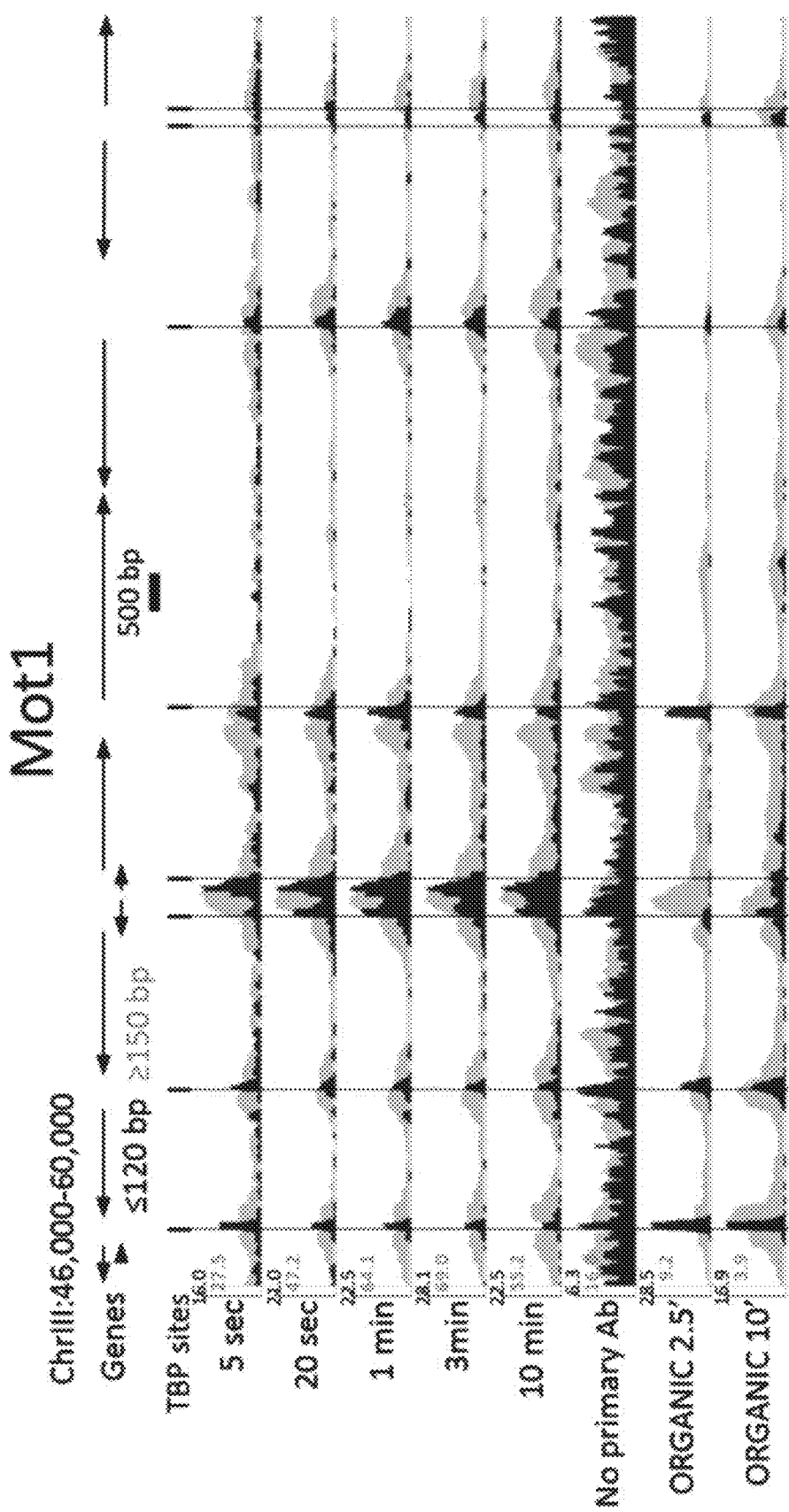
Figures 1, 2, 4B:
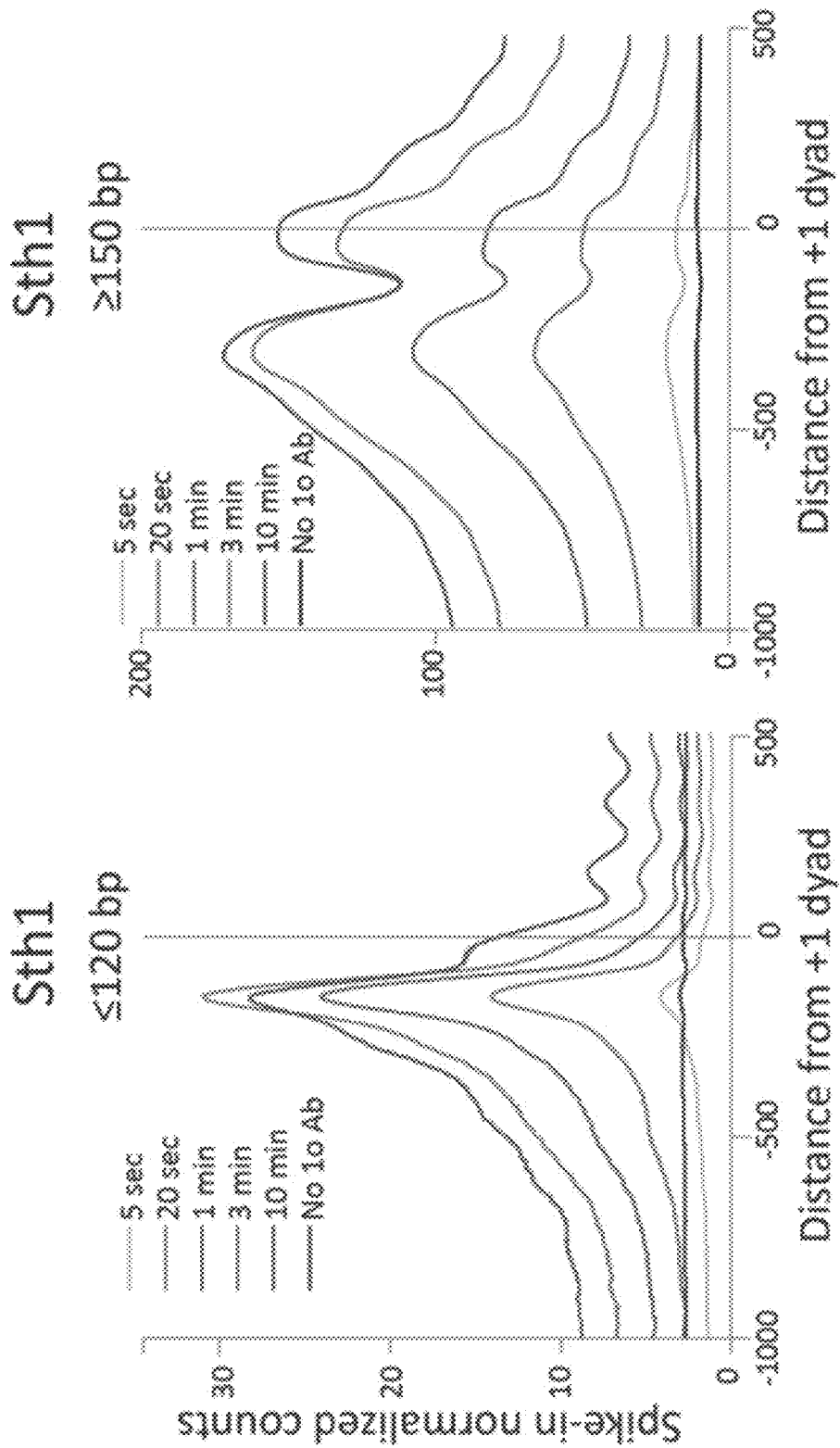
Figure 4C:
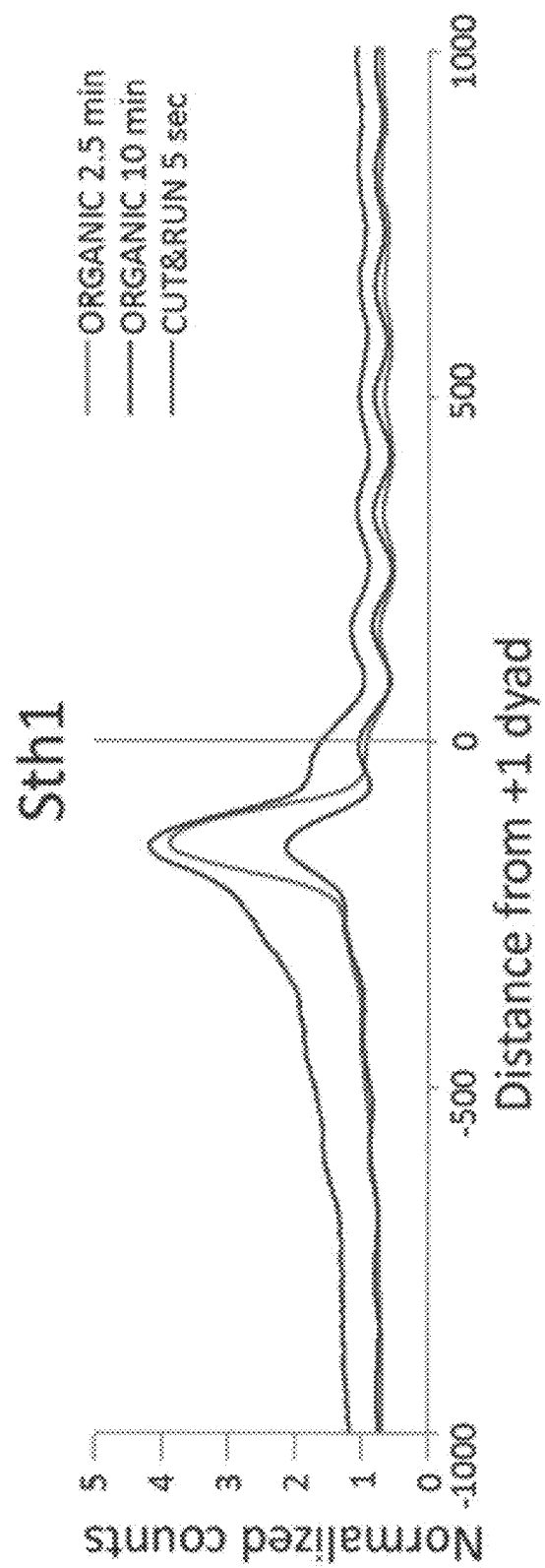
Figure 15A:
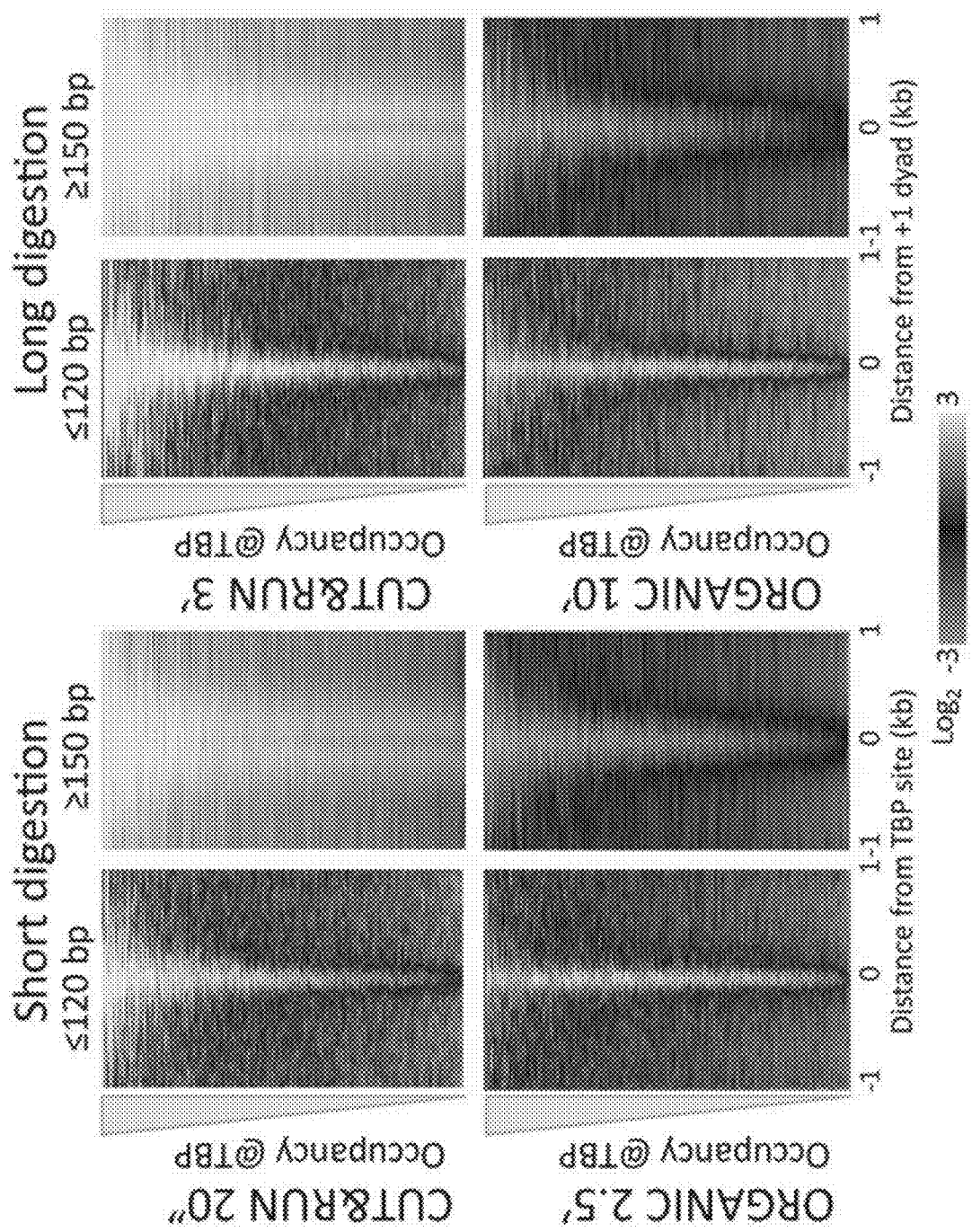
FIGS. 15A-15B show CUT&RUN and ORGANIC profiles for Mot1.
Figure 15B:
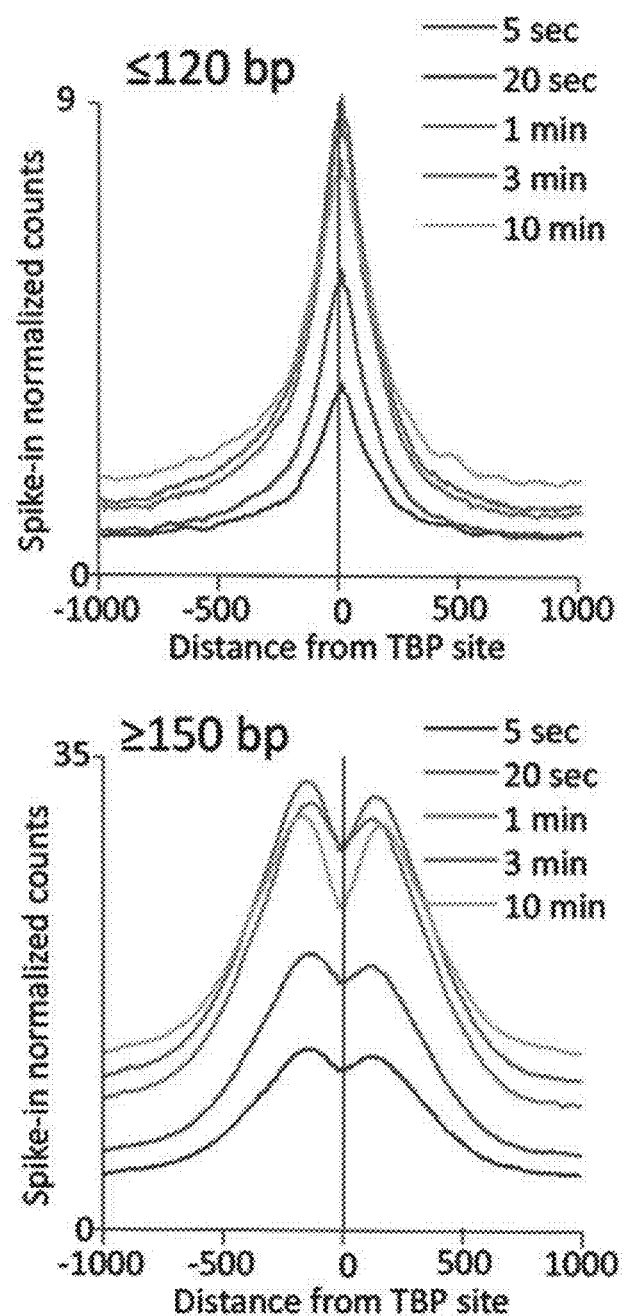
Figures 16A, 16B:
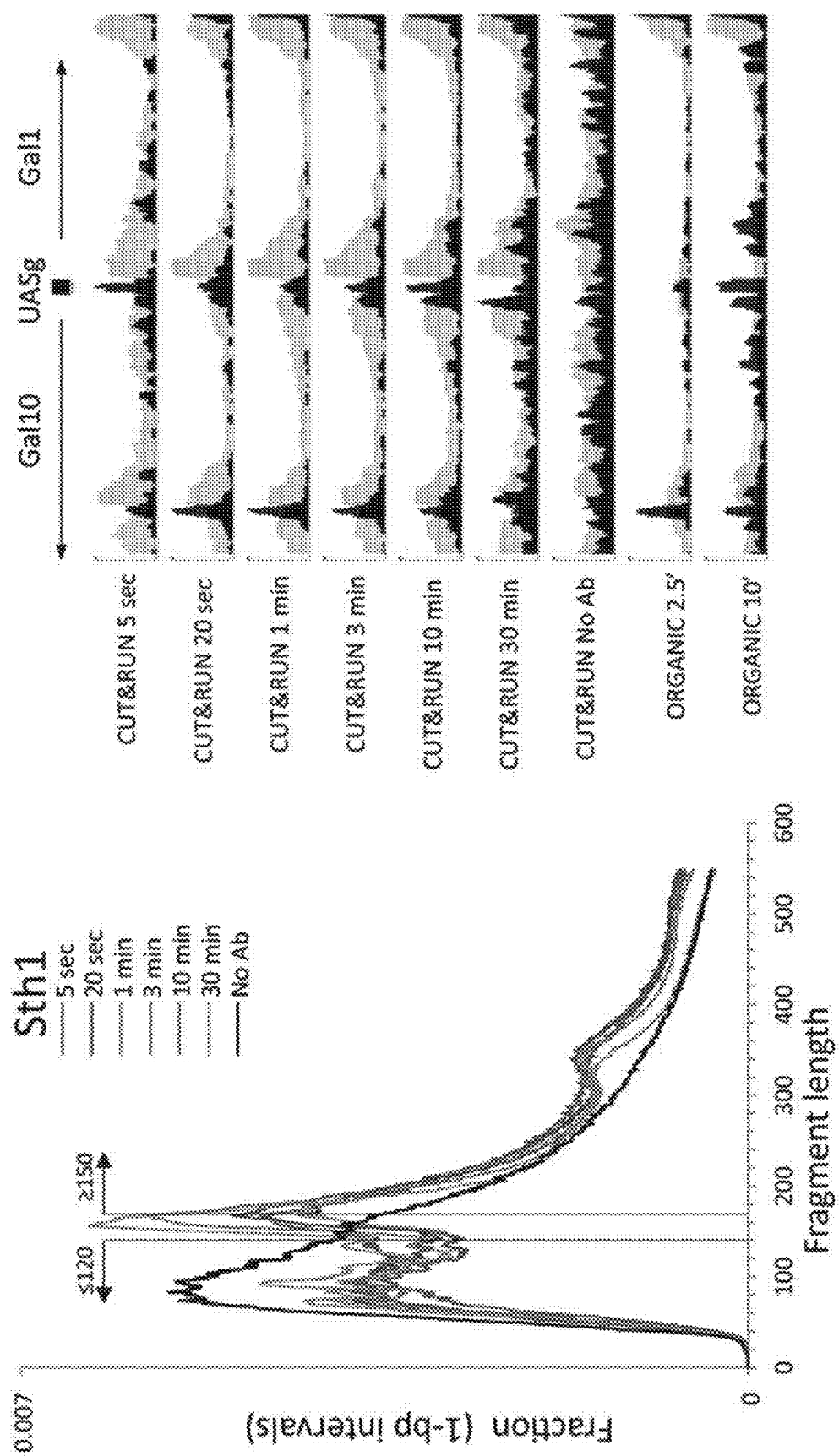
FIGS. 16A-16B show CUT&RUN and ORGANIC profiles for Sth1.

High-resolution mapping of mobile components of the chromatin landscape can be challenging for ChIP-based methods. For example, the ~1 megadalton 17-subunit RSC nucleosome remodeling complex dynamically slides a nucleosome that it transiently engulfs (Lorch et al., 2010, Ramachandran et al., 2015), and the Mot1 DNA translocase dynamically removes TATA-binding protein (TBP) from sites of high-affinity binding (Zentner and Henikoff, 2013; Auble et al., 1997). Although X-ChIP crosslinks nucleosome remodeling complexes to their nearest nucleosomes, native ChIP successfully captures yeast chromatin remodelers at their sites of action, both in nucleosome-depleted regions (NDRs) and on nucleosomes (Zentner et al., 2013). For CUT&RUN to profile such large chromatin-associated complexes it was found optimal to extract total DNA rather than chromatin solubilized by CUT&RUN in situ, which may be too large to diffuse through nuclear pores. Therefore, all DNA was extracted and large DNA fragments were preferentially removed with AMPure beads. When this modified protocol was applied to Mot1 over a >2 order-of-magnitude digestion range, it was observed that the chromatin profiles that were very similar to those obtained using ORGANIC profiling, but with only ~15% the number of paired-end reads (FIG. 4A). Mot1 peaks on the upstream side of TBP binding sites are seen for both CUT&RUN and ORGANIC profiles, confirming that Mot1 approaches TBP from the upstream side in vivo (Zentner and Henikoff, 2013) as it does in vitro (Wollmann et al., 2011). Heat map and average plot analyses show that the ≤120 bp fragments track closely with TBP sites, whereas the ≥150 bp fragments are diffusely distributed in the local vicinity, perhaps representing Mot1 translocation dynamics (FIGS. 15A-15B). CUT&RUN was also applied to Sth1, the catalytic component of the RSC complex. RSC acts to slide nucleosomes at NDRs. and yeast genes were aligned at the inferred dyad axis of the +1 nucleosome just downstream of the transcriptional start site (Ramachandran et al., 2015). Uniform digestion was observed over a 5 s to 30 min time course (FIG. 16A) and confirmation of the abundance of RSC directly over the GAL4 UAS (FIG. 16B) (Floer et al., 2010). Sth1 peaks are most abundant in the NDRs, where CUT&RUN profiles show a gradual increase in yield with digestion times between 5 s and 10 min (FIG. 4B-1, 4B-2), indicating that quantitative limit digestions are obtained using the CUT&RUN protocol. A nearly flat line was observed for a negative control derived from 3×FLAG-Sth1 nuclei treated in parallel for the maximum digestion time, but where the primary anti-FLAG antibody was omitted. The results for Sth1 CUT&RUN are similar to results for Sth1 ORGANIC profiling (Ramachandran et al., 2015), but with much higher yield (FIG. 4C). It was concluded that CUT&RUN provides efficient high-resolution mapping of chromatin-associated complexes, even those that are very large and dynamic.

CUT&RUN Resolves Rare Insoluble DNA-Binding Protein Complexes

Figures 2, 5C:
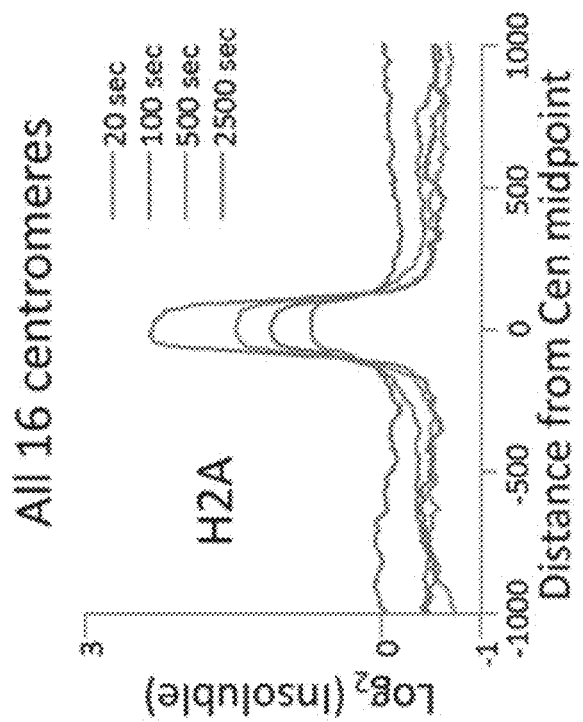
Figures 1, 5C:
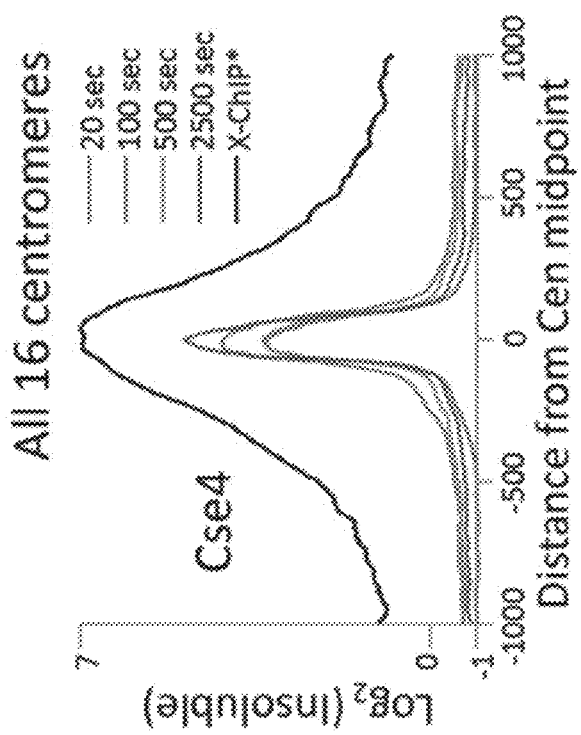
Figures 2, 5D:
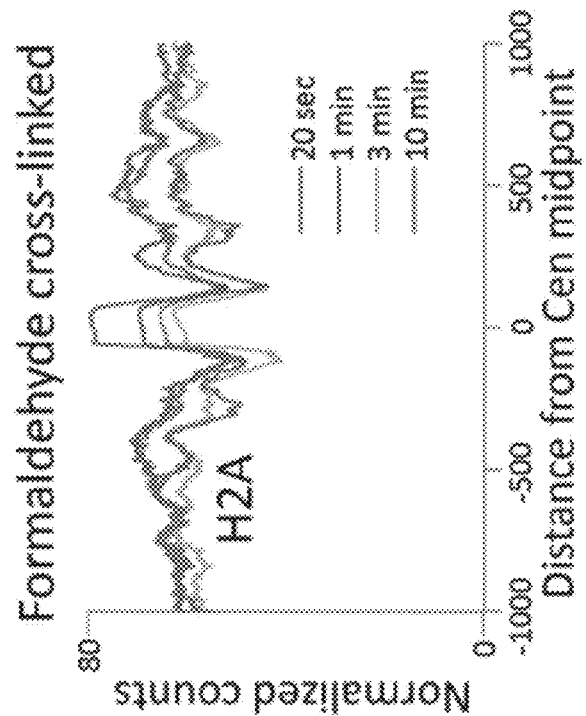
Figures 1, 5D:
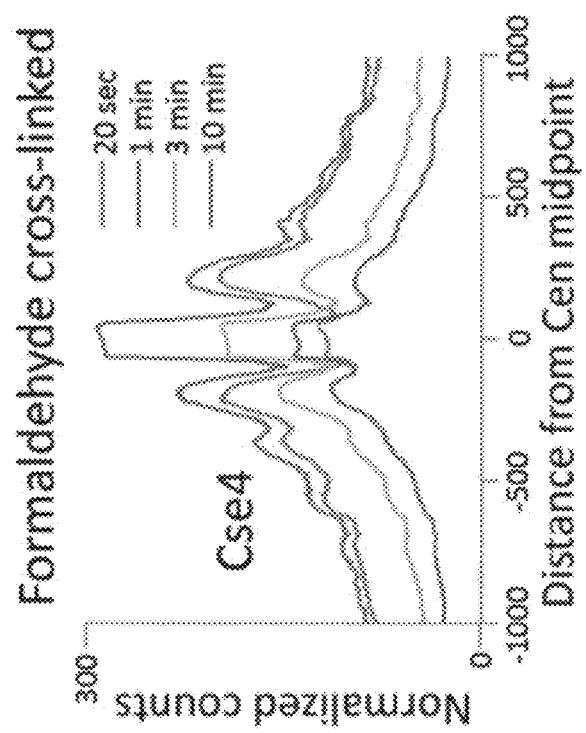

Abf1 and Reb1 are relatively abundant TFs, but many DNA-binding proteins of interest are rare, and so can be challenging to profile by ChIP. In budding yeast, there is only one centromeric nucleosome per chromosome, which is only ~1% the molar abundance of Abf1 or Reb1. An additional challenge to studying the centromeric nucleosome, which contains the CenH3 (Cse4) histone variant in place of H3, is that it is part of the multi-megadalton kinetochore complex throughout the cell cycle (Akiyoshi et al., 2010), which renders it highly insoluble (Krassovsky et al., 2012). To profile the Cse4 nucleosome by CUT&RUN, the samples were split after digestion, extracting just the supernatant from one aliquot, and total DNA from the other. In this way the recovery of the soluble and the insoluble kinetochore complex could be compared. In parallel, histone H2A was similarly profiled. By taking the difference between total and soluble chromatin, one can infer the occupancy of each histone in the insoluble pellet. As expected for the insoluble kinetochore, the highest Cse4 occupancy on the chromosome is seen at the centromere (FIG. 5A). Strikingly, occupancy of insoluble H2A, which is present in every nucleosome throughout the genome, is also maximum at the centromere. Indeed, at all 16 yeast centromeres we observe very similar enrichments of Cse4 and H2A con-fined to the ~120 bp functional centromere over the digestion timecourse, with resolution that is 4-fold better than that of standard X-ChIP (FIG. 5B). We also extracted total DNA from the bead-bound chromatin derived from cells that had been formaldehyde crosslinked prior to applying CUT&RUN, with similar results (FIG. 5C-1, 5C-2). Interestingly, crosslinking results in a more distinct profile and the appearance of phased nucleosomes on either side, which are interpreted as a reduction in chromatin flexibility with crosslinking, while demonstrating that the basic strategy can be applied to crosslinked cells.

Figures 17A, 17B, 17C:
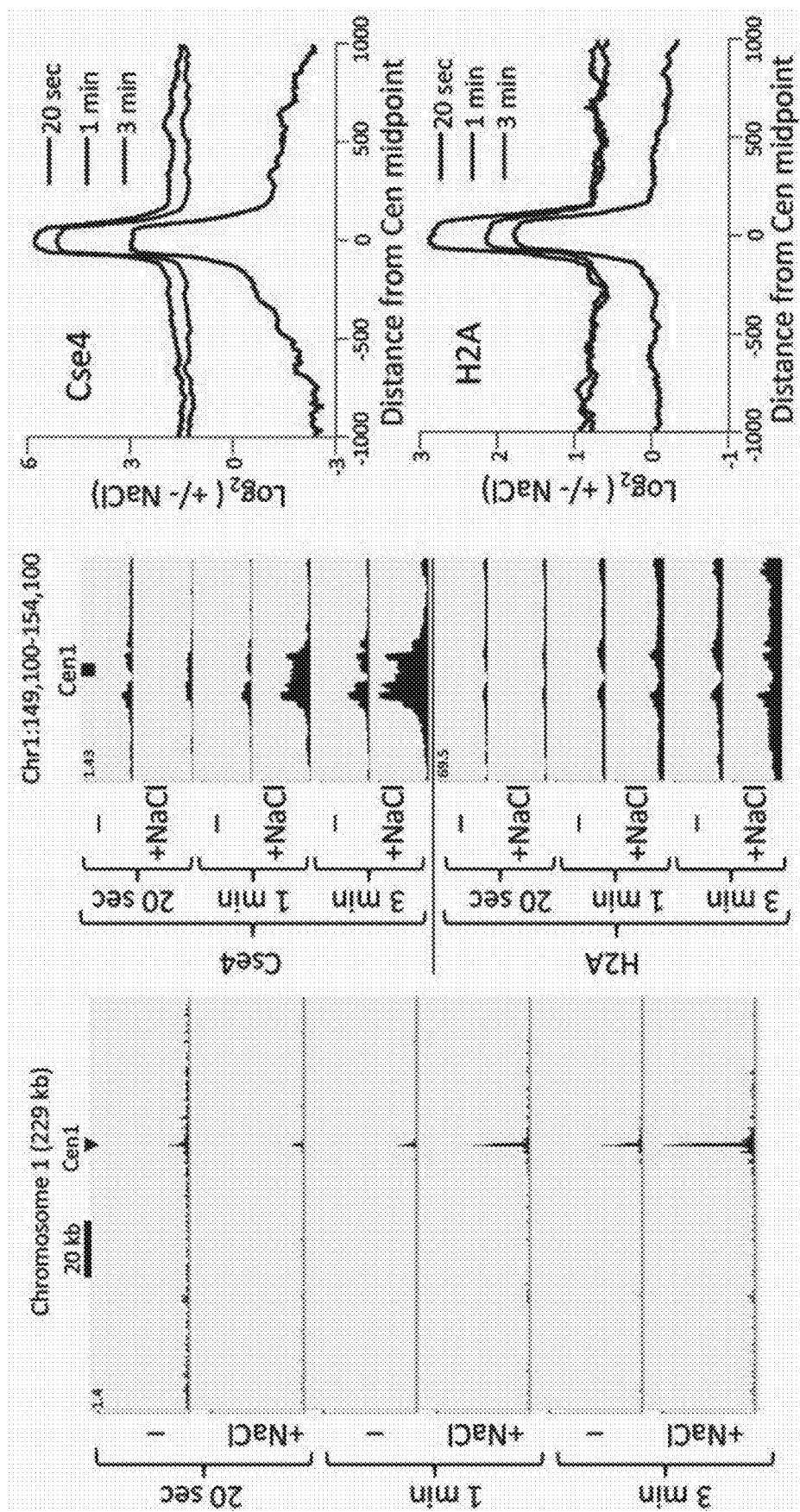
FIGS. 17A-17C show that CUT&RUN maps the rare highly insoluble S. cerevisiae kinetochore complex.

To confirm that the differences observed between the CUT&RUN supernatant and total DNA were due to differential solubility of kinetochore chromatin, the samples were split before digestion, and for one aliquot the cleavage reaction was stopped with 2 M NaCl and the supernatant recovered for sequencing. Similar results were obtained for the high-salt fraction as for total DNA (FIGS. 17A-17C). The unequivocal presence of insoluble H2A in the centromeric nucleosome directly addresses the continuing controversy over its composition (Wisniewski et al., 2014; Henikoff et al., 2014; Aravamudhan et al., 2013; Shivaraju et al., 2012). Moreover, as the yeast centromeric nucleosome wraps DNA that is >90% A+T (Krassovsky et al., 2012), the intactness of the centromeric particle over a >100 fold digestion time-course (FIGS. 5A to 5D-2) demonstrates that CUT&RUN is not biased by the inherent preference of MNase for AT-rich DNA (Chung et al., 2010; McGhee and Felsenfeld, 1983). It was concluded that CUT&RUN can map large DNA-binding complexes, even those that are rare, insoluble and AT-rich.

CUT&RUN Probes Nearby Chromatin

Examination of the ≥150 bp profiles (FIG. 1D and FIGS. 4A-4C) reveals broad peaks around the binding sites, sometimes with 'notches' corresponding to the sites themselves that deepen with time of digestion. This pattern was interpreted as representing the gradual release of fragments with one end resulting from cleavage around the TF-DNA complex and a second cleavage that is close enough to the TF-bound site to produce a soluble fragment. Heat map analysis of the ≥150 bp fragments also showed occupancy of Abf1 and Reb1 fragments over their respective binding motifs, extending ~0.5 kb on either side (FIGS. 2A-1 to 2B-3). Such extended local cleavage is reminiscent of the >1 kb reach of DamID (van Steensel et al., 2001), which suggests that the flexibility of the tether results in probing of nearby chromatin.

CUT&RUN Maps Human Transcription Factor Binding Sites at High Resolution

Figure 6A:
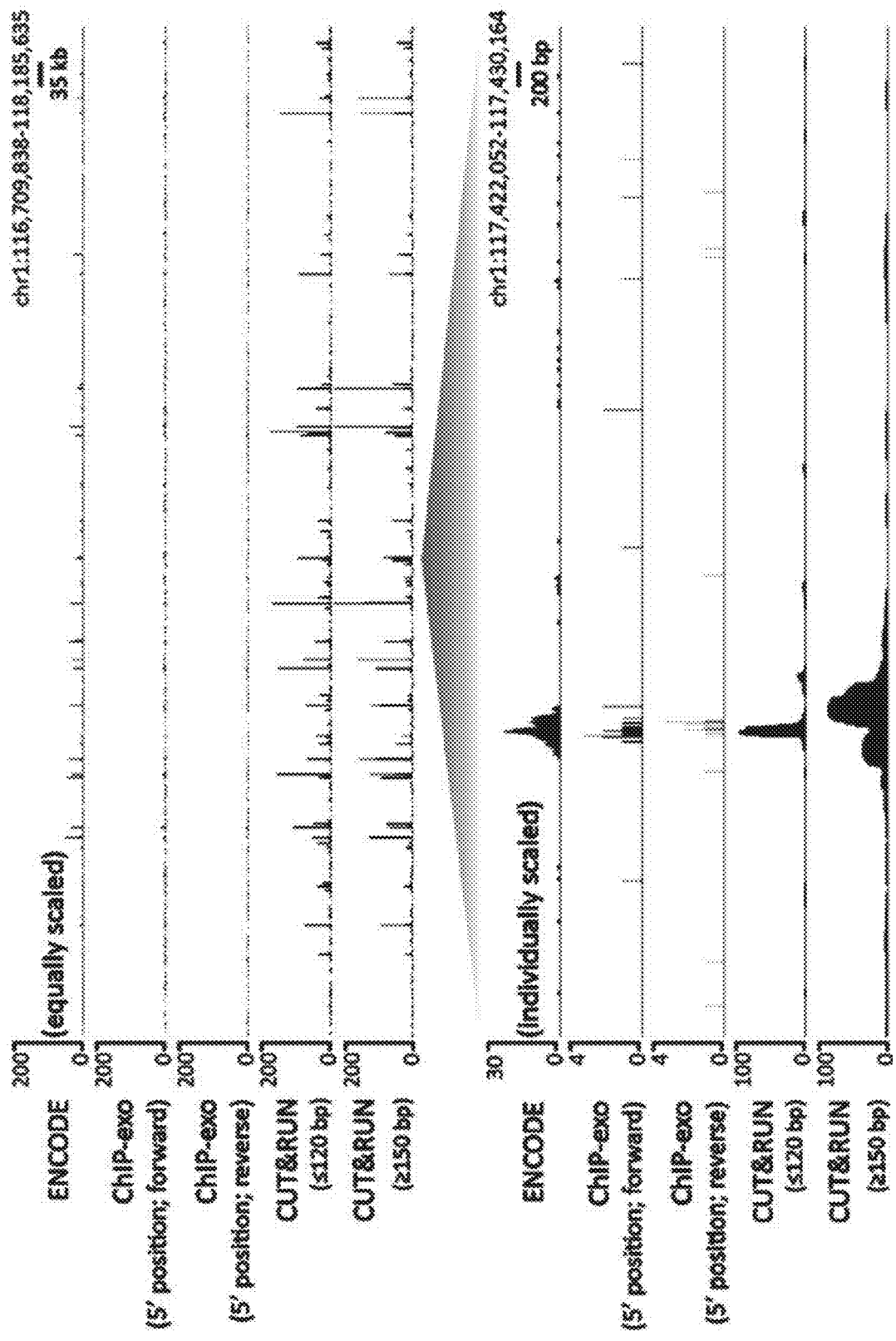
FIGS. 6A-6C show that CUT&RUN maps high-resolution footprints of CTCF.
Figure 6B:
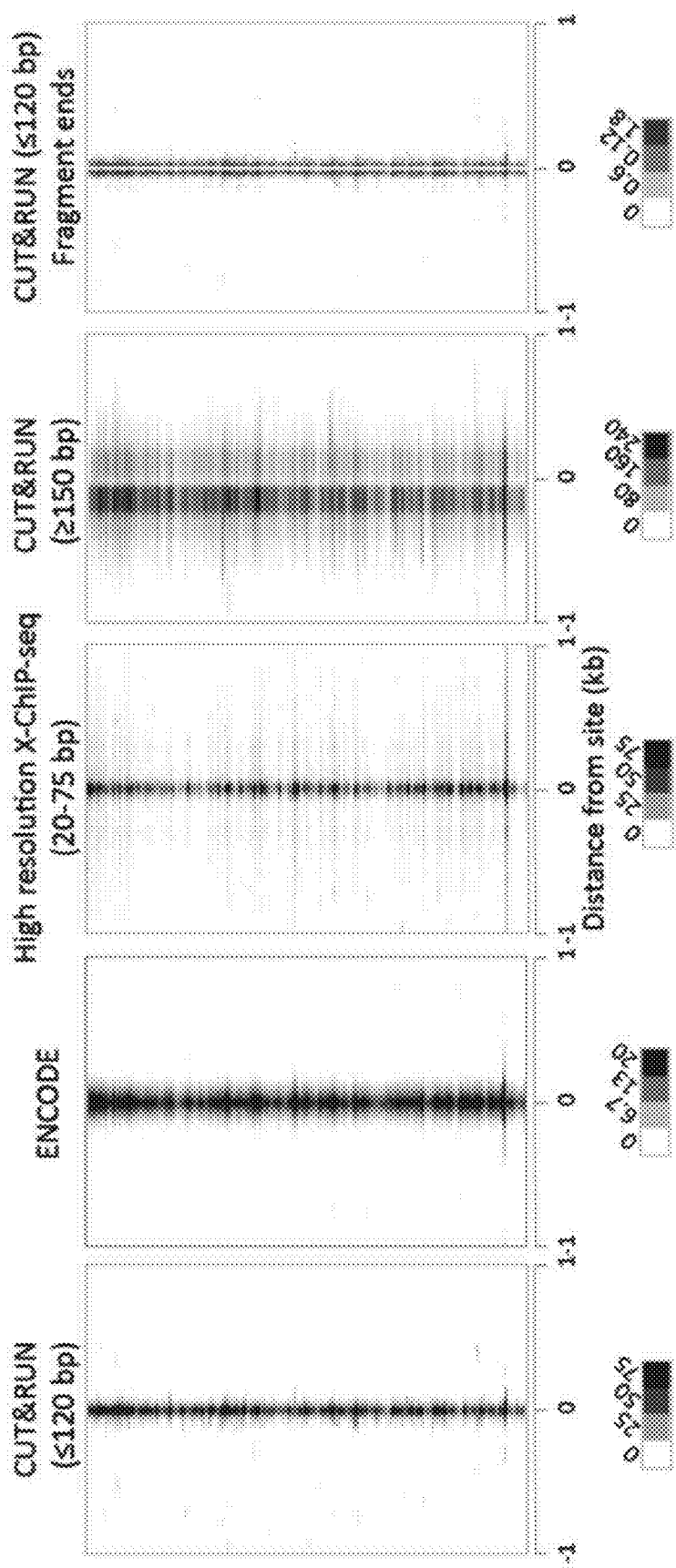
Figure 6C:
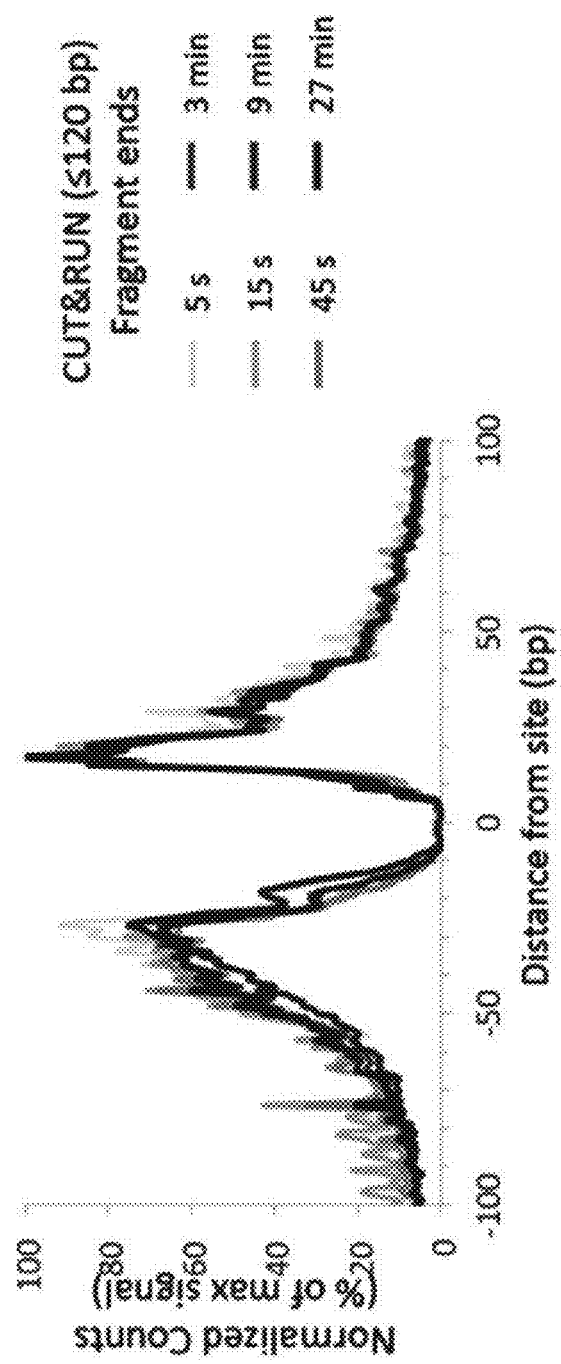
Figure 18:
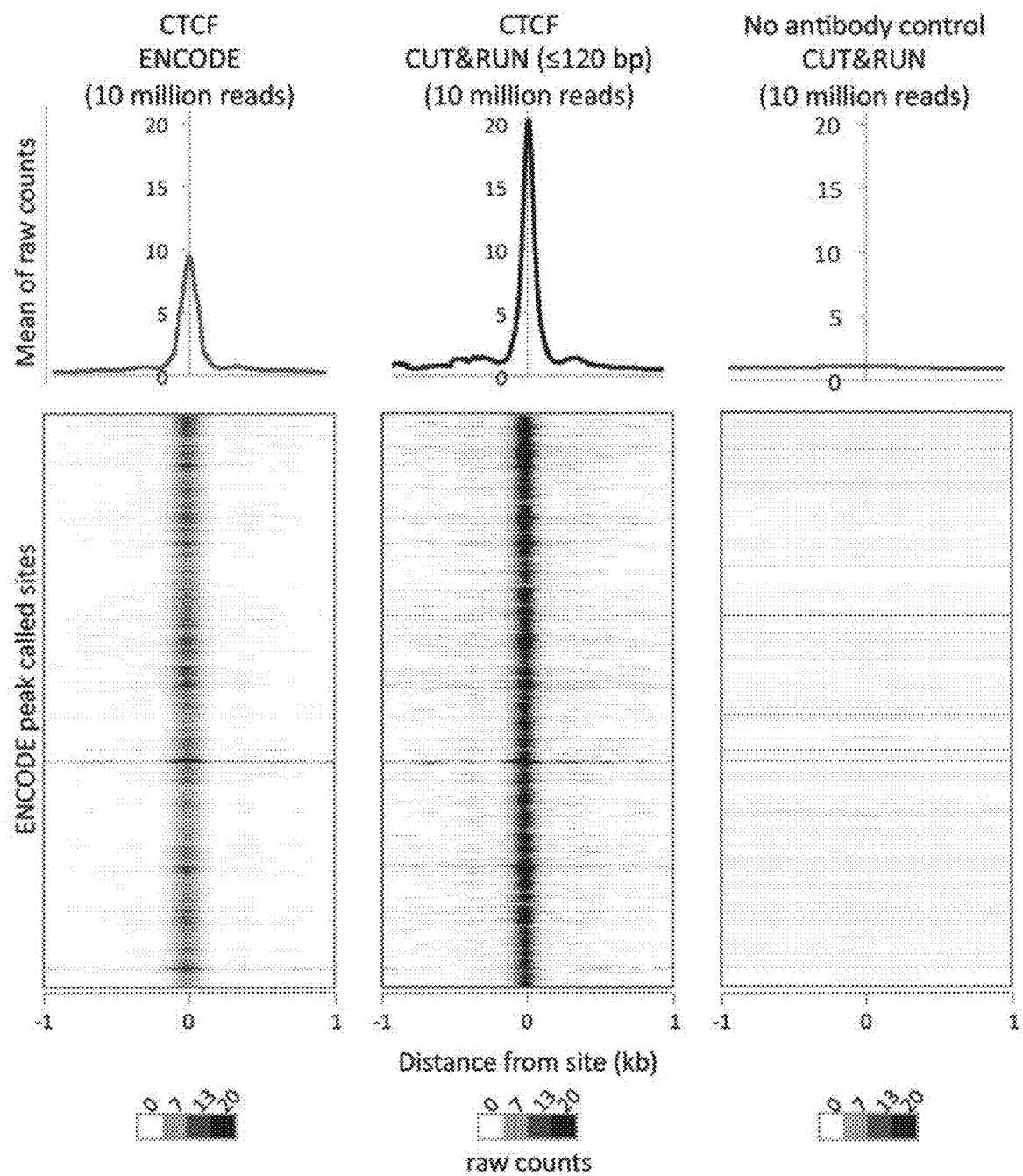
FIG. 18 shows that CUT&RUN recapitulates X-ChIP-seq but with higher dynamic range. For a direct comparison of genome wide dynamic range at previously identified CTCF binding sites, 10 million reads were randomly selected from ENCODE CTCF X-ChIP-seq (GSM749690) and CUT&RUN datasets and plotted at ENCODE peak called sites (GSM749690_narrowPeak). The upper plot shows the mean average of raw counts over these sites and heat maps below are ordered by genomic location.
Figure 19A:
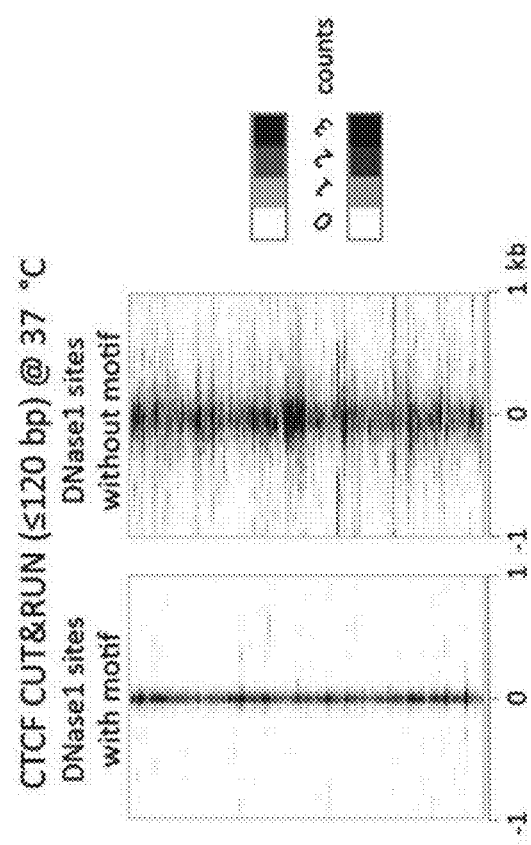
FIGS. 19A-19D show that CUT&RUN has low background when performed on ice. During protocol optimization, the cleavage reactions were performed over a range of temperatures.
Figure 19B:
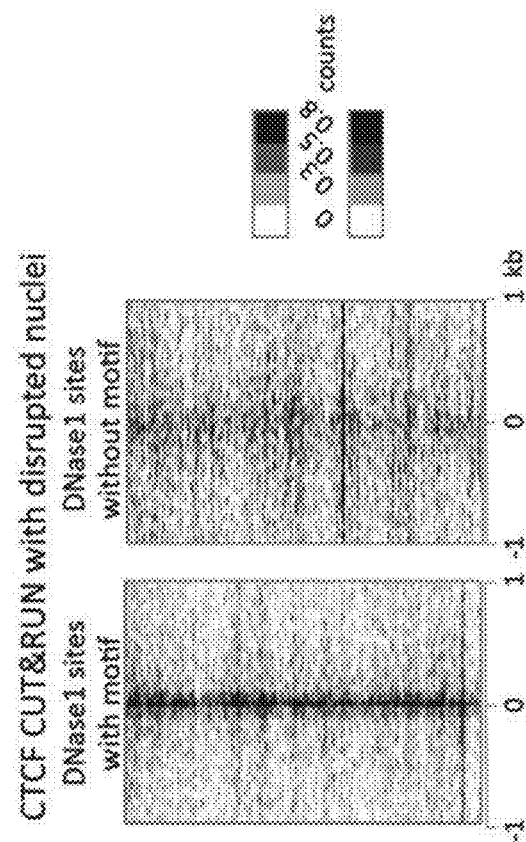
Figure 19C:
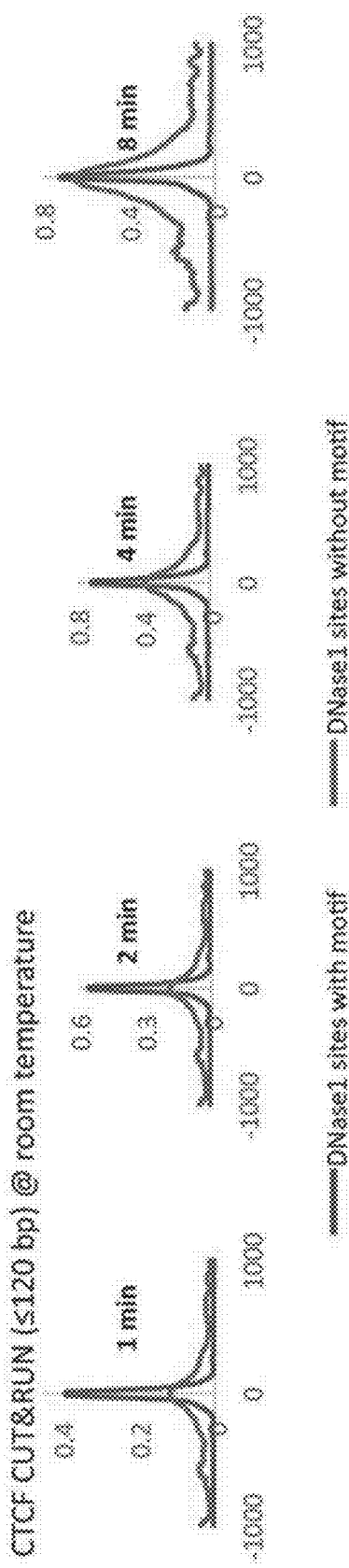
Figure 19D:
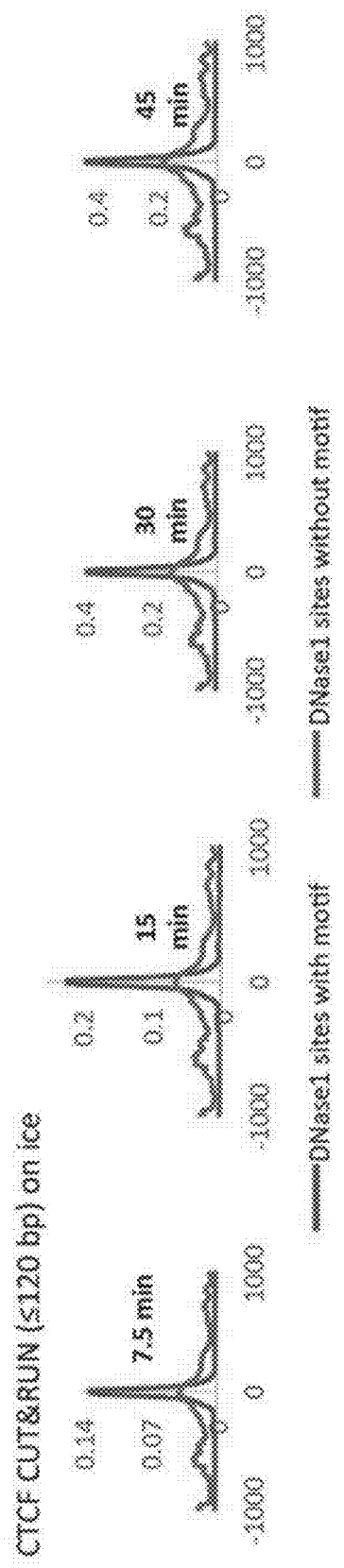

Having established proof-of-principle in a simple well-studied genome, CUT&RUN was applied to CCCTC-binding factor (CTCF) in human K562 cells. To directly compare the efficiency of various methods, 10 million reads were randomly selected for each technique and the raw scores plotted as an indication of information content per sequenced read. As was the case for yeast TFs, CTCF CUT&RUN showed higher dynamic range than other profiling methods, including standard X-ChIP-seq and ChIP-exo (FIG. 6A). When aligned to CTCF motifs found within DNaseI hypersensitive sites or previously identified binding sites, CUT&RUN and X-ChIP-seq CTCF heat maps showed strong concordance, with CUT&RUN having a higher dynamic range (FIG. 6B). A no antibody control showed undetectable background (FIG. 18) when CUT&RUN is performed at low temperature (FIGS. 19A-19D). As was the case for budding yeast TFs, the release of the neighboring fragments was observed, which correspond to phased nucleosomes immediately adjacent to CTCF sites. By plotting just the end positions of the short CUT&RUN fragments that are the cleavage positions of the tethered MNase, pronounced 'tram-tracks' were observed separated by 44 bp at defined positions relative to the CTCF motif. Furthermore, the exact cleavage pattern is consistent over a ~300 fold time-course digestion range, with a predominant single base-pair cut site on either side of the CTCF-bound site, highlighting the limit digest obtained (FIG. 6C). This pattern indicates that the cleavage positions are precise and highly homogeneous within the population of cells. The results suggest that CUT&RUN accurately maps both the TFs and their flanking chromatin in the same experiment. CTCF has 11 zinc fingers and therefore may represent an unusually stable protein-DNA interaction. CUT&RUN was therefore tested using Myc and Max which are basic-loop-helix proteins that bind to a short E-box motif and have b residence times (Phair et al., 2004). CUT&RUN successfully mapped both Myc and Max at high resolution (FIG. 20A). In the case of Max, a quantitative comparison with ENCODE ChIP-seq data is possible as the same antibody was used, and here CUT&RUN had a much higher dynamic range and therefore was able to robustly identify a much larger number of Max binding sites (FIG. 20B). To bind DNA at E-boxes, Myc forms a heterodimer with Max (Blackwood et al., 1991) but in addition Max has other binding partners (Ayer and Eisenman, 1993), As expected, a very high overlap was seen with Max present at almost all Myc binding sites. In contrast, there is poor overlap between previously identified binding sites by ENCODE X-ChIP-seq for Myc and Max, as 10-fold fewer Max sites were identified. However, when the Max ENCODE X-ChIP-seq data was lined up over Max CUT&RUN sites, \high occupancy (FIG. 20C) was seen, suggesting that the lower dynamic range of X-ChIP-seq relative to CUT&RUN was responsible for the failure to identify these Max binding sites by X-ChIP-seq.

CUT&RUN Maps Histone Modifications in Compacted Chromatin

Figure 21:
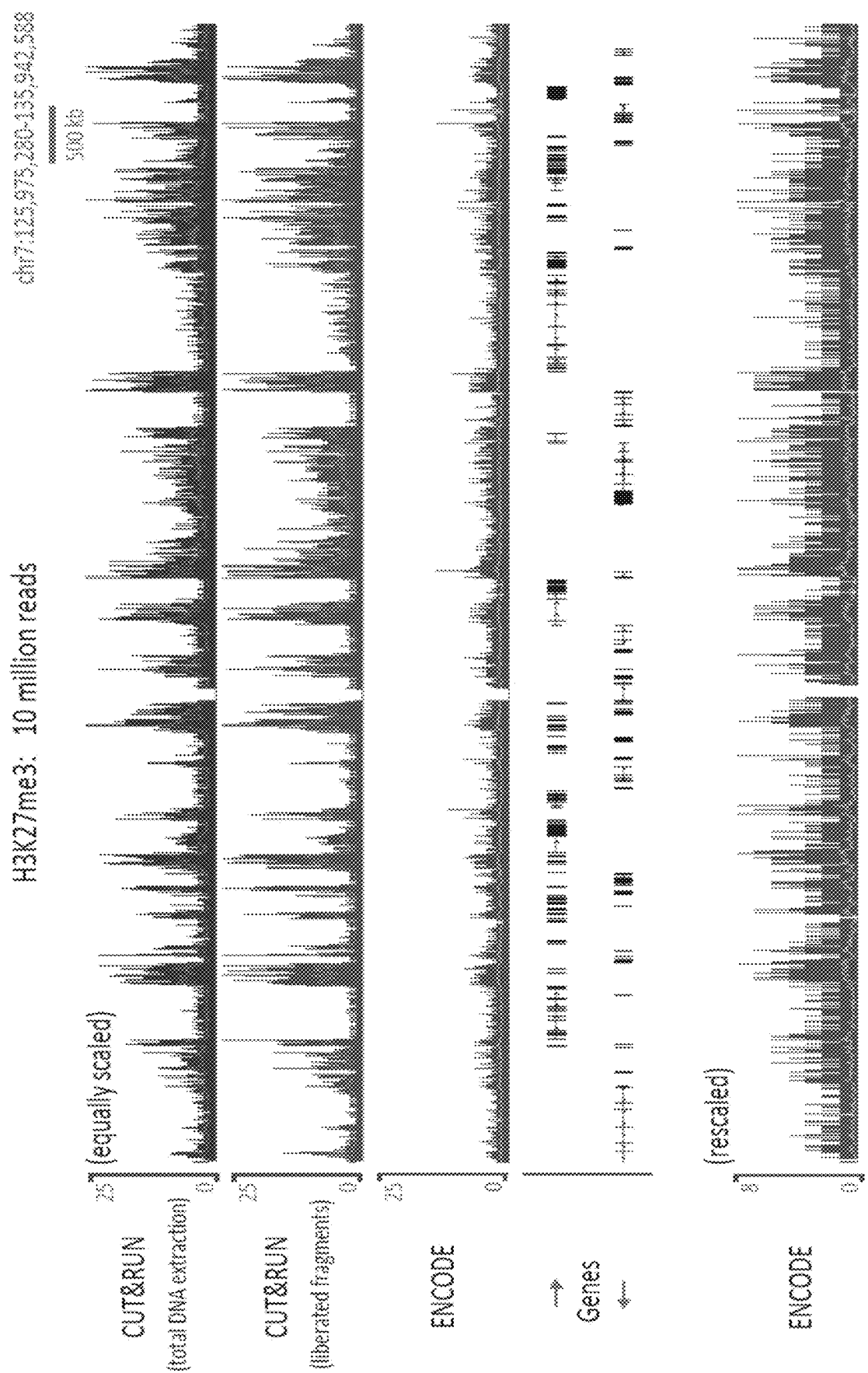
FIG. 21 shows that CUT&RUN can map compacted chromatin with a high dynamic range. CUT&RUN was performed for H3K27me3 in K562 cells either by extracting all the DNA after digestion followed by size selection or allowing cut fragments to diffuse out of the nuclei. For comparison an ENCODE H3K27me3 X-ChIP-seq (GSM733658) dataset was analyzed. For each dataset 10 million reads were randomly selected and a typical genomic region is shown with the upper panels equally scaled and the lower panel rescaled for the ENCODE dataset.

The possibility was considered that antibody-tethered MNase may be excluded from highly compacted heterochromatic regions in higher eukaryotes and as such CUT&RUN might be limited to analysis of protein-DNA interactions in euchromatic regions. Therefore, CUT&RUN was performed for the repressive histone mark H3K27me3. Analyzing 10 million reads from CUT&RUN and ENCODE X-ChIP-seq, similar H3K27me3 landscapes, but at a much higher dynamic range for CUT&RUN were observed, which demonstrates that Protein A-MNase is able to access compacted chromatin (FIG. 21). Furthermore, H3K27me3 cleaved chromatin is readily released from the intact nuclei into the soluble fraction, indicating that CUT&RUN is applicable to probing protein-DNA interactions in compacted chromatin.

CUT&RUN Directionally Maps Long-Range Genomic Contacts

Figure 7A:
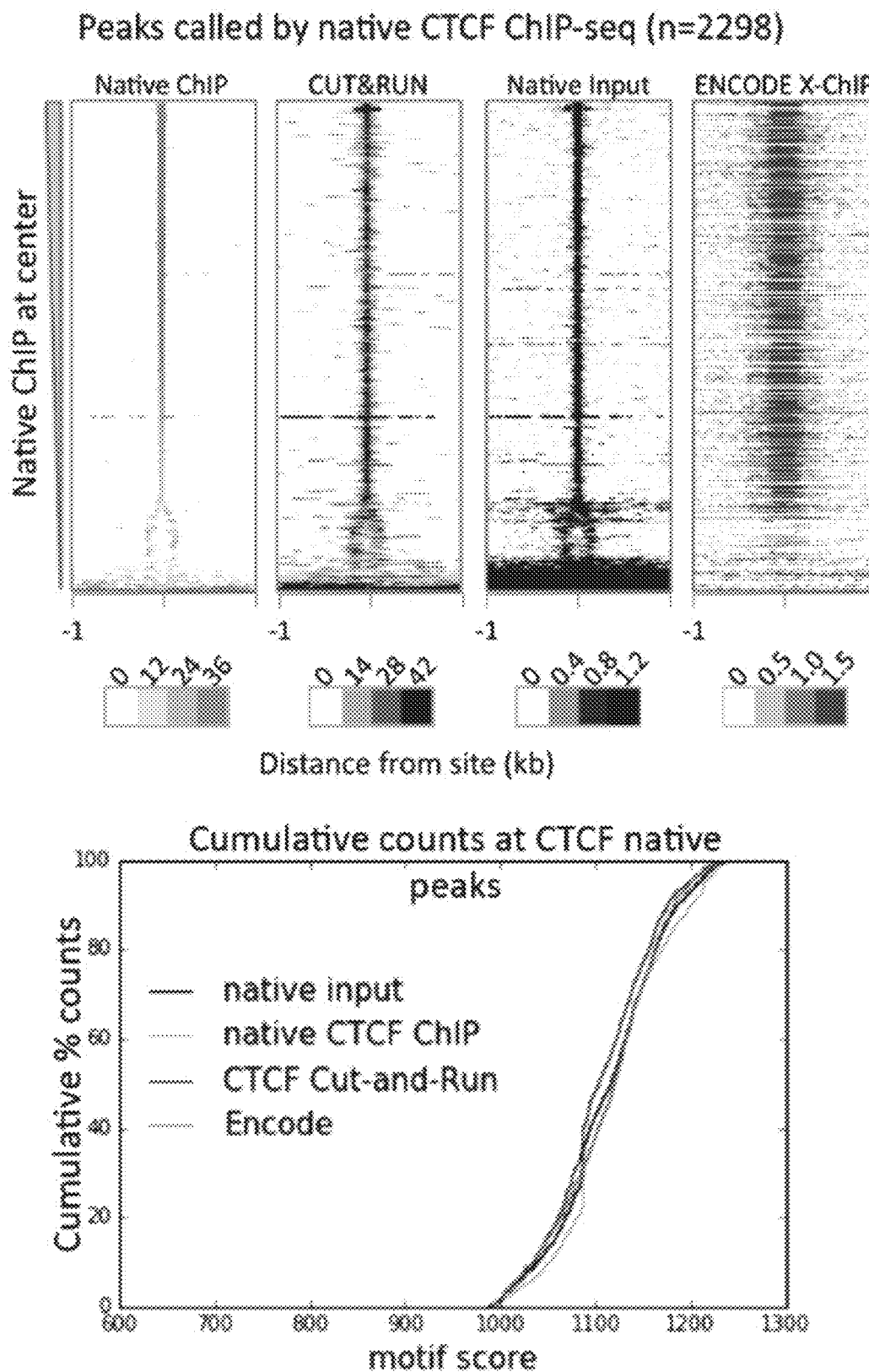
FIGS. 7A and 7B show that CTCF directly binds a subset of CUT&RUN peaks despite a robust footprint at all sites.
Figure 7B:
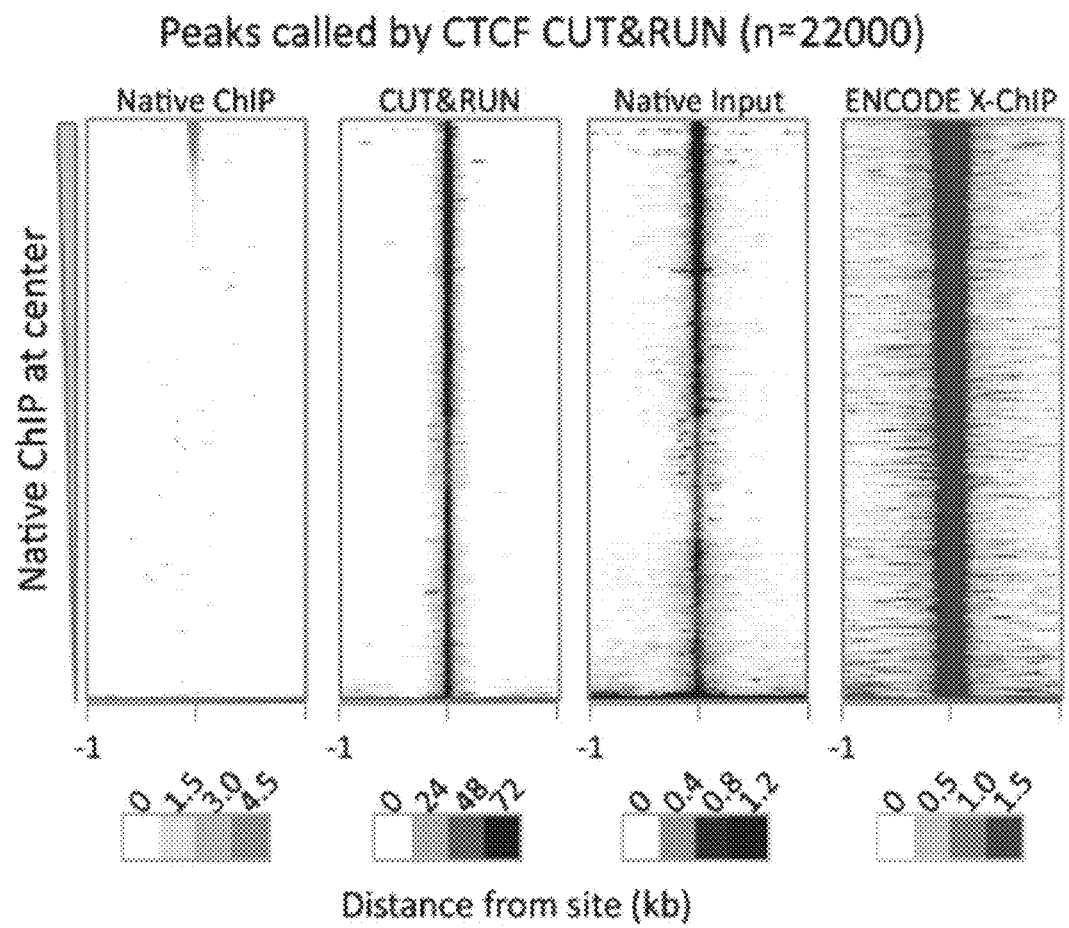
Figure 7B:
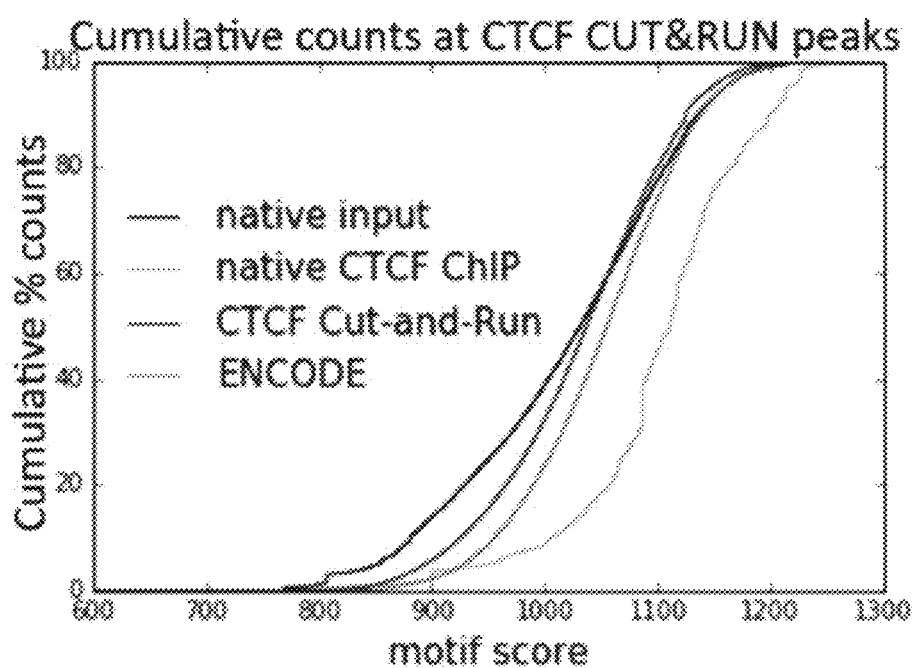
Figure 22A:
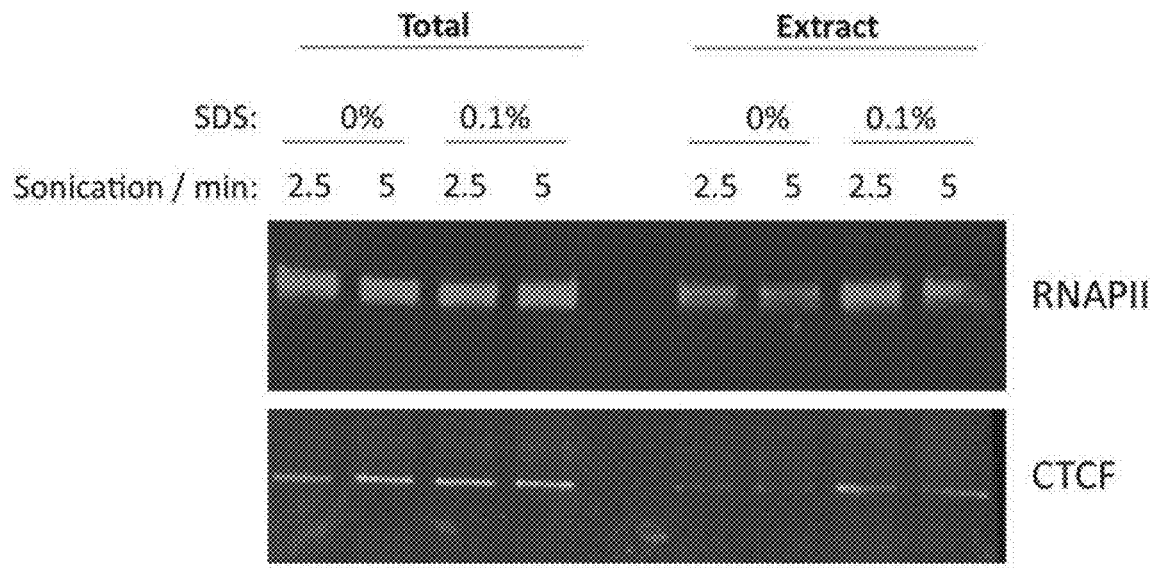
FIGS. 22A and 22B show that a modified native ChIP protocol allows complete protein extraction.
Figure 22B:
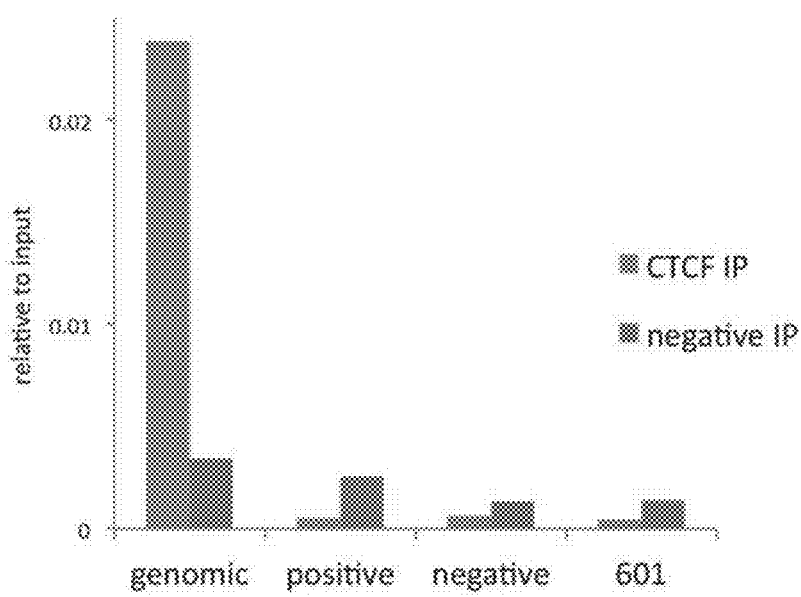
Figure 23:
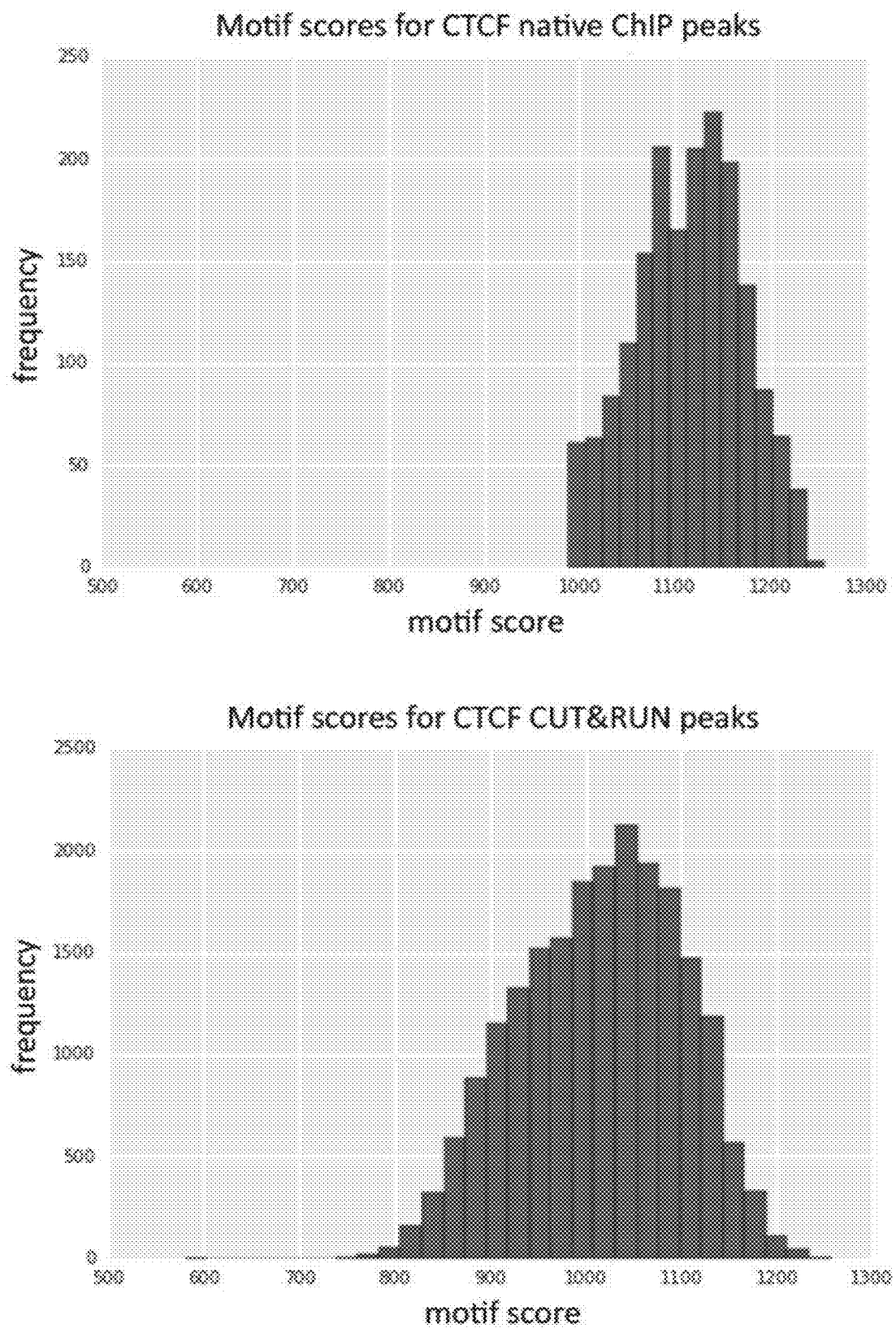
FIG. 23 shows that peaks identified by CUT&RUN have a more diverse range of motif scores than peaks from native ChIP. Peak calling was performed on native CTCF ChIP (false positives were removed that did not contain a clear peak) and CUT&RUN. The underlying DNA sequence was extended in both directions by 100 bp and the best match and score to the JASPAR position frequency matrix (MA0139.1) calculated. Histograms plot the distribution of motif scores.

As nucleosome-sized fragments adjacent to TFs are released together with TF-containing fragments, it was asked whether 3D adjacencies might also be subject to cleavage and release. Chromosome-Conformation-Capture (3C) methods, such as Hi-C and ChIA-PET (Tang et al., 2015; Lieberman-Aiden et al., 2009), are the preferred techniques for mapping 3D genome-wide contacts. These methods use the same formaldehyde crosslinking protocol as X-ChIP to identify 3D interactions, such as between a TF bound at an enhancer and its contact with a promoter via co-activators. In this example, the binding sites for a protein identified by X-ChIP will include both the promoter and the enhancer, even though one of the interactions is via indirect protein-protein interactions crosslinked by formaldehyde. But in both X-ChIP and 3C-based mapping there is no systematic way to distinguish between direct and indirect sites. It was therefore attempted to map CTCF binding sites using native ChIP, which have previously shown results in mapping only direct binding sites containing the TF-specific DNA-binding motif, due to the transient nature of protein-protein interactions (Kasinathan et al., 2014). A new native ChIP protocol (see below), was developed that achieved near-complete protein extraction with no evidence of protein redistribution (FIGS. 22A-22B). Under native conditions, 2298 sites were identified with high motif scores. In contrast, CUT&RUN mapping of CTCF detected ~22,000 sites that were also present in X-ChIP, with a diverse range of motif scores (FIG. 23). As expected, all sites identified by native ChIP also were robustly detected by CUT&RUN and X-ChIP, showing a similar signal distribution (FIG. 7A). CUT&RUN sites lacking a significant native ChIP signal nevertheless showed a robust footprint in the native ChIP input with a similar cumulative distribution of counts (FIG. 7B), indicating the presence of unknown bound factors, as would be expected for 3D genomic interactions. This indicates that CUT&RUN, as with X-ChIP, can discover both direct (native CTCF peak) and indirect (CUT&RUN peak only) chromatin interactions at high resolution.

Figure 8A:
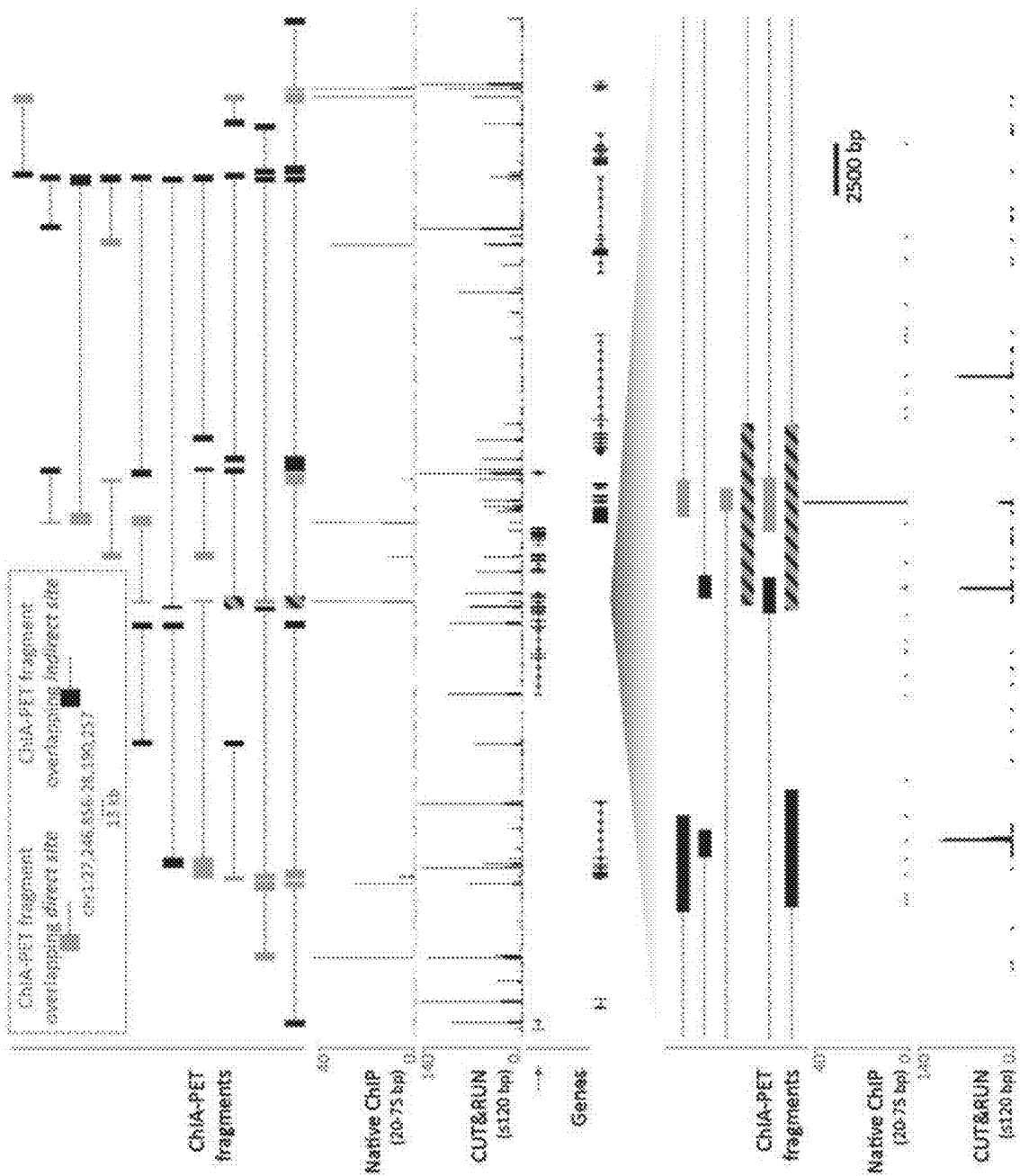
FIGS. 8A-8C show that CUT&RUN in combination with native ChIP can discern direct and indirect 3D contact sites.

To confirm that CTCF CUT&RUN sites not observed by native ChIP correspond to contact sites, direct and indirect sites were compared to contact sites observed by ChIA-PET. CTCF ChIA-PET identifies interacting genomic regions mediated through CTCF, but cannot discern between directly CTCF bound regions and the interacting indirectly bound region. For a typical ~1 Mb genomic region all high-scoring ChIA-PET fragments overlap with direct and indirect sites (FIG. 8A). Whereas mapped CTCF ChIA-PET fusion fragments are in the several kb range, determined by the distance between sites for the 6-cutter restriction enzyme used, both direct and indirect CUT&RUN CTCF sites are mapped with near base-pair resolution. Moreover, 91% of the direct sites are present in CTCF ChIA-PET data, with 43% of these ChIA-PET fragments interacting with an indirect site, and the remainder contained a high CUT&RUN signal (FIG. 8C), which indicates these are indirect sites involved in multiple contacts, just below the peak calling threshold.

Figure 8B:
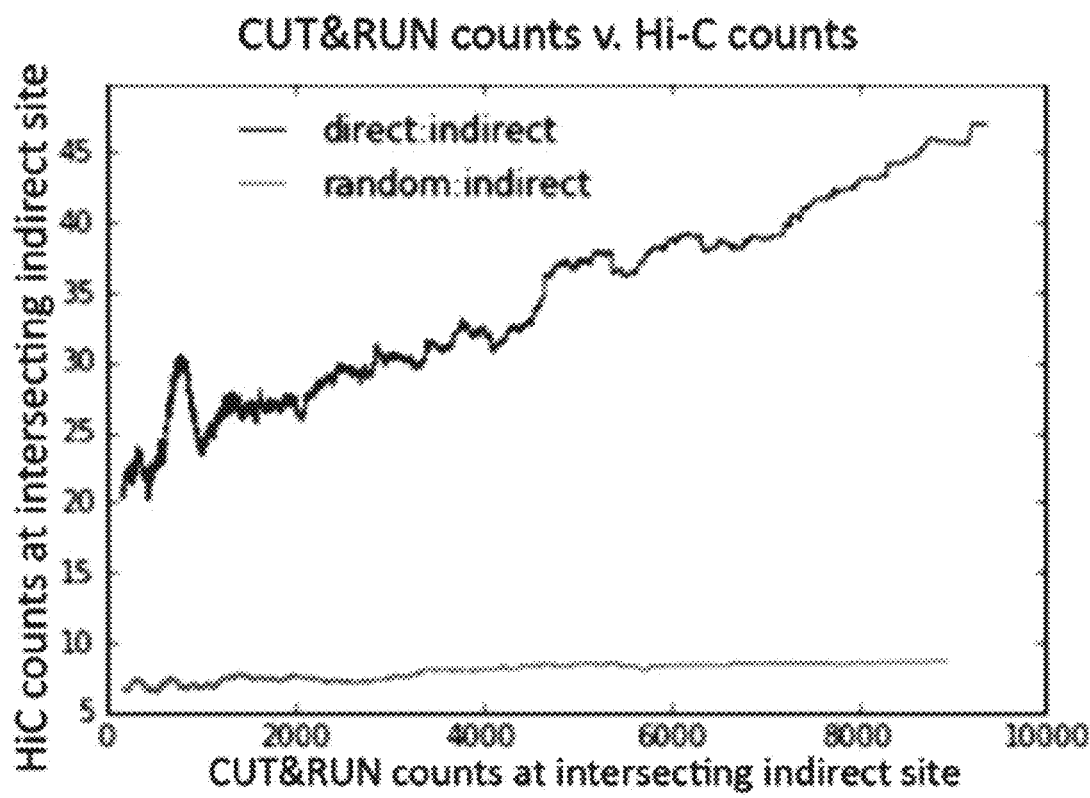
Figure 8C:
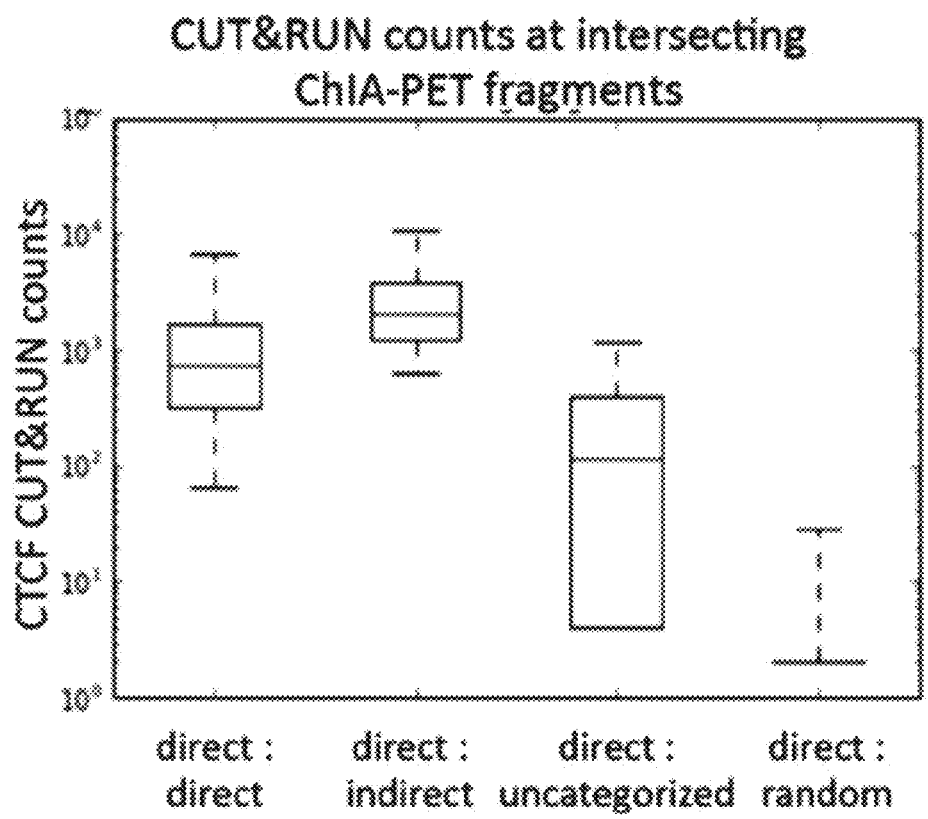
Figures 1, 2, 9B:
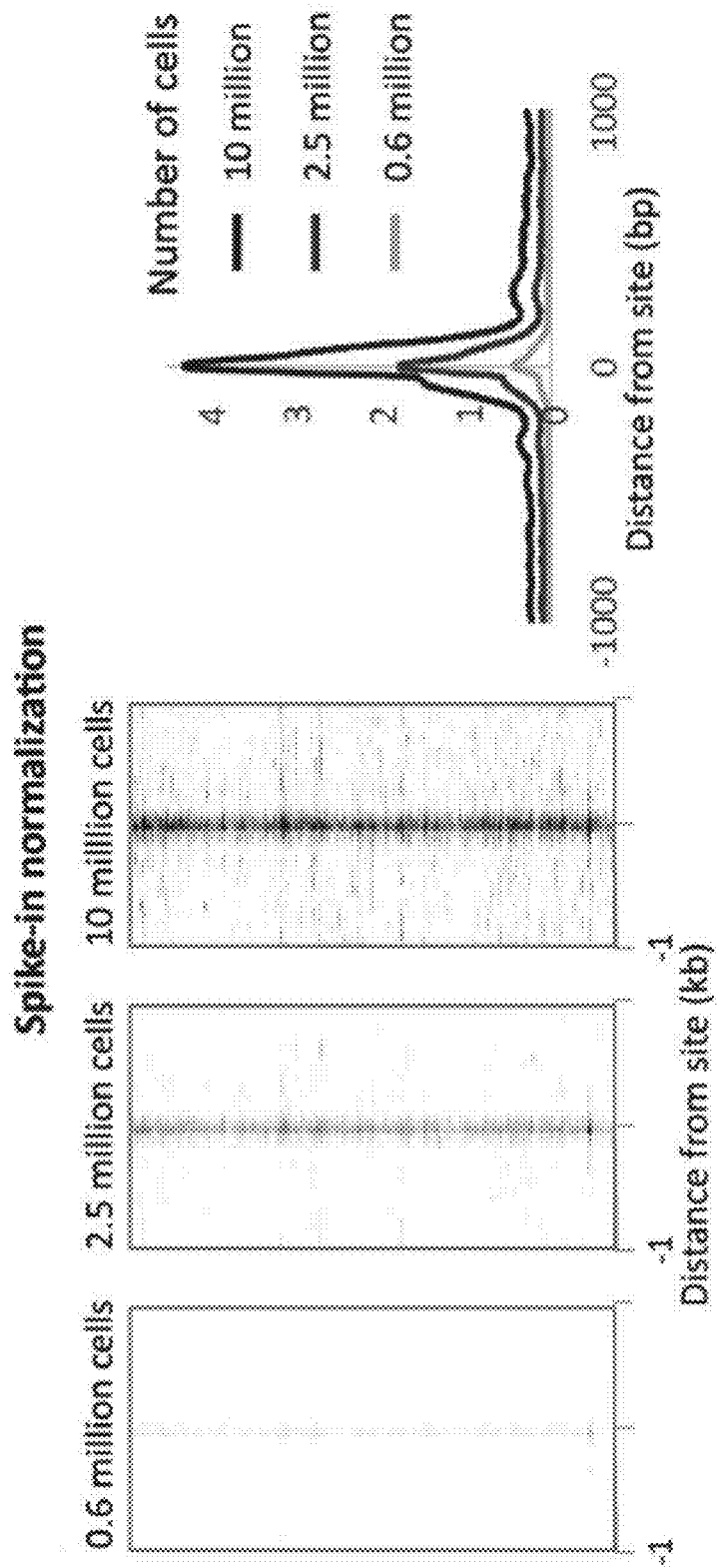
Figures 3, 4, 9B:
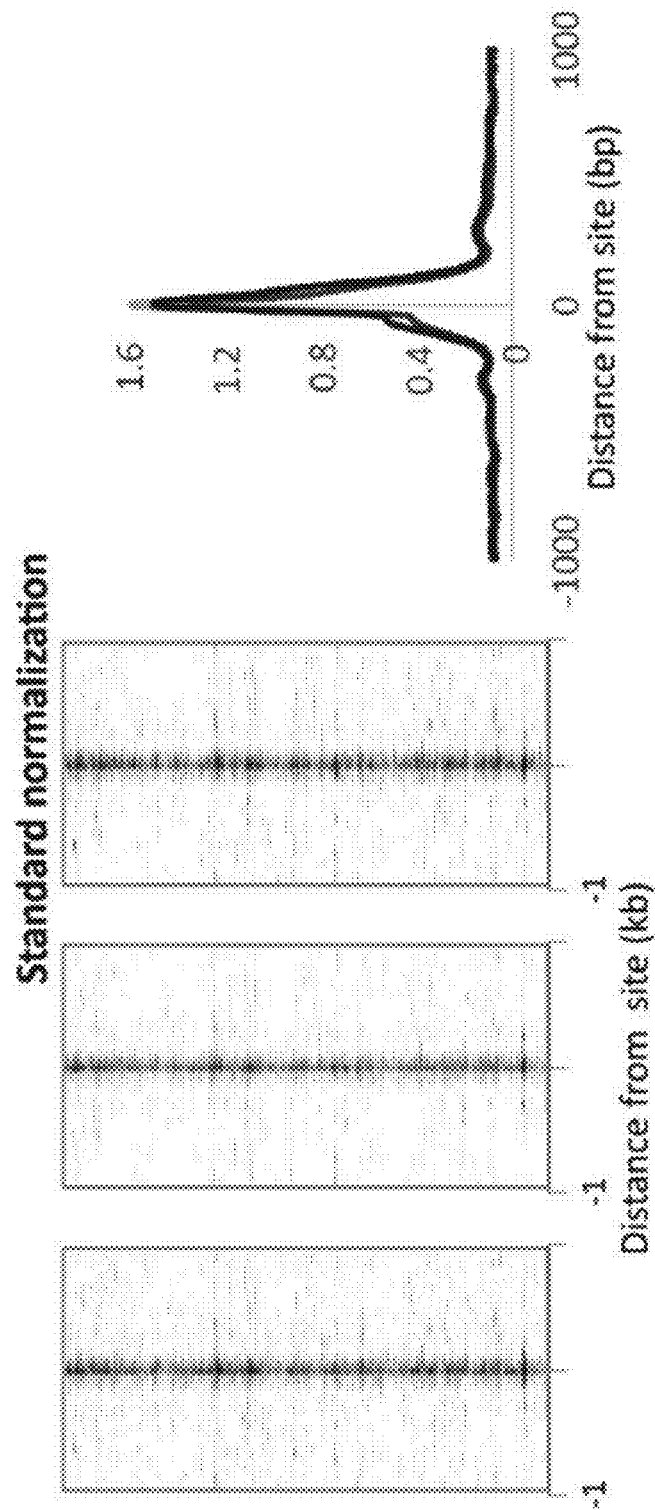

As further evidence that CUT&RUN can detect indirect contact interactions, a high frequency of Hi-C interactions were found between direct sites and indirect sites and a quantitative correlation between Hi-C score and CUT&RUN signal at the indirect sites (FIG. 8B). Therefore, by comparing CUT&RUN and native ChIP it is possible to map contact sites at near base-pair resolution, to distinguish direct from indirect protein binding sites that result from long-range genomic interactions, and to determine the directionality to these contacts, not feasible by other methods.

CUT&RUN Allows Quantitative Measurements with Low Cell Numbers

Typical ChIP-seq experiments require large numbers of cells, and low cell number ChIP has been limited to abundant proteins (Kasinathan et al., 2014; Brind'Amour et al., 2015). CTCF CUT&RUN was performed with starting K562 cell numbers ranging from 600,000 to 10 million. To compare absolute occupancies between datasets, a spike-in strategy was used (see Materials and methods below), allowing accurate quantitative measurements of protein occupancy. When normalized to spike-in DNA, the number of cleavage events was observed to be proportional to the starting cell number (FIGS. 9A-1 to 9B-4). Furthermore, when the data are normalized to the total number of reads aligning to the human genome, there is no clear difference in the samples, indicating that high data quality is maintained with low input material.

Discussion

A Simple Method for Chromatin Profiling

CUT&RUN is based on the ChIC antibody-tethered nuclease strategy of Laemmli and co-workers (Schmid et al., 2004). To adapt ChIC into a genome-wide profiling method, five critical modifications were made. First, permeabilized cells or crude nuclei were immobilized to magnetic beads, allowing for rapid and efficient solution changes, so that CUT&RUN is performed in a day and is suitable for automation. Second, antibodies and pA-MNase were bound to native unfixed nuclei, where epitopes are preserved and accessible. Third, as cleavage by immobilized MNase is a zero-order reaction, digestion was performed at ice-cold temperature, which limits diffusion of released fragments, thus reducing background. Fourth, native chromatin was used, which allows us to fractionate cleaved fragments based on solubility (Sanders, 1978; Teves and Henikoff, 2012; Jahan et al., 2016) to enrich specifically for the released chromatin complex. The insoluble bulk chromatin was removed, and only chromatin fragments with cleavages on both sides of a particle enter the supernatant. Fifth, after DNA extraction these soluble fragments were used for Illumina library preparation and paired-end DNA sequencing. CUT&RUN performs as well as or better than ChIP-seq with respect to simplicity, resolution, robustness, efficiency, data quality, and applicability to highly insoluble complexes. CUT&RUN requires only ~1/10th of the sequencing depth of other high resolution methodologies due to the intrinsically low background achieved by performing the reaction in situ. As nuclei are intact when MNase is activated, CUT&RUN can probe the local environment around the targeted site. Indeed, CUT&RUN recovers sites of 3D contacts with base-pair resolution at relatively low sequencing depth in human cells.

CUT&RUN is Widely Applicable

Although ChIC was described as a basic mapping method using Southern blotting 12 years ago, we are unaware of a single publication using it. Meanwhile, ChIP-seq alone has been mentioned in ~30,000 publications for profiling almost every type of chromatin component, including histone modifications, transcription factors and chromatin-associated proteins. Like ChIP, CUT&RUN is antibody-based, so that it can be applied to any epitope on chromatin, making it a general method for chromatin profiling that takes advantage of the large antibody production infrastructure developed for ChIP. CUT&RUN provides quantitative occupancy profiles with standard and spike-in normalization options implemented by our custom software for processing and comparing ChIP-seq and CUT&RUN datasets. The only non-standard feature of CUT&RUN is the requirement for the pA-MN fusion protein, which can be produced and purified in a batch from bacterial culture that yields enough pA-MN for profiling >100,000 samples. As CUT&RUN is based on different principles from ChIP, it can resolve crosslinking-, sonication- and solubilization-related issues. Backgrounds are low with CUT&RUN, because cleavages occur only around binding sites, whereas ChIP first pulverizes the entire genome, and these fragments contribute to a genome-wide background noise that must still be sequenced. The near absence of detectable background under the brief low-temperature conditions that we used, the lack of preference for accessible or AT-rich DNA, and the recovery of essentially all Abf1 and Reb1 motifs in the yeast genome, suggests that CUT&RUN is not subject to the types of artifacts that sometimes have plagued ChIP (Teytelman et al., 2013; Park et al., 2013; Jain et al., 2015; Baranello et al., 2016; Kasinathan et al., 2014). Furthermore, CUT&RUN antibody binding takes place in an intact nuclear environment resembling conditions for immunofluorescence microscopy, so that it should be successful for antibodies that are validated cytologically, even those that fail in ChIP. As CUT&RUN solubilizes chromatin only after the targeted cleavage reaction, it is appropriate for extending classical chromatin salt-fractionation (Sanders, 1978; Teves and Henikoff, 2012; Jahan et al., 2016) to specific TFs and chromatin complexes.

CUT&RUN Precisely Maps Long-Range Contacts

A consequence of using intact nuclei for CUT&RUN is that the long reach of antibody-tethered MNase can probe the local environment. In yeast, cleavages were observed on one surface of the DNA flanking the TF, gradually decreasing with distance. In human cells cleavages were observed at sites previously identified as contact sites for CTCF. Recently, Hi-C contact sites have been predicted computationally with a high degree of confidence given sites of CTCF binding (Sanborn et al., 2015). As CUT&RUN maps both CTCF binding sites and interactions, and the native ChIP protocol identifies those sites that are directly TF-bound, it can provide a complete high-resolution 1D map of a genome while enriching its 3D contact map with high-resolution distinctions between direct and indirect TF binding sites.

Low Background Levels Reduce Sequencing Costs

ChIP-seq analysis typically includes normalization to compensate for different numbers of reads between samples. In ChIP-seq, whole genome fragmentation leads to a constant low density genome-wide background that provides a basis for normalization, for example, in comparing wild-type and knockdown cell lines. Although normalization fails on abundant proteins, this can be corrected by the use of spike-in controls (Bonhoure et al., 2014; Chen et al., 2015; Orlando et al., 2014). However, a rigorous spike-in strategy requires the addition of cells from a different species, and quantification is reliant upon antibody cross-reactivity (Orlando et al., 2014). To normalize between samples despite the low background in CUT&RUN, adding a constant low amount of fragmented spike-in DNA from a different species suffices and allows accurate quantification of protein occupancy. The low background levels of cleavage with CUT&RUN require fewer reads to crisply define peaks. For example only ~10 million paired-end reads were required for each CTCF time point, similar to the requirement for low-resolution ChIP-seq, and many fewer than for ChIP-exo, which required ~100 million reads for CTCF (Rhee and Pugh, 2011). Furthermore, in the cases of Max and H3K27me3, 10 million reads for CUT&RUN provided very high dynamic range, but 10 million reads were insufficient for calling peaks from Max ENCODE X-ChIP-seq. This cost-effectiveness makes CUT&RUN attractive as a replacement for ChIP-seq especially where depth of sequencing is limiting. The high efficiency of CUT&RUN may be attributed to fundamental differences between in situ pro-filing and ChIP: CUT&RUN retains the in vivo 3D conformation, so antibodies access only exposed surfaces in a first-order binding reaction, whereas in ChIP, antibodies interact with the solubilizable genome-wide content of the pulverized cells or nuclei. Furthermore, CUT&RUN cleavage is effectively a zero-order reaction, resulting in steady particle release during the brief low temperature time-course for all bound epitopes in the genome. Accounting for epitope abundances, it is estimated that the mapping of ~22,000 direct and indirect CTCF sites with 600,000 cells is comparable to the sensitivity of ultra-low input ChIP-seq protocols that are typically restricted to abundant histone modifications, such as H3K27me3, with ~5000 cells (Brind'Amour et al., 2015). Whereas ultra-low-input ChIP provides only ~2 kb resolution, CUT&RUN provides near base-pair resolution. The inherent robustness, high information content, low input and sequencing requirements and suitability for automation of the disclosed method indicates that CUT&RUN profiling of CTCF and other TFs might be applied to epigenome diagnostics. In summary, CUT&RUN has a number of practical advantages over ChIP and its derivatives: with low background resulting in low sequence depth requirements, the ease of use makes it amenable to robotic automation, while allowing accurate quantification with a simple spike-in strategy. Thus, in all important respects CUT&RUN provides an attractive alternative to ChIP-based strategies.

Materials and Methods

Biological W1588-4C S. cerevisiae strains carrying Flag-tagged H2A (SBY2688), Cse4 (SBY5146), Abf1 and Reb1 under the control of their respective endogenous promoters were previously described (Kasinathan et al., 2014; Krassovsky et al., 2012; Gelbart et al., 2001). Yeast nuclei were pre-pared as described (Kasinathan et al., 2014), flash frozen in 0.5-0.6 ml aliquots and stored at −80° C. Human K562 cells were cultured under standard conditions. Standard protocols were used for electrophoretic gel analysis and immunoblotting. Antibodies used were Mouse anti-FLAG (M2, Sigma. St. Louis, MO, Catalog #F1804), Rabbit anti-mouse (Abcam, Cambridge, UK, Catalog #ab46540), CTCF (Millipore Billerica, MA, Catalog #07-729), H3K27me3 (Millipore Catalog #07-449), c-Myc (Cell Signaling Technology Beverly, MA, Catalog #D3N8F), Max (Santa Cruz Biotechnology. Dallas, TX, Catalog #sc-197) and RNA Pol II (8WG16, Abcam Catalog #ab817). The pK19 pA-MN plasmid was a gift from Ulrich Laemmli and pA-MN protein was prepared from E. coli cells as described (Schmid et al., 2004). CUT&RUN for yeast nuclei CUT&RUN begins with crude nuclei prepared according to published procedures. The following protocol is provided in step-by-step format (see below). Nuclei from ~×10$^8$ cells at OD600 ~0.7 were prepared as described (Orsi et al., 2015), divided into 10 600 mL aliquots, snap-frozen and held at −80° C., then thawed on ice before use. Bio-Mag Plus Concanavalin A (lectin) coated beads were equilibrated with HNT (20 mM HEPES pH7.5, 100 mM NaCl and 0.1% Tween 20) that was supplemented with 1 mM each MgCl2, CaCl2 and MnCl2. Only Ca++ and Mn++ are needed to activate lectins, and omitting MgCl2 had no effect on binding of permeabilized cells to beads. The beads (300 mL) were rapidly mixed with a thawed nuclei aliquot and held at room temperature (RT) ≥5 min. placed on a magnet stand to clear (<1 min), and decanted on a magnet stand. The beads were then incubated 5 min RT in HNT supplemented with protease inhibitors (Roche Complete tablets) and 1 mM phenylmethylsulfonyl fluoride (PMSF) (=HNT-PPi) containing 3% bovine serum albumen (BSA) and 2 mM EDTA pH 8, then incubated 5' with HNT-PPi+0.1% BSA (blocking buffer), using the magnet stand to decant. The beads were incubated 2 hr at 4° C. with mouse anti-FLAG antibody (1:200-1:350), decanted, washed once in HNT+PMSF, then incubated 1 hr at 4° C. with rabbit anti-mouse IgG antibody (1:200) in blocking buffer. The beads were washed once in HNT+PMSF, then incubated 1 hr at 4° C. with pA-MN (600 mg/ml, 1:200) in blocking buffer. The beads were washed twice in HNT+PMSF and once in 20 mM HEPES pH 7.5, 100 mM NaCl (Digestion buffer), optionally including 10% polyethylene glycol 8000 for Sth1 and Mot1. The beads were brought up in 1.2 ml Digestion buffer, divided into 8×150 mL aliquots, equilibrated to 0° C., then quickly mixed with CaCl$_2$, stopping the reaction with 150 mL 2×STOP 1200 mM NaCl, 20 mM EDTA, 4 mM EGTA, 50 mg/ml RNase A (Thermo Scientific, Waltham. MA, Catalog #EN0531) and 40 mg/ml glycogen (Sigma, Catalog #10901393001), containing 5-50 pg/ml heterologous mostly mononucleosome-sized DNA fragments extracted from formaldehyde crosslinked MNase-treated *Drosophila* chromatin as a spike-in]. After incubating at 37° C. for 20 min, the beads were centrifuged 5 min at 13,000 rpm at 4° C., the supernatant was removed on a magnet stand and mixed with 3 mL 10% SDS and 2 mL Proteinase K (Invitrogen, Carlsbad, CA, Catalog #25530049), incubated at 70° C. 10 min, then extracted at room temperature once with buffered phenol-chloroform-isoamyl alcohol (25:24:1, Sigma P2069), transferred to a phase-lock tube (Qiagen, Hilden, Germany, Catalog #129046), re-extracted with one vol CHCl$_3$, transferred to a fresh tube containing 2 mL 2 mg/ml glycogen, precipitated by addition of 2-2.5 vol ethanol, chilled in ice and centrifuged 10 min at 13,000 rpm at 4° C. The pellet was rinsed with 100% ethanol, air-dried and dissolved in 25 mL 0.1× TE8 (=1 mM Tris pH 8, 0.1 mM EDTA). To extend CUT&RUN for high-salt extraction, digestions were performed in a 50 mL volume, stopped with 50 mL 2×STOP, omitting RNase and substituting the standard 200 mM NaCl with 4 M NaCl. After 20 min at 37° C., 200 mL 67 mg/ml RNase A was added, incubated 20 min, then centrifuged 13,000 rpm to clarify the supernatant. CUT&RUN for mammalian cells Human K562 cells were purchased from ATCC (Manassas, VA, Catalog #CCL-243). CUT&RUN was performed using a centrifugation-based protocol. Ten million cells were harvested by centrifugation (600 g, 3 min in a swinging bucket rotor) and washed in ice cold phosphate-buffered saline (PBS). Nuclei were isolated by hypotonic lysis in 1 ml NE1 (20 mM HEPES-KOH pH 7.9; 10 mM KCl; 1 mM MgCl2; 0.1% Triton X-100; 20% Glycerol) for 5 min on ice followed by centrifugation as above (nucleases in some cells caused Mg++-dependent degradation of DNA, in which case 0.5 mM spermidine can be substituted for 1 mM MgCl2). Nuclei were briefly washed in 1.5 ml Buffer 1 (20 mM HEPES pH 7.5; 150 mM NaCl; 2 mM EDTA; 0.5 mM Spermidine; 0.1% BSA) and then washed in 1.5 ml Buffer 2 (20 mM HEPES pH 7.5; 150 mM NaCl; 0.5 mM Spermidine; 0.1% BSA). Nuclei were resuspended in 500 ml Buffer 2 and 10 ml antibody was added and incubated at 4° C. for 2 hr. Nuclei were washed 3× in 1 ml Buffer 2 to remove unbound antibody. Nuclei were resuspended in 300 ml Buffer 2 and 5 ml pA-MN added and incubated at 4° C. for 1 hr. Nuclei were washed 3× in 0.5 ml Buffer 2 to remove unbound pA-MN. Tubes were placed in a metal block in ice-water and quickly mixed with 100 mM CaCl$_2$) to a final concentration of 2 mM. The reaction was quenched by the addition of EDTA and EGTA to a final concentration of 10 mM and 20 mM respectively and 1 ng of mononucleosome-sized DNA fragments from *Drosophila*

DNA added as a spike-in. Cleaved fragments were liberated into the supernatant by incubating the nuclei at 4° C. for 1 hr, and nuclei were pelleted by centrifugation as above. DNA fragments were extracted from the supernatant and used for the construction of sequencing libraries. This protocol was also adapted for use with magnetic beads (shown below). Spike-in normalization Genome-wide background in TF ChIP-seq datasets is typically sufficiently high to provide a constant background level for normalization to compensate for variations between samples in library preparation and sequencing. For standard normalization, the number of fragment ends corresponding to each base position in the genome was divided by the total number of read ends mapped. However, the inherently low background levels of CUT&RUN necessitate a spike-in control for quantitative comparisons (Hu et al., 2014). For spike-in normalization of human CUT&RUN, a low constant amount of *Drosophila melanogaster* DNA was added to each reaction. The paired-end reads were mapped to both human and fly genomes, normalizing human profiles to the number of fly reads (FIGS. 9A-1 to 9B-4). Using internal normalization, no increase in cleavages were observed over a digestion time-course. However, by normalizing to the fly spike-in DNA, an ~4 fold increase in cleavage level over time was observed. As such, CUT&RUN is amenable to accurate quantification of protein-DNA interactions. Library preparation, sequencing and data processing Sequencing libraries were prepared from DNA fragments as described (Kasinathan et al., 2014; Henikoff et al., 2011) but without six-selection, following the KAPA DNA polymerase library preparation kit protocol (www.kapabiosystems.com/product-applications/products/next-generation-sequencing-2/dna-library-preparation/kapa-hyper-prep-kits/) and amplifying for eight or more cycles. To deplete total DNA samples of large fragments originating from insoluble chromatin, samples were mixed with %2 volume of Agencourt AMPure XP beads, held 5-10 min, placed on a magnet stand, and the supernatant was retained, discarding the beads. To reduce the representation of the remaining large fragments, the number of PCR cycles using the KAPA polymerase library preparation method was increased to 14 cycles and adapter concentrations were increased accordingly. Increasing the number of PCR cycles favors exponential amplification of shorter fragments over linear amplification of fragments that are too long for poly merase to completely transit. Libraries were sequenced for 25 cycles in paired-end mode on the Illumina HiSeq 2500. Paired-end fragments were mapped to the sacCer3/V64 genome and build and to release r5.51 (May 2013) of the *D. melanogaster* genomic sequence obtained from FlyBase using Novoalign (Novocraft) as described to generate SAM files. For human samples, paired-end fragments were mapped to hg19 using Bowtie2. Custom scripts for data processing are provided in Supplementary Software and can be downloaded from github.com/peteskene. For comparative analyses, publicly available datasets downloaded from the NCBI SRA archive were: ERR718799 (Abf1). SRR2568522 (Reb1). GSM749690 (CTCF: 150 bp sliding window at a 20 bp step across the genome with a false discovery rate of 1%), and the CTCF ChIP-exo BAM file was kindly provided by Frank Pugh. To obtain sets of TF-specific motifs without biasing towards CUT&RUN peaks, the MEME motif-finding program was applied to yeast ORGANIC ChIP-seq peak calls. The resulting log-odds position-specific scoring matrix (PSSM) was used for MAST searching of the *S. cerevisiae* genome to identify sites with significant log-odds motif scores. This identified 1899 Abf1 sites and 1413 Reb1 sites. Following previous studies, correspondence of a yeast TF binding site to the motif for that TF was used to be the 'gold-standard' for a true-positive call (Rhee and Pugh, 2011; Kasinathan et al., 2014; Zentner et al., 2015; Ganapathi et al., 2011). MEME was used to construct log-odds PSSMs from peaks called using the threshold method of Kasinathan et al. (Kasinathan et al., 2014). Peak-calling cut-off was the 99.5th percentile of normalized counts for pooled 1 s to 32 s≤120 bp Abf1 and Reb1 datasets, where the interpeak distance=100, minimum peak width=50, and maximum peak width=1000. To compare CUT&RUN and ORGANIC motif recovery, peak-call thresholds were adjusted to report similar numbers of peaks. Log-odds sequence logos were produced using PWMTools (ccg.vital-it.ch/pwmtools/). Track screen shots were produced using IGV (Thorvaldsdottir et al., 2013).

References for Example 1 (Each of which is Incorporated by Reference in its Entirety)

Akiyoshi B, Sarangapani K K, Powers A F, Nelson C R, Reichow S L, Arellano-Santoyo H, Gonen T, Ranish J A, Asbury C L, Biggins S. 2010. Tension directly stabilizes reconstituted kinetochore-microtubule attachments. Nature 468:576-579. doi: 10.1038/nature09594, PMID: 21107429

Aravamudhan P, Felzer-Kim I, Joglekar A P. 2013. The budding yeast point centromere associates with two Cse4 molecules during mitosis. Current Biology 23:770-774. doi: 10.1016/j.cub.2013.03.042, PMID: 23623551

Auble D T, Wang D, Post K W, Hahn S. 1997. Molecular analysis of the SNF2/SWI2 protein family member MOT1, an ATP-driven enzyme that dissociates TATA-binding protein from DNA. Molecular and Cellular Biology 17: 4842-4851. doi: 10.1128/MCB.17.8.4842

Aughey G N, Southall T D. 2016. Dam it's good! DamID profiling of protein-DNA interactions. Wiley Interdisciplinary Reviews: Developmental Biology 5:25-37. doi: 10.1002/wdev.205, PMID: 26383089

Ayer D E, Eisenman R N. 1993. A switch from Myc:Max to Mad:Max heterocomplexes accompanies monocyte/macrophage differentiation. Genes & Development 7:2110-2119. doi: 10.1101/gad.7.11.2110, PMID: 8224841

Baranello L, Kouzine F, Sanford S, Levens D. 2016. ChIP bias as a function of cross-linking time. Chromosome Research 24:175-181. doi: 10.1007/s10577-015-9509-1, PMID: 26685864

Blackwood E M, Eisenman R N. 1991. Max: a helix-loop-helix zipper protein that forms a sequence-specific DNA-binding complex with Myc. Science 251:1211-1217. doi: 10.1126/science.2006410, PMID: 2006410

Bonhoure N, Bounova G, Bernasconi D, Praz V, Lammers F, Canella D, Willis I M, Herr W, Hernandez N, Delorenzi M, CycliX Consortium. 2014. Quantifying ChIP-seq data: a spiking method providing an internal reference for sample-to-sample normalization. Genome Research 24:1157-1168. doi: 10.1101/gr.168260.113, PMID: 24709819

Brind'Amour J, Liu S, Hudson M, Chen C, Karimi M M, Lorincz M C. 2015. An ultra-low-input native ChIP-seq protocol for genome-wide profiling of rare cell populations.
Nature Communications 6:6033. doi: 10.1038/ncomms7033, PMID: 25607992 Chen K, Hu Z, Xia Z, Zhao D, Li W, Tyler J K. 2015. The overlooked fact: Fundamental need for Spike-In control for virtually all Genome-Wide analyses. Molecular and Cellular Biology 36:662-667. doi: 10.1128/MCB.00970-14, PMID: 26711261

Cho G, Kim J, Rho H M, Jung G. 1995. Structure-function analysis of the DNA binding domain of *Saccharomyces cerevisiae* ABF1. Nucleic Acids Research 23:2980-2987. doi: 10.1093/nar/23.15.2980, PMID: 7659521

Chung H R, Dunkel I, Heise F, Linke C, Krobitsch S, Ehrenhofer-Murray A E, Sperling S R, Vingron M. 2010. The effect of micrococcal nuclease digestion on nucleosome positioning data. PLoS One 5:e15754. doi: 10.1371/journal.pone.0015754, PMID: 21206756

Floer M, Wang X, Prabhu V, Berrozpe G, Narayan S, Spagna D, Alvarez D, Kendall J, Krasnitz A, Stepansky A, Hicks J, Bryant G O, Ptashne M. 2010. A RSC/nucleosome complex determines chromatin architecture and facilitates activator binding. Cell 141:407-418. doi: 10.1016/j.cell.2010.03.048, PMID: 20434983

Ganapathi M, Palumbo M J, Ansari S A, He Q, Tsui K, Nislow C, Morse R H. 2011. Extensive role of the general regulatory factors, Abf1 and Rap1, in determining genome-wide chromatin structure in budding yeast. Nucleic Acids Research 39:2032-2044. doi: 10.1093/nar/gkq1161, PMID: 21081559

Gelbart M E, Rechsteiner T, Richmond T J, Tsukiyama T. 2001. Interactions of Isw2 chromatin remodeling complex with nucleosomal arrays: analyses using recombinant yeast histones and immobilized templates. Molecular and Cellular Biology 21:2098-2106. doi: 10.1128/MCB.21.6.2098-2106.2001, PMID: 11238944

Hass M R, Liow H H, Chen X, Sharma A, Inoue Y U, Inoue T, Reeb A, Martens A, Fulbright M, Raju S, Stevens M, Boyle S, Park J S, Weirauch M T, Brent M R, Kopan R. 2015. SpDamID: Marking DNA bound by protein complexes identifies Notch-Dimer responsive enhancers. Molecular Cell 59:685-697. doi: 10.1016/j.molcel.2015.07.008, PMID: 26257285

He Q, Johnston J, Zeitlinger J. 2015. ChIP-nexus enables improved detection of in vivo transcription factor binding footprints. Nature Biotechnology 33:395-401. doi: 10.1038/nbt.3121

Henikoff J G, Belsky J A, Krassovsky K, MacAlpine D M, Henikoff S. 2011. Epigenome characterization at single base-pair resolution. PNAS 108:18318-18323. doi: 10.1073/pnas.1110731108, PMID: 22025700

Henikoff S, Ramachandran S, Krassovsky K, Bryson T D, Codomo C A, Brogaard K, Widom J, Wang J P, Henikoff J G. 2014. The budding yeast centromere DNA element II wraps a stable Cse4 hemisome in either orientation in vivo. eLife 3:e01861. doi: 10.7554/eLife.01861, PMID: 24737863

Hu Z, Chen K, Xia Z, Chavez M, Pal S, Seol J H, Chen C C, Li W, Tyler J K. 2014. Nucleosome loss leads to global transcriptional up-regulation and genomic instability during yeast aging. Genes & Development 28:396-408. doi: 10.1101/gad.233221.113, PMID: 24532716

Jahan S, Xu W, He S, Gonzalez C, Delcuve G P, Davie J R. 2016. The chicken erythrocyte epigenome. Epigenetics & Chromatin 9:19. doi: 10.1186/s13072-016-0068-2, PMID: 27226810

Jain D, Baldi S, Zabel A, Straub T, Becker P B. 2015. Active promoters give rise to false positive 'Phantom Peaks' in ChIP-seq experiments. Nucleic Acids Research 43:6959-6968. doi: 10.1093/nar/gkv637, PMID: 26117547

Kasinathan S, Orsi G A, Zentner G E, Ahmad K, Henikoff S. 2014. High-resolution mapping of transcription factor-binding sites on native chromatin. Nature Methods 11:203-209. doi: 10.1038/nmeth.2766, PMID: 24336359

Krassovsky K, Henikoff J G, Henikoff S. 2012. Tripartite organization of centromeric chromatin in budding yeast. PNAS 109:243-248. doi: 10.1073/pnas.1118898109, PMID: 22184235

Lieberman-Aiden E, van Berkum N L, Williams L, Imakaev M, Ragoczy T, Telling A, Amit I, Lajoie B R, Sabo P J, Dorschner M O, Sandstrom R, Bernstein B, Bender M A, Groudine M, Gnirke A, Stamatoyannopoulos J, Mimy L A, Lander E S, Dekker J. 2009. Comprehensive mapping of long-range interactions reveals folding principles of the human genome. Science 326:289-293. doi: 10.1126/science.1181369, PMID: 19815776

Lorch Y, Maier-Davis B, Kornberg R D. 2010. Mechanism of chromatin remodeling. PNAS 107:3458-3462. doi: 10.1073/pnas.1000398107, PMID: 20142505

McGhee J D, Felsenfeld G. 1983. Another potential artifact in the study of nucleosome phasing by chromatin digestion with micrococcal nuclease. Cell 32:1205-1215. doi: 10.1016/0092-8674(83)90303-3, PMID: 6301684

Meyer C A, Liu X S. 2014. Identifying and mitigating bias in next-generation sequencing methods for chromatin biology. Nature Reviews Genetics 15:709-721. doi: 10.1038/nrg3788, PMID: 25223782

Morrow B E, Ju Q, Warner J R. 1990. Purification and characterization of the yeast rDNA binding protein REB1. The Journal of Biological Chemistry 265:20778-20783. PMID: 2249986

O'Neill L P, VerMilyea M D, Turner B M. 2006. Epigenetic characterization of the early embryo with a chromatin immunoprecipitation protocol applicable to small cell populations. Nature Genetics 38:835-841. doi: 10.1038/ng1820, PMID: 16767102

Orlando D A, Chen M W, Brown V E, Solanki S, Choi Y J, Olson E R, Fritz C C, Bradner J E, Guenther M G. 2014. Quantitative ChIP-Seq normalization reveals global modulation of the epigenome. Cell Reports 9:1163-1170. doi: 10.1016/j.celrep.2014.10.018, PMID: 25437568

Orsi G A, Kasinathan S, Zentner G E, Henikoff S, Ahmad K. 2015. Mapping regulatory factors by immunoprecipitation from native chromatin. Current Protocols in Molecular Biology 110:21.31.1-21.3121. doi: 10.1002/0471142727.mb2131s110

Park D, Lee Y, Bhupindersingh G, Iyer V R. 2013. Widespread misinterpretable ChIP-seqbias inyeast. PLoS One 8:e83506. doi: 10.1371/journal.pone.0083506, PMID: 24349523

Paul E, Tirosh I, Lai W, Buck M J, Palumbo M J, Morse R H. 2015. Chromatin mediation of a transcriptional memory effect in yeast. G3(Bethesda) 5:829-838. doi: 10.1534/g3.115.017418, PMID: 25748434

Pekgoz Altunkaya G, Malvezzi F, Demianova Z, Zimniak T, Litos G, Weissmann F, Mechtler K, Herzog F, Westermann S. 2016. CCAN Assembly configures composite binding interfaces to promote Cross-Linking of Ndc80 complexes at the kinetochore. Current Biology 26:2370-2378. doi: 10.1016/j.cub.2016.07.005, PMID: 27524485

Phair R D, Scaffidi P, Elbi C, Vecerova' J, Dey A, Ozato K, Brown D T, Hager G, Bustin M, Misteli T. 2004. Global nature of dynamic protein-chromatin interactions in vivo: three-dimensional genome scanning and dynamic interaction networks of chromatin proteins. Molecular and Cellular Biology 24:6393-6402. doi: 10.1128/MCB.24.14.6393-6402.2004, PMID: 15226439

Ramachandran S, Zentner G E, Henikoff S. 2015. Asymmetric nucleosomes flank promoters in the budding yeast genome. Genome Research 25:381-390. doi: 10.1101/gr.182618.114, PMID: 25491770

Rhee H S, Pugh B F. 2011. Comprehensive genome-wide protein-DNA interactions detected at single-nucleotide resolution. Cell 147:1408-1419. doi: 10.1016/j.cell.2011.11.013, PMID: 22153082

Sanborn A L, Rao S S, Huang S C, Durand N C, Huntley M H, Jewett A I, Bochkov I D, Chinnappan D, Cutkosky A, Li J, Geeting K P, Gnirke A, Melnikov A, McKenna D, Stamenova E K, Lander E S, Aiden E L. 2015. Chromatin extrusion explains key features of loop and domain formation in wild-type and engineered genomes. PNAS 112:E6456-E6465. doi: 10.1073/pnas.1518552112, PMID: 26499245

Sanders M M. 1978. Fractionation of nucleosomes by salt elution from micrococcal nuclease-digested nuclei. The Journal of Cell Biology 79:97-109. doi: 10.1083/jcb.79.1.97, PMID: 701381

Schmid M, Durussel T, Laemmli U K. 2004. ChIC and ChEC; genomic mapping of chromatin proteins. Molecular Cell 16:147-157. doi: 10.1016/j.molcel.2004.09.007, PMID: 15469830

Shivaraju M, Unruh J R, Slaughter B D, Mattingly M, Berman J, Gerton J L. 2012. Cell-cycle-coupled structural oscillation of centromeric nucleosomes in yeast. Cell 150:304-316. doi: 10.1016/j.cell.2012.05.034, PMID: 22817893

Skene P J, Henikoff S. 2015. A simple method for generating high-resolution maps of genome-wide protein binding. eLife 4:e09225. doi: 10.7554/eLife.09225, PMID: 26079792

Solomon M J, Varshavsky A. 1985. Formaldehyde-mediated DNA-protein crosslinking: a probe for in vivo chromatin structures. PNAS 82:6470-6474. doi: 10.1073/pnas.82.19.6470, PMID: 2995966

Southall T D, Gold K S, Egger B, Davidson C M, Caygill E E, Marshall O J, Brand A H. 2013. Cell-type-specific profiling of gene expression and chromatin binding without cell isolation: assaying RNA Pol II occupancy in neural stem cells. Developmental Cell 26:101-112. doi: 10.1016/j.devcel.2013.05.020, PMID: 23792147

Tang Z, Luo O J, Li X, Zheng M, Zhu J J, Szalaj P, Trzaskoma P, Magalska A, Wlodarczyk J, Ruszczycki B, Michalski P, Piecuch E, Wang P, Wang D, Tian S Z, Penrad-Mobayed M, Sachs L M, Ruan X, Wei C L, Liu E T, et al. 2015. CTCF-Mediated human 3D genome architecture reveals chromatin topology for transcription. Cell 163:1611-1627. doi: 10.1016/j.cell.2015.11.024, PMID: 26686651

Teves S S, Henikoff S. 2012. Salt fractionation of nucleosomes for genome-wide profiling. Methods in Molecular Biology 833:421-432. doi: 10.1007/978-1-61779-477-3_25, PMID: 22183608

Teytelman L, Thurtle D M, Rine J, van Oudenaarden A. 2013. Highly expressed loci are vulnerable to misleading ChIP localization of multiple unrelated proteins. PNAS 110:18602-18607. doi: 10.1073/pnas.1316064110, PMID: 24173036

Thorvaldsdo' ttir H, Robinson J T, Mesirov J P. 2013. Integrative Genomics Viewer (IGV): high-performance genomics data visualization and exploration. Briefings in Bioinformatics 14:178-192. doi: 10.1093/bib/bbs017, PMID: 22517427 van Steensel B, Delrow J, Henikoff S. 2001. Chromatin profiling using targeted DNA adenine methyltransferase. Nature Genetics 27:304-308. doi: 10.1038/85871, PMID: 11242113

Wisniewski J, Hajj B, Chen J, Mizuguchi G, Xiao H, Wei D, Dahan M, Wu C. 2014. Imaging the fate of histone Cse4 reveals de novo replacement in S phase and subsequent stable residence at centromeres. eLife 3:e02203. doi: 10.7554/eLife.02203, PMID: 24844245

Wollmann P, Cui S, Viswanathan R, Berninghausen O, Wells M N, Moldt M, Witte G, Butryn A, Wendler P, Beckmann R, Auble D T, Hopfner K P. 2011. Structure and mechanism of the Swi2/Snf2 remodeler Mot1 in complex with its substrate TBP. Nature 475:403-407. doi: 10.1038/nature10215, PMID: 21734658

Zentner G E, Henikoff S. 2013. Mot1 redistributes TBP from TATA-containing to TATA-less promoters. Molecular and Cellular Biology 33:4996-5004. doi: 10.1128/MCB.01218-13, PMID: 24144978

Zentner G E, Kasinathan S, Xin B, Rohs R, Henikoff S. 2015. ChEC-seq kinetics discriminates transcription factor binding sites by DNA sequence and shape in vivo. Nature Communications 6:8733. doi: 10.1038/ncomms9733, PMID: 26490019

Zentner G E, Tsukiyama T, Henikoff S. 2013. ISWI and CHD chromatin remodelers bind promoters but act in gene bodies. PLoS Genetics 9:e1003317. doi: 10.1371/journal.pgen.1003317, PMID: 23468649.

CUT&RUN protocol for yeast Nuclei: from $\sim 5 \times 10^8$ S. cerevisiae cells @ OD600 ~-0.7 (Orsi et al., 2015). Other methods for preparing nuclei are expected to give equivalent results. Bio-Mag Plus Concanavalin A coated beads can be purchased from Polysciences, Inc. (Warrington, PA, Catalog #86057). Digestion buffer (150 ml) 3 ml 1M HEPES pH 7.5, 20 mM 3 ml 5M NaCl 100 mM water to 150 ml. Add 1 mM phenylmethanylsulfonyl fluoride (PMSF, 100 mM stock in ethanol) just before use and hold on ice after addition. HNT wash buffer (100 ml) 100 ml Digestion buffer 100 mL Tween 20 0.1% 1 mM PMSF just before use (=HNT-Pi) For preparing beads. HNT++ =HNT+1 mM $CaCl_2$, +1 mM $MnCl_2$. $Ca^{++}$ and $Mn^{++}$ are needed to activate lectins. Although the manufacturer recommends 1 mM $MgCl_2$ as well, this can cause DNA degradation and omitting $MgCl_2$ had no effect on binding of permeabilized nuclei to beads. HNT-PPi blocking buffer (20 ml): 20 ml HNT wash buffer 67 mL 30% BSA 0.1% 2 mini-Complete Ultra (Roche) protease inhibitor tablets 1 mM PMSF just before use HNT-preblock (per 1 ml) 900 mL HNT-PPi 100 mL 30% BSA 3% 4 mL 0.5M EDTA 2 mM 1 mM PMSF just before use 2×STOP (10 ml) 400 ml 5M NaCl 200 mM 400 mL 0.5M EDTA 20 mM 200 mL 0.2M EGTA 4 mM+50 mL Thermo RNase A (10 mg/ml) 50 mg/ml+20 mL glycogen (20 mg/ml) 40 g/ml water to 10 ml. For spike-in add ~10 pg/ml spike-in DNA (e.g. mononucleosome-sized fragments from MNase digestion of formaldehyde crosslinked *Drosophila* S2 cells). 1×STOP (10 ml) 200 ml 5M NaCl 100 mM 200 mL 0.5M EDTA 10 mM 100 mL 0.2M EGTA 2 mM water to 10 ml.

Procedure:

Pre-blocking: Add 1 ml HNT-preblock with gentle pipetting. Let sit 5 min, then spin, place on the magnet stand, pull off the supernatant and continue to the next step. Antibody binding: Block 5 min in 1 ml blocking buffer (HNT-PPi with 0.1% BSA). Place on the magnet stand and pull off the supernatant and bring up in 500 mL blocking buffer. While vortexing gently add 500 mL anti-FLAG (containing 5 mL Sigma M2 mouse anti-FLAG anti-body—1:200 final). Incubate on rotator 2 hr at 4° C. Spin and wash once in 1 ml HNT-Pi Wash buffer.

Secondary antibody binding (optional): If a mouse monoclonal antibody was used, a rabbit anti-mouse secondary antibody (e.g. Abcam ab46540) is needed to provide high specificity of pA-MN binding. Use of a secondary antibody amplifies the cleavage rate by 1-2 orders of magnitude. Follow the same procedure as in Step 3, except incubate for 1 hr.

Bind pA-MN: Pull off the supernatant and bring up in 500 mL blocking buffer. While vortexing add 500 mL of blocking buffer containing 5 mL pA-MN (600 mg/ml). Incubate 1 hr on rotator at 4° C. Spin and wash twice in 1 ml HNT-Pi Wash buffer.

Digestion: Decant and wash once in 1 ml Digestion buffer, bring up in 1.2 ml Digestion buffer, and divide each into 8×150 mL time-point aliquots, placing directly on the bottom of the tube. Equilibrate to 0° C. on blocks fitted for 1.7 ml tubes in ice-water. Place a 3 mL 100 mM $CaCl_2$ (to 2 mM) drop on the side of each tube. To obtain a time course, begin digestion by vortexing tubes and replacing in the ice-water holder. Stop by addition of 150 mL 2×STOP (optionally with spike-in DNA added). For total DNA extraction: Add 3 mL 10% SDS (to 0.1%), and 2.5 mL Proteinase K (20 mg/ml) to samples and vortex. Incubate at 70° C. for 10 min with occasional inversion to mix. (For formaldehyde crosslinked cells incubate 4 hr at 65° C. to reverse the crosslinks.) Mix with 300 mL phenol-chloroform-isoamyl, spin 5 min 13 krpm and decant to afresh tube. Add ½ volume (150 mL) AMPure beads and mix well. Let sit 10 min and place on a magnet stand. Transfer the supernatant to a fresh tube to remove remaining beads, then precipitate the supernatant with 1 ml ethanol, chill and spin. Wash in 1 ml 100% ethanol and bring up in 25 mL 0.1×TE8 for library preparation. For chromatin-associated complexes: Follow the total DNA extraction procedure. Include 0.5 mM spermidine in the HMT, Digestion and STOP buffers. For salt fractionation: Reduce the volume of the digestion slurry from 150 mL to 50 mL and stop the reaction with 2×STOP where 4M NaCl is substituted for 200 mM NaCl, and leave out the RNase. After incubation at 37° C. add 200 mL RNase (100 mg/ml) in water, incubate 20 min at 37° C., then continue with the 5' 13,000 rpm spin to separate the supernatant from the pellet.

Isolating excised fragments: Incubate 37° C. 20 min. Spin 5' 13,000 rpm 4° C., place on magnet stand and pull off supernatants to fresh tubes. Bring the bead pellet up in 300 mL 1×STOP (no RNase or glycogen). Add 3 mL 10% SDS (to 0.1%), vortex, and add 2.5 mL Proteinase K (20 mg/ml) to samples. Incubate at 70° C. for 10 min with occasional inversion to mix.

Extract supernatant DNA for libraries: Mix with 300 mL phenol-chloroform-isoamyl alcohol, transfer to phase-lock tubes, spin, then extract with 300 mL chloroform. Remove to a fresh tube containing 2 mL of 2 mg/ml glycogen in the tube before addition. Add 750 mL ethanol, chill and spin. Wash the pellet in 1 ml 100% ethanol, air dry and dissolve in 25 mL 0.1×TE8. Some of the DNA represents on the order of ~1% of the high molecular weight DNA that becomes solubilized, but which will not appreciably amplify during library preparation.

Extract pellet fraction for gel analysis (optional): Mix with 300 mL phenol-chloroform-isoamyl alcohol, spin 5 min 13,000 rpm, put on a magnet stand for ~5 min and pull off. Remove aqueous layer to a fresh tube containing 2 mL of 2 mg/ml glycogen in the tube before addition. Add 750 mL ethanol, chill and spin. Wash the pellet in 1 ml 100% ethanol, air dry and dissolve in 25 mL 0.1×TE8, then centrifuge 10 min 13 krpm to pellet most of the insoluble brown material that came off the beads. Protocol has been used to map CTCF, Myc, Max and H3K27me3 in human K562 cells. A very low background was observed. This protocol relies on the cut chromatin fragments 'leaching' out of the intact nuclei into the reaction volume. The intact nuclei are spun down at the end of the experiment and the DNA extracted from the supernatant fraction. This isolates the liberated chromatin fragments and therefore does not need further size selection. The protocol can either use centrifugation (600 g; 3 min; swing-bucket rotor) or concanavalin A coated magnetic beads (BioMag Plus #86057) to isolate nuclei at each step.

Typical experimental samples: ($10 \times 10^6$ cells per reaction): i. no antibody; free pA-MNase (i.e. PA-MNase not washed out); ii. no antibody+pA-MNase (controls for background MNase activity); iii. antibody+pA-MNase (experimental sample) We take small QC samples before $CaCl_2$ addition ('input') and after the reaction has been stopped ('end') to assay how the MNase reaction proceeded prior to fractionation. Protease inhibitors (Roche complete EDTA-free) are added to buffers at a final concentration of 1× from 50× stock.

1. Optional: Prepare beads (use 50 ml beads per $10 \times 10^6$). Wash 3 times in 3 volumes of binding buffer. Resuspend in 1 volume binding buffer 2. Harvest cells; spin down at 600 g 3 min in swing bucket rotor (typically 10 million cells per sample).

3. Wash cells by resuspending in 1 ml cold Phosphate Buffered Saline (scale up if greater than 10 million cells) by gently pipetting. Spin down as above.

4. Resuspend cells in 1 ml NE1 by gently pipetting (scale up if greater than 10 million cells). Place on ice for 10 min. Magnetic beads: Spin down as above and resuspend in NE1. Add beads directly to resuspended in nuclei, with gentle pipetting. 5 min @ room temp on mixing platform. Bind to magnet for ~2 min, discard supernatant. or Centrifugation: pellet nuclei at 600 g 3 min in swing bucket rotor.

5. Resuspend in 1.7 ml CUT&RUN Buffer 1 by gently pipetting and transfer to 1.7 ml Eppendorf tubes. Place on ice for 5 min. Collect nuclei by magnet or centrifugation as above.

6. Resuspend in 1.5 ml CUT&RUN Buffer 2 by gently pipetting. Collect nuclei by magnet or centrifugation as above.

7. Resuspend in CUT&RUN Buffer 2 by gently pipetting. Use 10 million cells in 500 ml volume in 0.5 ml Eppendorf tubes. Add antibody as required including secondary antibody. Place on mixing platform at 4° C. for 2 hr (0.5 ml tubes give a tighter pellet for centrifugation and reduce the sloshing of liquid during the incubation to maintain nuclear integrity).

8. Three 5 min washes with 500 ml CUT&RUN Buffer 2 on a mixing platform at 4° C. Collect nuclei by magnet or centrifugation as above.

9. Resuspend in 300 ml CUT&RUN Buffer 2. Add 3 mg protein A-MNase fusion (5 ml @ 600 ng/ml or 8.3 ml @ 360 ng/ml). Place on mixing platform at 4° C. for 1 hr (300 ml reaction volume allows the supernatant fraction to be easily extracted/EtOH ppt in a 1.7 ml tube).

10. Three 5 min washes with 300 ml CUT&RUN Buffer 2 on a mixing platform at 4° C. NOT for free MNase sample (keep on mixing platform). Collect nuclei by magnet or centrifugation as above.

11. Resuspend in 300 ml CUT&RUN Buffer 2. Take 12 ml as 'input' and place into 288 mL DNA extraction buffer 12. Place tubes in wet ice (it is imperative the digestion is performed at 0° C. —preferably use an aluminum block to maintain the temperature). Add CaCl$_2$ to final concentration of 2 mM (6 ml of 100 mM CaCl$_2$). Mix rapidly by inverting and place on wet ice. Incubate for desired time (e.g. 15 min). Typically place free MNase sample at 37° C. for 5 min. This allows digestion to be evaluated by agarose gel electrophoresis.

13. Stop by adding a master mix of EDTA to 10 mM and EGTA to 20 mM. Mix rapidly by inverting and place on ice. Take 12 ml as 'end' and place into 288 mL DNA extraction buffer. Option: add spike-in DNA Option A 14. Place on a mixing platform at 4° C. for 1 hr to let the chromatin fragments leach out. Spin down at 600 g 3 min SW rotor (even if using the magnetic bead approach). Take supernatant.

15. Extract DNA from supernatant by adding: 3 ml 10% SDS (final concentration 0.1%), 5 ml proteinase K at 10 mg/ml, 2 ml RNaseA at 1 mg/ml and 5 ml 5 M NaCl (final concentration 300 mM). Vortex and place at 55° C. for 1 hr. Phenol extract; EtOH precipitate (add 1 ml glycogen); EtOH wash. Resuspend in 20 ml H20

Option B

14. Extract all DNA and then use a very simple size selection to separate the large uncut pieces of the genome from the small footprints. This may be better for large, potentially insoluble protein complexes that might not diffuse through the nuclear pores.

Extract DNA from entire reaction: 3 ml 10% SDS (final concentration 0.1%), 5 ml proteinase K at 10 mg/ml, 2 ml RNaseA at 1 mg/ml and 5 ml 5 M NaCl (final concentration 300 mM). Vortex and place at 55° C. for 1 hr. Phenol extract and then EtOH precipitate (add 1 ml glycogen); EtOH wash and resuspend in 150 ml H20

15. Size selection of cut fragments (~700 bp) using Beckmann Agencourt AMPure XP beads (A63881)

Allow beads to warm up to room temp before use;
Add 75 ml beads, mix by pipetting 10×;
Incubate at room temp for 5 min;
Place on magnet for 2 min;
Take supernatant fraction (it is imperative not to take any of high MW DNA attached to the beads, one can spin down the supernatant fraction to check for beads);
precipitate by adding 700 ml EtOH and 1 ml glycogen (no additional salt required); 70% EtOH wash;
Resuspend in 20 ml H$_2$O.
Buffers:
Protease inhibitors (Roche complete EDTA-free) added to 1× from 50× stock in water Binding buffer
1×PBS;
1 mM CaCl$_2$;
1 mM MgCl$_2$;
1 mM MnCl$_2$;

NB: We have found that nucleases in some cells cause Mg++-dependent degradation of DNA. The presence of Mg++ in the binding buffer follows the manufacturer's recommendation, but only Ca++ and Mn++ are needed to activate lectins. Omitting MgCl$_2$ had no effect on binding of permeabilized cells to beads.

NE1:
20 mM Hepes-KOH pH 7.9;
10 mM KCl;
1 mM MgCl$_2$;
0.1% Triton X-100; and
20% Glycerol.

NB: We find that substituting 0.5 mM spermidine for 1 mM MgCl$_2$ can be used to avoid Mg++-dependent DNA degradation.

CUT&RUN Buffer 1:
20 mM Hepes pH 7.5;
150 mM NaCl;
2 mM EDTA;
0.5 mM Spermidine;
0.1% BSA.
CUT&RUN Buffer 2:
20 mM Hepes pH 7.5;
150 mM NaCl;
0.5 mM Spermidine;
0.1% BSA.
Other Reagents:
100 mM CaCl$_2$;
10% SDS;
5M NaCl;
500 mM EDTA;
Proteinase K;
500 mM EGTA;
RNaseA;
Extraction buffer.

DNA extraction for 12 ml QC samples taken during Protocol:
Phenol extract;
Ethanol precipitate;
Ethanol wash;
Resuspend in 20 mL H$_2$O;
RNase-treat;
Electrophorese on 0.7% agarose gel.

Example 2

Cleavage Under Targets and Release Using Nuclease (CUT&RUN) is an epigenomic profiling strategy in which antibody-targeted controlled cleavage by micrococcal nuclease releases specific protein-DNA complexes into the supernatant for paired-end DNA sequencing. As only the targeted fragments enter into solution, and the vast majority of DNA is left behind, CUT&RUN has exceptionally low background levels. CUT&RUN outperforms the most widely used Chromatin Immunoprecipitation (ChIP) protocols in resolution, signal-to-noise, and depth of sequencing required. In contrast to ChIP, CUT&RUN is free of solubility and DNA accessibility artifacts and can be used to profile insoluble chromatin and to detect long-range 3D contacts without cross-linking. Here we present an improved CUT&RUN protocol that does not require isolation of nuclei and provides high-quality data starting with only 100 cells for a histone modification and 1000 cells for a transcription factor. From cells to purified DNA CUT&RUN requires less than a day at the lab bench.

Introduction

Development of the Protocol

Figure 24:
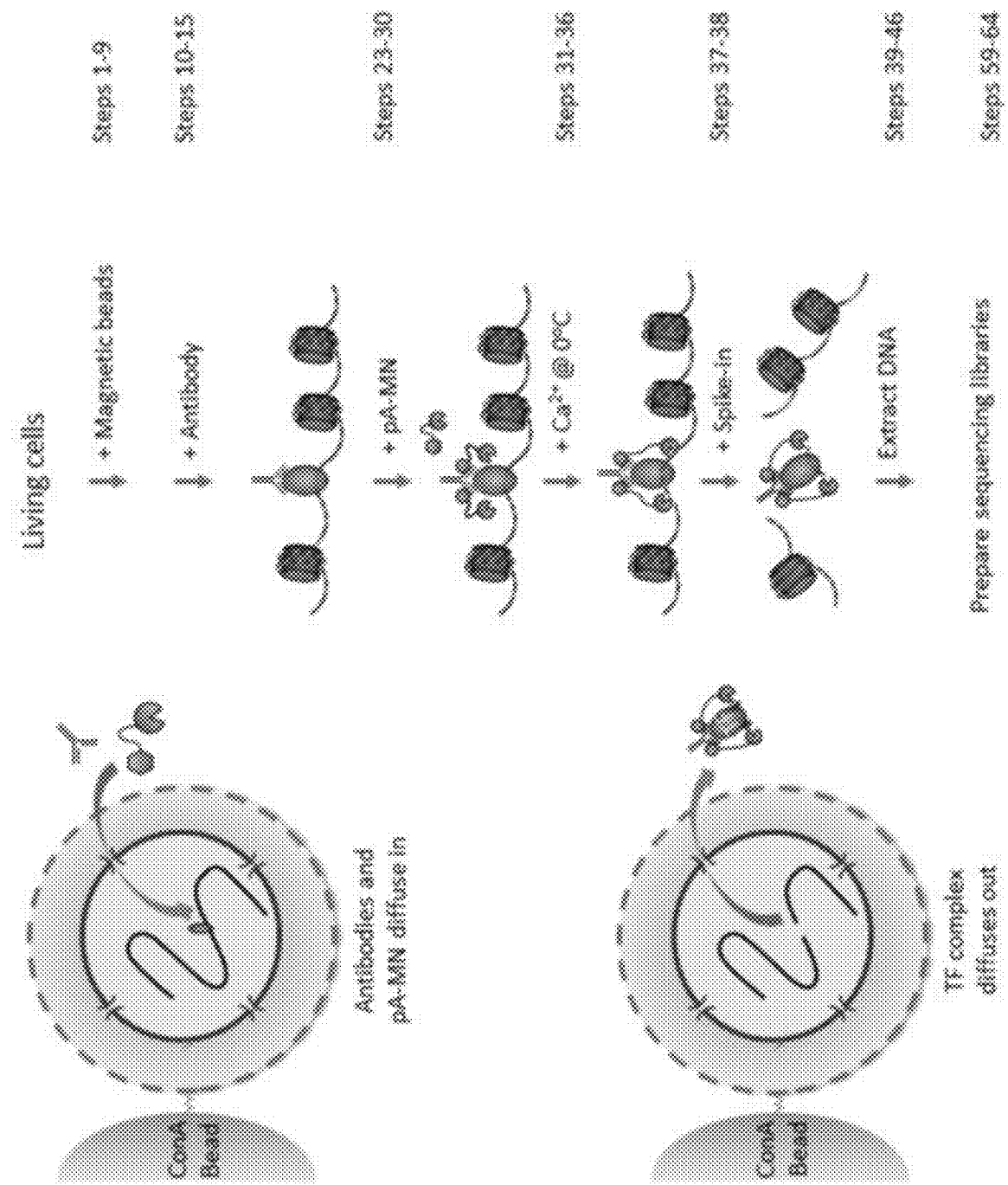
FIG. 24 shows that CUT&RUN requires less than a day from cells to DNA. A schematic overview of the CUT&RUN protocol. Cells are harvested and bound to concanavalin A-coated magnetic beads. Cell membranes are permeabilized with digitonin to allow the specific antibody to find its target. After incubation with antibody, beads are briefly washed, and then incubated with pA-MN. Cells are chilled to 0° C., and digestion begins with addition of $Ca^{2+}$. Reactions are stopped by chelation including spike-in DNA and the DNA fragments released into solution by cleavage are extracted from the supernatant.

All of the cells in a multicellular organism have the same genomic sequence, but different gene expression patterns underpin tissue specification. Differences in gene expression arise from the binding of transcription factors (TFs) and their recruitment of chromatin-associated complexes that modify and mobilize nucleosomes. As a result, genome-wide mapping of TFs, chromatin associated complexes and chromatin states, including histone variants and post-translational modifications (PTMs), has become a major focus of research. For over 30 years, chromatin immunoprecipitation (ChIP) has been the predominant method of mapping protein-DNA interactions. With ChIP, cells are crosslinked with formaldehyde, then the entire cellular content is solubilized to fragment the chromatin fiber, and an antibody is added to isolate the chromatin fragments of interest. Whereas the readout strategies for ChIP have evolved over 30 years from gel electrophoresis[1] to massively parallel sequencing[2,3], the fundamentals of ChIP have remained largely unchanged. Although ChIP-seq allows base-pair resolution mapping of TFs[4,5], issues remain with high background that limits sensitivity, requirements for large number of cells, and artifacts resulting from cross-linking and solubilization[6-10]. Without an alternative method that is based on different principles from ChIP, it has been difficult to distinguish true positives from misleading false positive artifacts. Alternative strategies have been used for the genome-wide mapping of protein-DNA interactions that can address some of these limitations of ChIP. For example, several methods, including DNase1 footpinting[11], FAIRE-seq[12], Sono-seq[13], MNase-seq[14,15] and ATAC-seq[16], are being used to map TF binding genome-wide using a sequencing read-out. However, as these approaches are not targeted to specific proteins, they are not specific to any one TF. Furthermore they cannot be used to map specific chromatin states such as those demarcated by histone PTMs, which may be used to clinically differentiate healthy and disease states[17]. Other methods provide target-specific mapping by genetically engineering a fusion between the protein of interest and an enzyme that methylates the surrounding DNA in the case of DamID[18], or targeted cleavage of the protein's footprint in the case of chromatin endogenous cleavage (ChEC)[19]. Enzyme tethering approaches are performed in vivo (DamID) or in situ (ChEC) without the need to fragment and solubilize chromatin. However, as they require a transgenic approach, this limits the scalability to large infrastructural consortiums such as ENCODE and the transferability to a clinical setting. In addition, these methods cannot map histone PTMs. These limitations were partially overcome by the chromatin immunocleavage (ChIC) method, whereby crude nuclei from crosslinked cells were first treated with a TF-specific antibody and then a fusion protein between protein A and Micrococcal Nuclease (pA-MN), which can be activated by calcium ions[19]. However, ChIC was developed using a Southern blot read-out, and so its applicability to genome-wide profiling remained unclear for over a decade. We recently developed a ChIC strategy that we termed CUT&RUN (cleavage under targets & release using nuclease; FIG. 24)[20]. The disclosed protocol took unfixed nuclei and attached them to a solid support using concanavalin-A coated magnetic beads to allow simple handling. Following in situ binding of antibody and pA-MN specifically to the target protein, seconds after exposure to calcium at 0° C., cleavage occurred on either side of the TF. As noncrosslinked nuclei were used, cleaved fragments released with two cuts were free to diffuse out of the nuclei, and so by simply pelleting the intact nuclei, the supernatant containing released chromatin fragments was used to extract DNA directly for sequencing. It was discovered that performing the Ca$^{2+}$-dependent digestion reaction at 0° C. was essential to limit the diffusion of the cleaved chromatin complexes, which would otherwise cleave and release accessible DNA. Overall, it was shown that CUT&RUN has a much higher signal-to-noise ratio than crosslinking ChIP-seq, thereby allowing identification of previously unknown genomic features. CUT&RUN achieved base-pair resolution of mammalian TFs with only 10 million sequenced reads.

The need for quantitative mapping of protein-DNA interactions has become increasingly apparent[21]. However, due to the complexity of ChIP, which involves genome-wide solubilization of chromatin and immunoprecipitation, an involved quantitation strategy is required whereby a fixed number of cells from a different species that has antibody cross-reactivity is spiked-in[22]. The requirement for conserved epitopes limits general applicability. In contrast, due to the inherent simplicity of CUT&RUN, a straightforward spike-in strategy with heterologous DNA sufficed to accurately quantify binding events. In summary, CUT&RUN has several advantages over ChIP-seq: (1) The method is performed in situ in non-crosslinked cells and does not require chromatin fragmentation or solubilization; (2) The intrinsically low background allows low sequence depth and identification of low signal genomic features invisible to ChIP; (3) The simple procedure can be completed within a day and is suitable for robotic automation; (4) The method can be used with low cell numbers compared to existing methodologies; (5) A simple spike-in strategy can be used for accurate quantitation of protein-DNA interactions. As such, CUT&RUN represents an attractive replacement for ChIPseq, which is one of the most popular methods in biological research.

Experimental Design

Figure 25:
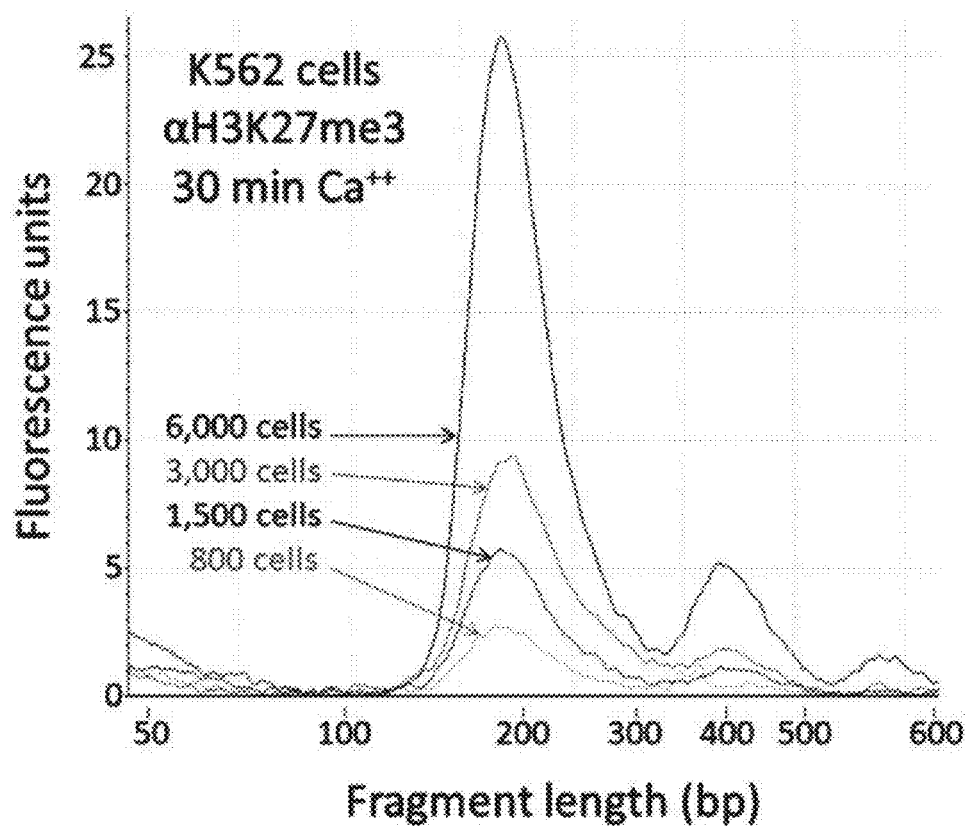
FIG. 25 shows tapestation analysis of an abundant histone epitope (H3K27me3) as a same-day positive control. The remainder of these samples were used to make libraries for sequencing, with results shown in FIG. 28.
Figure 26:
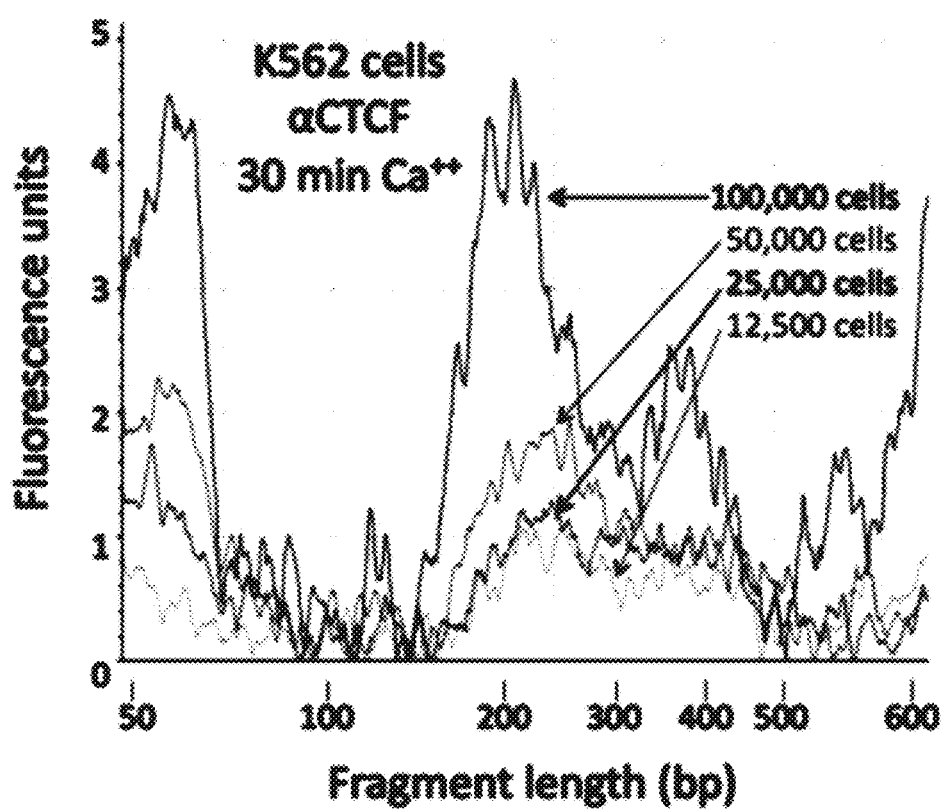
FIG. 26 shows tapestation analysis of CUT&RUN cleaved fragments using an anti-CTCF antibody. The remainder of these samples were used to make libraries for sequencing, with results shown in FIG. 29.
Figure 27:
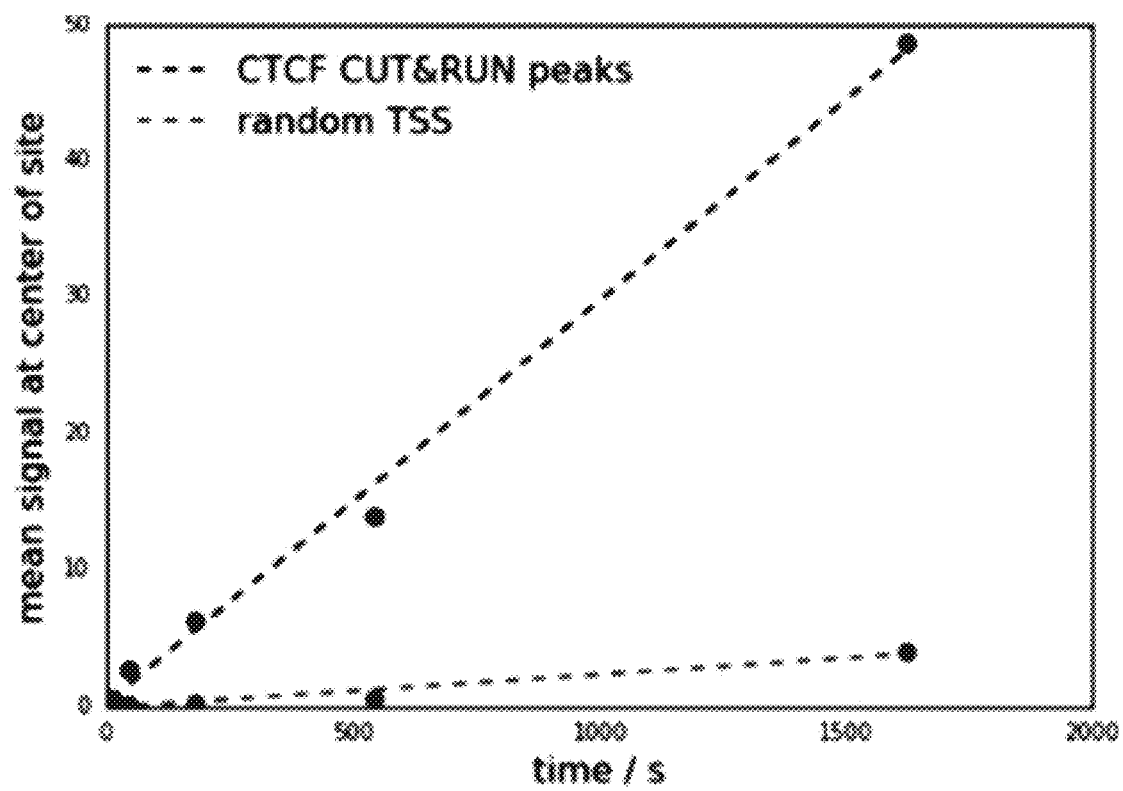
FIG. 27 shows yield increases with digestion time with little change in signal-to-noise. By scaling to spike-in DNA, quantitative measurement of the amount of cleaved DNA fragments is possible. The average signal over ~20,000 CTCF CUT&RUN binding sites is compared to an equal number of non-overlapping transcriptional start sites (TSS) as a negative control regions. Spike in scaled signal was summed over the −50 to +50 bp region relative to the center of the site or TSS.

The CUT&RUN method for the in situ targeted cleavage and release of chromatin complexes is straightforward and can be completed in under a day using standard lab equipment. Herein is provided a detailed protocol and various options that might be used to tailor the protocol to specific situations. One of the strengths of CUT&RUN is that the entire reaction is performed in situ, whereby the antibody and pA-MN are free to diffuse into the nucleus. The original protocol used nuclei prepared by a combination of hypotonic lysis and treatment of cells with Triton X-100. This has been successful with a number of cell lines, but we have recently adapted the protocol to use cells permeabilized by the non-ionic detergent digitonin, which has been successfully used in other in situ methods, including ChEC-seq[23] and ATAC-seq[24]. Digitonin partitions into membranes and extracts cholesterol. Membranes that lack cholesterol are minimally impacted by digitonin[25,26]. Nuclear envelopes are relatively devoid of cholesterol compared to plasma membranes. As such, treatment of cells with digitonin represents a robust method for permeabilizing cells without compromising nuclear integrity[26]. The protocol described here uses digitonin, but it is possible that individual experimental situations call for generating intact nuclei by other means, and such nuclei can be prepared by a suitable method, bound to concanavalin A-coated beads and then enter the protocol below at step 10[20]. One of the limitations of a protocol that has inherently low background and is amenable to low cell numbers is that the amount of DNA recovered can be very low, such that analysis even by sensitive capillary electrophoresis orpicogreen assays (e.g. Agilent Tapestation and Qubit) are problematic. In addition, high resolution mapping techniques that cleave a minimal footprint are not suitable to PCR-based analysis of known binding loci, as it is not commonly possible to design ~50 bp PCR amplicons. As such, it is recommended to use a positive control antibody that targets an abundant epitope and therefore the DNA can be readily detected. A rabbit monoclonal antibody raised against H3K27me3 has been successfully used, with capillary electrophoresis showing with the amount of cleaved fragments being proportional to the number of starting cells. A nucleosomal ladder is expected by Tapestation or other sensitive electrophoretic analysis method (FIG. 25), and the use of a monoclonal antibody avoids potential lot-to-lot variation that can complicate troubleshooting. For less abundant epitopes such as CTCF, it is harder to detect the cleaved fragments by even sensitive electrophoretic analysis (FIG. 26). Once the expected digested DNA pattern is observed for the positive control by capillary electrophoresis such as H3K37me3, it is not necessary to sequence this sample. As a negative control, the use of a non-specific rabbit IgG antibody that will randomly coat the chromatin at low efficiency without sequence bias is recommended. A no-antibody control is not recommended, as the lack of tethering increases the possibility that slight carry-over of pA-MN will result in preferential fragmentation of hyper-accessible DNA. Targeted cleavage has been shown to occur within seconds of adding $Ca^{2+}$ ions, and by virtue of being a sterically regulated tethered reaction, the cleavage pattern was constant over time. However, longer digestion times release more material with no apparent change in the signal-to-noise ratio (FIG. 27). Therefore, it is recommended to digest for 30 minutes as a starting point that can be tailored based upon epitope abundance and antibody concentration. Applications of the method CUT&RUN has the potential to replace all ChIP-based applications. For a typical research project in which ChIP-seq is currently used, transitioning to CUT&RUN can be done efficiently, as it can be done entirely on the benchtop using standard equipment that is already present in most molecular biology laboratories. Furthermore, as CUT&RUN is performed in situ in permeabilized cells that can readily be attached to a solid support such as magnetic beads, coated plates or glass slides, this method will readily transfer to robotics allowing high-throughput from cell to sequencing library. CUT&RUN to robotics should be more straightforward than is the case for ChIP-seq, as CUT&RUN does not require equipment such as sonicators or high speed spin steps to remove insoluble material that are difficult to automate. Standard crosslinking ChIP protocols are not suitable for low cell numbers that are often obtained after fluorescence activated cell sorting or dissection, or in clinical settings. In light of this limitation, ATAC-seq has been used down to 5000 cells[24]. But ATAC-seq is limited to nonspecific identification of TFs that are in accessible regions of chromatin and is unable to distinguish chromatin states demarcated by histone PTMs. Problems of epitope masking in crosslinking ChIP leading to low efficiency can be mitigated by using a native ChIP strategy, which was shown to provide high-quality data with as few as 5000 cells for abundant nucleosome epitopes, but was not applied to TFs[27]. Here, it is shown that CUT&RUN is suitable for application to 100 cells for profiling H3K27me3 or 1000 cells for CTCF sequence-specific DNA binding protein. Therefore, CUT&RUN makes possible targeted genome-wide maps of protein-DNA interactions for rare cell types. A recent advance in single-cell genomic analysis is single-cell combinatorial indexing ("sci"), whereby split-pool barcoding is used to uniquely label a large number of intact individual cells without ever having to perform reactions on individual isolated cells. This approach has been successfully used for profiling transcriptomes[28], chromatin accessibility (sci-ATAC-seq[29]), and 3-D interactions (sci-Hi-C[30]) in single cells. CUT&RUN, unlike ChIP, is performed inside intact permeabilized cells and therefore is amenable to combinatorial barcoding to map single-cell epitope-specific epigenomic landscapes. Further development of the protocol could include a replacement for sequential ChIP to map cooccupancy of subunits within a protein complex. Sequential ChIP-seq has typically been challenging, and because of the very low yield after the second immunoprecipitation step, it is suitable only for abundant chromatin complexes. However, by first performing CUT&RUN, the cleaved chromatin complexes that are liberated into the supernatant at high efficiency could be immunoprecipitated with a second antibody. This application allows compositional analysis and mapping of chromatin complexes genome-wide. It was shown that by virtue of CUT&RUN being an in situ cleavage approach and the inherent flexibility of the chromatin fiber, it is possible to probe the local chromatin structure including adjacent nucleosomes and 3D contacts. Hi-C, ChIA-PET and HiChIP, which are popular technologies for genome-wide mapping of 3D nuclear organization, rely on formaldehyde crosslinking to stabilize protein-protein interactions[31-33]. As such, these techniques have no formal distance constraint for mapping a positive genomic interaction, as very large nuclear structures could be crosslinked. In contrast, TSA-seq[34] and genome architecture mapping[35] have distance constraints and therefore measure cytological distance, either by the limited diffusion of a reactive species or the cryosectioning of cells. Similarly, in CUT&RUN, the reach of protein A-MNase provides an intrinsic limit to how far cleavage can occur from an epitope and therefore how close two interacting DNA loci need to be in order to be cleaved by tethering to one of them. By combining CUT&RUN with a proximity based ligation method, it is possible to generate factor-specific high resolution maps of nuclear architecture. Other novel applications can be envisioned. Any epitope for which an antibody is available can potentially be subjected to profiling using CUT&RUN, and CUT&RUN in situ mapping of lncRNAs would seem to be an attractive alternative to DRIP-seq[36]. In addition, the ability of CUT&RUN to profile insoluble chromatin[20] indicates that combining CUT&RUN with salt fractionation will allow for an epigenomic map to be based on chromatin solubility, which has traditionally been used to define classical "active" chromatin[37-39]. In this way, each DNA-binding protein or chromatin feature being profiled can be enriched with information about its solubility, a key physical property. Although salt-fractionation can be performed with MNase-based ChIP-seq[39] high salt can disrupt the complex and cause loss of the epitope prior to antibody binding, whereas with CUT&RUN, salt fractionation is performed only after the antibody is bound and the fragments cleaved Comparison with Other Methods Table 1 lists metrics for CUT&RUN and three ChIP-seq methods, X-ChIP-seq[3], ChIP-exo[4] and NChIP-seq[40]. Compared to these ChIP-seq methods, CUT&RUN requires fewer cells and fewer reads, has a higher signal-to-noise ratio, has no fragmentation bias, is faster and is amenable to spike-in for quantitation.

TABLE 1

Comparison of CUT&RUN to ChIP-seq protocols

| Method | CUT&RUN | X-ChIP-seq | ChIP-exo | N-ChIP-seq |
| --- | --- | --- | --- | --- |
| Number of cells required | ~100 | ~5 million | ~50 million | ~5000 |
| Resolution | <5 bp | ~300 bp | <5 bp | <5 bp |
| Number of reads required | ~3 million | ~20 million | ~100 million | ~40 million |

TABLE 1-continued

Comparison of CUT&RUN to ChIP-seq protocols

| Method | CUT&RUN | X-ChIP-seq | ChIP-exo | N-ChIP-seq |
|---|---|---|---|---|
| Profiles insoluble complexes | Yes | Yes | Yes | No |
| Signal-to-noise ratio | High | Low | Low | Medium |
| Fragmentation bias | No | Yes | Probably | Yes |
| Speed (cells to DNA) | 1 day | 3 days | 1 week | 2 days |
| Spike-in for quantitation | Simple | Possible | Complicated | Possible |

An important advancement in ChIP-based technologies has been to leverage next generation sequencing to generate base-pair resolution genome-wide maps of protein-DNA interactions[41]. In contrast to standard crosslinking ChIP where sonication is used to fragment the chromatin to a minimum of ~200 bp fragments, exonuclease treatment in ChIP-exo or MNase digestion in high-resolution X-ChIP-seq or native ChIP approaches allows limit or near-limit digestion[4,5,20,40,42]. However, this improvement in resolution in crosslinking strategies has often come at the price of increases in sequence depth requirements and the number of cells required. For example, in ChIP-exo, any sonicated fragments that contain more than just the target protein, such as an adjacent nucleosome, will form a block to the exonuclease in generating minimal TF footprints and as such contribute to an apparent localized background, requiring increased cell numbers and sequencing depths to call high resolution peak pairs. Native ChIP often does not suffer from these associated problems, but has limited general applicability due to the requirement to generate soluble chromatin extracts in the absence of harsh detergents and therefore is best suited to stably bound proteins and may require optimization on a case-by-case basis. It has previously been shown that sonication, such as is used for cross-linking ChIP methods, is nonrandom and therefore is subject to a fragmentation bias[5,43]. As CUT&RUN is performed on intact cells or nuclei without fragmentation, it can be used to probe all genomic compartments. Technologies that use MNase for genome-wide digestion can suffer from A/T bias of the enzyme[44] and will preferentially digest open chromatin. In contrast, CUT&RUN involves a sterically regulated cleavage reaction, and we have shown that it does not suffer from any detectable A/T or DNA accessibility bias[20].

As is the case with ChIP, the success of CUT&RUN depends in large part on the affinity of the antibody for its target and its specificity under the conditions used for binding. Because antibodies bind to their epitopes in the solid state using CUT&RUN, antibodies that successfully tested for specificity by immunofluorescence (IF) would be likely to work with CUT&RUN, with the caveat that IF generally involves fixation, whereas formaldehyde fixation decreases the efficiency of CUT&RUN. In the standard CUT&RUN protocol, we recommend allowing the cleaved chromatin complexes to diffuse out of the nuclei, thereby permitting simple isolation of the cut DNA from the supernatant fraction with the undigested genome retained in the intact nuclei. However, it is possible that a chromatin complex is too large to diffuse out or that protein-protein interactions retain the cleaved complex. In such cases, total DNA may be extracted after the digestion. By doing a very simple size selection using volume of paramagnetic carboxylated beads (e.g. Agencourt AMPure XP beads) fragments below ~700 bp will be selected for. This strategy was successful for the ~1 MDa yeast RSC complex[20].

Materials
Reagents
Cell suspension. Human K562 cells, Drosophila S2 cells were used and dissected Drosophila tissues such as brains and imaginal disks, and spheroplasted yeast.
Concanavalin-coated magnetic beads (Bangs Laboratories, ca. no. BP531)
Antibody to an epitope of interest. For example, rabbit α-CTCF polyclonal antibody (Millipore 07-729) for mapping 1D and 3D interactions by CUT&RUN
Positive control antibody to an abundant epitope, e.g. α-H3K27me3 rabbit monoclonal antibody (Cell Signaling Technology, cat. no. 9733)
Negative control antibody to an absent epitope, e.g. guinea pig α-rabbit antibody
5% Digitonin (EMD Millipore, cat. no. 300410)
Protein A-Micrococcal Nuclease (pA-MNase) fusion protein. Store at −20° C.
Spike-in DNA (e.g., from Saccharomyces cerevisiae micrococcal nuclease-treated chromatin, provided by authors upon request)
Distilled, deionized or RNAse-free H2O (dH2O e.g., Promega, cat. no. P1197)
1 M Manganese Chloride ($MnCl_2$; Sigma-Aldrich, cat. no. 203734)
1 M Calcium Chloride ($CaCl_2$); Fisher, cat. no. BP510)
1 M Potassium Chloride (KCl; Sigma-Aldrich, cat. no. P3911)
1 M Hydroxyethyl piperazineethanesulfonic acid pH 7.5 (HEPES (Na+); Sigma-Aldrich, cat. no. H3375)
1 M Hydroxyethyl piperazineethanesulfonic acid pH 7.9 (HEPES (K+); Sigma-Aldrich, cat. no. H3375)
5 M Sodium chloride (NaCl; Sigma-Aldrich, cat. no. 55150-1L)
0.5 M Ethylenediaminetetraacetic acid (EDTA; Research Organics, cat. no. 3002E)
0.2 M Ethylene glycol-bis(β-aminoethyl ether)-N,N,N', N'-tetraacetic acid (EGTA; Sigma-Aldrich, cat. no. E3889)
2 M Spermidine (Sigma-Aldrich, cat. no. S2501)
Roche Complete Protease Inhibitor EDTA-Free tablets (Sigma-Aldrich, cat. no. 5056489001)
2 mg/ml Glycogen (1:10 dilution of Sigma-Aldrich, cat. no. 10930193001)
RNase A, DNase and protease-free (10 mg/ml; Thermo Fisher Scientific, cat. no. EN0531)
Gel and PCR Clean-up kit (Macherey-Nagel NucleoSpinR, cat. no. 740609.250)
Agencourt AMPure XP magnetic beads (Beckman Coulter, cat. no. A63880)
10% Sodium dodecyl sulfate (SDS; Sigma-Aldrich, cat. no. L4509)
Proteinase K (Thermo Fisher Scientific, cat. no. E00492)
Phenol-chloroform-isoamyl alcohol 25:24:1 (PCI; Invitrogen, cat. no. 15593049)

Chloroform (Sigma, cat. no. 366919-1L)
1 M Tris-HCl pH 8.0
Ethanol (DeconLabs, cat. no. 2716)
Qubit dsDNA HS kit (Life Technologies, cat. no. Q32851)

Reagent Setup

5% Digitonin: To reconstitute enough digitonin for an experiment, the powder was weighed in a 2 ml microcentrifuge tube, water boiled in a small beaker in a microwave oven, and pipetted in and out to warm the 1000 µL pipette tip. The hot water was pipetted into the tube with the digitonin powder to make 5% (w/v), the cap closed and quickly vortexed on full until the digitonin was completely dissolved. If refrigerated, this stock can be used within a week, but will need reheating as the digitonin slowly precipitates. The effectiveness of digitonin varies between batches, so testing permeability of Trypan blue is recommended to determine the concentration to use for a cell type. Excellent results were obtained for K562 cells with 0.02-0.1% digitonin.

Digitonin is toxic and care should be taken especially when weighing out the powder. A digitonin stock may be prepared by dissolving in dimethylsulfoxide (DMSO), but be aware that DMSO can absorb through the skin.

Binding buffer: Mix 400 µL 1M HEPES-KOH pH 7.9, 200 µL 1M KCl, 20 µL 1M $CaCl_2$) and 20 µL 1M MnCl2, and bring the final volume to 20 ml with dH2O. Store the buffer at 4° C. for 6 months.

Concanavalin A-coated beads: Gently resuspend and withdraw enough of the slurry such that there will be 10 µL for each final sample and/or digestion time point. Transfer into 1.5 ml Binding buffer in a 2 ml tube. Place the tube on a magnet stand to clear (30 s to 2 min). Withdraw the liquid, and remove from the magnet stand. Add 1.5 ml Binding buffer, mix by inversion or gentle pipetting, remove liquid from the cap and side with a quick pulse on a microcentrifuge. Resuspend in a volume of Binding buffer equal to the volume of bead slurry (10 µL per final sample). Wash buffer Mix 1 ml 1 M HEPES pH 7.5, 1.5 ml 5 M NaCl, 12.5 µL 2 M Spermidine, bring the final volume to 50 ml with dH2O, and add 1 Roche Complete Protease Inhibitor EDTA-Free tablet. Store the buffer at 4° C. for up to 1 week. Dig-wash buffer Mix 160-800 µL 5% Digitonin with 40 ml Wash buffer. The effectiveness of digitonin varies between batches, so testing permeability of Trypan blue is recommended to determine the concentration to use. Excellent results were obtained for K562 cells with 0.02-0.1% digitonin. Store the buffer at 4° C. for up to 1 day.

Antibody buffer: Mix 8 µL 0.5 M EDTA with 2 ml Dig-wash buffer and place on ice. Divide into aliquots for each antibody and add antibody solution or serum to a final concentration of 1:100 or to the manufacturer's recommended concentration for immunofluorescence. 2×STOP To 4.2 ml dH2O add 340 µl 5M NaCl, 200 µL 0.5M EDTA, 100 µL 0.2M EGTA, 20 µL 5% Digitonin, 25 µL RNase A, 125 µL 2 mg/ml glycogen and 2 pg/ml heterologous spike-in DNA. Store the buffer at 4° C. for up to 1 week.

Heterologous spike-in DNA for calibration should be fragmented down to ~200 bp mean size, for example an MNase-treated sample of mononucleosome-sized fragments. As we use the total number of mapped reads as a normalization factor only, very little spike-in DNA is needed. For example, addition of 1.5 pg results in 1,000-10,000 mapped spike-in reads for 1-10 million mapped experimental reads (in inverse proportion).

Procedure

Binding Cells to Beads

TIMING 30 min

All steps prior to the addition of antibody are performed at room temperature to minimize stress on the cells. Because it is crucial that DNA breakage is minimized throughout the protocol, we recommend that cavitation during resuspension and vigorous vortexing be avoided.

1) Harvest fresh culture(s) at room temperature and count cells. The same protocol can be used for 100 to 250,000 mammalian cells per sample and/or digestion time point.

PAUSE POINT: If necessary, cells can be cryopreserved in 10% DMSO using a Mr. Frosty isopropyl alcohol chamber. Flash freezing is not recommended, as this can cause background DNA breakage that may impact final data quality.

2) Centrifuge 3 min 600×g at room temperature and withdraw liquid.

3) Resuspend in 1.5 ml room temperature Wash buffer by gently pipetting and transfer if necessary to a 2 ml tube.

4) Centrifuge 3 min 600×g at room temperature and withdraw liquid.

5) Repeat steps 3 and 4.

6) Resuspend in 1 ml room temperature Wash buffer by gently pipetting.

7) While gently vortexing the cells at room temperature, add the bead slurry.

8) Rotate 5-10 min at room temperature.

9) Divide into aliquots in 1.5-ml tubes, one for each antibody to be used.

To evaluate success of the procedure without requiring library preparation, include in parallel a positive control antibody (e.g. α-H3K27me3) and a negative control antibody (e.g. α-rabbit). Do not include a no-antibody control, as the lack of tethering may allow any unbound pA-MN to act as a "time-bomb" and digest accessible DNA, resulting in a background of DNA-accessible sites.

Bind (Primary) Antibodies

TIMING 15 min-overnight, with longer incubations providing higher yields

10) Place on the magnet stand to clear and pull off the liquid.

Although low-retention pipette tips are preferred for accurate solution transfers, use only conventional (not low-binding) microcentrifuge tubes to avoid loss of beads while decanting.

11) Place each tube at a low angle on the vortex mixer set to low (~1100 rpm) and squirt 50 µL of the Antibody buffer (per sample and/or digestion time point) along the side while gently vortexing to allow the solution to dislodge most or all of the beads. Tap to dislodge the remaining beads.

The presence of EDTA during antibody treatment removes excess divalent cation used to activate the ConA, because carry-over of Ca++ from the beads can prematurely initiate strand cleavage after addition of pA-MN. Chelation of divalent cations when cells are permeabilized also serves to quickly halt metabolic processes and prevent endogenous DNAse activity. Washing out the EDTA before pA-MN addition avoids inactivating the enzyme. Spermidine in the wash buffer is intended to compensate for removal of Mg++, which might otherwise affect chromatin properties.

12) Place on the tube rotator at 4° C. for ~2 hr, or at room temperature for 5-10 min.

PAUSE POINT Antibody incubation may proceed overnight at 4° C.

13) Remove liquid from the cap and side with a quick pulse on a micro-centrifuge.

14) Place on the magnet stand to clear (~30 s) and pull off all of the liquid.

15) Add 1 ml Dig-wash buffer, mix by inversion, or by gentle pipetting using a 1 ml tip if clumps persist, and remove liquid from the cap and side with a quick pulse on a micro-centrifuge. Bind secondary antibody (as required)
TIMING 15 min-1.5 hr The binding efficiency of Protein A to the primary antibody depends on host species and IgG isotype. For example, Protein A binds well to rabbit and guinea pig IgG but poorly to mouse and goat IgG, and so for these latter antibodies a secondary antibody, such as rabbit α-mouse is recommended.

16) Place on the magnet stand to clear and pull off all of the liquid.

17) Place each tube at a low angle on the vortex mixer set to low (~1100 rpm) and squirt 50 μL of the Dig-wash buffer (per sample and/or digestion time point) along the side while gently vortexing to allow the solution to dislodge most or all of the beads. Tap to dislodge the remaining beads.

18) Mix in the secondary antibody to a final concentration of 1:100 or to the manufacturer's recommended concentration for immunofluorescence.

19) Place on the tube rotator at 4° C. for ~1 hr, or at room temperature for 5-10 min.

20) Remove liquid from the cap and side with a quick pulse on a micro-centrifuge.

21) Place on the magnet stand to clear and pull off all of the liquid.

22) Add 1 ml Dig-Wash buffer, mix by inversion, or by gentle pipetting if clumps persist, and remove liquid from the cap and side with a quick pulse on a micro-centrifuge.
Bind Protein A-MNase Fusion Protein
TIMING 15 min-1.5 hr 23) Place on the magnet stand to clear and pull off all of the liquid.

24) Place each tube at a low angle on the vortex mixer set to low (~1100 rpm) and squirt 50 μL of the Dig-wash buffer (per sample and/or digestion time point) along the side while gently vortexing to allow the solution to dislodge most or all of the beads. Tap to dislodge the remaining beads.

25) Mix in the pA-MNase to a final concentration of ~700 ng/ml (e.g. 2.5 μL/50 μL of a 1:10 dilution of the 140 μg/ml glycerol stock provided upon request).

26) Place on the tube rotator at 4° C. for ~1 hr, or at room temperature for 5-10 min.

27) Remove liquid from the cap and side with a quick pulse on a micro-centrifuge.

28) Place on the magnet stand to clear and pull off all of the liquid.

29) Add 1 ml Dig-wash buffer, mix by inversion, or by gentle pipetting if clumps persist, and remove liquid from the cap and side with a quick pulse on a micro-centrifuge.

30) Repeat Dig-wash steps 28-29.
Targeted Digestion
TIMING 45 min

31) Place on the magnet stand to clear and pull off all of the liquid.

32) Place each tube at a low angle on the vortex mixer set to low (~1100 rpm) and add 100 μL of the Dig-wash buffer (per sample and/or digestion time point) along the side while gently vortexing to allow the solution to dislodge most or all of the beads. Tap to dislodge the remaining beads.

33) Insert tubes into the 1.5 ml wells of a heater block sitting in wet ice to chill down to 0° C.

34) Remove each tube from the block, mix in 2 μL 100 mM $CaCl_2$) (diluted 1:10 from a 1 M stock) with gentle vortexing and immediately replace the tube in the 0° C. block.

35) Incubate at 0° C. for the desired digestion time (default is 30 min).

MNase binds DNA but only cleaves when Ca++ is present, so that digestion is a zero-order reaction that seems to be less temperature-dependent than the subsequent diffusion of released pA-MNase-bound particles that can digest accessible regions of the genome. Cleavage and release of particles in most of the cell population can be obtained at 0° C. while minimizing background cleavages attributable to diffusion. We have found that digestion at ambient temperature or higher results in unacceptable background cleavage levels.

36) Add 100 μL 2×STOP and mix by gentle vortexing. When there are multiple time points, remove 100 μL to 100 μL 2×STOP and mix by gentle vortexing.

Heterologous spike-in DNA should be present in the 2×STOP to calibrate DNA amounts, for example to compare treatments or digestion time points. This is especially important for CUT&RUN, as there is too little background cleavage for normalization of samples.
Target Chromatin Release
TIMING 20 min 37) Incubate 10 min 37° C. to release CUT&RUN fragments from the insoluble nuclear chromatin.

38) Centrifuge 5 min 4° C. 16,000×g and place on magnet stand.
Option A: Fast DNA Extraction by Spin Column
TIMING 20 min 39) Place a spin column into a collection tube and add 400 μL Buffer NT1 (from Nucleo Spin kit or equivalent).

40) Decant the supernatant cleanly from the pellet and transfer to the NT1 in the spin column pipetting gently up and down to mix.

41) Centrifuge 30 s at 11,000×g. Discard flow-through.

42) Add 700 μL Buffer NT3. Centrifuge 30 s 11,000×g. Discard flow-through.

43) Add 700 μL Buffer NT3. Centrifuge 30 s @11,000×g. Discard flow-through and replace in rotor.

44) Centrifuge for 1 min 11,000×g. Let dry 5 min.

45) Place in a fresh tube and add 20-40 μL Buffer NE to membrane.

46) After 1 min, centrifuge for 1 min @11,000×g.
Option B: Alternate DNA Extraction (Preferred for Quantitative Recovery of ≤80 bp Fragments)
TIMING 1.5 hr 47) Decant the supernatant cleanly from the pellet and transfer to a fresh 1.5-ml microcentrifuge tube.

48) To each sample add 2 μL 10% SDS (to 0.1%), and 2.5 μL Proteinase K (20 mg/ml). Mix by inversion and incubate 10 min 70° C.

49) Add 300 μL PCI and mix by full-speed vortexing ~2 s.

50) Transfer to a phase-lock tube, and centrifuge 5 min room temperature at 16,000×g.

51) Add 300 μL chloroform and invert ~10× to mix.

52) Remove liquid by pipetting to a fresh tube containing 2 μL 2 mg/ml glycogen.

53) Add 750 μL 100% ethanol and mix by vortexing or tube inversion.

54) Chill on ice and centrifuge 10 min at 4° C. 16,000×g.

55) Pour off the liquid and drain on a paper towel.

56) Rinse the pellet in 1 ml 100% ethanol and centrifuge 1 min at 4° C. 16,000×g.

57) Carefully pour off the liquid and drain on a paper towel. Air dry.

58) When the pellet is dry, dissolve in 25-50 μL 1 mM Tris-HCl pH8 0.1 mM EDTA.

Library Preparation and Sequencing

TIMING 2-4 days

59) Optional: Quantify 1-2 μL, for example using fluorescence detection with a Qubit instrument.

60) Optional: Evaluate the presence of cleaved fragments and the size distribution by capillary electrophoresis with fluorescence detection, for example using a Tapestation instrument.

Some long undigested DNA will leak through, and this is what will dominate the Qubit fluorescence for CUT&RUN of typical transcription factors. For these, the targeted DNA recovered is too low in amount and too small in size to be detected by gel analysis or even by Tapestation. In such cases it may be necessary to make a PCR-amplified library to quantify by Tapestation or Bioanalyzer analysis.

61) Prepare barcoded libraries for Illumina sequencing with Tru-Seq adapters using a single-tube protocol, following the manufacturer's instructions. Rapid PCR cycles favor exponential amplification of the desired CUT&RUN fragments over linear amplification of large DNA fragments that are too long for polymerase to complete.

To minimize the contribution of large DNA fragments, PCR cycles should be at least 12-14 cycles, preferably with a 10 s 60° C. combined annealing/extension step. Good results have been obtained with the Hyper-prep kit (KAPA Biosystems).

62) Quantify library yield using dsDNA-specific assay, such as Qubit.

63) Determine the size distribution of libraries by Agilent 4200 TapeStation analysis.

64) Perform paired-end Illumina sequencing on the barcoded libraries following the manufacturer's instructions.

Because of the very low background with CUT&RUN, typically 5 million paired-end reads suffices for transcription factors or nucleosome modifications, even for the human genome. For maximum economy, we mix up to 24 barcoded samples per lane on a 2-lane flow cell, and perform paired-end 25×25 bp sequencing. Single-end sequencing is not recommended for CUT&RUN, as it sacrifices resolution and discrimination between transcription factors and neighboring nucleosomes.

Data Processing and Analysis

TIMING 1 d (variable)

65) We align paired-end reads using Bowtie2 version 2.2.5 with options: -local—very sensitive-local -no-unal -no-mixed -no-discordant -phred33 -I 10 -X 700. For mapping spike-in fragments, we also use the -no-overlap -no-dovetail options to avoid cross-mapping of the experimental genome to that of the spike-in DNA.

Separation of sequenced fragments into ≤120 bp and ≥150 bp size classes provides mapping of the local vicinity of a DNA-binding protein, but this can vary depending on the steric access to the DNA by the tethered MNase. Single-end sequencing is not recommended for CUT&RUN, as it sacrifices resolution and discrimination between transcription factors and neighboring nucleosomes.

66) Scripts available from on the world wide web at domain name github.com/peteskene are customized for processing, spike-in calibration, and analysis CUT&RUN data.

Results

Figure 28:
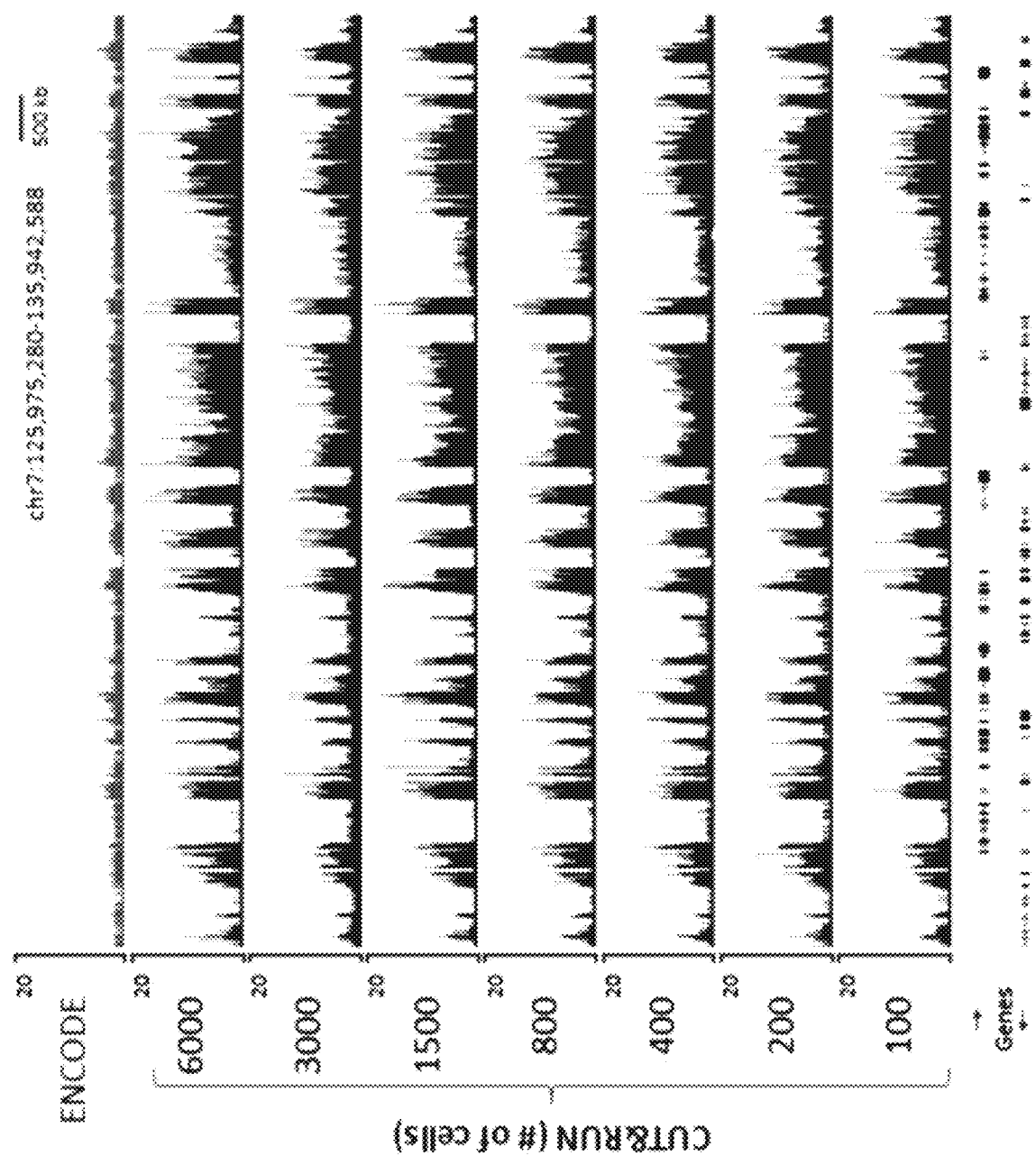
FIG. 28 shows that CUT&RUN of H3K27me3 requires only 100 cells to profile the human Polycomb chromatin landscape. A varying number of K562 cells was used as the starting material for profiling H3K27me3 by CUT&RUN. Following paired-end 25×25 bp Illumina sequencing and removal of duplicates, 7.5 million reads were randomly selected and used to generate bedgraphs representing raw counts, as indicated on the y-axis. For comparison, ENCODE XChIP-seq data (GSM733658) was similarly analyzed.
Figure 29:
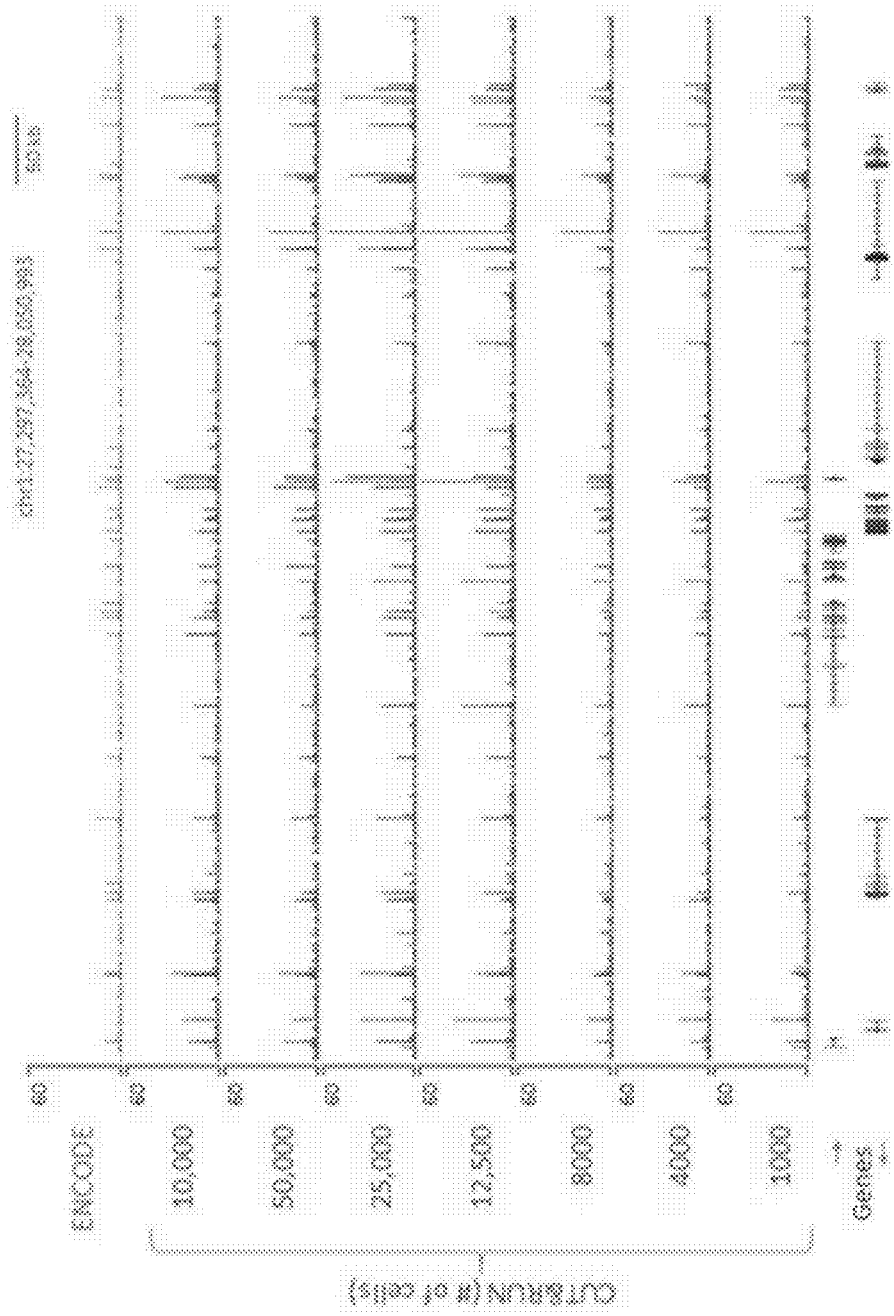
FIG. 29 shows that CUT&RUN requires only 1000 cells and 4 million reads to delineate human CTCF peaks. CUT&RUN was used to map CTCF binding sites in varying numbers of K562 cells. Following paired-end sequencing, 4 million non-duplicated reads were randomly selected and used to generate bedgraphs representing raw counts, as indicated on the y-axis. For comparison, ENCODE X-ChIP-seq data (GSM749690) was similarly analyzed.
Figure 30:
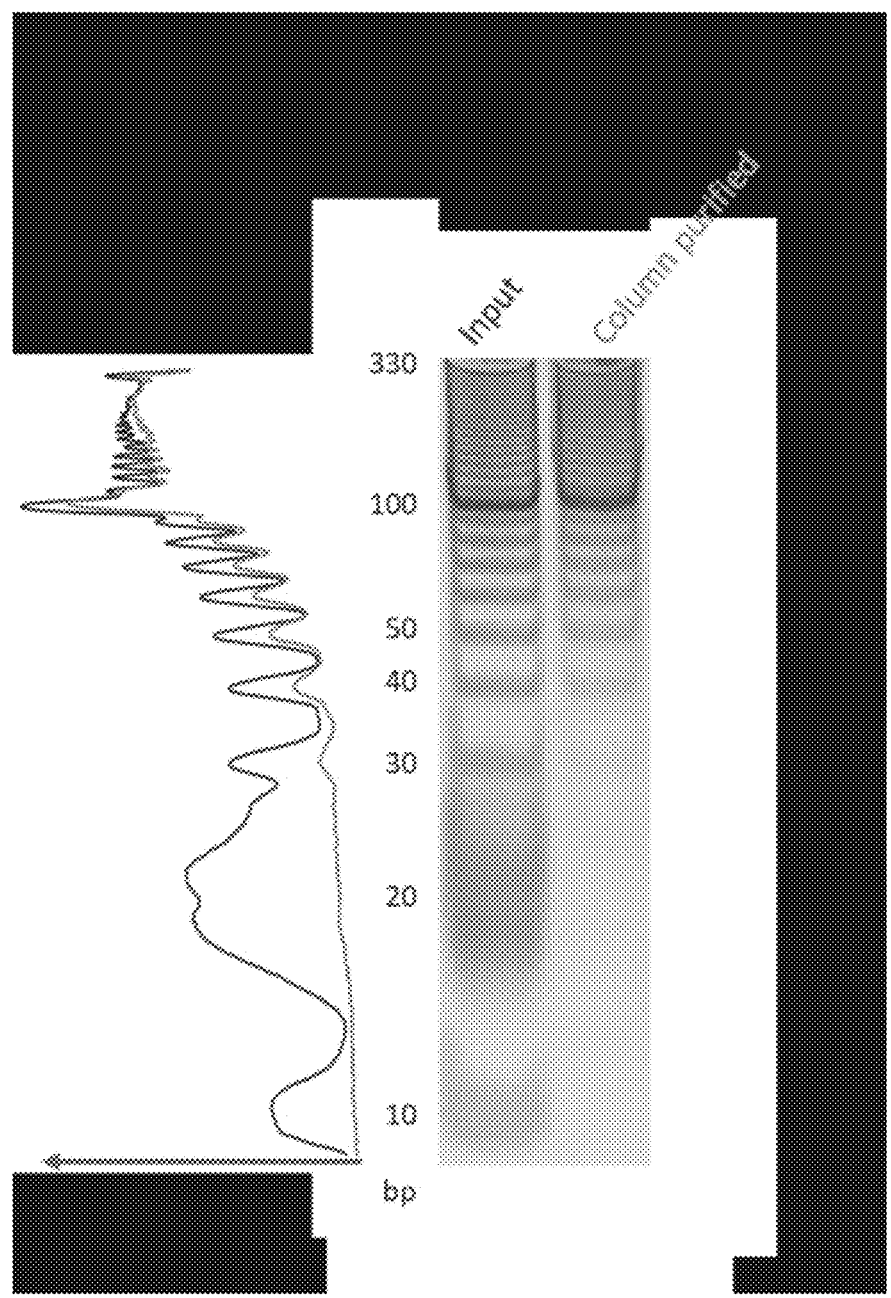
FIG. 30 shows that spin-column DNA purification partially excludes both large and small fragments. To test the efficiency of spin columns in binding different length DNA fragments, 2 µg of 10 bp ladder was purified through the column and compared to 2 µg as input. DNA was resolved by 10% polyacrylamide gel electrophoresis and stained with SYBRgold. Densitometry is shown on the left. For CUT&RUN, removal of large fragments reduces background, but removal of small fragments impacts recovery when profiling DNA-binding proteins. Therefore, spin-column purification (Steps 39-46) is preferred for nucleosomes, but might be less desirable for transcription factors and very low cell numbers, in which case the alternative PCI protocol (Steps 47-58) is recommended.

Human K562 cells were cultured at 37° C., counted, harvested at 1×10$^6$ cells/ml by low-speed centrifugation, suspended and pelleted twice in Wash buffer, then diluted and mixed with wash buffer in a 300 μL volume to achieve a doubling series between 50 and 6,000 cells. Ten μL of a $Ca^{2+}$- and $Mn^{2+}$-washed ConA-coated magnetic bead slurry was added in binding buffer to each cell suspension with gentle vortexing. After 10 min, cells were collected on a magnet stand, decanted, resuspended in 50 μL Antibody buffer containing anti-H3K27me3 (1:100, CST #9733), 2 mM EDTA and 0.05% digitonin and incubated at 4° C. for 15 hr. After collecting the beads on a magnet stand and washing once in 1 ml cold Dig-wash, cells were resuspended in 100 μL pA-MN (1:500 360 μg/ml) in Dig-wash and incubated at 4° C. for 1 hr. Beads were collected on a magnet stand, washed twice in 1 ml Dig-wash, resuspended in 150 μL Dig-wash, and chilled to 0° C. Three μL 100 mM $CaCl_2$ was added, and 0° C. incubation was continued for 30 min. Reactions were terminated with 1 vol 2×STOP, incubated at 37° C. for 20' and centrifuged at 4° C. for 5' 16,000×g. Both the supernatant and pellet were extracted following Steps 47-58). DNA from pellets was quantified by Qubit fluorescence. DNA from selected supernatant fractions was resolved by Tapestation analysis (FIG. 26) and subjected to Illumina PE25×25 sequencing. Typical ChIP-seq experiments use high starting cell numbers that result in a large number of unique sonicated fragments that are immunoprecipitated. In contrast, as CUT&RUN allows low cell numbers and has a relatively low background, the number of unique fragments is less than typical sequence depths. Therefore, high sequencing depths from low cell number experiments could result in redundant sequencing of PCR duplicates. Presumed PCR duplicates were removed and mapped fragments were randomly sampled without replacement, resulting in 7.5 million unique reads per sample, displayed as normalized counts from stacked reads (FIG. 28). For comparison, a sample of 7.5 million unique reads were sampled from an ENCODE dataset for H3K27me3 in K562 cells. It is evident that very little loss of data quality occurred with reduction in cell number down to 100 cells. In contrast, the ENCODE profile sampled at the same depth shows a blurry profile owing to the high background inherent to ChIP. CUT&RUN using an anti-CTCF antibody (1:100, Millipore 07-729) was performed similarly, yielding profiles with little loss of data quality down to 1000 cells (FIG. 29). Spin-column extraction (Steps 39-46) is simple and fast providing good recovery of fragments in the range of nucleosomes, while reducing the concentration of very large fragments that can interfere with library preparation (FIG. 30). Therefore, this DNA extraction option is preferred for most applications of CUT&RUN. However, for CUT&RUN of TFs at low cell numbers, organic extraction (Steps 47-58) is preferred for better recovery of small fragments.

References for Example 2 (Each of which is Incorporated by Reference in its Entirety)

1. Solomon, M. J. & Varshavsky, A. Formaldehyde-mediated DNA-protein crosslinking: a probe for in vivo chromatin structures. Proc Natl Acad Sci USA 82, 6470-4 (1985).
2. Johnson, D. S., Mortazavi, A., Myers, R. M. & Wold, B. Genome-wide mapping of in vivo protein-DNA interactions. Science 316, 1497-502 (2007).
3. Barski, A. et al. High-resolution profiling of histone methylations in the human genome. Cell 129, 823-37 (2007).

4. Rhee, H. S. & Pugh, B. F. Comprehensive genome-wide protein-DNA interactions detected at single-nucleotide resolution. Cell 147, 1408-19 (2011).
5. Skene, P. J. & Henikoff, S. A simple method for generating high-resolution maps of genome-wide protein binding. eLife 4, e09225 (2015).
6. Teytelman, L., Thurtle, D. M., Rine, J. & van Oudenaarden, A. Highly expressed loci are vulnerable to misleading ChIP localization of multiple unrelated proteins. Proceedings of the National Academy of Sciences of the United States of America 110, 18602-7 (2013).
7. Park, D., Lee, Y., Bhupindersingh, G. & Iyer, V. R. Widespread misinterpretable ChIP-seq bias in yeast. PloS one 8, e83506 (2013).
8. Jain, D., Baldi, S., Zabel, A., Straub, T. & Becker, P. B. Active promoters give rise to false positive 'Phantom Peaks' in ChIP-seq experiments. Nucleic Acids Res 43, 6959-68 (2015).
9. Baranello, L., Kouzine, F., Sanford, S. & Levens, D. ChIP bias as a function of cross-linking time. Chromosome Res 24, 175-81 (2016).
10. Meyer, C. A. & Liu, X. S. Identifying and mitigating bias in next-generation sequencing methods for chromatin biology. Nat Rev Genet 15, 709-21 (2014).
11. Crawford, G. E. et al. Genome-wide mapping of DNase hypersensitive sites using massively parallel signature sequencing (MPSS). Genome Res 16, 123-31 (2006).
12. Giresi, P. G., Kim, J., McDaniell, R. M., Iyer, V. R. & Lieb, J. D. FAIRE (Formaldehyde-Assisted Isolation of Regulatory Elements) isolates active regulatory elements from human chromatin. Genome Res 17, 877-85 (2007).
13. Auerbach, R. K. et al. Mapping accessible chromatin regions using Sono-Seq. Proc Natl Acad Sci USA 106, 14926-31 (2009).
14. Kent, N. A., Adams, S., Moorhouse, A. & Paszkiewicz, K. Chromatin particle spectrum analysis: a method for comparative chromatin structure analysis using paired-end mode next-generation DNA sequencing. Nucleic Acids Res 39, e26 (2011).
15. Henikoff, J. G., Belsky, J. A., Krassovsky, K., Macalpine, D. M. & Henikoff, S. Epigenome characterization at single base-pair resolution. Proc Natl Acad Sci USA 108, 18318-23 (2011).
16. Buenrostro, J. D., Giresi, P. G., Zaba, L. C., Chang, H. Y. & Greenleaf, W. J. Transposition of native chromatin for fast and sensitive epigenomic profiling of open chromatin, DNA binding proteins and nucleosome position. Nat Methods 10, 1213-8 (2013).
17. Bert, K. M. et al. MLL-rearranged leukemia is dependent on aberrant H3K79 methylation by DOT1L. Cancer Cell 20, 66-78 (2011).
18. van Steensel, B., Delrow, J. & Henikoff, S. Chromatin profiling using targeted DNA adenine methyltransferase. Nat Genet 27, 304-8 (2001).
19. Schmid, M., Durussel, T. & Laemmli, U.K. ChIC and ChEC; genomic mapping of chromatin proteins. Mol Cell 16, 147-57 (2004).
20. Skene, P. J. & Henikoff, S. An efficient targeted nuclease strategy for high-resolution mapping of DNA binding sites. Elife 6(2017).
21. Hu, Z. et al. Nucleosome loss leads to global transcriptional up-regulation and genomic instability during yeast aging. Genes & development 28, 396-408 (2014).
22. Orlando, D. A. et al. Quantitative ChIP-Seq normalization reveals global modulation of the epigenome. Cell Rep 9, 1163-70 (2014).
23. Zentner, G. E., Kasinathan, S., Xin, B., Rohs, R. & Henikoff, S. ChEC-seq kinetics discriminate transcription factor binding sites by DNA sequence and shape in vivo. Nature Communications 6, 8733 (2015).
24. Corces, M. R. et al. Lineage-specific and single-cell chromatin accessibility charts human hematopoiesis and leukemia evolution. Nat Genet 48, 1193-203 (2016).
25. Liu, X. & Fagotto, F. A method to separate nuclear, cytosolic, and membrane-associated signaling molecules in cultured cells. Sci Signal 4, p12 (2011).
26. Adam, S. A., Marr, R. S. & Gerace, L. Nuclear protein import in permeabilized mammalian cells requires soluble cytoplasmic factors. J Cell Biol 111, 807-16 (1990).
27. Brind'Amour, J. et al. An ultra-low-input native ChIP-seq protocol for genome-wide profiling of rare cell populations. Nat Commun 6, 6033 (2015).
28. Porreca, G. J. et al. Multiplex amplification of large sets of human exons. Nat Methods 4, 931-6 (2007).
29. Cusanovich, D. A. et al. Multiplex single cell profiling of chromatin accessibility by combinatorial cellular indexing. Science 348, 910-4 (2015).
30. Ramani, V. et al. Massively multiplex single-cell Hi-C. Nat Methods 14, 263-266 (2017).
31. Lieberman-Aiden, E. et al. Comprehensive mapping of long-range interactions reveals folding principles of the human genome. Science 326, 289-93 (2009).
32. Tang, Z. et al. CTCF-Mediated Human 3D Genome Architecture Reveals Chromatin Topology for Transcription. Cell 163, 1611-27 (2015).
33. Mumbach, M. R. et al. HiChIP: efficient and sensitive analysis of protein-directed genome architecture. Nat Methods 13, 919-922 (2016).
34. Chen, Y. B., A. "TSA-Seq": a novel proximity mapping approach for studying three dimensional genome organization and function. (2016).
35. Beagrie, R. A. et al. Complex multi-enhancer contacts captured by genome architecture mapping. Nature 543, 519-524 (2017).
36. Wahba, L., Costantino, L., Tan, F. J., Zimmer, A. & Koshland, D. S1-DRIP-seq identifies high expression and polyA tracts as major contributors to R-loop formation. Genes Dev 30, 1327-38 (2016).
37. Sanders, M.M. Fractionation of nucleosomes by salt elution from micrococcal nuclease digested nuclei. J Cell Biol 79, 97-109 (1978).
38. Davie, J. R. & Saunders, C. A. Chemical composition of nucleosomes among domains of calf thymus chromatin differing in micrococcal nuclease accessibility and solubility properties. J Biol Chem 256, 12574-80 (1981).
39. Henikoff, S., Henikoff, J. G., Sakai, A., Loeb, G. B. & Ahmad, K. Genome-wide profiling of salt fractions maps physical properties of chromatin. Genome Res 19, 460-9 (2009).
40. Kasinathan, S., Orsi, G. A., Zentner, G. E., Ahmad, K. & Henikoff, S. High-resolution mapping of transcription factor binding sites on native chromatin. Nature methods 11, 203-9 (2014).
41. Zentner, G. E. & Henikoff, S. High-resolution digital profiling of the epigenome. Nat Rev Genet 15, 814-27 (2014).
42. Fan, X., Lamarre-Vincent, N., Wang, Q. & Struhl, K. Extensive chromatin fragmentation improves enrichment of protein binding sites in chromatin immunoprecipitation experiments. Nucleic acids research 36, e125 (2008).
43. Teytelman, L. et al. Impact of chromatin structures on DNA processing for genomic analyses. PloS one 4, e6700 (2009).

44. Chung, H. R. et al. TFfhe effect of micrococcal nuclease digestion on nucleosome positioning data. PLoS One 5, e15754 (2010).

Example 3

CUT&RUN.ChIP as a High-Efficiency Alternative to Sequential ChIP.

Chromatin factors form complexes to bind DNA, but current methods to identify co-occupancy are severely limited by the inefficiencies of sequential ChIP. Sequential ChIP is performed by using the chromatin immunoprecipitate recovered after a first cross-linking ChIP reaction as input for a second ChIP pull-down. However, because of the inefficiency of cross-linking ChIP, the amount of material recovered after the second ChIP can be vanishingly small, typically limiting Sequential ChIP to PCR and only rarely if ever allowing for Sequential ChIP-seq for genome-wide application. For example, in [6] we successfully performed Sequential ChIP-seq on the human kinetochore complex, but only because the complex resides on tandemly repetitive α-satellite sequences that are present in thousands of copies at centromeres. However, as CUT&RUN is far more efficient than ChIP, we reasoned that we could use the CUT&RUN supernatant as input for ChIP. We use the high efficiency of CUT&RUN to release chromatin particles, and find that ChIP with this material for a second chromatin component is much more efficient with negligible background.

Figure 31A:
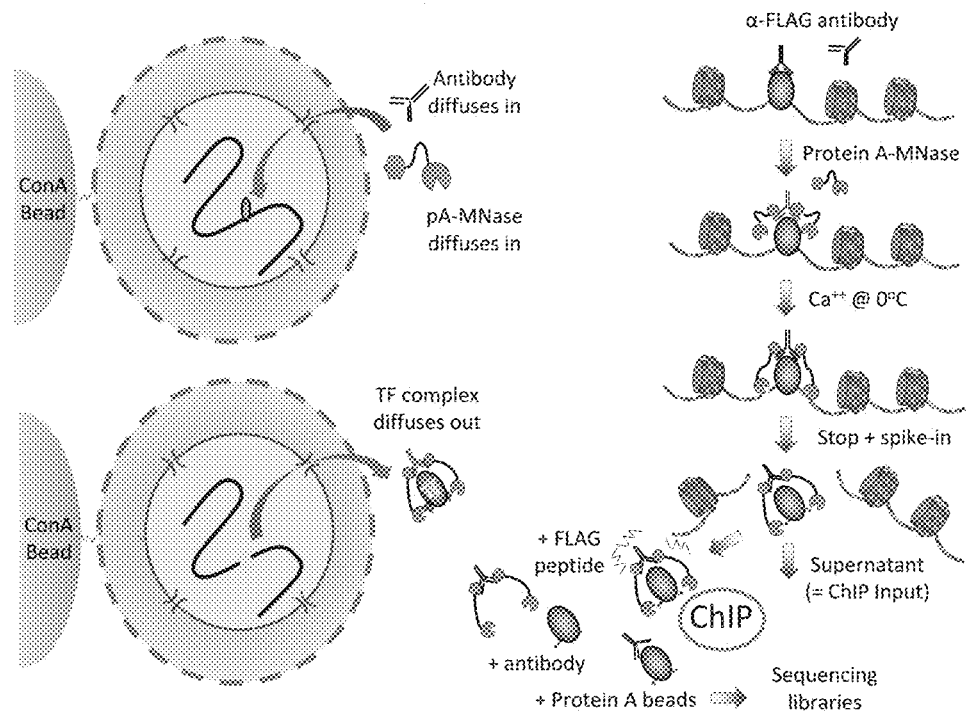
FIGS. 31A and 31B show that CUT&RUN.ChIP efficiently maps components of multiprotein complexes.
Figure 31B:
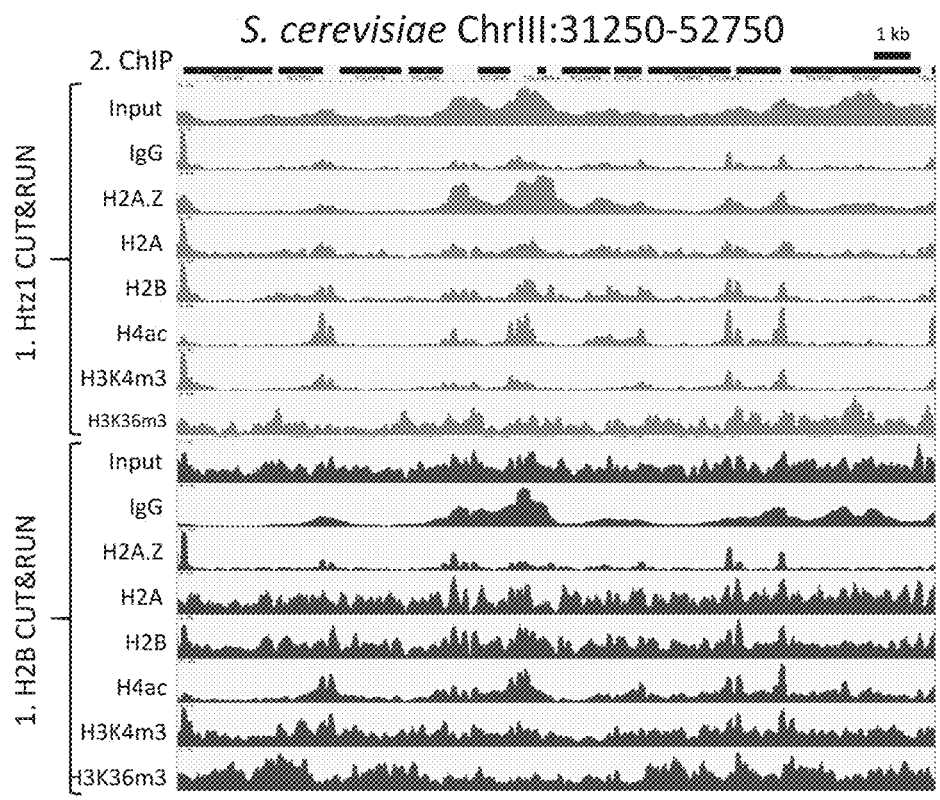

To test the CUT&RUN.ChIP, we applied CUT&RUN to FLAG-tagged histones, then competed off the pA-MN-bound antibody from the particles present in the supernatant using a FLAG peptide, and added a second antibody to other histone marks for native ChIP of the CUT&RUN supernatant (FIG. 31A). A representative nucleosome landscape shows that relative to H2B, which is a marker for all nucleosomes, the histone variant H2A is enriched for H4 acetylation and H3K4 trimethylation, but depleted for H3K36 trimethylation (FIG. 31B) over promoter-proximal nucleosomes, consistent with previous studies mapping these modifications using ChIP [7, 8]. Whereas single ChIP studies had already established that promoter-proximal nucleosomes are enriched or depleted for these modifications, they had not established the degree to which they are on the same nucleosome. This CUT&RUN.ChIP procedure can for example be used to define the status of bivalent chromatin states in promoters to address the mechanism of transcriptional poising at developmentally regulated genes in mammalian cells [9].

Example 4

CUT&RUN Protein Identification.

Figure 32A:
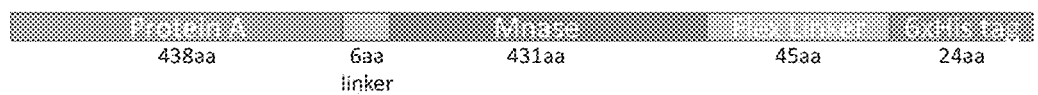
FIGS. 32A and 32B show that CUT&RUN.Proteomics for identifying protein components of multiprotein complexes.
Figure 32B:
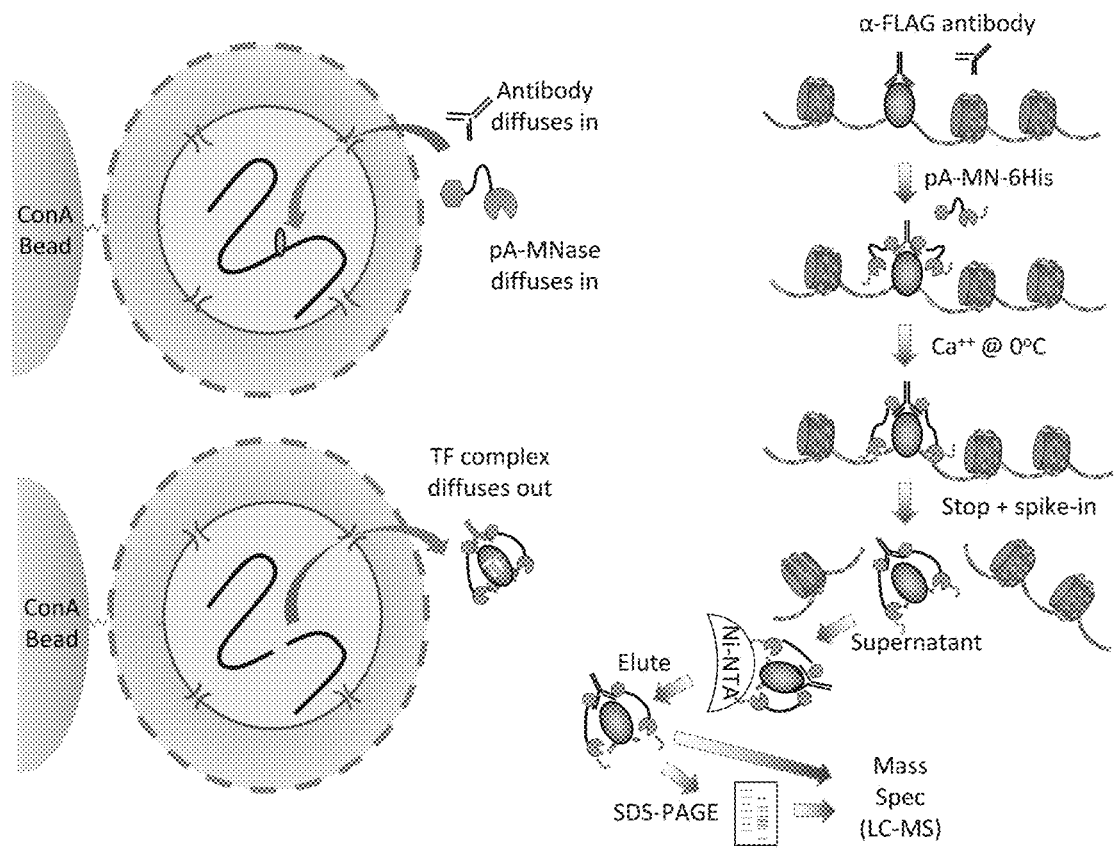

CUT&RUN.ChIP can only identify protein components of a DNA-protein complex when they are known in advance and an antibody is available, however a different strategy is needed to identify unknown components in the complex. Because of the low efficiency of ChIP, it is difficult to obtain enough immunoprecipitate to perform protein identification, however, the high efficiency of particle release into the CUT&RUN supernatant provides sufficient material for downstream proteomic analysis. However, we have found that the released particles comprise only a fraction of the total material released into the CUT&RUN supernatant, and so we have designed and produced a version of Protein A-MNase with a 6-His tag (FIG. 32A) that can be used for purifying pA-MN/antibody-bound complexes for downstream proteomic analysis. The procedure is to bind the particles released into the CUT&RUN supernatant to an affinity matrix such as nickel-agarose (for example Ni-NTA Agarose available from Qiagen and other vendors). After washing and eluting following the manufacturer's recommendations, a sufficient amount of pure complex should be obtained for silver-stained SDS-PAGE analysis and Liquid Chromatography-Mass Spectrometric determination of the protein components of a complex (FIG. 32B).

References for Example 4 (Each of which is Incorporated by Reference in its Entirety)

1. Schmid, M., Durussel, T., and Laemmli, U. K. (2004). ChIC and ChEC; genomic mapping of chromatin proteins. Mol. Cell 16, 147-157.
2. Zentner, G. E., Kasinathan, S., Xin, B., Rohs, R., and Henikoff, S. (2015). ChEC-seq kinetics discriminate transcription factor binding sites by DNA sequence and shape in vivo. Nat Commun 6, 8733.
3. Skene, P. J., and Henikoff, S. (2017). An efficient targeted nuclease strategy for high-resolution mapping of DNA binding sites. eLife 6.
4. Skene, P. J., and Henikoff, S. (2017). CUT&RUN: Targeted in situ genome-wide profiling with high efficiency for low cell numbers. Submitted for publication.
5. Henikoff, S., Henikoff, J. G., Sakai, A., Loeb, G. B., and Ahmad, K. (2009). Genome-wide profiling of salt fractions maps physical properties of chromatin. Genome Res. 19, 460-469.
6. Thakur, J., and Henikoff, S. (2016). CENPT bridges adjacent CENPA nucleosomes on young human alpha-satellite dimers. Genome Res. 26, 1178-1187.
7. Weiner, A., Hughes, A., Yassour, M., Rando, O. J., and Friedman, N. (2010). High-resolution nucleosome mapping reveals transcription-dependent promoter packaging. Genome Res. 20, 90-100.
8. Luk, E., Ranjan, A., Fitzgerald, P. C., Mizuguchi, G., Huang, Y., Wei, D., and Wu, C. (2010). Stepwise histone replacement by SWR1 requires dual activation with histone H2A.Z and canonical nucleosome. Cell 143, 725-736.
9. Shema, E., Jones, D., Shoresh, N., Donohue, L., Ram, O., and Bernstein, B. E. (2016). Single-molecule decoding of combinatorially modified nucleosomes. Science 352, 717-721.

Example 5

Coexistence of Stem Cell-Like PRC2 Activity and Activated Developmental Programs Define Diffuse Midline Glioma Chromatin Landscapes Introduction Diffuse midline gliomas are lethal pediatric CNS tumors with a 5-year overall survival of <5% (Mackay et al. 2017). Approximately 80% of these tumors have mutations in genes encoding either histone H3.1 or H3.3, most prominent of which is the lysine 27-to-methionine "oncohistone" mutation (H3K27M) (Schwartzentruber et al. 2012; Wu et al. 2012). Despite mutant histone H3 comprising ~5-15% of total H3 within the cell, these tumors have low levels of lysine 27 trimethylation (H3K27me3) (Chan et al. 2013; Lewis et al. 2013), an H3 tail modification catalyzed by the Polycomb Repressive Complex 2 (PRC2) methyltransferase EZH2 and associated with transcriptionally silent chromatin. In vitro studies demonstrating that the H3K27M tail binds the EZH2 active site and inhibits its catalytic activity (Bender et al. 2013; Lewis et al. 2013; Justin et al. 2016), ectopic expression studies of H3K27M showing that it can globally reprogram PRC2 landscapes (Bender et al. 2013; Chan et al. 2013), and the finding of low total H3K27me3 in DMG patient samples (Chan et al. 2013; Lewis et al. 2013) led to a model positing that global inhibition of EZH2 activity by H3K27M leads to gliomagenesis (Morgan and Shilatifard 2013; Weinberg et al. 2017).

More recent results have called this model into question. First, in a reconstituted nucleosome model, PRC2 bound H3K27M-containing nucleosomes with similar affinity to wildtype nucleosomes, which is inconsistent with EZH2 having high affinity for H3K27M (Wang et al. 2017). Second, large-scale genomic analyses of 1,000 patient samples did not identify EZH2 mutations that would phenocopy a global PRC inhibitor (Mackay et al. 2017). Finally, recent ChIP-Seq assays in DMGs demonstrated surprising residual H3K27me3 domains, some of which contained more H3K27me3 than histone-wildtype DMGs (Mohammad et al. 2017; Piunti et al. 2017). The regulatory logic underlying the retention of specific PRC2 domains despite the presence of a PRC2 inhibitor remains unknown (Weinberg et al. 2017; Funato and Tabar 2018). It has also become clear that H3K27M may require specific developmental cues or secondary mutations to promote tumorigenesis. For example, H3K27M alone is insufficient to induce gliomas in murine models except within a very narrow developmental window (Pathania et al. 2017). In addition, single-cell RNA-seq analysis from DMG cell populations suggests that a specific undifferentiated progenitor cell-of-origin gives rise to the tumor (Filbin et al. 2018). Furthermore, the observed co-occurrence of ACVR1 mutations with H3.1K27M and PDGFRA amplification with H3.3K27M indicates that H3 mutations need genetic modifiers to contribute to oncogenesis. The impact of developmental cues and secondary mutations on chromatin landscapes in DMGs have yet to be fully elucidated.

Figure 33A:
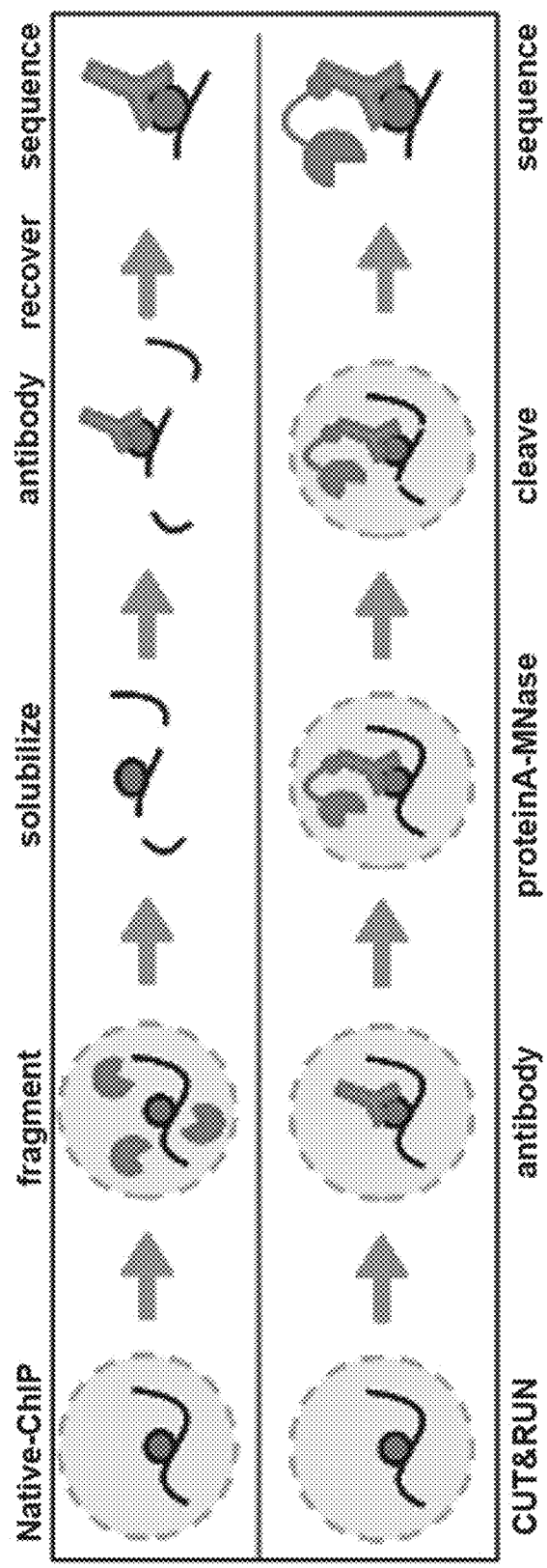
FIGS. 33A-33D show H3K27M incorporation in H3 mutant DMGs is H3 variant-dependent.

To better understand the diseased chromatin landscapes observed in H3K27M-containing DMGs, we have applied Cleavage Under Targets and Release Using Nuclease (CUT&RUN), a recently described method for mapping protein:DNA interactions genome-wide (Skene and Henikoff 2017; Skene et al. 2018), to a panel of patient-derived DMG cell lines either lacking a histone mutation or containing a lysine-to-methionine substitution in H3.1 or H3.3 at position 27 in the H3 tail (FIG. 33A). This method allows for profiling of the genome-wide localization of mutant H3K27M histone with high resolution and provides highly quantitative comparisons of H3K27me3 occupancy genome-wide through the use of an exogenous cell spike-in as a normalization control. Application of quantitative CUT&RUN to a representative panel of DMG cell lines and untransformed stem cells reveals that the residual PRC2 activity in histone-mutant DMGs is highly concordant with PRC2 activity in embryonic stem cells, despite DMGs concurrently expressing a mixture of stem-like and differentiated cell markers. These results indicate that retention of a primitive stem cell-like PRC2 landscape in the face of differentiation cues and reduced PRC2 activity are defining features of H3K27M-DMGs and potential vulnerabilities for these fatal pediatric tumors.

Results

H3K27M Deposition in DMGs is H3 Variant-Dependent

Figure 33B:
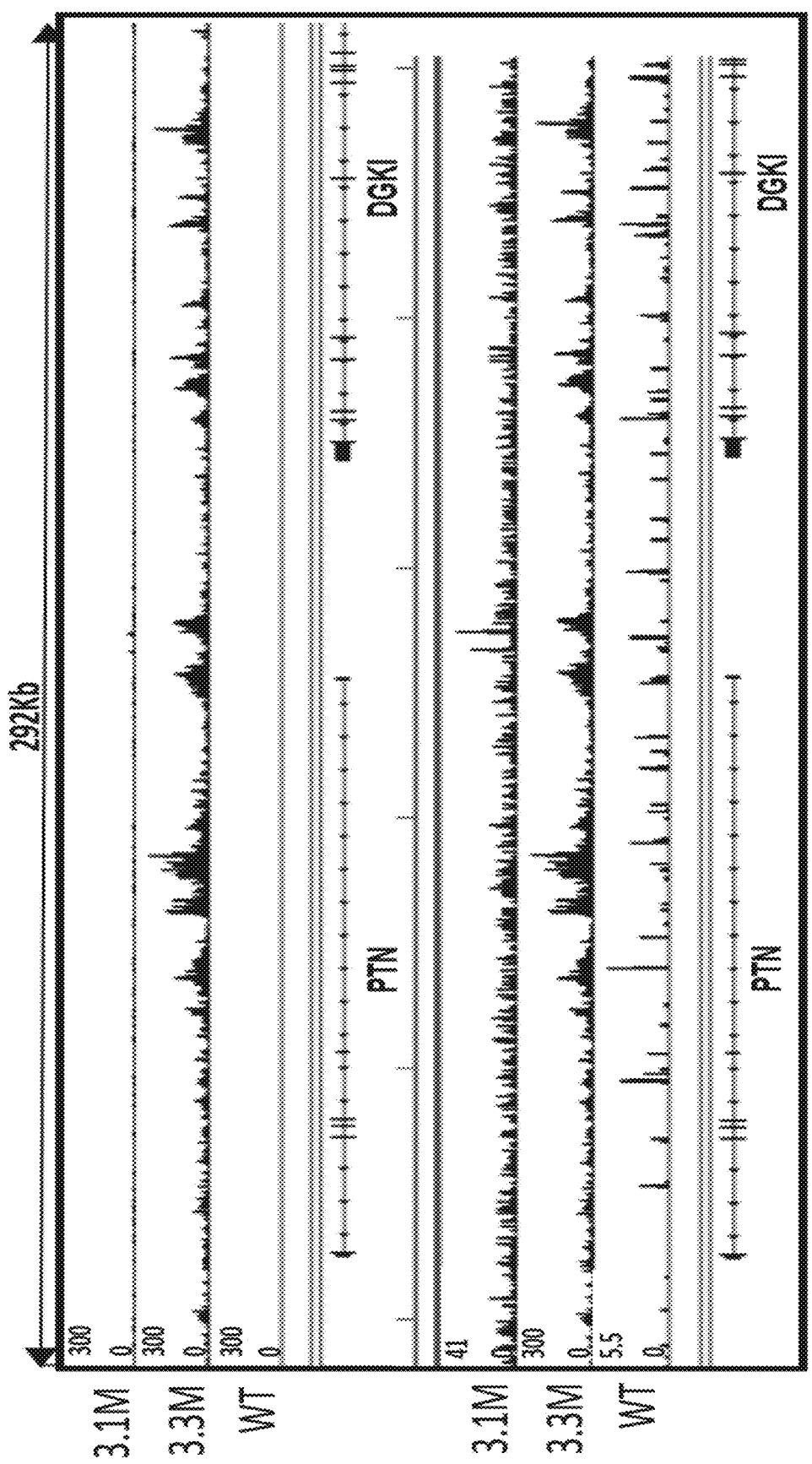
Figure 33C:
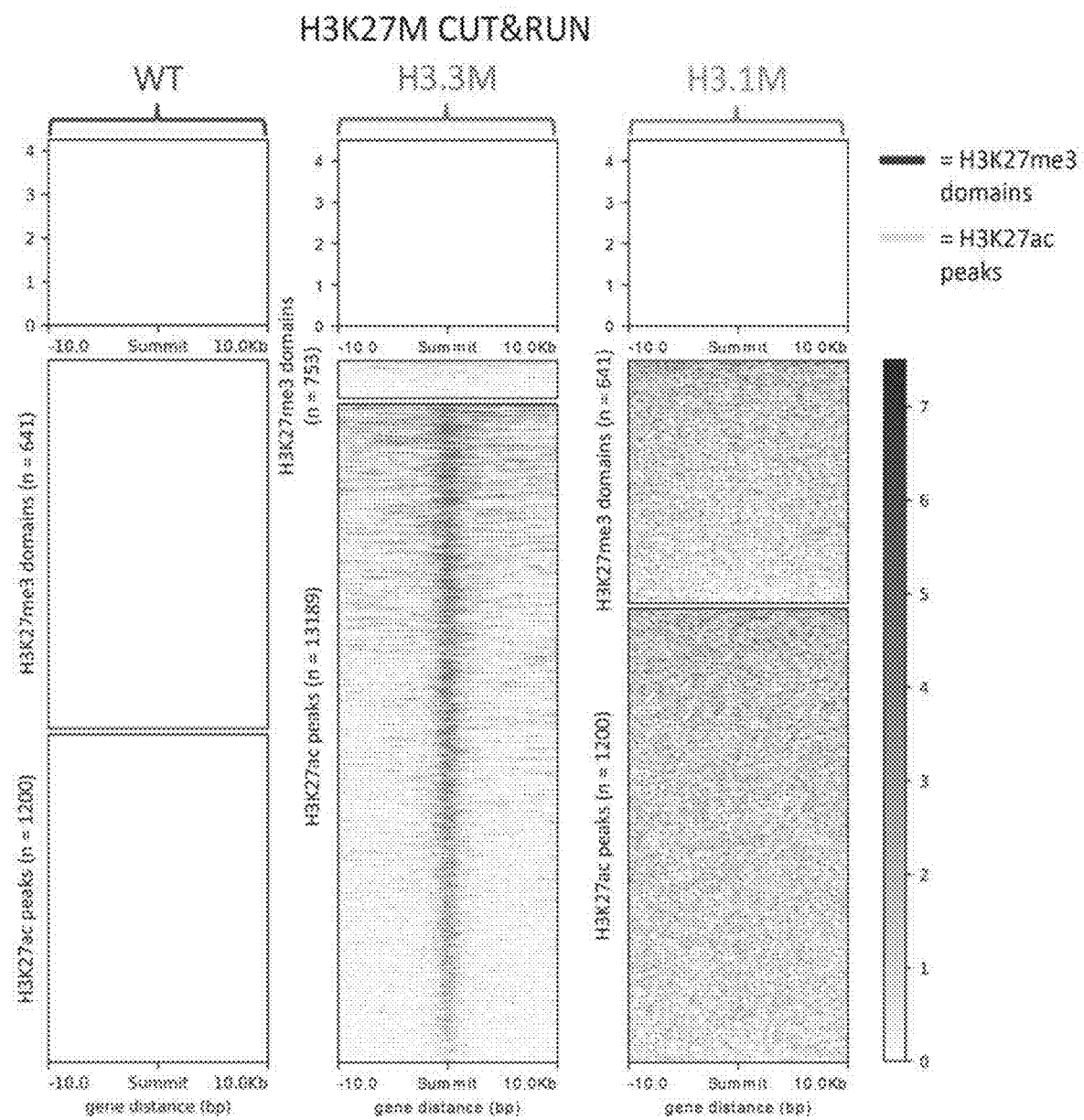

We first sought to analyze the genome-wide localization of the H3K27M oncohistone in patient DMG cell lines bearing K27M mutations in either H3.1 or H3.3. H3.1 is a histone variant that is deposited in chromatin in a replication-dependent manner, resulting in uniform distribution throughout the genome (Maze et al. 2014). In contrast, the H3.3 variant is deposited in a replication-independent manner and accumulates at sites of high histone turnover (Maze et al. 2014). To assess genome-wide localization of H3K27M in H3.1K27M- and H3.3K27M-DMGs, an antibody against H3K27M was used in CUT&RUN reactions in three DMG cell lines, SU-DIPG-IV (H3.1K27M), SU-DIPG-XIII (H3.3K27M) and VUMC-10 (MYCN-amplified, H3 wildtype). The anti-H3K27M antibody is highly specific for H3K27M but cannot distinguish between H3.1K27M and H3.3K27M (Piunti et al. 2017; Fang et al. 2018). H3K27M CUT&RUN profiles in H3.3K27M DMG cells show that H3.3K27M accumulates in defined domains (FIG. 33B). Moreover, when we compared H3K27M with H3K27me3 and H3K27ac CUT&RUN in the same cell lines, H3.3K27M peaks correlated closely with H3K27ac peaks, and had minimal overlap with H3K27me3 domains, consistent with H3.3 incorporation at sites of active histone turnover (FIG. 33C). Analysis of genome-wide localization of H3K27M in the H3.3K27M cell line shows accumulation at several genes with important roles in DMG oncogenesis, including PTN (FIG. 33B), H3F3A and MYC (Mackay et al. 2017; Qin et al. 2017). In addition, H3.3K27M is present at loci that are transcriptionally active in embryonic stem cells (ESCs), including the ESC reprogramming factors Sox2, and MYC (Takahashi and Yamanaka 2006), suggesting a primitive cell-of-origin. Components of the SHH signaling pathway, including DHH, SUFU, PTCH1, GLI1 and GLI2 are also sites of H3K27M accumulation, indicating activation of the hedgehog pathway (Monje et al. 2011).

Figure 33D:
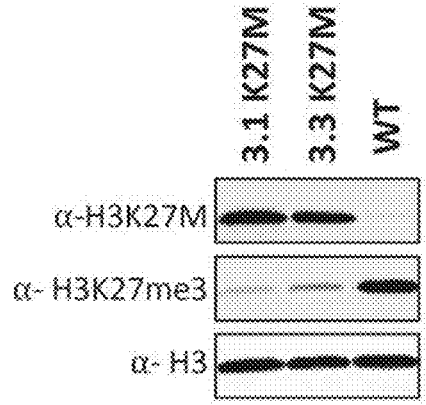

In contrast to H3.3K27M, CUT&RUN profiling with the H3K27M antibody in the H3.1K27M cell line shows uniform distribution throughout the genome without defined domains of enrichment, consistent with replication-dependent incorporation (FIG. 33B, 33C). The lack of identifiable peaks in the H3.1K27M cell line is not due to expression, as H3.1K27M and H3.3K27M are expressed at similar levels (FIG. 33D). Heat maps of H3.3K27M and H3.1K27M clearly demonstrate defined peaks (FIG. 33C) in the H3.3K27M-DMG cell line but not in the H3.1K27M-line. These data also demonstrate that H3.1K27M is present at levels above the background observed in the H3.3K27M background, indicating detectable incorporation genome-wide (FIG. 33C). As a control, the H3K27M antibody was used in a CUT&RUN reaction in VUMC-10. No significant signal was observed, nor was signal observed in a Western blot, verifying the specificity of the antibody for H3K27M (FIG. 33C, 33D).

H3K27M-DMGs Contain Unique H3K27Me3 Domains Absent in Wildtype Gliomas

The finding of different patterns of H3K27M localization in H3.1K27M and H3.3K27M DMG cell lines afforded an opportunity to investigate the relationship between H3K27M and H3K27me3 localization. It has been proposed that H3K27M binds and inhibits EZH2 activity directly (Weinberg et al. 2017; Funato and Tabar 2018), which implies that H3K27me3 and H3K27M should not co-occupy large domains. To determine whether H3K27me3 and H3K27M are mutually exclusive within large domains, we performed CUT&RUN with an H3K27me3-specific antibody in the DMG cell lines. We also capitalized on the ability of CUT&RUN to quantitatively measure PRC2 domain size and robustness across DMG cell lines with vastly different H3K27me3 content via an exogenous spike-in. We added Drosophila S2 cells to CUT&RUN reactions at a fixed ratio of $1\times10^6$ human to $5\times10^4$ Drosophila cells.

Figure 34A:
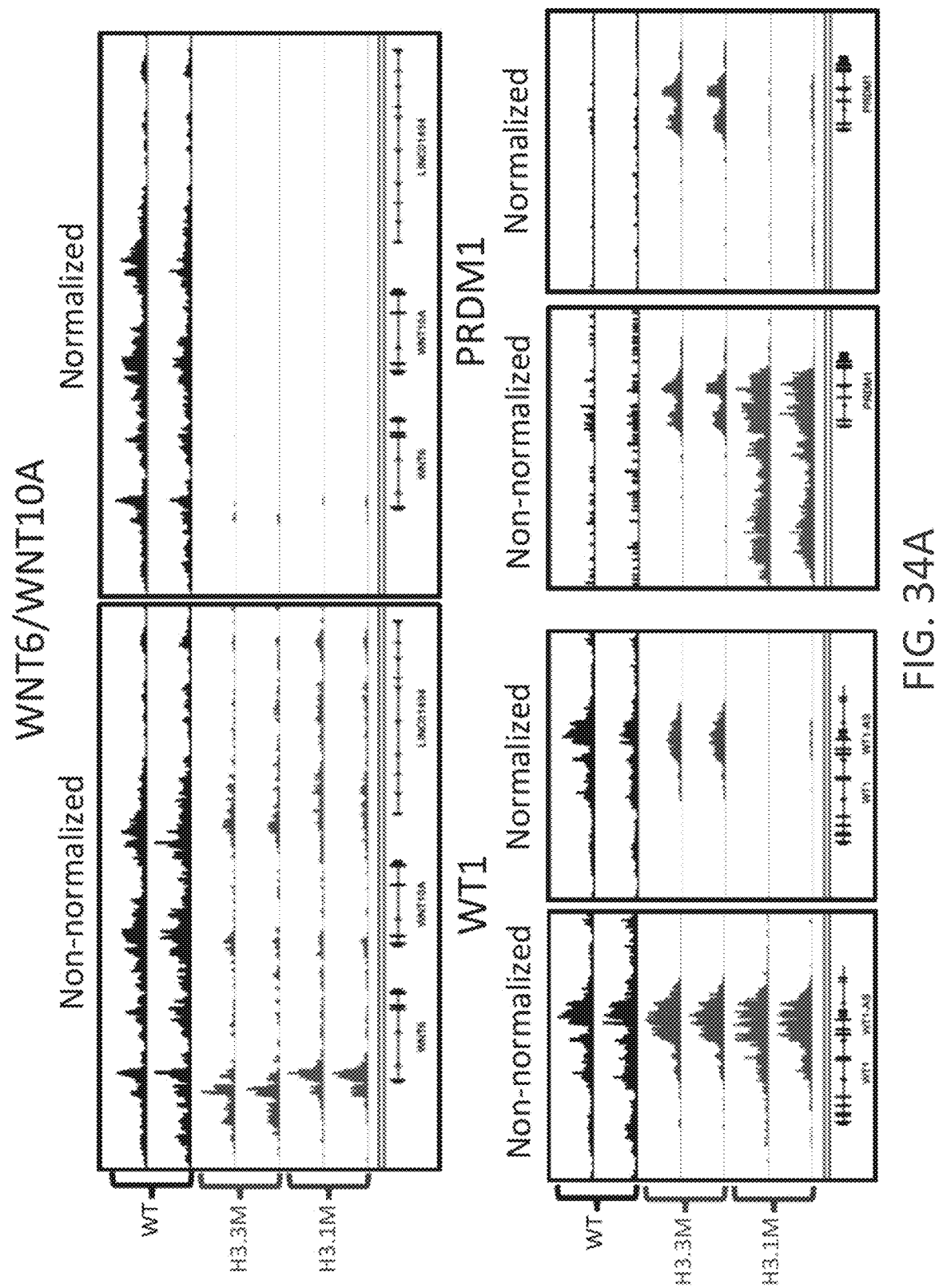
FIGS. 34A-34C show H3 mutant DMGs exhibit unique H3K27me3 domains.
Figure 34B:
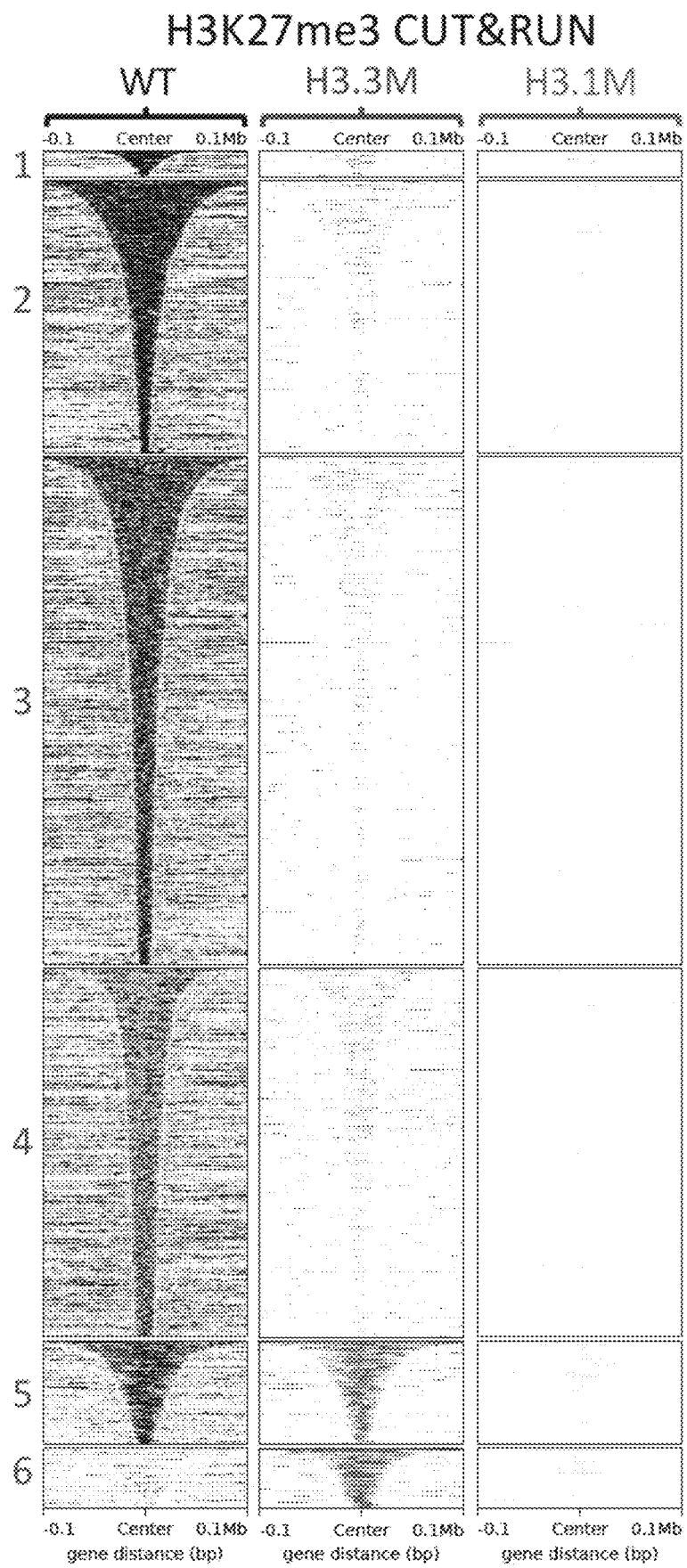

Since the H3K27me3 antibody recognizes both *Drosophila* and human H3K27me3, sequencing of human and *Drosophila* reads allowed for normalization to a consistent control and direct comparison between human samples. Spike-in reads tracked closely with quantitative western blot results between cell lines, confirming the validity of our quantitative normalization strategy. Interestingly, though the H3K27me3 content varied significantly between DMG cell lines (FIG. 33D), H3K27me3 domains were identified in all of them, including both H3.1K27M and H3.3K27M cell lines that have been previously reported to have almost undetectable levels of H3K27me3 (Grasso et al. 2015; Piunti et al. 2017) (FIG. 34A). Pearson's correlation analysis demonstrates higher similarity in H3K27me3 distribution between H3.1K27M and H3.3K27M tumors than with their wildtype counterpart, consistent with similar relationships observed in genomic and transcriptomic analyses of DMGs (Mackay et al. 2017) (FIG. 34B). However, correlation analysis using normalization-sensitive Lin's correlation to observe combined differences in distribution and signal intensity shows segregation of H3.3 and H3.1, which is the result of the reduced H3K27me3 deposition in the H3.1K27M DMG cell line (FIG. 34B). We uncovered many enriched regions in histone mutant DMGs at numerous loci of interest, including the tumor suppressor WT1 (FIG. 34A). Known tumor suppressors such as CDKN2a were PRC2 targets in the H3.3K27M and the histone wildtype cell line, but not in the H3.1K27M cell line, consistent with previous reports (Piunti et al. 2017).

Figure 34C:
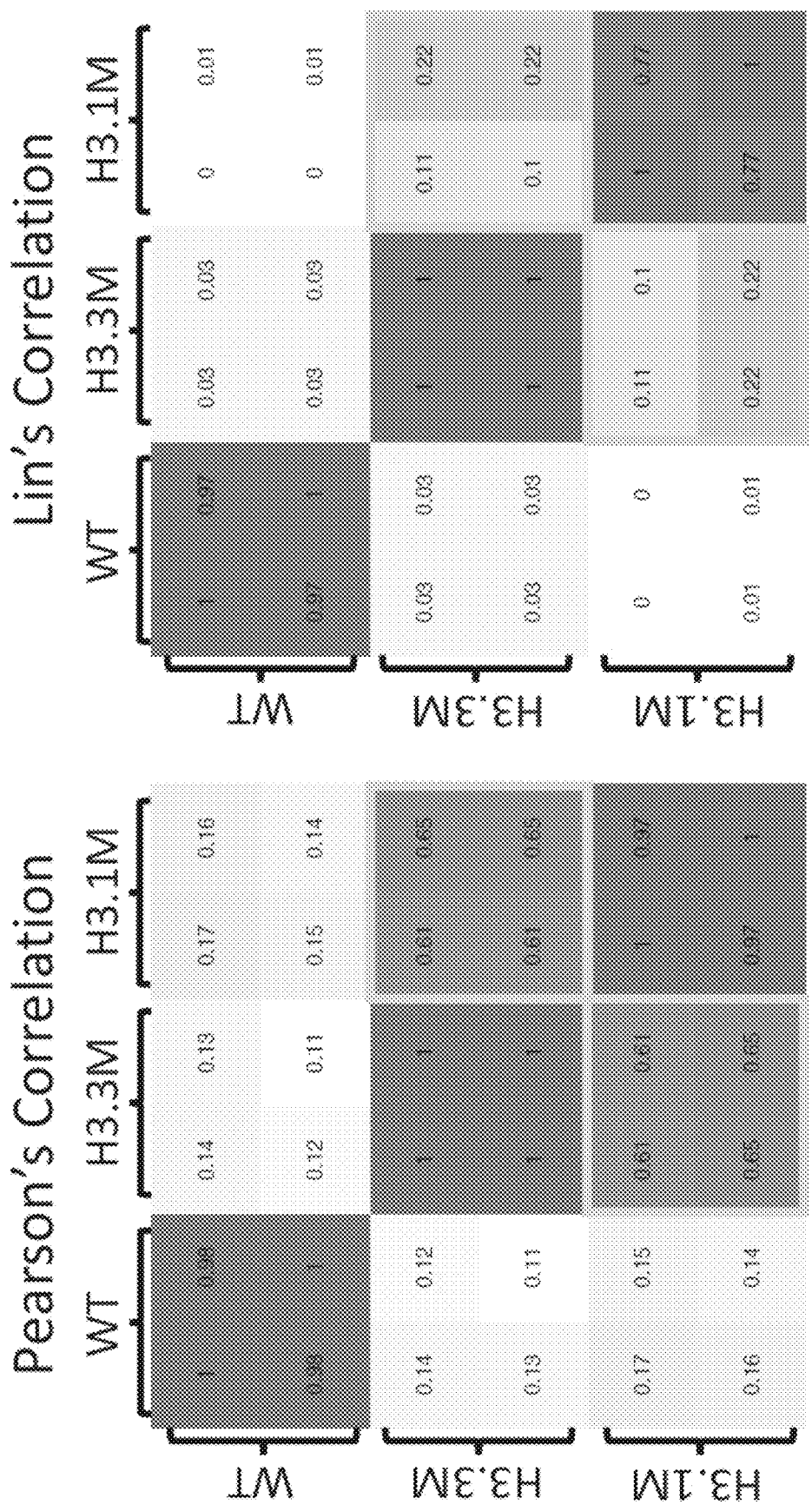

To determine specific H3K27me3 regions unique to each cell line, we used genome-wide normalized signal for each line to define the maximum difference in signal between any two lines at every base pair in the genome, and called "peaks" based on contiguous regions of high differential signal. We then used k-means clustering to group differential H3K27me3 peaks based on H3K27me3 signal in each cell line, resulting in an optimal solution containing 6 clusters. Comparison of differential H3K27me3 domains in the different DMG cell lines shows several clusters of PRC2 domains present in the wildtype cell line that are not present in the H3.1K27M and H3.3K27M cell lines (FIG. 34C). Though the majority of differential H3K27me3 regions (Top 4 clusters) are specific to wildtype, there remain hundreds of regions (Cluster 5) that retain H3K27me3 in the H3.3K27M cells, as well as several more (Cluster 6) that are heavily enriched for H3K27me3 in H3.3K27M in the absence of any enrichment in wildtype (FIG. 34C). Cluster 6 domains overlap with cell type-specific transcription factors including numerous T-box, Forkhead and Distal-less family members, suggesting cell-of-origin differences from histone wildtype tumors. Cluster 6 also contains several known tumor suppressors including PRDM1 and VGLL3, which are often mutated in hematological and ovarian malignancies, respectively (FIG. 34A) (Mandelbaum et al. 2010; Karube et al. 2011).

The identification of very low residual H3K27me3 domains in the H3.1K27M cell line is intriguing given that H3K27M is deposited genome-wide in these cells (FIG. 33C, 34A). This result suggests that PRC2 is active but less efficient in the local presence of H3.1K27M. Although we did not find areas devoid of H3.1K27M in PRC2 domains, it is also possible that a fraction of H3.1 may be locally evicted and replaced by wildtype H3.3, a suitable EZH2 substrate that would allow for restoration of PRC2 domains. To investigate this possibility, wildtype H3.3 localization in the H3.1K27M cell line was assessed using CUT&RUN. No enrichment for H3.3 is seen in K27me3 domains. Given the uniform distribution of H3.1K27M in the H3.1K27M cell line and consistent signal observed within PRC2 domains, these data suggest that H3K27M and H3K27me3 can co-exist locally in chromatin.

H3K27M-DMGs have a Primitive Stem Cell-Like H3K27Me3 Configuration

The identification of H3K27me3 domains specifically retained in H3K27M-DMGs that are absent in the wildtype gliomas, and the coexistence of H3K27M and H3K27me3-containing loci, indicates that DMG chromatin landscapes may not solely be determined by the impact of H3K27M on EZH2 activity. The unique H3K27me3 patterns observed in histone mutant DMGs might instead be derived from the cell-of-origin for the tumors. To investigate this, we sought to quantitatively compare H3K27me3 domains in DMGs with those in a panel of neural stem cells (NSC) and ESCs that represent an artificial developmental trajectory from which the putative precursor for DMGs Is likely to have arisen. ESCs have low H3K27me3 and have previously served as a model for H3K27M-gliomagenesis (Funato et al. 2014), making for a relevant comparison to H3-mutant DMGs, while fetal forebrain-derived NSCs are an established control for glioblastoma (Pollard et al. 2009).

Figures 35A, 35B:
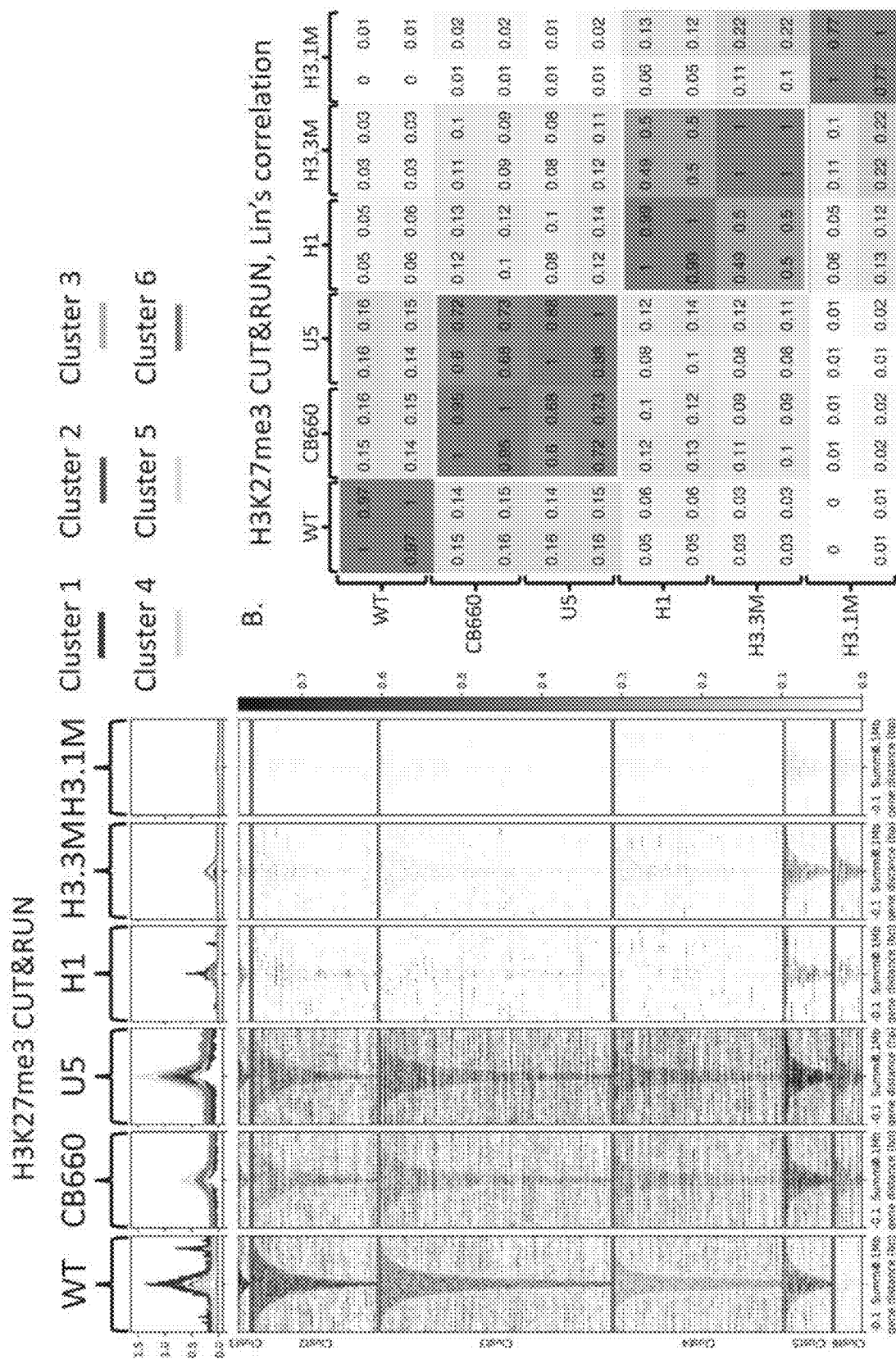
FIGS. 35A-35C show H3K27me3 adopts a primitive stem cell-like configuration in H3 mutant DMGs.
Figure 35C:
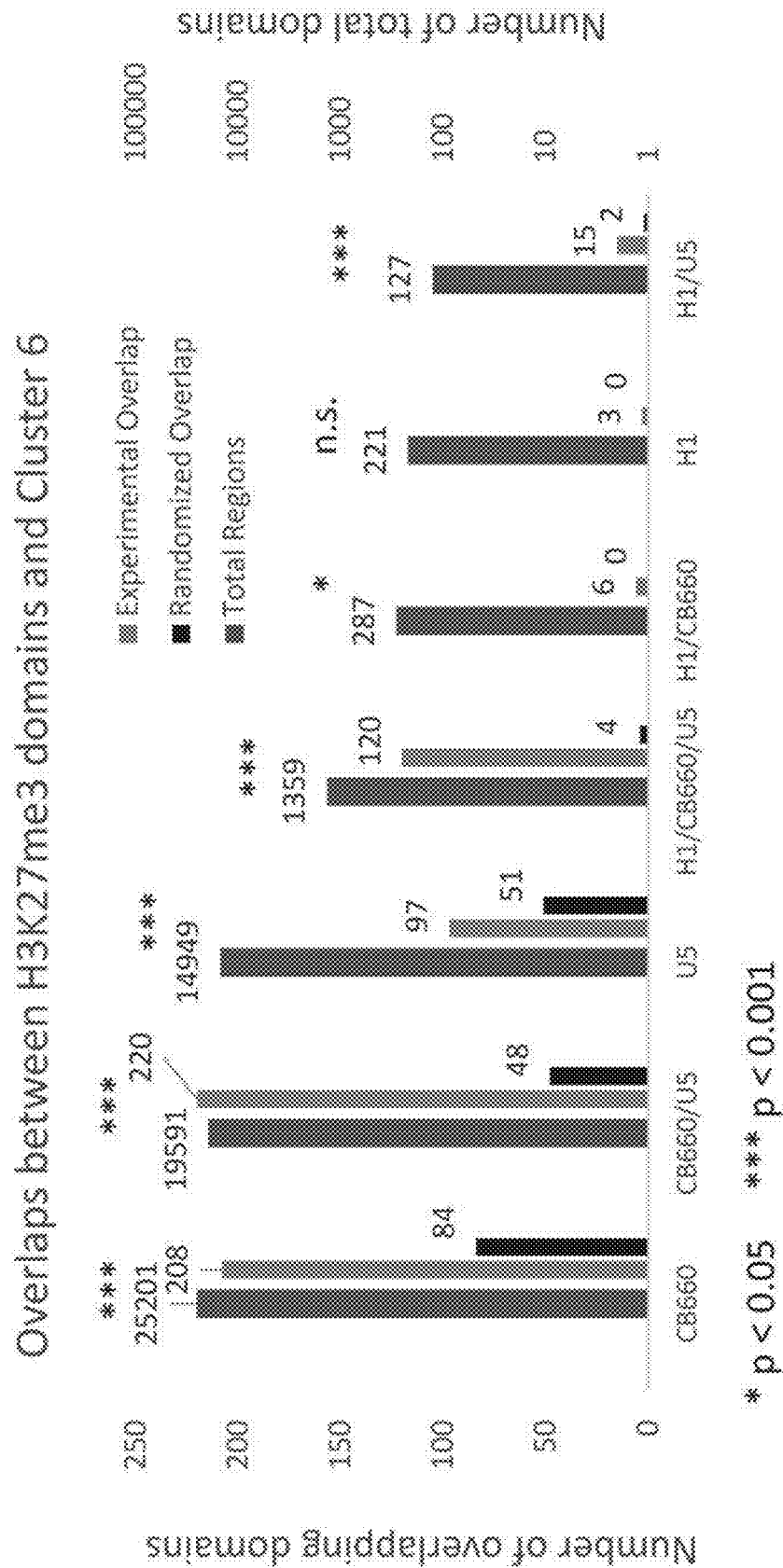

We performed CUT&RUN for H3K27me3 in untransformed H1 ESCs and the NSC lines CB660 and U5 using the spike-in strategy described above to enable quantitative comparisons. Robust PRC2 domains were identified in all cell types (FIG. 35A). Genome-wide profiles for H3K27me3 in H3.1K27M and H3.3K27M cell lines are consistently more highly correlated with the ESC and NSC lines than with the histone wildtype DMG. Strikingly, quantitative comparisons that incorporate absolute H3K27me3 levels via Lin's correlation demonstrate high relatedness between the ESC line and H3.3K27M, suggesting a primitive stem-like configuration of H3K27me3 domains in H3.3K27M (FIG. 35B). To further investigate unique H3K27me3 domains, we focused on H3K27me3-enriched regions contained in the histone mutant DMG-specific cluster (Cluster 6) from the previous differential H3K27me3 analysis. Comparison of H3K27me3 domains in Cluster 6 between the ESC and NSC lines shows that they have substantial overlap with domains identified in Cluster 6 in the H3.3K27M cell line (FIG. 35C). This is intriguing given that global H3K27me3 is low in ESCs and indicates that these are important sites for maintenance of a primitive stem cell state. In addition, a substantial number of transcription factors associated with mutually exclusive differentiation pathways are present within cluster 6, representing a set of PRC2 targets either likely to already be present in the DMG progenitor cell or generated de novo during the accumulation of secondary mutations. Cluster 6 genes specific to DMGs but absent in untransformed stem cells include tumor suppressor genes PRDM1 and VGLL3 as well as other tissue-specific transcription factors.

H3K27M-DMGs Contain Chromatin Signatures of Activated Developmental Pathways

Figure 36A:
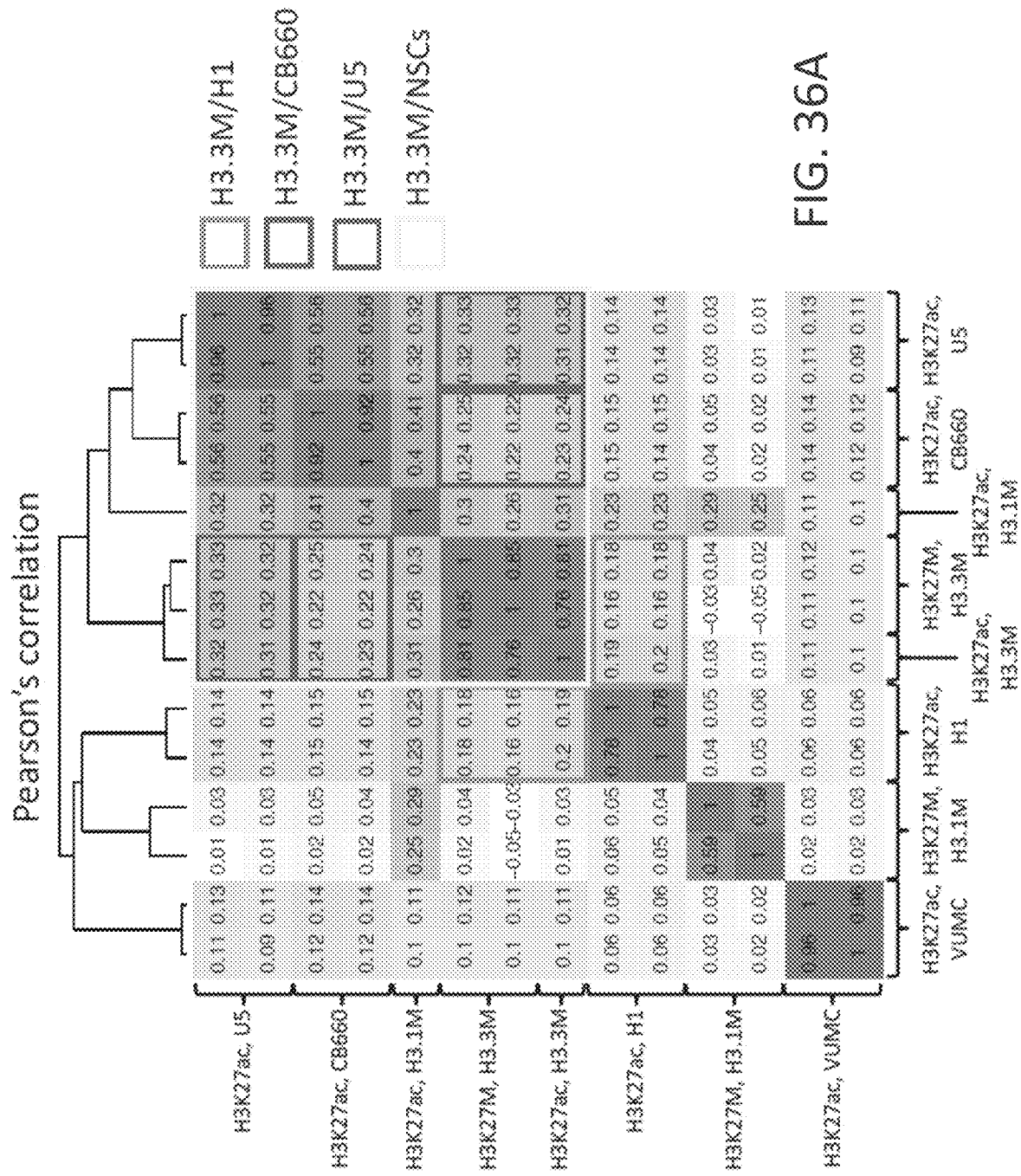
FIGS. 36A-36B shows H3K27M incorporates at a combination of hESC and neural-specific genes in H3.3 mutant DMGs.

H3K27me3 profiling showed that H3K27M-DMGs have a primitive stem-like state; thus, we sought to determine whether H3K27ac and H3.3K27M enrichment in DMGs reflects a stem cell-like profile as well. We generated a correlation matrix comparing H3K27ac peaks in ESCs, NSCs, and DMGs, and H3.3K27M peaks in DMGs, to identify similarity in active chromatin profiles between the different cell lines. H3K27ac and H3K27M in the H3.3K27M DMG cell line had high correlation coefficients of 0.76 and 0.81 (Piunti et al. 2017) (FIG. 36A). The histone wildtype DMG line demonstrated poor correlation to the other DMG cell lines (FIG. 36A), consistent with a different constellation of secondary mutations and a putatively different cell-of-origin (Mackay et al. 2017). Interestingly, the H3-mutant DMG lines were more closely related to NSC lines than ESCs (FIG. 36A), which contrasts with the finding that the H3K27me3 domains in the H3-mutant DMGs resembled ESCs rather than NSCs (FIG. 35B). H3.3K27M enrichment in H3.3 mutant DMG cells was more consistent with H3K27ac enrichment in NSCs than in ESCs, indicating that H3.3K27M incorporates into an active chromatin environment that is globally more similar to NSCs.

Figure 36B:
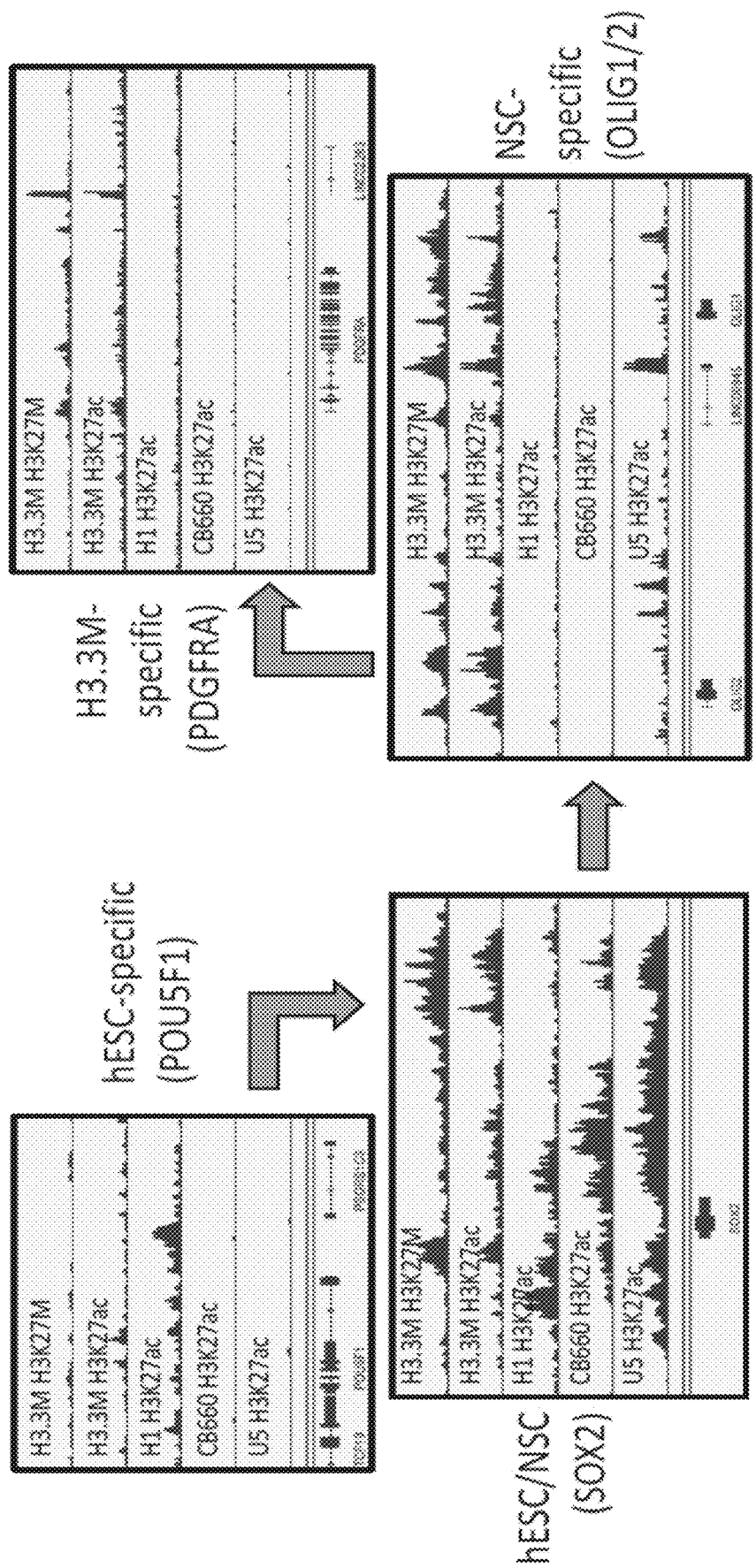

Shared H3K27M/H3K27ac peaks present in the H3-mutant DMG samples include genes involved in glial maturation such as Olig1, Olig2 (FIG. 36B) and GFAP, which are shared most closely with the U5 cell line, and general neural regulators NEUROD1 and NES, which are shared with both NSC lines. Moreover, H3K27M/H3K27ac peaks not shared between ESCs or NSCs include components of the Sonic Hedgehog and WNT signaling pathways, and oligodendrocyte precursor-specific active genes such as PDGFRA (FIG. 36B), indicating activation of genes developmentally downstream of NSCs (Filbin et al. 2018). Though hESC-specific regulators such as POU5F1 lack DMG H3K27ac/H3K27M peaks, they are present at the SOX2 and MYC loci, which are strongly active in both ESCs and NSCs (FIG. 36B). Taken together, these data are consistent with primitive DMG progenitor cells attempting to differentiate but being unable terminate stem cell-specific chromatin regulatory mechanisms, resulting in a differentiation block and aberrant coexistence of stem- and differentiation-associated active genes.

H3.3K27M does not Globally Alter PRC2 Landscapes

Figure 37A:
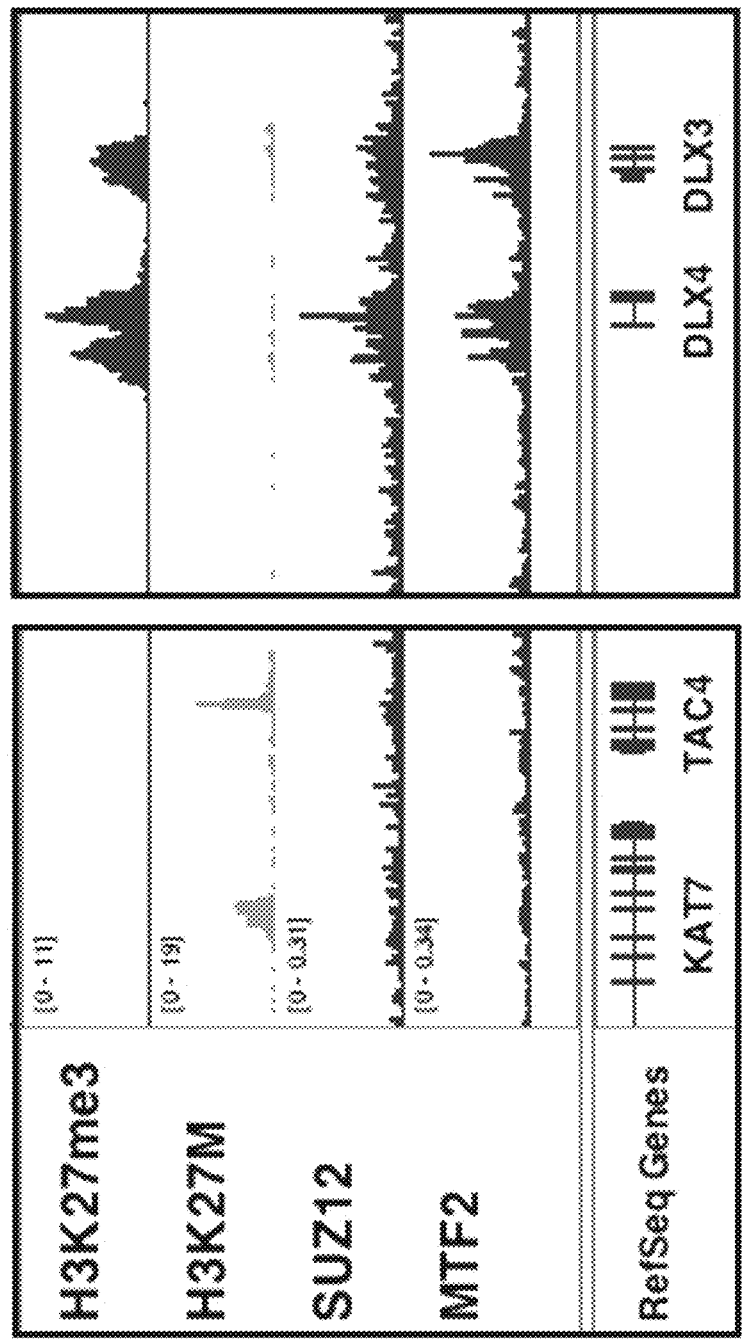
FIGS. 37A-37C show H3K27M does not sequester PRC2 in DMGs.
Figure 37B:
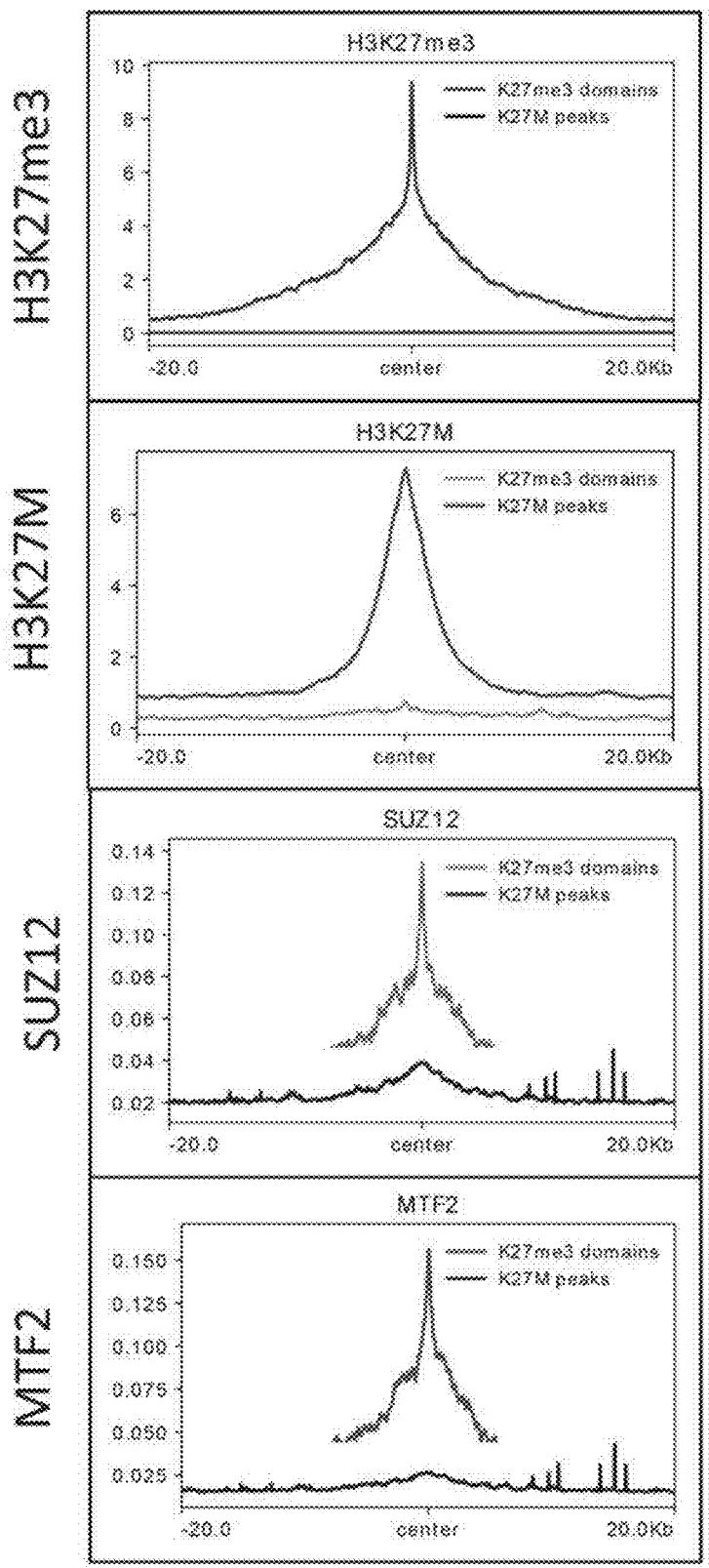
Figure 37C:
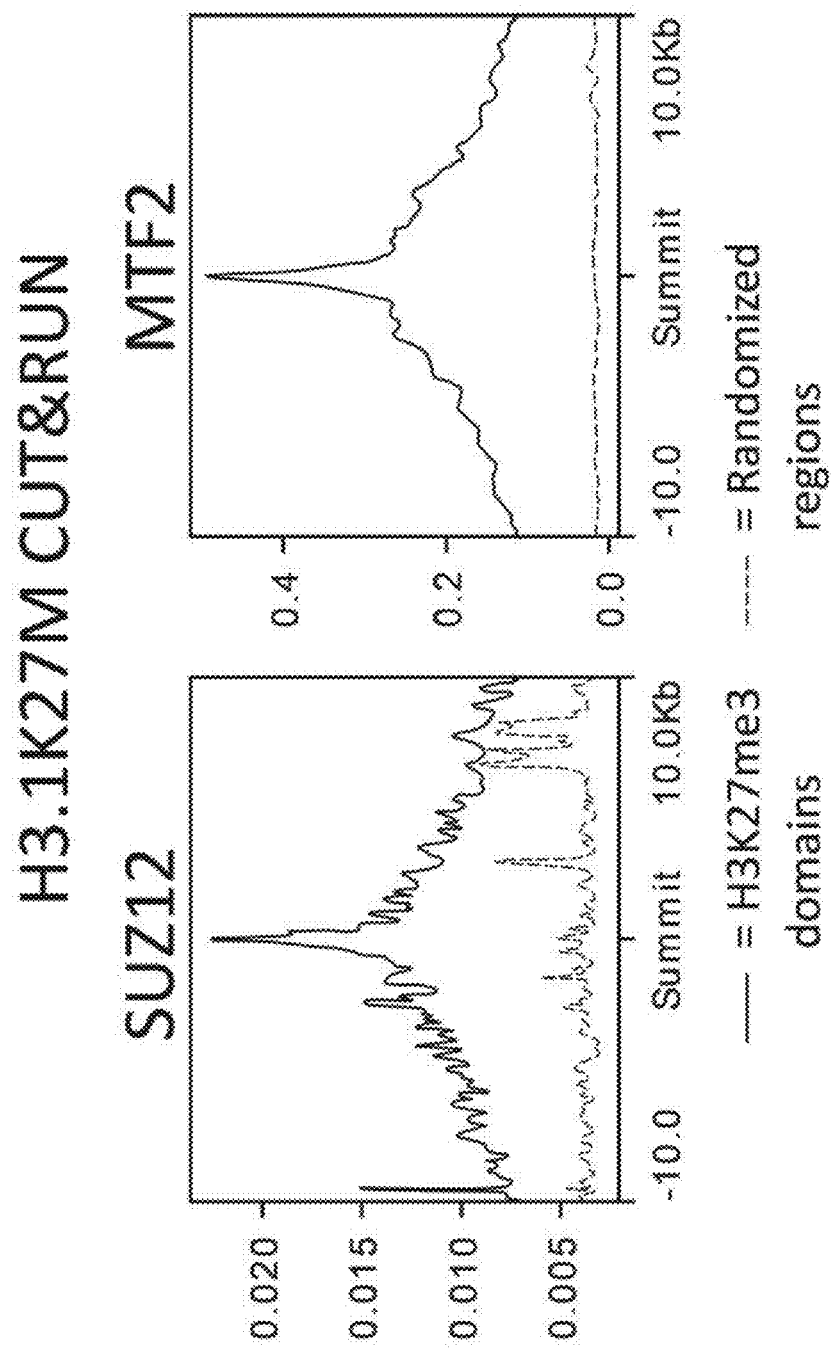

The data presented here are consistent with a model where a stem cell-like cell-of-origin and secondary mutations are the major determinants of chromatin landscapes in DMGs. Previous studies suggested that expression of H3K27M can reduce H3K27me3 levels to those observed in histone-mutant DMGs and reshape PRC2 distribution, though the extent and timeframes of H3K27me3 loss varied widely (Bender et al. 2013; Chan et al. 2013; Lewis et al. 2013). In addition, a more recent report using ESCs found that H3.3K27M can recruit EZH2 to chromatin directly, inhibiting EZH2 at some loci while facilitating PRC2 activity at others (Fang et al. 2018). To investigate PRC2 localization in our DMG panel we used antibodies against the obligate PRC2 subunit SUZ12 and alternate subunit MTF2 in CUT&RUN reactions. SUZ12 and MTF2 signals were highly enriched within H3K27me3 peaks in both H3-mutant DMG cell lines, consistent with PRC2 components mediating deposition of H3K27me3 by EZH2 (FIG. 37A, 37B). However, SUZ12 and MTF2 co-localized poorly with H3K27M-enriched domains relative to H3K27me3-enriched domains (FIG. 37B) in the H3.3K27M cell line. Moreover, SUZ12 and MTF2 signals did not show evidence of genome-wide distribution in the H3.1K27M cell line that would be expected by H3K27M-mediated recruitment, as their enrichment in H3K27me3 domains is significantly elevated above randomly-sampled regions, which contrasts with H3K27M distribution (FIG. 37C). Moreover, SUZ12 and MTF2 signals correlate poorly with H3K27M signal in H3K27M regions in either cell line, indicating it is unlikely that SUZ12 and MTF2 interact with the genome in an H3K27M-dependent manner. We conclude that sequestration of PRC2 by H3K27M is unlikely.

Figure 38:
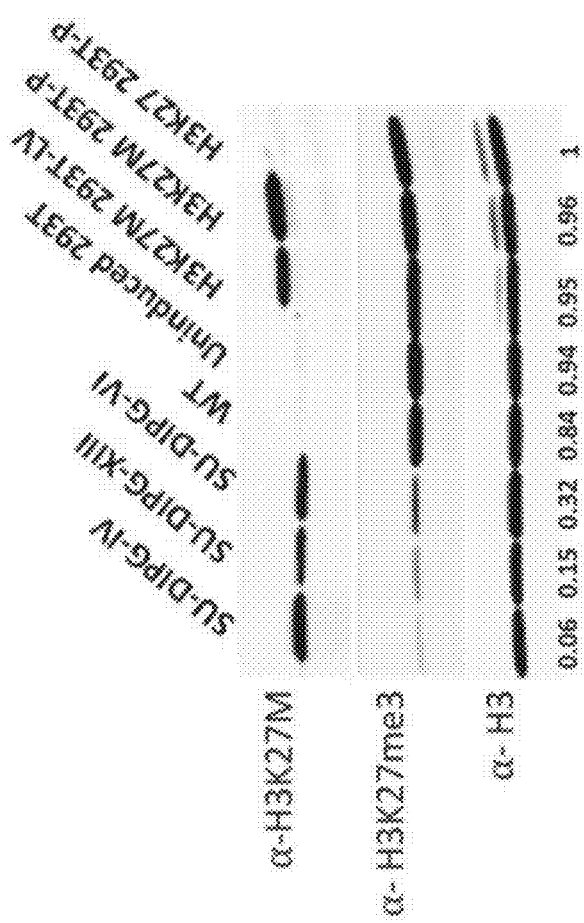
FIG. 38 shows H3.3K27M Western Blot of 293T cells expressing H3.3K27M or wildtype H3.3, LV=lentiviral infected, P=transfected. Numbers represent densitometry values of H3K27me3 band intensity normalized to H3 as percentage relative to 293T expressing FLAG-wildtype H3.3.
Figure 39A:
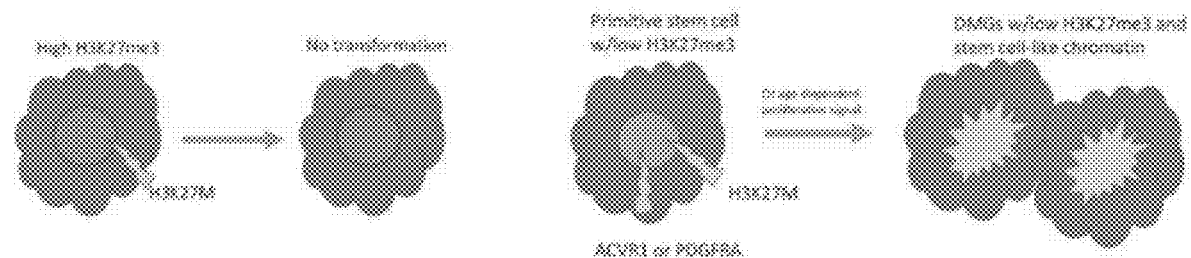
FIGS. 39A-39B show a model showing sensitivity to H3K27M depends on stem-like cell of origin, secondary mutations and developmental context.

Our data indicate that H3.3K27M should not potently inhibit EZH2 activity when expressed at physiological levels. To test this hypothesis, we introduced H3.3K27M in 293T cells at levels similar to those seen in DMGs using both a lentiviral transduction system at low MOI and a plasmid-based transfection system. Antibiotic selection was used to ensure that all cells contained the appropriate constructs. Western blotting demonstrates that after 6 days of expression H3.3K27M is present at similar levels to those observed in the H3.1K27M and H3.3K27M cell lines (FIG. 38). Importantly, compared to total H3 levels, the ectopic H3.3K27M represents a minor fraction of total H3, which is consistent with physiological H3 levels from one H3F3A or HIST1H3b allele (FIG. 38). Despite robust expression of H3.3K27M, minimal reduction in H3K27me3 levels is seen (FIG. 38). These data are not consistent with H3.3K27M potently inhibiting EZH2 globally and instead further supports a model where PRC2 landscapes in DMGs are shaped by a combination of cell-of-origin and secondary mutations (FIG. 39A).

Discussion

DMGs are developmentally-restricted fatal pediatric CNS tumors that have few treatment options. Characterization of chromatin landscapes in these tumors may lead to new therapeutic strategies but has been limited by a paucity of patient-derived samples and cell lines. A recent report using single-cell transcriptomic analysis demonstrated that while DMGs are most transcriptionally similar to oligodendrocyte precursor cells, they aberrantly express markers of both stem cells and mature glia (Filbin et al. 2018). Whether another critical regulator of developmental trajectory, PRC2 activity, also reflects a dysfunctional combination of primitive and mature states in DMGs was not known. Here we used CUT&RUN to profile chromatin landscapes in a representative panel of DMG cell lines and untransformed stem cells. Our data show that low levels of residual PRC2 activity present in H3K27M-DMGs most closely resemble ESC PRC2 landscapes. Probing of transcriptionally active regions of chromatin shows expression of SOX2 and MYC alongside markers of mature glia including GFAP. Taken together, our data are consistent with a stem cell-specific chromatin regulatory network driving ES-like PRC2 activity despite activation of developmental programs and the presence of H3K27M.

Our CUT&RUN approach also allowed us to dissect current models for the contribution of H3.1K27M and H3.3K27M to PRC2 landscapes in DMGs, some of which are centered on the increased affinity of EZH2 for H3K27M (Weinberg et al. 2017; Fang et al. 2018; Funato and Tabar 2018). A recent study suggested that H3.3K27M can inappropriately sequester and inhibit EZH2 at some poised enhancers while facilitating PRC2 activity at other loci in mouse ESCs (Fang et al. 2018). Their model predicts that PRC2 components should localize to a large subset of H3K27M sites in the H3.3K27M-DMG cell line due to sequestration, otherwise PRC2 activity would not be significantly altered. In our data set, we observed minimal overlap between H3K27M-enriched sites and PRC2 components, which is inconsistent with sequestration. Furthermore, we also found that ectopic expression of H3.3K27M in 293T at physiological levels did not decrease H3K27me3 levels, which does not support the concept of H3.3K27M potently inhibiting EZH2 globally (Weinberg et al. 2017). Our data indicate that the interaction of H3.3K27M with EZH2 is unlikely to be the primary determinant of the reduced PRC2 activity seen in H3.3K27M-DMGs.

The impact of H3.1K27M on PRC2 landscapes in H3.1-mutant DMGs is unknown. We used our H3K27me3, H3K27M and H3K27ac data to better understand the aberrant chromatin landscapes observed in H3.1K27M-DMGs.

Figure 39B:
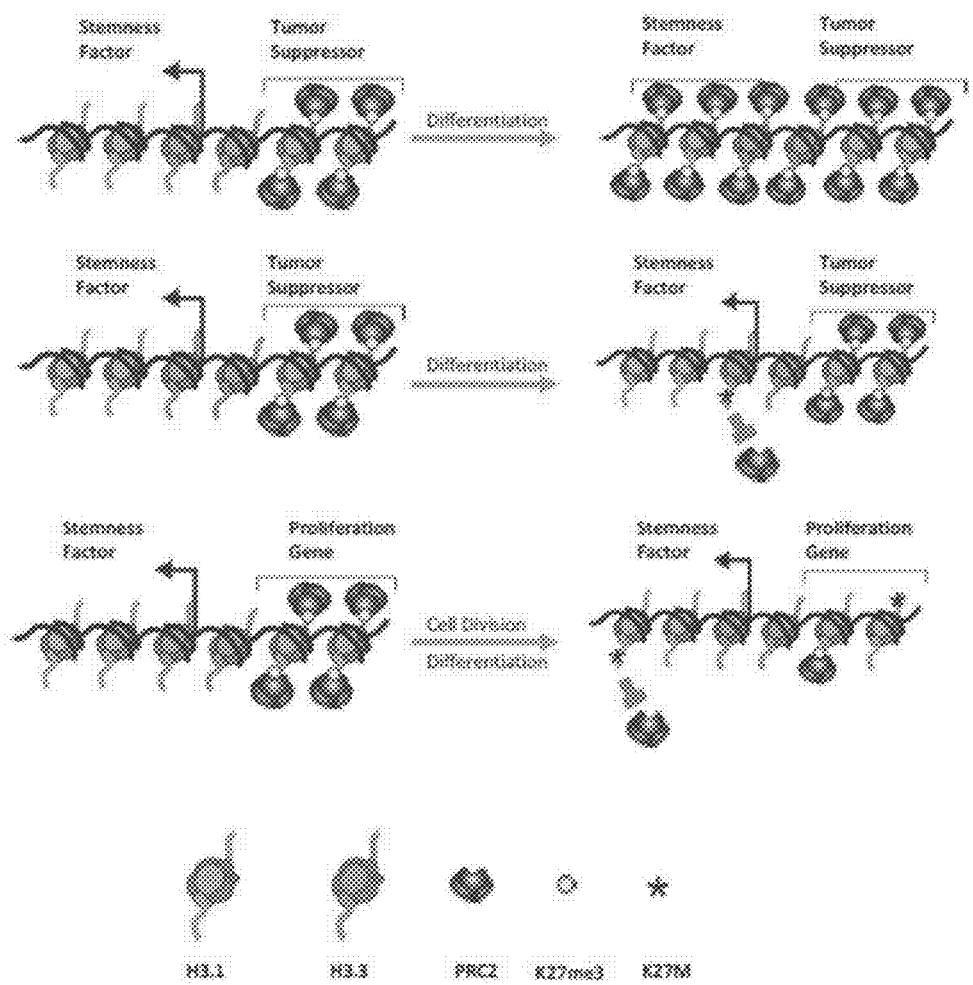

Our profiling of H3.1-mutant DMGs revealed that H3.1K27M is deposited genome-wide in a replication-dependent manner. Quantitative CUT&RUN identified extraordinarily low residual PRC2 activity and co-occupancy with H3.1K27M. The remaining sites of PRC2 activity were similar to those present in H3.3K27M-DMGs and ESCs. We also did not observe evidence for genome-wide deposition of PRC2 components recruited by H3.1K27M, which is another prediction of sequestration models. Instead, our data are consistent with chromatin-associated H3K27M locally inhibiting PRC2 activity, but stem cell-specific PRC2-recruitment mechanisms overcoming H3K27M inhibition at a subset of loci to facilitate tumorigenesis by repressing tumor suppressor loci such as WT1 (FIG. 39B).

If H3K27M is not the major determinant of the aberrant PRC2 landscapes seen in DMGs then how do they arise Our data indicate that cell-of-origin, developmental context and secondary mutations synergize to dictate the PRC2 landscape upon which H3K27M acts in DMGs (FIG. 39A). These data also support a model whereby H3.3K27M exerts its effect in a cell with a primitive stem-like chromatin configuration, which may already be present in the cell-of-origin or acquired during dedifferentiation mediated by a secondary mutation. Phylogenetic analysis demonstrating that H3K27M is an early event in gliomagenesis argues that it needs to be present prior to the acquisition of secondary mutations and activation of developmentally-regulated signaling cascades (Nikbakht et al. 2016) to facilitate tumorigenesis. It is likely that H3.3K27M contributes to oncogenesis by preventing new PRC2 domains from arising when incorporated at transcriptionally active loci in need of silencing during differentiation, such as SOX2 and MYC, preserving activation of stem-cell regulatory networks but allowing response to differentiation cues (FIG. 39B). In contrast, the genome-wide distribution of H3.1K27M may make chromatin refractory to PRC2 activity, preventing silencing of certain pro-proliferative genes while a stem-cell specific PRC2 recruitment mechanism facilitates inefficient but effective repression of tumor suppressors (FIG. 39B). We speculate that chromodomain-containing proteins may be the target of H3K27M, as a recent report showed that H3.3K27M reduces the association of Cbx7 with chromatin (Tatavosian et al. 2018) and Cbx proteins have well-demonstrated roles in establishment of developmentally-regulated PRC2 domains (Morey et al. 2012).

Our model suggesting that H3K27M can only contribute to tumorigenesis in certain chromatin contexts is supported by other studies showing differential sensitivity to H3K27M depending on cell type and developmental stage (Funato et al. 2014; Pathania et al. 2017). Furthermore, the recent identification of infantile ependymomas and radial glia with H3K27me3 levels similar to H3K27M-mutant DMGs shows that H3K27 mutations are not necessary to promote aberrantly low levels of PRC2 activity (Bayliss et al. 2016). In addition, the recent identification of H3K27M in a subset of acute myelogenous leukemias found only in combination with RUNX1 mutations further supports a model whereby the impact of H3K27M is most profound in stem-like chromatin states defined by low H3K27me3 (Lehnertz et al. 2017). In that report, RUNX1 mutations alone had lower levels of H3K27me3 than RUNX1 wildtype blasts, and the combination of RUNX1 mutations and H3.1K27M had lower levels than RUNX1-mutant histone wildtype cells. ACVR1 mutations and PDGFRA amplification may play a similar role in DMGs to RUNX1 mutations in AML, sensitizing cells to the effects of H3K27M. Taken together, these findings demonstrate that secondary mutations and developmental context can be sufficient to reduce PRC2 activity, providing an environment in which H3K27M oncohistones can exert their effects.

The finding of stem-like PRC2 landscapes co-existing with activated developmental programs in DMGs also has clinical and therapeutic implications. Inducing differentiation with conventional strategies such as retinoic acid combined with small molecule inhibitors of chromatin-modifying enzymes that can facilitate resolution of stem-like PRC2 activity, such as EZH2 inhibitors or HDAC inhibitors, is likely to be more efficacious than use of either as monotherapy. The model presented here also suggests that DMGs are unlikely to be more sensitive to EZH2 inhibitor monotherapy than are other primitive stem cells, as they contain a subset of PRC2 domains that have higher levels of H3K27me3 than primitive stem cells. The recent report of a secondary T-cell lymphoma developing in a pediatric patient receiving an EZH2 inhibitor of a CNS tumor is consistent with stem cell sensitivity to EZH2 inhibitors and argues for the benefit of combinatorial therapies that facilitate differentiation while relieving PRC2-mediated repression. Targeting of secondary mutations such as PDGFRA amplification with tyrosine kinase inhibitors combined with induction of differentiation and chromatin modifying agents in DMGs may also be a productive therapeutic approach for these invariably fatal pediatric malignancies.

Materials and Methods Cell Culture

SU-DIPG-IV (H3.1K27M), SU-DIPG-VI (H3.3K27M) and SU-DIPG-XIII (H3.3K27M) cells were generously provided by the laboratory of M. Monje, Stanford University. VUMC-10 cells were obtained. Cells were grown in NeuroCult medium (StemCell Technologies, Vancouver, BC) supplemented with human-EGF at 20 ng/mL and human-bFGF at 20 ng/mL supplemented with penicillin/streptomycin. Cells were passaged with Accutase for dissociation. *Drosophila* S2 cells were grown to log phase in HYQ-SFX insect medium (ThermoFisher) supplemented with 18 mM L-Glutamine and harvested by scraping. 293T cells were grown in DMEM (ThermoFisher) with supplemented with 10% fetal bovine serum and 2 mM L-glutamine.

Whole Cell Lysate Preparation:

For each sample, ~3-5×106 cells were pelleted, washed once with PBS and 200 µL standard protein sample buffer was added to the pellet. Samples were vortexed, boiled for 5 minutes at 1000C and cooled to room temperature. Benzonase (1 µL) was added and samples were incubated at room temperature for 5 minutes before freezing for further use.

CUT&RUN

CUT&RUN was performed as described (Skene et al. 2018). Antibodies used include H3K27me3 (Cell Signaling Technologies 9733), H3K27M (Abcam ab190631), H3K27ac (Millipore MABE647), H3 (Abcam ab24834), H3.3 (Abnova), MTF2 (ThermoFisher), SUZ12 (Abcam ab12073) and rabbit IgG isotype control EPR25A (Abcam ab172730). For CUT&RUN reactions, all antibodies were used at 1:100 dilutions, except SUZ12 and MTF2, which were used at 1:50. Spike-in normalization was performed with *Drosophila* S2 cells at a ratio of 1,000,000 human cells to 50,000 S2 cells, as counted by a ViCell (ThermoFisher).

Library Preparation and Sequencing

Extracted DNA was subjected to the KAPA Hyper-prep library preparation kit protocol (Roche, Inc.) and amplified as previously described (Skene and Henikoff 2017), with the modification that the end-repair reaction and poly-A tailing reactions were performed at <60° C. to preserve small fragments, as described (Lu et al Orkin Cell 2018). Human reads were aligned to hg19 using Bowtie2. Custom scripts for identification of sites of enrichment relative to an IgG control are available at github.com/Henikoff/Cut-and-Run.

Data Analysis

Sequencing reads were mapped to the hg19 genome build using Bowtie2 (Langmead et al. 2012), and paired-end fragment bed files and spike-normalized bedgraphs generated using bedtools (Quinlan and Hall 2010). Correlation heatmaps were generated in R (r-project.org), using normalized fragment counts mapping to 10 kb windows spanning the hg19 genome. Enriched regions and region summits were called using custom scripts. CUT&RUN scatterplots were generated using the ggplot utility in R (ggplot2.tidyverse.org). CUT&RUN signal heatmaps and metaplot profiles were generated using deeptools (Ramirez et al. 2014). Enriched region intersections were quantified using the bedtools intersect utility. Datasets were visualized using Integrative Genomics Viewer (Robinson et al. 2011).

References for Example 5 (Each of which is Incorporated by Reference in its Entirety)

Bayliss J, Mukherjee P, Lu C, Jain S U, Chung C, Martinez D, Sabari B, Margol A S, Panwalkar P, Parolia A et al. 2016. Lowered H3K27me3 and DNA hypomethylation define poorly prognostic pediatric posterior fossa ependymomas. Sci Transl Med 8: 366ra161.

Bender S, Tang Y, Lindroth A M, Hovestadt V, Jones D T, Kool M, Zapatka M, Northcott P A, Sturm D, Wang W et al. 2013. Reduced H3K27me3 and DNA hypomethylation are major drivers of gene expression in K27M mutant pediatric high-grade gliomas. Cancer Cell 24: 660-672.

Chan K M, Fang D, Gan H, Hashizume R, Yu C, Schroeder M, Gupta N, Mueller S, James C D, Jenkins R et al. 2013. The histone H3.3K27M mutation in pediatric glioma reprograms H3K27 methylation and gene expression. Genes Dev 27: 985-990.

Fang D, Gan H, Cheng L, Lee J H, Zhou H, Sarkaria J N, Daniels D J, Zhang Z. 2018. H3.3K27M mutant proteins reprogram epigenome by sequestering the PRC2 complex to poised enhancers. Elife 7.

Filbin M G, Tirosh I, Hovestadt V, Shaw M L, Escalante L E, Mathewson N D, Neftel C, Frank N, Pelton K, Hebert C M et al. 2018. Developmental and oncogenic programs in H3K27M gliomas dissected by single-cell RNA-seq. Science 360: 331-335.

Funato K, Major T, Lewis P W, Allis C D, Tabar V. 2014. Use of human embryonic stem cells to model pediatric gliomas with H3.3K27M histone mutation. Science 346: 1529-1533.

Funato K, Tabar V. 2018. Histone Mutations in Cancer. Annual Review of Cancer Biology 2: 337-351.

Grasso C S, Tang Y, Truffaux N, Berlow N E, Liu L, Debily M A, Quist M J, Davis L E, Huang E C, Woo P J et al. 2015. Functionally defined therapeutic targets in diffuse intrinsic pontine glioma. Nat Med 21: 555-559.

Justin N, Zhang Y, Tarricone C, Martin S R, Chen S, Underwood E, De Marco V, Haire L F, Walker P A, Reinberg D et al. 2016. Structural basis of oncogenic histone H3K27M inhibition of human polycomb repressive complex 2. Nat Commun 7: 11316.

Karube K, Nakagawa M, Tsuzuki S, Takeuchi I, Honma K, Nakashima Y, Shimizu N, Ko Y H, Morishima Y, Ohshima K et al. 2011. Identification of FOXO3 and PRDM1 as tumor-suppressor gene candidates in NK-cell neoplasms by genomic and functional analyses. Blood 118: 3195-3204.

Lehnertz B, Zhang Y W, Boivin I, Mayotte N, Tomellini E, Chagraoui J, Lavallee V P, Hebert J, Sauvageau G. 2017. H3(K27M/I) mutations promote context-dependent transformation in acute myeloid leukemia with RUNX1 alterations. Blood 130: 2204-2214.

Lewis P W, Muller M M, Koletsky M S, Cordero F, Lin S, Banaszynski L A, Garcia B A, Muir T W, Becher O J, Allis C D. 2013. Inhibition of PRC2 activity by a gain-of-function H3 mutation found in pediatric glioblastoma. Science 340: 857-861.

Mackay A, Burford A, Carvalho D, Izquierdo E, Fazal-Salom J, Taylor K R, Bjerke L, Clarke M, Vinci M, Nandhabalan M et al. 2017. Integrated Molecular Meta-Analysis of 1,000 Pediatric High-Grade and Diffuse Intrinsic Pontine Glioma. Cancer Cell 32: 520-537 e525.

Mandelbaum J, Bhagat G, Tang H, Mo T, Brahmachary M, Shen Q, Chadburn A, Rajewsky K, Tarakhovsky A, Pasqualucci L et al. 2010. BLIMP1 is a tumor suppressor gene frequently disrupted in activated B cell-like diffuse large B cell lymphoma. Cancer Cell 18: 568-579.

Maze I, Noh K M, Soshnev A A, Allis C D. 2014. Every amino acid matters: essential contributions of histone variants to mammalian development and disease. Nat Rev Genet 15: 259-271.

Mohammad F, Weissmann S, Leblanc B, Pandey D P, Hojfeldt J W, Comet I, Zheng C, Johansen J V, Rapin N, Porse B T et al. 2017. EZH2 is a potential therapeutic target for H3K27M-mutant pediatric gliomas. Nat Med 23: 483-492.

Monje M, Mitra S S, Freret M E, Raveh T B, Kim J, Masek M, Attema J L, Li G, Haddix T, Edwards M S et al. 2011. Hedgehog-responsive candidate cell of origin for diffuse intrinsic pontine glioma. Proc Natl Acad Sci USA 108: 4453-4458.

Morey L, Pascual G, Cozzuto L, Roma G, Wutz A, Benitah S A, Di Croce L. 2012. Nonoverlapping functions of the Polycomb group Cbx family of proteins in embryonic stem cells. Cell Stem Cell 10: 47-62.

Morgan M A, Shilatifard A. 2013. Medicine. (Poly)combing the pediatric cancer genome for answers. Science 340: 823-824.

Nikbakht H, Panditharatna E, Mikael L G, Li R, Gayden T, Osmond M, Ho C Y, Kambhampati M, Hwang E I, Faury D et al. 2016. Spatial and temporal homogeneity of driver mutations in diffuse intrinsic pontine glioma. Nat Commun 7: 11185.

Pathania M, De Jay N, Maestro N, Harutyunyan A S, Nitarska J, Pahlavan P, Henderson S, Mikael L G, Richard-Londt A, Zhang Y et al. 2017. H3.3(K27M) Cooperates with Trp53 Loss and PDGFRA Gain in Mouse Embryonic Neural Progenitor Cells to Induce Invasive High-Grade Gliomas. Cancer Cell 32: 684-700 e689.

Piunti A, Hashizume R, Morgan M A, Bartom E T, Horbinski C M, Marshall S A, Rendleman E J, Ma Q, Takahashi Y H, Woodfin A R et al. 2017. Therapeutic targeting of polycomb and BET bromodomain proteins in diffuse intrinsic pontine gliomas. Nat Med 23: 493-500.

Pollard S M, Yoshikawa K, Clarke I D, Danovi D, Stricker S, Russell R, Bayani J, Head R, Lee M, Bernstein M et al. 2009. Glioma stem cell lines expanded in adherent culture have tumor-specific phenotypes and are suitable for chemical and genetic screens. Cell Stem Cell 4: 568-580.

Qin E Y, Cooper D D, Abbott K L, Lennon J, Nagaraja S, Mackay A, Jones C, Vogel H, Jackson P K, Monje M. 2017. Neural Precursor-Derived Pleiotrophin Mediates Subventricular Zone Invasion by Glioma. Cell 170: 845-859 e819.

Schwartzentruber J, Korshunov A, Liu X Y, Jones D T, Pfaff E, Jacob K, Sturm D, Fontebasso A M, Quang D A, Tonjes M et al. 2012. Driver mutations in histone H3.3 and chromatin remodelling genes in paediatric glioblastoma. Nature 482: 226-231.

Skene P J, Henikoff J G, Henikoff S. 2018. Targeted in situ genome-wide profiling with high efficiency for low cell numbers. Nat Protoc 13: 1006-1019.

Skene P J, Henikoff S. 2017. An efficient targeted nuclease strategy for high-resolution mapping of DNA binding sites. Elife 6.

Takahashi K, Yamanaka S. 2006. Induction of pluripotent stem cells from mouse embryonic and adult fibroblast cultures by defined factors. Cell 126: 663-676.

Tatavosian R, Duc H N, Huynh T N, Fang D, Schmitt B, Shi X, Deng Y, Phiel C, Yao T, Zhang Z et al. 2018. Live-cell single-molecule dynamics of PcG proteins imposed by the DIPG H3.3K27M mutation. Nat Commun 9: 2080.

Wang X, Paucek R D, Gooding A R, Brown Z Z, Ge E J, Muir T W, Cech T R. 2017. Molecular analysis of PRC2 recruitment to DNA in chromatin and its inhibition by RNA. Nat Struct Mol Biol 24: 1028-1038.

Weinberg D N, Allis C D, Lu C. 2017. Oncogenic Mechanisms of Histone H3 Mutations. Cold Spring Harb Perspect Med 7.

Wu G, Broniscer A, McEachron T A, Lu C, Paugh B S, Becksfort J, Qu C, Ding L, Huether R, Parker M et al. 2012. Somatic histone H3 alterations in pediatric diffuse intrinsic pontine gliomas and non-brainstem glioblastomas. Nat Genet 44: 251-253.

Example 6

Unexpected Conformational Variations of the Human Centromeric Chromatin Complex

The fidelity of chromosome segregation depends on the efficient capture of chromosomes by spindle microtubules via proteinaceous kinetochores, which assemble at specific chromosomal loci called centromeres. Human centromeres comprise 0.5- to 5-Mb-long tandem arrays of an ~170-base-pair (bp) α-satellite repeat unit (Alexandrov et al. 2001). α-Satellite DNA originated in the primate lineage and has since evolved by repeat expansion, resulting in highly homogenous young arrays at the core, with more diverged α-satellite sequences occupying centromere edges. Assembly of these homogenous α-satellite arrays into contiguous maps has presented a serious challenge to existing sequence assembly technologies. To address this problem, we recently used bottom-up hierarchical clustering of sequences bound by centromere proteins for de novo identification of functional centromeric α satellites. We found that the most abundant α-satellite arrays contain a basic 340-bp or 342-bp dimeric unit (Henikoff et al. 2015), which belongs to previously characterized SF1 and SF2 suprachromosomal families of α satellites, respectively (Alexandrov et al. 2001).

Centromeric α satellites are included in specialized chromatin, where canonical histone H3 is replaced by its cenH3 variant, called centromere protein A (CENP-A) (Palmer et al. 1987; Fukagawa and Earnshaw 2014). CENP-A is part of the constitutive centromere-associated network (CCAN) complex, which includes CENP-B, CENP-C, CENP-N, CENP-T, CENP-W, CENP-S, and CENP-X (Hori et al. 2008). Using a comparative chromatin immunoprecipitation (ChIP) with DNA sequencing (ChIP-seq) strategy that included native ChIP (N-ChIP), cross-linking ChIP (X-ChIP), and sequential ChIP (ReChIP), we showed previously that CENP-B, CENP-C, and CENP-T are physically integrated and form a coherent complex with CENP-A nucleosomes. Micrococcal nuclease (MNase) digestion of CENP-A, CENP-C, and CENPT X-ChIP resulted in >165-bp protection over α-satellite dimers (Thakur and Henikoff 2016), whereas under native conditions, MNase digestion resulted primarily in shorter CENP-A-bound α-satellite fragments ranging from ~100 to ~135 bp (Hasson et al. 2013; Henikoff et al. 2015; Nechemia-Arbely et al. 2017).

We and others have found that centromeric chromatin is stable when extracted with 350-500 mM NaCl (Zhang et al. 2012; Hasson et al. 2013; Henikoff et al. 2015). We also found that 500 mM NaCl increased the recovery of centromeric chromatin relative to low-salt conditions (Thakur and Henikoff 2016), raising the question of whether the differences in recovery reflect qualitative differences in the nature of centromeric chromatin. As classical chromatin salt fractionation has been used to separate nucleosomes with different physical properties (Sanders 1978), functions (Rocha et al. 1984), and genome-wide distributions (Henikoff et al. 2009; Jahan et al. 2016),we wondered whether most of the centromeric chromatin had been rendered insoluble by the presence of CCAN components that are absent from the soluble fraction that is typically recovered in native MNase-ChIP studies.

To address the possibility that differential solubility under native conditions reflects qualitative differences in centromeric chromatin, we subjected salt-fractionated chromatin to N-ChIP of centromeric proteins. We further explore differences in salt solubility by adapting our recently developed CUT&RUN (cleavage under targets and release using nuclease) in situ targeted mapping method for profiling specific centromeric components. We found that minor sequence differences between dimeric repeats belonging to the same α-satellite subfamily correspond to differences in both centromere protein binding and the structure of the complex itself.

Results and Discussion

CUT&RUN Salt Fractionation (CUT&RUN.Salt) Releases Discrete CENP-A-Containing Complexes Although ChIP has been the dominant method for mapping specific protein-DNA interactions for more than three decades, recent reports of ChIP-seq artifacts (Park et al. 2013; Teytelman et al. 2013; Jain et al. 2015) have emphasized the importance of validation using non-ChIP methods (Zentner et al. 2015). Of particular concern for centromere studies is the tendency of MNase, which is used for N-ChIP, to cause nibbling and internal cleavages (Brogaard et al. 2012), leading to uncertainty as to whether particles are fully or partially wrapped (Hasson et al. 2013). We recently introduced CUT&RUN, an efficient targeted nuclease method that is unrelated to ChIP in that it causes precise cleavage and release of intact antibody targeted particles without solubilizing the rest of the genome (Skene and Henikoff 2017b). In our most recent CUT&RUN protocol (Skene and Henikoff 2017a), antibodies are added to permeabilized cells bound to magnetic beads followed by addition of a protein fusion between MNase and protein A (pA-MN), which binds to the antibody. MNase is activated by calcium and then stopped by chelation with EDTA and EGTA in the presence of 175 mM NaCl. When MNase is tethered to specific sites in CUT&RUN, there is no detectable nibbling, accessibility bias, or internal cleavages over a range of more than two orders of magnitude in digestion times even for highly AT-rich DNA. Moreover, because there is no chromatin solubilization, the CUT&RUN cleavage pattern of DNA extracted from the insoluble pellet can also be profiled (Skene and Henikoff 2017b). To adapt CUT&RUN for salt fractionation (CUT&RUN.Salt), chelation stop buffer was added without RNase, and, after removing the supernatant, we incubated the cell/bead pellet with 500 mM NaCl. We then extracted DNA from the low-salt and high-salt supernatants and the final pellet (FIG. 49A). CUT&RUN is well suited for salt fractionation in that antibody recognition occurs before the DNA is cleaved, whereas in ChIP, antibody recognition or DNA recovery might be affected by changes in salt-induced particle conformation, such as loss of particle integrity. For all three fractions, we observed a clear enrichment of centromeric α satellites in qPCR assays on DNA from CENP-A, CENP-B, and CENP-C but not in the negative control H3K27me3 CUT&RUN.Salt sequencing libraries (FIG. 49B). Consistent with our N-ChIP results, the majority of chromatin (~70%-80%) was amplified in the high-salt CUT&RUN. Salt fractions (FIG. 49C).

When subjected to paired-end 25-bp×25-bp DNA sequencing and mapped to consensus α-satellite arrays, all three fractions showed strong enrichment for CENP-A, CENP-B, and CENP-C over homogeneous dimeric α satellites (SFI, D5Z2, D7Z1, and SF2) relative to a background control and weak enrichment over noncentromeric α satellites (D5Z1 and D7Z2). Pericentric histone marks (H3K9me2 and H3K9me3) showed weak enrichment over α satellites, as expected, whereas euchromatic marks (H3K27me2 and H3K27me3) showed strong depletion.

Figures 40A, 40B:
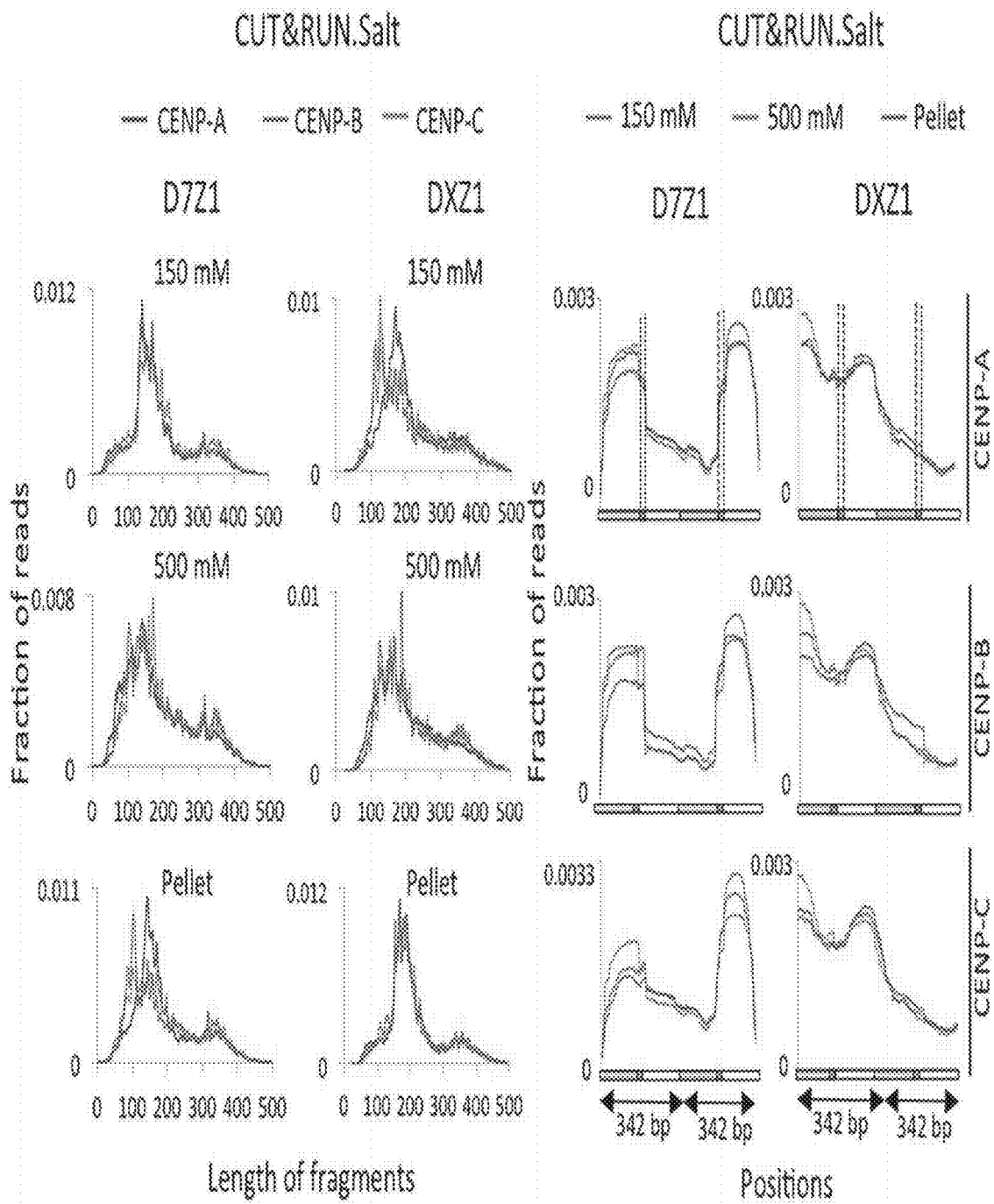
FIGS. 40A-40B show CUT&RUN.Salt releases a discrete CENP-A/B/C complex.

To analyze the fragment length distribution of CUT&RUN.Salt fragments, we performed paired-end 250-bp×250-bp sequencing on CUT&RUN.Salt fractions and mapped merged pairs to active centromeric α-satellite contigs. In contrast to the heterogeneous size distribution seen between N-ChIP salt fractions, we observed much more uniform size distributions between low-salt and high-salt CUT&RUN.Salt fractions (FIG. 40A). For CENP-A, CENPB, and CENP-CCUT&RUN.Salt, all three fractions showed a major peak at ~160-185 bp and a minor peak at ~340 bp. The CENP-A CUT&RUN.Salt profiles on α-satellite contigs revealed discrete CCAN complexes in low-salt, highsalt, and pellet fractions (FIG. 40B) similar to those observed using X-ChIP (Thakur and Henikoff 2016). Thus, CUT&RUN.Salt not only releases the intact CENP-A/B/C complex under native conditions (thereby avoiding potential cross-linking artifacts) but also preserves the particles from disruption, in contrast to N-ChIP, in which untethered MNase produces 100-bp subparticles.

Strong and Dense CENP-B Boxes Stabilize the CENP-A/B/C Complex

As seen above for CENP-A N-ChIP, differential solubility for CENP-A, CENP-B, and CENP-C CUT&RUN.Salt was most evident over the CENP-B boxes, with increasing occupancy seen with increasing salt over the same α-satellite contigs. Interestingly, when averaged over multiple 340-bp units, a peak of CENP-B CUT&RUN occupancy was observed precisely over the CENP-B box in high salt and pellet fractions but not over the low-salt fraction (FIG. 41A). Taken together with the preservation of CCAN particles in CUT&RUN, this absence of an average peak indicates that there are two distinct classes of particles: stable particles that resist disruption and are enriched for CENP-B and less stable particles that are depleted for CENP-B.

We wondered whether CCAN integrity as measured by CUT&RUN.Salt reflects a stabilizing role of CENP-B. The presence of α-satellite sequences with a gradient of divergence at human centromeres provides an opportunity to test this possibility (Henikoff et al. 2015). The most recently expanded abundant CENP-A-enriched α-satellite dimeric arrays contain a high density of CENP-B boxes (approximately one CENP-B box per 340-bp dimer). Older α satellites become more divergent due to an accumulation of random mutations over evolutionary time, which leads to either complete loss or degeneration of CENP-B boxes. We asked whether the divergence of the CENP-B box sequence from the ancestral motif corresponds to the ability of α satellites to bind CENP-A/B/C and therefore the ability to form centromeres.

To address this question, we first identified the middle 15 bp of the 17-bp CENP-B box as being ancestral, as it is present in the large majority of homogeneous SF1 (e.g., D5Z2), SF2 (e.g., Cen13-like), and SF3 (e.g., DXZ1) α-satellite contigs at regular intervals. We then identified statistically significant occurrences of this motif using motif alignment and search tool (MAST) and scored them between 0 (more than three mismatches) and 1 (identical). We found that the increase in CENP-B motif score correlated with enrichment of CENP-A relative to nonspecific IgG CUT&RUN occupancy (FIG. 41B). Specifically, when averaged over two biological replicates, we observed Pearson correlations of r=0.66-0.83 for all three salt fractions. We conclude that the presence of a strong CENP-B box is associated with stabilization of CENP-A/B/C.

CENP-B box density varies from being highest on the dimeric arrays to the least on heterogeneous monomeric arrays. As CENP-B binds to the CENP-B box in a sequence-dependent manner, CENP-B protein density is also expected to be higher on younger homogenous arrays. We tested whether the degree of loss of CENP-B boxes (decrease in CENP-B box density) from old sequences correlates with the reduction in CENP-A binding on these sequences. We plotted the CENP-B density against CENP-A enrichment on longer α-satellite contigs and observed strong correlations (r=0.62-0.75) between CENP-B motif density and CENP-A enrichment (FIG. 41C). This indicates that maintenance of strong and dense CENP-B boxes increases the efficiency of CENP-A/B/C binding to α-satellite centromeres. Our evidence that CENP-B boxes within homogeneous functional α-satellite arrays have evolved to stabilize the resident CENP-A/B/C particles provides support for the proposal that CENP-B contributes to segregation fidelity by stabilizing CENP-C (Fachinetti et al. 2015).

Divergent α Satellites Retain Some Competence for CENPA Assembly

Although the highest CENP-A enrichment occurred on highly homogenous arrays with dense CENP-B boxes, qPCR assays also revealed a low amount of CENP-A on divergent sequences that contained either sparse or no CENP-B boxes in CUT&RUN.Salt and salt fractionation N-ChIP experiments (FIG. 41C). Detecting low levels of CENP-A cytologically on divergent α satellites is difficult due to their low copy number when compared with the detection of homogenous dimers that are brightly stained with CENP-A. For example, homogenous D7Z1 (1.5-3.8 Mb) shows a strong cytological colocalization with CENP-A, whereas divergent D7Z2 (0.1-0.5 Mb) was reported to be negative for CENP-A binding (Slee et al. 2012). We compared the CENP-A enrichment in CUT&RUN.Salt samples on heterogeneous monomeric α satellites with noncentromeric sequences, including β satellites—a 68- to 69-bp pericentric tandem repeat array. We found more than three-fold CENP-A enrichment on D7Z2 relative to the repeat-masked genome and to β-satellite arrays (FIG. 41D), indicating that even a divergent α-satellite array that completely lacks CENP-B motifs retains some competence for CENP-A assembly.

Figure 42:
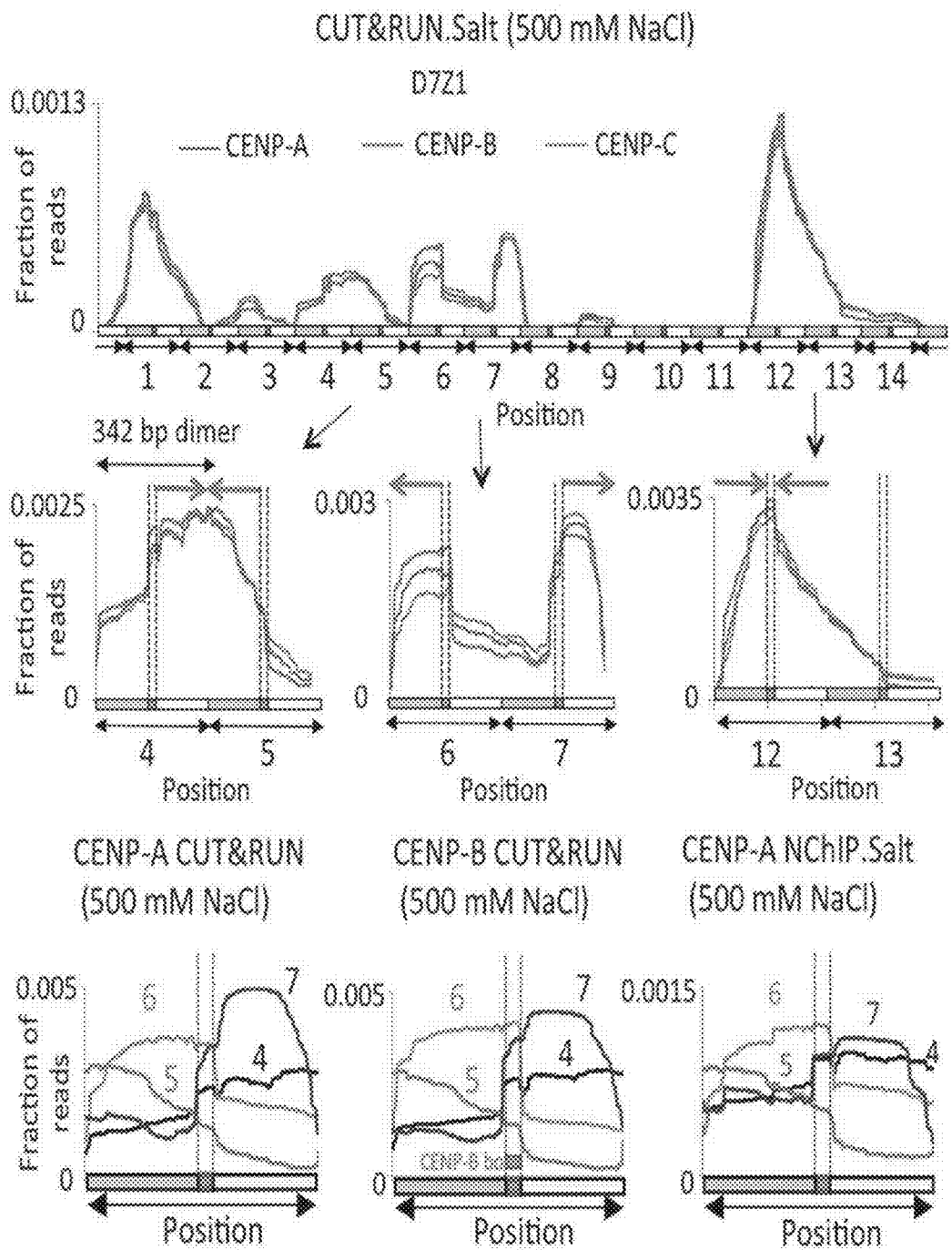
FIG. 42 shows structural and conformational variations of CENP-A/B/C at human centromeres. (Top panels) High-stringency mapping of the CENP CUT&RUN.Salt 250-bp× 250-bp merged pairs averaged over D7Z1. CENP CUT&RUN.Salt profiles of two tandem dimers are shown below the D7Z1 contig. (Bottom panels) Overlaying of CENP-A profiles from different dimeric units to show the orientation of CENP-A/B/C in either direction in CENP-A and CENP-B CUT&RUN.Salt as well as CENP-A N-ChIP.

Unexpected Structural and Conformational Variations of CENP-A/B/C on Nearly Homogenous α-Satellite Arrays Although perfectly homogeneous α-satellite arrays cannot be uniquely assembled from standard sequencing reads, ~5% divergence is enough to assemble some sequenced reads into contigs. As we had expected that all copies of highly homogeneous arrays would show identical patterns, we were surprised to find major differences between adjacent repeats when we mapped 250-bp×250-bp merged pairs to them. We observed three major types of variations within homogeneous arrays corresponding to annotated BAC clones and genomic contigs (FIG. 42): (1) Differential occupancy of individual dimers by CENP-A/B/C. We observed up to ~50-fold differences in enrichment between the lowest and the highest occupied dimers within a single array. (2) Orientation of CENP-A/B/C with respect to the CENP-B box. The distance between two CENP-B boxes within an SF1 α-satellite dimeric array is 340 bp unidirectionally oriented in a head-to-tail fashion. Thus, the orientation of the CENPA/B/C-containing complex is expected to be unidirectional. Contrary to this expectation, we observed that CENPA/B/C could be oriented on either side with respect to the CENP-B box orientation (red arrows in FIG. 42) even within a single continuous α-satellite contig. (3) Structural variation. We observed different configurations of CENP-A/B/C on these contigs, including either a symmetric complex spanning the entire 340-bp dimer with almost equal CENP-A/B/C binding on both monomers of the dimer or an asymmetric complex preferentially occupying one monomer of the dimer. Such drastic structural variations of CENP-A-containing particles on α-satellite dimers were observed with remarkably little difference in sequence. For example, the four adjacent 340-bp D7Z1 repeat units shown superimposed in the bottom panels of FIG. 42 are 88%-96% identical in pairwise comparisons, and yet all four are different from one another in CCAN structure. Thus, it would appear that slight α-satellite sequence variations affect the binding behavior of CENP-A containing complexes. Evidently, multiple CCAN forms can recruit the outer kinetochore, although it is possible that only a single structural form is competent for recruitment. These differences could be inherent to the sequences to which the CCANs are bound or reflect exclusion by nonhistone satellite DNA-binding proteins analogous to *Drosophila* D1, GAGA factor, and Prod proteins (Levinger and Varshavsky 1982; Raff et al. 1994; Torok et al. 1997).

Our mapping of CENP-A/B/C using salt fractionation confirms our previous report in which we showed that homogeneous α-satellite arrays are occupied by a single coherent CCAN complex containing CENP-A, CENP-B, CENP-C, and CENP-T (Thakur and Henikoff 2016). Our mapping of the CENP-T subcomplex over the CENP-B box led us to propose a model in which each α-satellite dimeric unit wraps with right-handed superhelical chirality around the CENP-TWSX subparticle between two CENP-A/H4/H2A/H2B subnucleosomes. The sensitivity of the uncrosslinked CCAN to MNase digestion can account in part for the differences in DNA protection that led to conflicting conclusions about the structure of the CENP-A nucleosome. However, by following N-ChIP with salt fractionation, we now show that CENP-A particles observed using low-salt conditions (Lacoste et al. 2014; Nechemia-Arbely et al. 2017) comprise only a minor fraction of the total CENP-A genome-wide. In contrast, the major N-ChIP salt fraction consists of particles that protect much larger DNA fragments, consistent with the presence of an intact CCAN complex. Our evidence that CENP-B binding to CENP-B boxes in homogeneous α-satellite arrays promotes CCAN integrity provides evidence for a specific role for CENP-B. In addition, our finding that CCAN components are recruited at low levels to the D7Z2 α-satellite array that lacks CENP-B boxes and shows no enrichment of CENP-B suggests that there is inherent CCAN recruitment potential even in the absence of CENP-B. Thus, CCAN occupancy is determined by α-satellite sequence but can be enhanced by CENP-B binding to arrays.

Materials and Methods

Cell Lines, Antibodies, and Primers

Salt fractionation N-ChIP assays were performed in the CENP-A Flagtagged HT1080-1b cell line (Thakur and Henikoff 2016), and CUT&RUN.Salt experiments were performed in the K562 cell line. The antibodies used were anti-CENP-A (Abcam, ab13939), anti-CENP-B (Abcam, ab25734), anti-CENP-C(Abcam, ab33034), Histone H3K27me3 (Cell Signaling Technologies, 9733), IgG (Antibodies Online, ABIN102961) and MTPOL (GeneTex, GTX105137).

CUT&RUN.Salt

CUT&RUN of human K562 cells or nuclei was performed essentially as described (Skene and Henikoff 2017b) except that, after digestion, the protocol was modified to allow for salt fractionation. Experiments shown in FIG. 41 used permeabilized cells rather than nuclei (Skene and Henikoff 2017a). Paired-end 250-bp×250-bp or 25-bp×25-bp sequencing was performed.

Sequence Analysis

Paired-end 250-bp×250-bp reads were trimmed and merged using SeqPrep with parameters: -q 25 -L 25 -o 15 as described (Henikoff et al. 2015). Merged pairs and paired-end 25-bp×25-bp reads were mapped using Bowtie2 with following parameters: -end-to-end -very-sensitive -no-mixed -no-discordant -q -phred33 -I 10 -X 700. For CUT&RUN.Salt, read counts were calibrated using the spike-in control as described (Skene and Henikoff 2017b). Enrichment values represent the ratio of calibrated read counts for the specific antibody versus a nonspecific IgG control. To estimate motif strength and densities, we reasoned that the 15-bp CENP-B box motif is ancestral, as it is found at regular intervals in the most homogeneous SF1 (e.g., Cen1-like), SF2 (e.g., Cen13-like), and SF3 (e.g., DXZ1) α-satellite arrays. We scanned contigs for statistically significant occurrences as described (Zentner et al. 2015) to identify CENP-B motifs and calculate CENP-B box mismatches and density. We define a motif score as the degree of identity to the 15-bp consensus, where 15 out of 15 matches equals 1, more than three mismatches equals 0, and each mismatch subtracts a value of 0.25, for a scale of 0 (no significant motif) to 1 (perfect motif).

References for Example 6 (Each of which is Incorporated by Reference in its Entirety)

Alexandrov I, Kazakov A, Tumeneva I, Shepelev V, Yurov Y. 2001. α-Satellite DNA of primates: old and new families. Chromosoma 110: 253-266.

Brogaard K R, Xi L, Wang J P, Widom J. 2012. A chemical approach to mapping nucleosomes at base pair resolution in yeast. Methods Enzymol 513: 315-334.

Chereji R V, Ocampo J, Clark D J. 2017.MNase-sensitive complexes in yeast: nucleosomes and non-histone barriers. Mol Cell 65: 565-577.e563.

Fachinetti D, Han J S, McMahon M A, Ly P, Abdullah A, Wong A J, Cleveland D W. 2015. DNA sequence-specific binding of CENP-B enhances the fidelity of human centromere function. Dev Cell 33: 314-327.

Fukagawa T, Earnshaw W C. 2014. The centromere: chromatin foundation for the kinetochore machinery. Dev Cell 30: 496-508.

Hasson D, Panchenko T, Salimian K J, Salman M U, Sekulic N, Alonso A, Warburton P E, Black B E. 2013. The octamer is the major form of CENP-A nucleosomes at human centromeres. Nat Struct Mol Biol 20: 687-695.

Henikoff S, Henikoff J G, Sakai A, Loeb G B, Ahmad K. 2009. Genome-wide profiling of salt fractions maps physical properties of chromatin. Genome Res 19: 460-469.

Henikoff J G, Thakur J, Kasinathan S, Henikoff S. 2015. A unique chromatin complex occupies young α-satellite arrays of human centromeres. Sci Adv 1: e1400234.

Hori T, Amano M, Suzuki A, Backer C B, Welburn J P, Dong Y, McEwen B F, Shang W H, Suzuki E, Okawa K, et al. 2008. CCAN makes multiple contacts with centromeric DNA to provide distinct pathways to the outer kinetochore. Cell 135: 1039-1052.

Jahan S, Xu W, He S, Gonzalez C, Delcuve G P, Davie J R. 2016. The chicken erythrocyte epigenome. Epigenetics Chromatin 9: 19. Jain D, Baldi S, Zabel A, Straub T, Becker P B. 2015. Active promoters give rise to false positive 'phantompeaks' in ChIP-seq experiments. Nucleic Acids Res 43: 6959-6968.

Lacoste N, Woolfe A, Tachiwana H, Garea A V, Barth T, Cantaloube S, Kurumizaka H, Imhof A, Almouzni G. 2014. Mislocalization of the centromeric histone variant CenH3/CENP-A in human cells depends on the chaperone DAXX. Mol Cell 53: 631-644.

Levinger L, Varshavsky A. 1982. Protein D1 preferentially binds A+T-rich DNA in vitro and is a component of Drosophila melanogaster nucleosomes containing A+T-rich satellite DNA. Proc Natl Acad Sci 79: 7152-7156.

McNulty S M, Sullivan L L, Sullivan B A. 2017. Human centromeres produce chromosome-specific and array-specific α satellite transcripts that are complexed with CENP-A and CENP-C. Dev Cell 42: 226-240.e226.

Mieczkowski J, Cook A, Bowman S K, Mueller B, Alver B H, Kundu S, Deaton A M, Urban J A, Larschan E, Park P J, et al. 2016. MNase titration reveals differences between nucleosome occupancy and chromatin accessibility. Nat Commun 7: 11485.

Nechemia-Arbely Y, Fachinetti D, Miga K H, Sekulic N, Soni G V, Kim D H, Wong A K, Lee A Y, Nguyen K, Dekker C, et al. 2017. Human centromeric CENP-A chromatin is a homotypic, octameric nucleosome at all cell cycle points. J Cell Biol 216: 607-621.

Palmer D K, O'Day K, Wener M H, Andrews B S, Margolis R L. 1987. A 17-kD centromere protein (CENP-A) copurifies with nucleosome core particles and with histones. J Cell Biol 104: 805-815.

Park D, Lee Y, Bhupindersingh G, Iyer V R. 2013. Widespread misinterpretable ChIP-seq bias in yeast. PLoS One 8: e83506. Raff J W, Kellum R, Alberts B. 1994. The Drosophila GAGA transcription factor is associated with specific regions of heterochromatin throughout the cell cycle. EMBO J 13: 5977-5983.

Rocha E, Davie J R, van Holde K E, Weintraub H. 1984. Differential salt fractionation of active and inactive genomic domains in chicken erythrocyte. J Biol Chem 259: 8558-8563.

Sanders M M. 1978. Fractionation of nucleosomes by salt elution from micrococcal nuclease-digested nuclei. J Cell Biol 79: 97-109.

Skene P J, Henikoff S. 2017a. CUT&RUN: targeted in situ genome-wide profiling with high efficiency for low cell numbers. bioRxiv doi: 10.1101/193219.

Skene P J, Henikoff S. 2017b. An efficient targeted nuclease strategy for high-resolution mapping of DNA binding sites. eLife 6: e21856.

Slee R B, Steiner C M, Herbert B S, Vance G H, Hickey R J, Schwarz T, Christan S, Radovich M, Schneider B P, Schindelhauer D, et al. 2012. Cancer-associated alteration of pericentromeric heterochromatin may contribute to chromosome instability. Oncogene 31: 3244-3253.

Teytelman L, Thurtle D M, Rine J, van Oudenaarden A. 2013. Highly expressed loci are vulnerable to misleading ChIP localization of multiple unrelated proteins. Proc Natl Acad Sci 110: 18602-18607.

Thakur J, Henikoff S. 2016. CENPT bridges adjacent CENPA nucleosomes on young human α-satellite dimers. Genome Res 26: 1178-1187. Torok T, Harvle P D, Buratovich M, Bryant P J. 1997. The product of proliferation disrupter is concentrated at centromeres and required for mitotic chromosome condensation and cell proliferation in Drosophila. Genes Dev 11: 213-225.

Xi Y, Yao J, Chen R, Li W, He X. 2011. Nucleosome fragility reveals novel functional states of chromatin and poises genes for activation. Genome Res 21: 718-724.

Zentner G E, Kasinathan S, Xin B, Rohs R, Henikoff S. 2015. ChEC-seq kinetics discriminate transcription factor binding sites by DNA sequence and shape in vivo. Nat Commun 6: 8733.

Zhang W, Colmenares S U, Karpen G H. 2012. Assembly of Drosophila centromeric nucleosomes requires CID dimerization. Mol Cell 45: 263-269.

Example 7

Automated In Situ Profiling of Chromatin Modifications Resolves Cell Types and Gene Regulatory Programs Introduction Cells establish their distinct identities and functional properties by altering activity of the cis-regulatory DNA elements that control gene-expression[1,2]. Promoter elements lie near the 5' transcriptional start sites (TSSs) of all genes, whereas distal cis-regulatory elements such as enhancers often bridge long stretches in the DNA to interact with select promoters and direct cell-type specific gene expression[1,2]. In addition to their genetic content (i.e. DNA sequence), our cells also transmit these distinct cis-regulatory confirmations across cell-divisions in the form of heritable epigenetic information, allowing them to pass on their unique cellular identities[3,4]. Defects in the nuclear proteins that recognize these cis-regulatory elements underlie many human diseases that often manifest in specific tissues and cell-types[5-9]. To provide a reference for molecular diagnosis of patient samples, efforts are underway to generate a comprehensive atlas of cells in the human body[10,11]. Characterizing cell-type specific chromatin landscapes in healthy and diseased cells is essential for this atlas, however, technical limitations have prevented implementation of traditional approaches for genome-wide profiling of chromatin proteins on the ambitious scales necessary for this project.

Despite the growing awareness that epigenetic malfunctions underlie many human diseases[12], very few methods for profiling the epigenomes of patient samples are available. Realizing the clinical potential of epigenomic technologies requires robust, scalable approaches that can profile large numbers of patient samples in parallel. Chromatin immunoprecipitation with antigen-specific antibodies combined with high-throughput sequencing has been used extensively for chromatin profiling, but this method is labor-intensive, prone to artifacts[13], and requires high sequencing depth to distinguish weak signals from genomic background noise, making it difficult to scale for clinical applications. Recently, we introduced CUT&RUN as an alternative chromatin profiling technique that uses factor-specific antibodies to tether micrococcal nuclease (MNase) to genomic binding sites[14,15]. The targeted nuclease cleaves chromatin around the binding sites, and the released DNA is easily sequenced using standard library preparation techniques, resulting in efficient mapping of protein-DNA interactions. CUT&RUN has very low backgrounds, which greatly reduces sample amounts and sequencing costs required to obtain high-quality genome-wide profiles[14,16].

Here we modify the CUT&RUN protocol to profile chromatin proteins and modifications in a 96-well format on a liquid handling robot. By applying this method to the H1 human embryonic stem cell (hESC) line and K562 leukemia cell line, we develop a robust quantitative metric to compare cell-types and identify their distinct gene regulatory programs. In addition, we show this method is able to define chromatin features from frozen tumor samples to determine their cellular identities. AutoCUT&RUN is ideal for high-throughput studies of chromatin-based gene regulation, and could make examination of the chromatin landscape of patient samples routine in the clinic.

Results

An Automated Platform for Genome-Wide Profiling of Chromatin Proteins

Figures 43A, 43B:
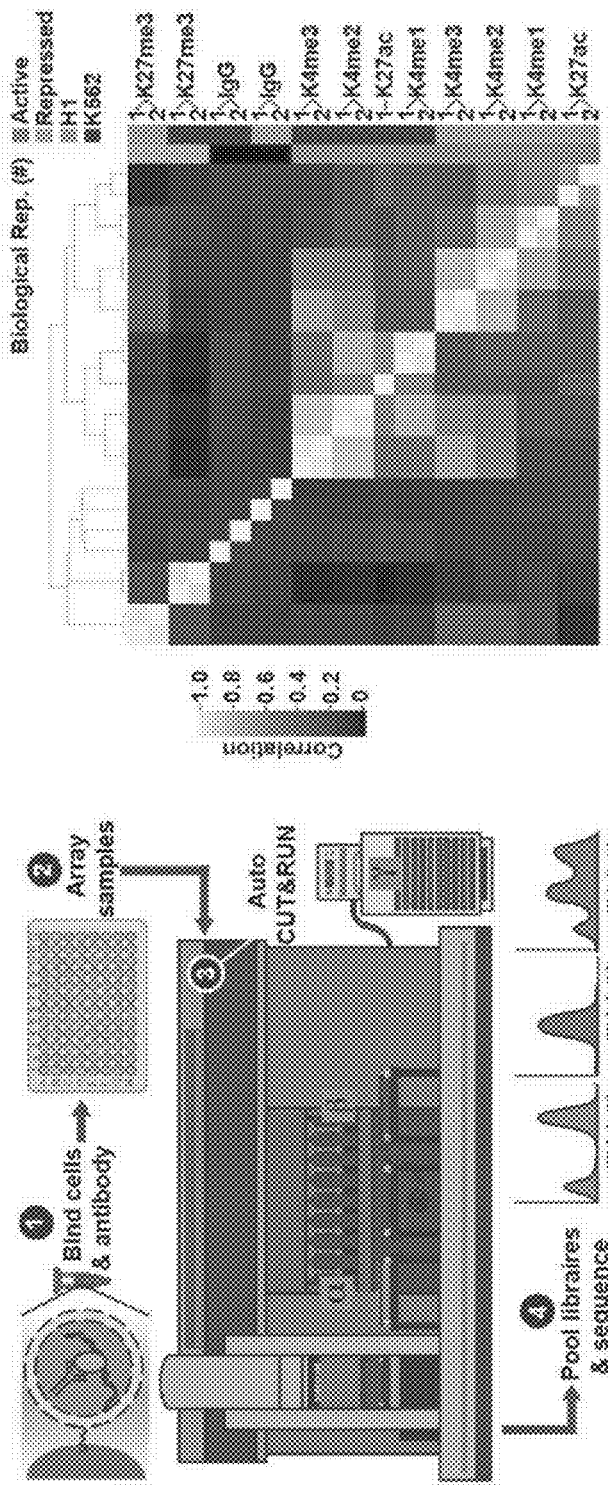
FIGS. 43A-43B show an automated platform for high-throughput in situ profiling of chromatin proteins.

To adapt CUT&RUN to an automated format we equipped a Beckman Biomek FX liquid handling robot to facilitate magnetic separation and temperature control (FIG. 43A). First, cells are bound to Concanavalin A-coated magnetic beads, allowing all subsequent washes to be performed by magnetic separation. Bead-coated samples are then incubated with an antibody, and up to 96 samples are arrayed in a plate (FIG. 43A). Successive washes, tethering of a proteinA-MNase fusion protein, cleavage of DNA, and release of cleaved chromatin fragments into the sample supernatant are performed on the Biomek (FIG. 49A). A major stumbling block to automating genomics protocols is they typically require purification of small amounts of nucleic-acid prior to library preparation. To overcome this hurdle, we developed a method to polish the DNA ends in chromatin fragments for direct ligation of Illumina library adapters (FIG. 49A). Indexed CUT&RUN libraries are then purified on the Biomeck using Ampure XP magnetic beads both before and after PCR enrichment. The end-polishing, adapter ligation, and PCR enrichment reactions are performed on a separate thermocycler. This AutoCUT&RUN protocol allows a single operator to generate up to 96 libraries in 2 days that are ready to be pooled sequenced (FIG. 43A).

To test the efficacy of AutoCUT&RUN, we simultaneously profiled two biological replicates of H1 hESCs and K562 cells using antibodies targeting four histone modifications that mark active chromatin states (H3K4me1, H3K4me2, H3K4me3, and H3K27ac) and one repressive modification (H3K27me3). Comparing the global distribution of reads for each histone mark, we found that samples highly correlate with their biological replicate, and cluster together in an unbiased hierarchical matrix (FIG. 43B). Additionally, the genome-wide profiles of the active histone marks clustered together within a given cell type, and separated away from the repressive histone mark H3K27me3 (FIG. 43B). These profiles represent antibody-specific signals, as they are poorly correlated with an IgG negative control. Together, these results indicate that AutoCUT&RUN chromatin profiling reproducibly captures the cell-type specific distributions of histone marks.

Histones are tightly associated with DNA in chromatin, so we also examined whether AutoCUT&RUN can be applied to mapping DNA-binding transcription factors that have lower residence times. We tested the performance of AutoCUT&RUN with two transcription factors, the histone locus-specific gene regulator NPAT, and the insulator protein CTCF[17,18]. AutoCUT&RUN profiles of both NPAT and CTCF are highly specific to their expected targets in both H1 and K562 cells (FIG. 49B, 49C), and the signal sensitivity of CTCF in K562 cells was comparable to our previous results[15]. Thus, AutoCUT&RUN is suitable for high-throughput, genome-wide profiling of diverse DNA binding proteins.

Figure 44B:
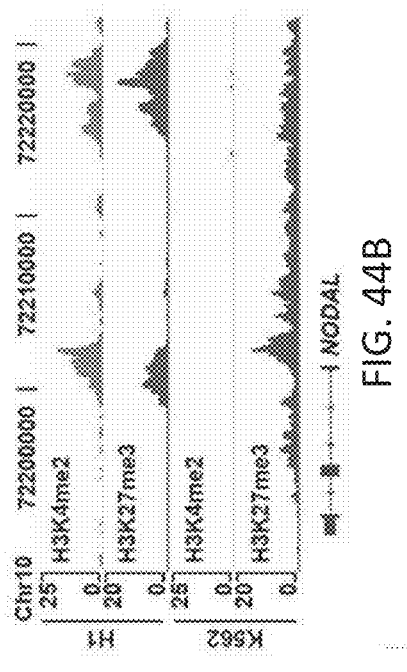
FIGS. 44A-44D show AutoCUT&RUN reproduces the expected chromatin landscape of H1 and K562 cells.
Figure 44D:
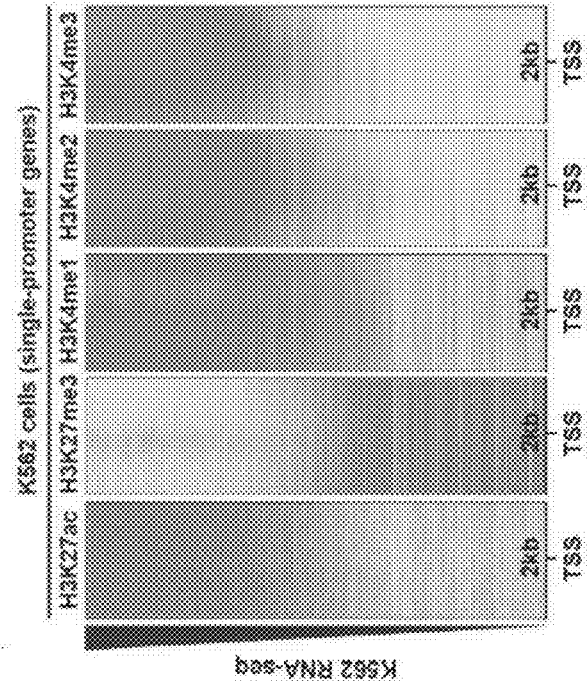
Figure 44A:
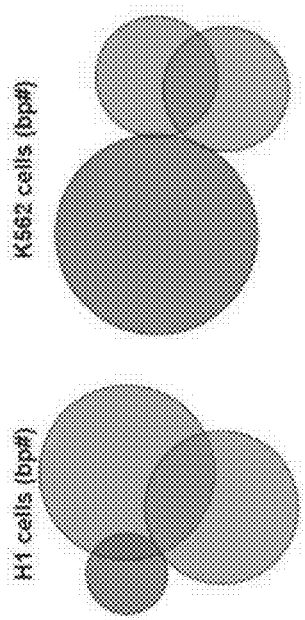

To maintain their developmental plasticity, hESCs have a generally open, hyper-acetylated chromatin landscape that is interspersed with repressed domains of facultative heterochromatin, marked by overlapping H3K27me3 and H3K4 methylation[19-22]. AutoCUT&RUN recapitulates these features in hESCs; we observed that H1 cells have increased H3K27ac as compared to the lineage-restricted K562 cell line, whereas domains of the repressive histone mark H3K27me3 are rare in H1 cells, but prevalent in K562 cells (FIG. 44A). We also observed extensive overlap between H3K27me3 and H3K4me2 signals in H1 cells, but not K562 cells (FIG. 44A, 44B). Thus, Auto CUT&RUN profiles are consistent with the specialized chromatin features found in hESCs.

Figure 44C:
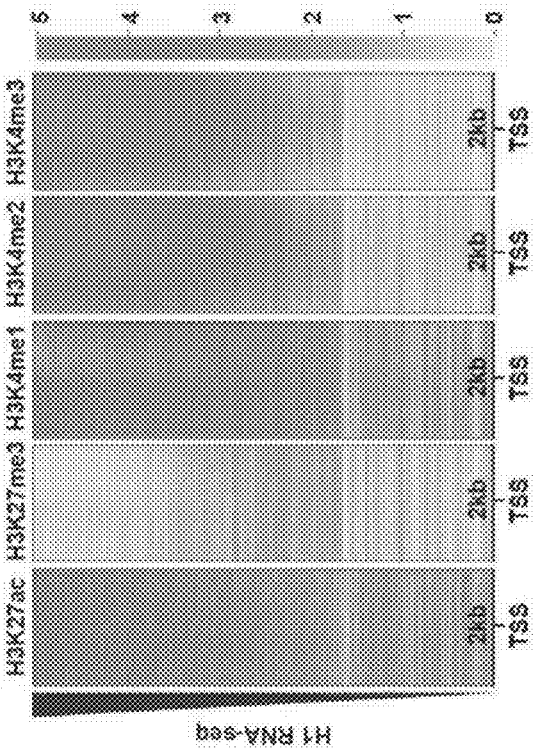

Post-translational modifications to the H3 histone tail have been well-documented to closely correlate with transcriptional activity. To determine whether our AutoCUT&RUN profiles of histone modifications are indicative of the transcriptional activity of cis-regulatory elements, we examined the distribution of the five histone marks around the transcriptional start sites (TSSs) of genes, rank-ordered according to RNA-seq expression data (FIGS. 44C, 44D)[23]. We find the active mark H3K4me3 is the most highly correlated with expression in both cell types (r=0.70 and 0.81 for H1 and K562 respectively), followed by H3K4me2 and H3K27ac (FIGS. 49D, 49E). The repressive histone mark H3K27me3 is anti-correlated with expression (r=-0.16 and -0.53 in H1 and K562 respectively) (FIGS. 49D, 49E). We conclude AutoCUT&RUN for these five marks broadly recapitulates transcriptional activity, providing a strategy to identify cell-type specific gene regulatory programs.

A Simple Chromatin Metric Resolves Gene Expression Programs from AutoCUT&RUN Data.

We wanted to develop a quantitative metric that could be applied to AutoCUT&RUN data to compare cell-types and distinguishing their gene regulatory programs. Because H3K4 methylation and H3K27ac primarily mark active promoters, whereas H3K27me3 is indicative of the degree of gene repression, we reasoned that by combining these marks into a single model we could develop a more robust metric of gene activities. RNA-seq has been widely used to identify cell-type specific gene expression programs[23], so we used RNA-seq data as a reference for training a weighted linear regression model that incorporates normalized H3K4me2, H3K27ac, and H3K27me3 read counts into a Cis-Regulatory Element Activity Model (CREAM) that assigns promoters a relative activity score. H3K4me2 was selected over H3K4me3 and H3K4me1 because these marks are interdependent, and because H3K4me2 is uniquely applicable for modeling the activity of both proximal and distal cis-regulatory elements (see below). When applied to the promoters of K562 cells, CREAM scores correlate very well with RNA-seq values (r=0.83) (FIG. 45A), providing a comparable power for predicting gene expression as similar models that used up to 39 histone modifications mapped by ChIP-seq (r=0.81)[24]. In addition, the weighted CREAM trained on K562 cells also performs well when applied to H1 cells (FIGS. 50A, 50B), indicating that the model and data quality is sufficiently robust to assign promoter scores to uncharacterized cell-types.

Using this model, we examined whether AutoCUT&RUN accurately identifies promoters with cell-type specific activity. We initially focused our analysis on genes with a single TSS, that can be unambiguously assigned RNA-seq values, and called promoters whose CREAM scores were enriched more than two-fold in either H1 or K562 cells (FIG. 45B). For comparison, we also called genes that were more than two-fold enriched in either H1 or K562 cells according to their RNA-seq expression values (FIG. 50C). By displaying the H1 and K562 specific genes identified by CREAM scores on the plot generated from RNA-seq values, we find that many of the genes identified by CREAM scores as cell-type specific are overlooked by RNA-seq (FIGS. 45B, 45C), and the inverse is also true (FIGS. 50C, 50D), suggesting that these methods show differential sensitivity to changes in the expression of numerous genes. Encouragingly, the 865 genes that are called as cell-type specific according to both CREAM scores and RNA-seq are highly enriched for developmental regulators, whereas the genes called by CREAM scores or RNA-seq alone are not enriched for developmental GO terms (FIGS. 45D, 50E-50G). In addition, only 35/2,014 genes called as cell-type specific by CREAM have the opposite cell-type specificities according to RNA-seq (FIG. 45D). Thus, AutoCUT&RUN can be applied to accurately identify cell-type specific developmental regulators.

To determine whether AutoCUT&RUN data recapitulates the cell-type specificities of highly characterized transcription factors, we expanded our CREAM analysis to include all promoters. We find that components of the hESC pluripotency network (NANOG, SOX2, SALL4, and OTX2) are highly enriched in H1 cells, while regulators of hematopoietic progenitor cell fate (PU.1, TAL1, GATA1, and GATA2) are highly enriched in K562 cells (FIG. 45E)[25,26]. Intriguingly, this method also identifies differences in alternative promoter activity (e.g. OTX2 and TAL1), providing an indication of the specific gene isoforms that are expressed in a given cell-type (FIG. 45E), a feature that is not possible using RNA-seq. We conclude that AutoCUT&RUN allows identification of master regulators of cellular identity, providing a powerful tool to characterize cell-types in a high-throughput format.

Profiling Tumors by AutoCUT&RUN

Figure 46B:
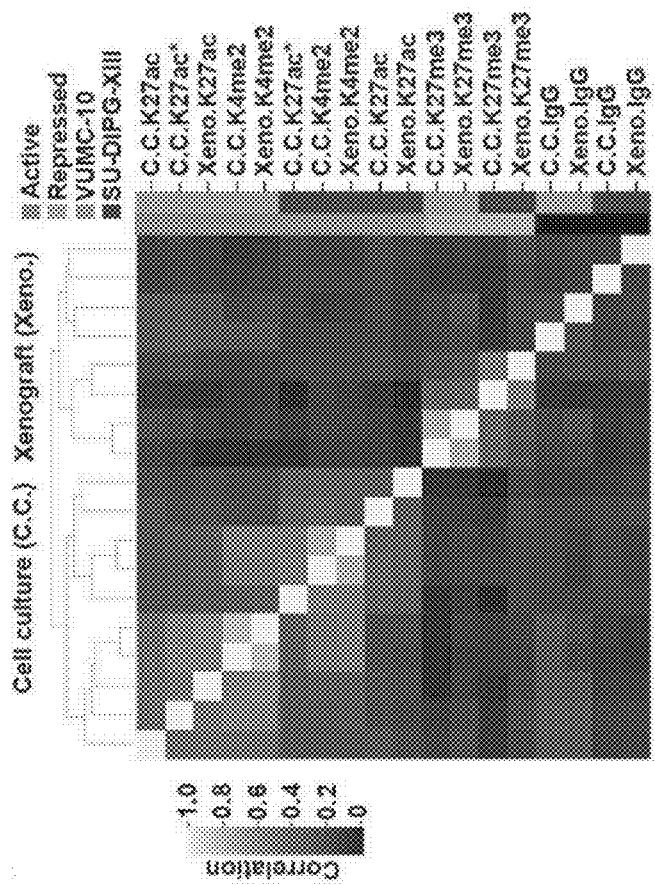
FIGS. 46A and 46B show AutoCUT&RUN is suitable for profiling the chromatin landscape of frozen tumor samples.
Figure 46A:
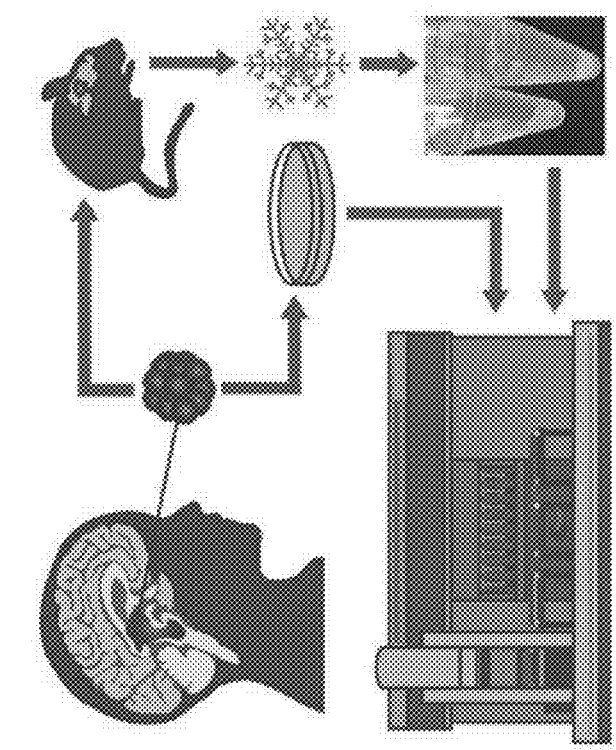
Figure 51:
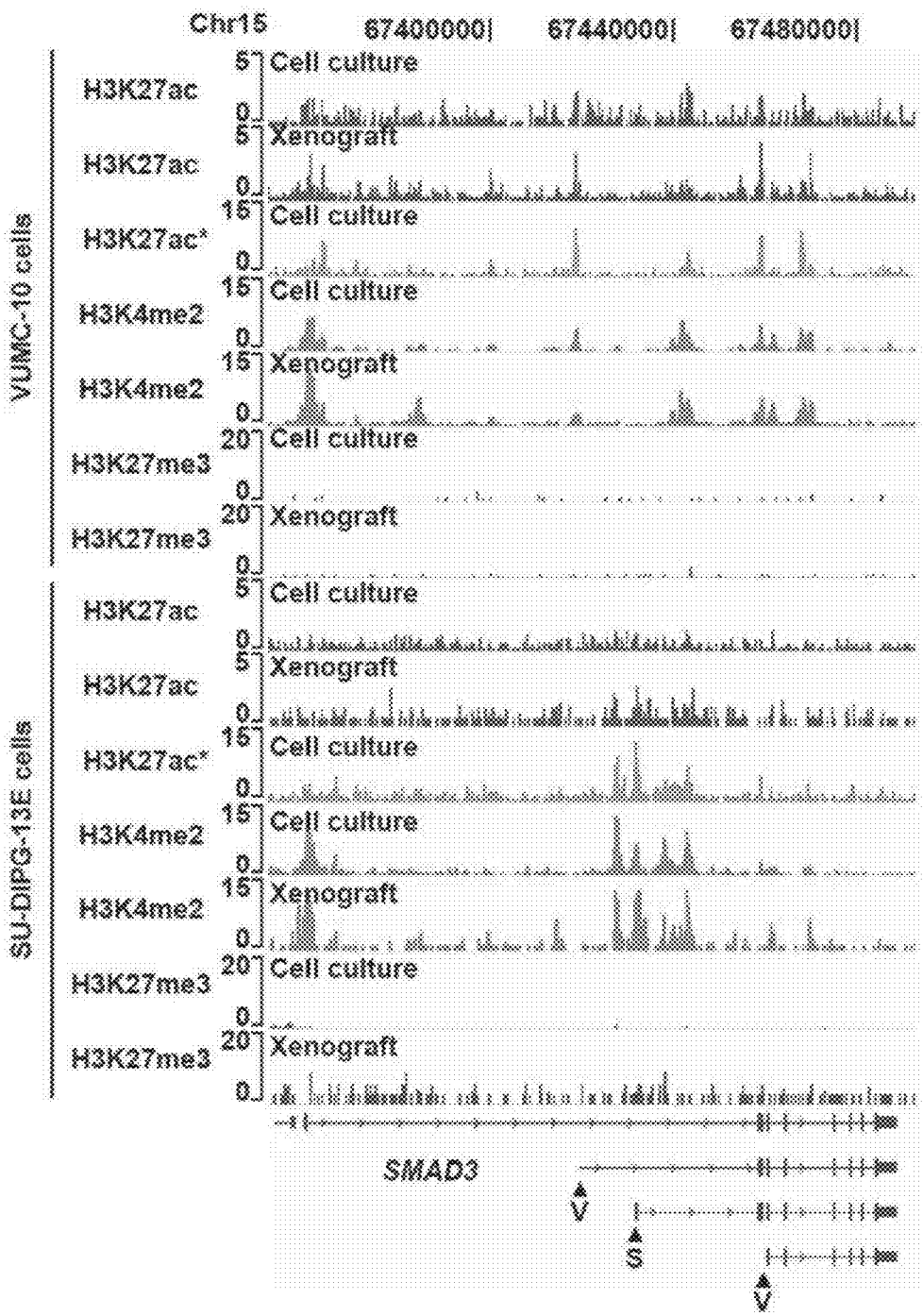
FIG. 51 shows DMG specific SMAD3 promoter activities. Genome browser tracks of histone marks profiled by Auto CUT&RUN in VUMC-10 and SU-DIPG-XIII cells at a representative locus (SMAD3) showing the concordance of profiles from cell culture and xenograft samples. The H3K27ac signal in SU-DIPG-XIII cells was noisy, but this issue is antibody specific. For comparison H3K27ac was also profiled manually using an alternative antibody (*). Arrowheads indicate promoters that are predicted to be specifically active in VUMC-10 (V) or SU-DIPG-XIII (S) cells.

Traditional methods to profile protein-DNA interactions (e.g. ChIP-seq) are generally unable to handle clinically-relevant samples, which often contain small amounts of starting material and have been flash-frozen. To test whether AutoCUT&RUN is suitable for profiling frozen tumor specimens we obtained two diffuse midline glioma (DMG) patient-derived cell lines (VUMC-10 and SU-DIPG-XIII) that were autopsied from similar regions of the brainstem, but differ in their oncogenic backgrounds[27]. Both of these DMG cell lines readily form xenografts in murine models, and we applied AutoCUT&RUN to profile histone modifications in VUMC-10 and SU-DIPG-XIII xenografts that were seeded in the brains of mice, and then resected upon tumor formation and frozen under typical clinical conditions (FIG. 46A). For comparison, we also harvested these DMGs directly from cell culture and profiled them on the same AutoCUT&RUN plate (FIG. 46A). Again, we found that replicates were extremely similar, so we combined them for further analysis. Importantly, cell culture samples were highly correlated with the same mark profiled in the corresponding frozen xenografts, and AutoCUT&RUN on xenograft tissues and cell culture samples produced similar data quality (FIG. 46B, FIG. 51). Thus, AutoCUT&RUN reliably generates genome-wide chromatin profiles from frozen tissue samples.

Figures 52A, 52B, 52C:
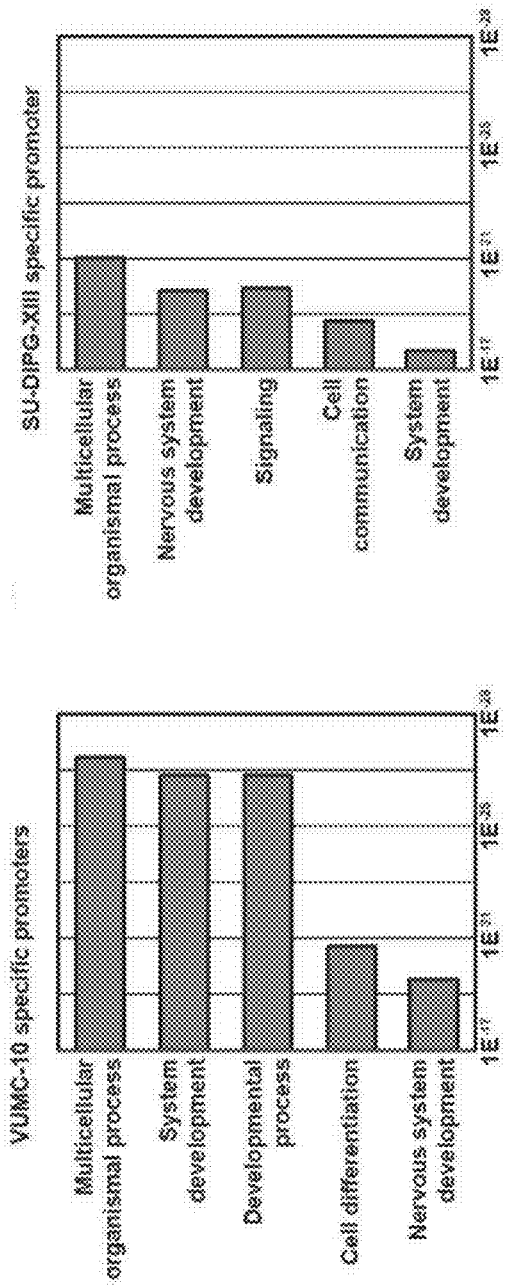
FIGS. 52A-52C show Promoter CREAM identifies DMG specific gene regulatory programs.

Stratifying cancer patients into effective treatment groups requires distinguishing tumor subtypes derived from the same tissues, making the VUMC-10 and SU-DIPG-XIII samples ideal for exploring the diagnostic potential of AutoCUT&RUN. By applying the CREAM to these samples, we identified 5,006 promoters that show differential activity between VUMC-10 and SU-DIPG-XIII cells (FIG. 47A). Consistent with the neuronal origins of these tumors, both the VUMC-10 and SU-DIPG-XIII specific promoters are significantly enriched for genes involved in neuronal development (FIGS. 52A, 52B). Genes involved in cell-signaling are also overrepresented in SU-DIPG-XIII cells (FIG. 52B); for example, the promoters of the PDGFR gene as well as its ligand PDGF are highly active in SU-DIPG-XIII cells (FIG. 47A). This is consistent with the observation that DMGs frequently contain activating mutations in PDGFR-$\alpha$ that promote tumor growth[7]. In addition, one promoter of the SMAD3 gene, a component of the TGF-$\beta$ signaling pathway[28], is specifically active in SU-DIPG-XIII cells, whereas two different SMAD3 promoters are active in VUMC-10 cells (FIG. 47A, FIG. 51). This suggests that AutoCUT&RUN can be applied to identify promoters that display tumor-specific activity, providing an indication of the signaling pathways that may be driving tumor growth and potential susceptibility to therapeutic agents.

As a diagnostic tool, we reasoned that AutoCUT&RUN with CREAM could be used to quantitatively assess cell-types and tissue samples and place them within a pre-defined reference map of healthy and diseased cell-types. Consistent with this idea, CREAM scores indicate that whereas 5,006 gene promoters display differential activity between VUMC-10 and SU-DIPG-XIII (FIG. 47A), only 388 promoters are differentially active between VUMC-10 frozen xenografts and VUMC-10 cultured cells (FIG. 47B), and only 1,619 promoters are differentially active between SU-DIPG-XIII xenografts and cultured cells (FIG. 52C). In addition, when we compare promoter CREAM scores of the four DMG samples with H1 and K562 cells, we find DMG xenografts are by far the most similar to their corresponding cell culture samples (FIG. 47C). We conclude that Auto CUT&RUN can be used as a reliable method to assign cellular identities to frozen tumor samples.

High-Throughput Mapping of Cell-Type Specific Enhancers

The cell-type specific activities of gene promoters are often established by incorporating signals from distal cis-regulatory elements, such as enhancers[1,2]. Similar to promoters, enhancers also display H3K4me2[29], and active enhancers are typically marked by H3K27ac, whereas repressed enhancers are marked by H3K27me3[22,30,31]. This suggests the AutoCUT&RUN profiles we used to assign promoter CREAM scores should also allow identification of cell-type specific enhancers. To investigate this possibility, we first compared our H1 data to available chromatin accessibility maps generated by ATAC-seq, which are enriched for both active promoters and enhancers[32,33]. Of the marks we profiled, we find H3K4me2 peaks show the highest overlap with ATAC-seq (FIG. 48A, FIG. 53A), and identify 36,725/52,270 ATAC-seq peaks (~70%). Interestingly, H3K4me2 is also prevalent at an additional 71,397 sites that were not called as peaks on ATAC-seq profiles (FIG. 48A, FIG. 53A). Many of these H3K4me2 specific sites show a low, but detectable ATAC-seq signal (FIG. 53B), indicating they may correspond to repressed promoters and enhancers. Consistent with this interpretation, on average H3K4me2+/ATAC− TSSs have higher H3K27me3 signals than ATAC+ TSSs (FIG. 53C). By dividing H3K4me2+/ATAC+ peaks into those that overlap with annotated TSSs and those that do not, we find that H3K4me3 is much more enriched at promoters, while H3K4me1 is more enriched at distal regulatory elements (FIG. 48B, 48C, FIG. 53D), which suggests these distal regulatory elements are likely enriched for enhancers[22,34]. Thus, mapping sites of H3K4me2 by AutoCUT&RUN provides a sensitive method for defining the repertoire of active and repressed cis-regulatory elements that control gene expression programs.

Finally, we examined whether AutoCUT&RUN can be used to identify cell-type specific enhancers. To expand the number of putative enhancer sites, we compiled a list of non-TSS peaks called on H3K4me2 profiles from all of our samples. Using our linear regression model, we then assigned these elements enhancer CREAM scores and examined their correlations between different cell types. We find the enhancer CREAM scores of DMG cell culture samples and xenografts are highly correlated (r=0.75 and 0.87 for SU-DIPG-XIII and VUMC-10 cells respectively) (FIG. 48D), and the enhancer CREAM scores of SU-DIPG-XIII cells show a weak positive correlation with VUMC-10 cells (e.g. r=0.19), likely reflecting cell-type-specific differences despite their common neural origins. For example, enhancers in the SOX2 pluripotency locus display differences between SU-DIPG-XIII and VUMC-10 cells (FIG. 48E) consistent with SU-DIPG-XIII cells resembling a more primitive neural stem cell-type than VUMC-10 cells, as has been previously suggested[35]. Thus, AutoCUT&RUN provides a stringent method for stratifying cell-types and tissue samples.

Discussion

We adapted the CUT&RUN technique to an automated platform by developing direct ligation of chromatin fragments for Illumina library preparation, and implemented magnetic separation for the wash steps and library purification. AutoCUT&RUN generates 96 genome-wide profiles of antibody-targeted chromatin proteins in just 2 days, dramatically increasing the throughput and potential scale of studies to interrogate the chromatin landscape. We show that profiling just three histone modifications (H3K27ac, H3K27me3 and H3K4me2) is sufficient to determine the cell-type specific activities of promoters and enhancers, providing a powerful quantitative metric to compare the epigenetic regulation of different cell-types. The automated workflow reduces technical variability between experiments, generating consistent profiles from biological replicates and from different sample types.

To continue optimizing AutoCUT&RUN one could envision hardware modifications and computational development. By screening various antibody collections, the repertoire of nuclear proteins that can be efficiently profiled using AutoCUT&RUN would expand dramatically. In addition, the current AutoCUT&RUN protocol is optimized for a popular liquid handling robot, but a custom robot incorporating a reversibly magnetic thermocycler block would allow the CUT&RUN reaction and library preparation to be carried out in place, streamlining the protocol even further. Last, metrics distinguishing cell types could be improved by incorporating additional aspects of the data, such as using a combination of both enhancer and promoter activities.

The excellent reproducibility of profiling frozen tissue samples by AutoCUT&RUN has the potential to transform the field of epigenetic medicine[12]. As compared to other genomics approaches that are currently used for patient diagnosis, AutoCUT&RUN has the unique capacity to profile chromatin proteins within diseased cells. For example, cancers caused by oncogenic fusions in chromatin proteins could be profiled by AutoCUT&RUN to provide a molecular diagnosis based on their chromatin landscapes, while simultaneously mapping the loci that are disrupted by the de novo mutant protein. This could provide a powerful tool for patient stratification, as well as a direct read-out of whether chromatin-modulating therapies such as histone deacetylase or histone methyltransferase inhibitors are having their intended effects.

Methods

AutoCUT&RUN

Briefly, cells or tissue samples are bound to Concanavalin A coated magnetic beads (Bangs Laboratories, ca. no. BP531), permeabilized with digitonin, and bound with a protein specific antibody as previously described[14]. Samples are then arrayed in a 96-well plate and processed on a Beckman Biomek FX liquid handling robot equipped with a 96S Super Magnet Plate (Alpaqua SKU A001322) for magnetic separation of samples during wash steps, and an Aluminum Heat Block Insert for PCR Plates (V&P Scientific, Inc. VP74I16A) routed to a cooling unit to perform the MNase digestion reaction at 0-4° C. after the addition of 2 mM $CaCl_2$. MNase digestion reactions are then stopped after 9 min by adding EGTA, which allows $Mg^{2+}$ addition for subsequent enzymatic reactions. This step circumvents the need for DNA purification prior to library preparation. Chromatin fragments released into the supernatant during digestion are then used as the substrate for end-repair and ligation with barcoded Y-adapters. Prior to ligation, the A-tailing step is performed at 58° C. to preserve sub-nucleosomal fragments in the library[36,37]. End-repair and adapter ligation reactions were performed on a separate thermocycler. Chromatin proteins were then digested with Proteinase K, and adapter ligated DNA fragments were purified on the Biomeck FX using two rounds of pre-PCR Ampure bead cleanups with size-selection. PCR enrichment reactions were performed on a thermocycler using the KAPA PCR kit (KAPA Cat #KK2502). Two rounds post-PCR Ampure bead cleanups with size-selection were performed on the Biomeck FX to remove unwanted proteins and self-ligated adapters. The size distributions of AutoCUT&RUN libraries were analyzed on an Agilent 4200 TapeStation, and library yield was quantified by Qubit Fluorometer (Life Technologies). Up to 24 barcoded AutoCUT&RUN libraries were pooled per lane at equimolar concentration for paired-end 25×25 bp sequencing on a 2-lane flow cell on the Illumina HiSeq 2500 platform at the Fred Hutchinson Cancer Research Center Genomics Shared Resource.

Antibodies

We used Rabbit anti-CTCF (1:100, Millipore Cat #07-729), Rabbit anti-NPAT (1:100, Thermo Fisher Cat #PA5-

66839), Rabbit anti-H3K4me1 (1:100, Abcam Cat #ab8895), Rabbit anti-H3K4me2 (1:100, Millipore Cat #07-030), Rabbit anti-H3K4me3 (1:100, Active Motif Cat #39159), Rabbit anti-H3K27me3 (1:100, Cell Signaling Tech Cat #9733S). Since pAMNase does not bind efficiently to many mouse antibodies, we used a rabbit anti-Mouse IgG (1:100, Abcam, Cat #ab46540) as an adapter. H3K27ac was profiled by AutoCUT&RUN in H1 and K562 cells and manually in VUMC-10 and SU-DIPG-XIII cell lines using Rabbit anti-H3K27ac (1:50, Millipore Cat #MABE647). H3K27ac was profiled by AutoCUT&RUN in VUMC-10 and SU-DIPG-XIII cell lines and xenografts using Rabbit anti-H3K27ac (1:100, Abcam Cat #ab45173).

Cell Culture

Human K562 cells were purchased from ATCC (Manassas, VA, Catalog #CCL-243) and cultured according to supplier's protocol. H1 hESCs were obtained from WiCell (Cat #WA01-lot #WB35186), and cultured in Matrigel™ (Corning) coated plates in mTeSR™ 1 Basal Media (STEMCELL Technologies cat #85851) containing mTeSR™ 1 Supplement (STEMCELL Technologies cat #85852). Pediatric DMG cell lines VUMC-DIPG-10 (Esther Hulleman, VU University Medical Center, Amsterdam, Netherlands) and SU-DIPG-XIII (Michelle Monje, Stanford University, CA) were obtained with material transfer agreements from the associated institutions. Cells were maintained in NeuroCult NS-A Basal Medium with NS-A Proliferation Supplement (STEMCELL Technologies, cat #05751), 100 U/mL of penicillin/streptomycin, 20 ng/mL epidermal growth factor (PeproTech, cat #AF-100-15), and 20 ng/mL fibroblast growth factor (PeproTech, cat #100-18B).

Patient Derived Xenografts

All mouse studies were conducted in accordance with Institute of Animal Care and Use Committee-approved protocols. NSG mice were bred in house and aged to 2-3 months prior to tumor initiation. Intracranial xenografts were established by stereotactic injection of 100,000 cells suspended in 3 uL at a position of 2 mm lateral and 1 mm posterior to lambda. Symptomatic mice were euthanized and their tumors resected for analysis.

Annotation and Data Analysis

We align paired-end reads using Bowtie2 version 2.2.5 with options: -local -very-sensitive-local -no-unal -no-mixed -no-discordant -phred33 -I 10 -X 700. For mapping spike-in fragments, we also use the -no-overlap -no-dovetail options to avoid cross-mapping of the experimental genome to that of the spike-in DNA. Files were processed using bedtools and UCSC bedGraphToBigWig programs.

To examine correlations between the genome-wide distribution of various samples, bins of 500 bp were generated for the genome, creating an array with approximately 6 million entries. Reads in each bin were counted and the log 2 transformed values of these bin counts were used to determine a Pearson correlation score between different experiments. Hierarchal clustering was then performed on a matrix of the Pearson scores.

To examine the distribution of histone mark profiles around promoters, a reference list of genes for build hg19 were downloaded from UCSC table browser (genome.ucsc.edu/cgi-bin/hgTables) and oriented according to the directionality of gene transcription for further analysis. Genes with TSSs within 1 kb of each other were removed, as were genes mapping to the mitochondrial genome, creating a list of 32,042 TSSs. RNA-sequencing data was obtained from the ENCODE project for H1 and K562 cells (ENCSR537BCG and ENCSR000AEL). RNA reads were counted using featureCounts (bioinf.wehi.au/feature-Counts/), and converted to Fragments Per Kilobase per Million mapped reads (FPKM) and assigned to the corresponding TSS as a gene expression value. ATAC-sequencing data for H1 cells was obtained from gene omnibus expression (GEO) (GSE85330) and mapped to hg19 using bowtie2. Mitochondrial DNA accounted for ~50% of the reads and were removed in this study.

Training the CREAM Algorithm

To ensure the accuracy of fitting histone modification data at promoters to RNA-seq values, genes with more than one promoter were removed from the previously generated TSS list. The genes RPPH1 and RMRP were expressed at extremely high levels in H1 cells, and so were considered to be outliers and were removed to avoid skewing the regression, leaving a list of n=12,805 genes.

To assign a relative CUT&RUN signal to these promoters for each histone mark, denoted by C, base pair read counts+/−1kb of the TSS were normalized by both sequencing depth over the promoters being scored and the total number of promoters examined. The prior normalization is to account for both sequencing depth and sensitivity differences amongst antibodies and the latter normalization is included so that the model can be applied to different numbers of cis-regulatory elements without changing the relative weight of each element. FPKM values were used for RNA-seq.

A linear model was trained using a linear combination of histone data fitted to the RNA-seq expression values: $y=C_1x_1+ \ldots +C_nx_n$, where $C_i$ is the weight for each histone modification and $x_i$ is denoted by $x_i=\ln(C_i+\alpha i)$, where C is the normalized base pairs counts described above and a is a pseudo-count to accommodate genes with no expression. The RNA-seq values were similarly transformed as $y_i=\ln(FPKM_i+\alpha_{y,i})$. Logarithmic transformations were used to linearize the data. A minimization step was then performed to calculate pseudo-counts and weights for each histone modification that would maximize a regression line between CUT&RUN data and RNA-seq.

We expected that the histone marks H3K27ac, H3K27me3, and H3K4me2 would provide the least redundant information. The optimized three histone mark model for K562 cells is described by:

$$=0.858 \ln(CH_{3K27ac}+0.058)-0.615 \ln(CH_{3K27me3}+0.0816)+1.609 \ln(CH_{3K4me2}+0.054).$$

This equation was used to generate all CREAM scores.

Calling Chromatin Domains

To compare the global chromatin landscape of H1 and K562 cells, chromatin domains were called using a custom script that enriched for regions relative to an IgG CUT&RUN control. Enriched regions amongst marks were compared and overlaps were identified by using bedtools intersect. Overlapping regions were quantified by the number of base pairs in the overlapping enriched regions and these were used to generate the Venn diagrams.

Venn Diagrams

All Venn Diagrams were generated using the BaRC webtool, publicly available from the Whitehead Institute (barc.wi.mit.edu/tools/venn/).

Calculating Cell-Type Specific Promoter Activities Using CREAM Scores

Raw promoter CREAM scores generally fall within a range from −10 to 10, where a smaller number is indicative of less transcriptional activity. To account for outliers in the data when comparing different cell types, CREAM scores within 2 standard deviations were z-normalized. Negative and zero values complicate calculating fold change, so the data was shifted in the x and y directions by the most negative values. The fold difference between promoter CREAM scores for various cell types was calculated by dividing the inverse log 10 normalized CREAM scores against each other. A conservative 2-fold cutoff was used to determine cell-type specific promoters in each case (FIGS. 45B, 45E, 47A, 47B). Each list of genes was classified by gene ontology (geneontology.org/) to identify statistically enriched biological processes.

To examine the relative similarities between cell-types based on their promoter activities, CREAM scores for all promoters >1kb apart were used to generate an array, and Spearman correlations were calculated for each pair-wise combination of the samples. Hierarchal clustering of the Spearman correlation values was used to visualize the relative similarities between cell-types.

Peak Calling on AutoCUT&RUN and ATAC-Seq Data

Biological replicates profiled by AutoCUT&RUN were shown to be highly correlated (FIG. 43B), so replicates were joined prior to calling peaks. The tool MACS2 was used to call peaks and the following command was used on the command line: "macs2 callpeak -t file -f BEDPE -n name -q 0.01 -keep-dup all -g 3.137e9". A FDR cutoff of 0.01 was used.

Calculating Cell-Type Specific DRE Activities from CREAM Scores

To assemble a list of distal cis-regulatory elements in the human genome, we used MACS2 to call peaks on H3K4me2 profiles from each of our samples using the same flags described in the 'Peak calling on AutoCUT&RUN and ATAC-seq' methods section. To distinguish between TSSs and putative enhancers, peaks <2.5 kb away from an annotated TSS were removed, and windows +/−1kb around these putative enhancers were assigned CREAM scores using the algorithm trained to predict promoter activity. Correlation matrices comparing the enhancer CREAM scores between samples were generated in the same manner as the correlation matrix comparing promoter CREAM scores between samples.

References for Example 7 (Each of which is Incorporated by Reference in its Entirety)

1 Levine, M., Cattoglio, C. & Tjian, R. Looping back to leap forward: transcription enters a new era. Cell 157, 13-25, doi:10.1016/j.cell.2014.02.009 (2014).
2 Heinz, S., Romanoski, C. E., Benner, C. & Glass, C. K. The selection and function of cell type-specific enhancers. Nat Rev Mol Cell Biol 16, 144-154, doi:10.1038/nrm3949 (2015).
3 Reinberg, D. & Vales, L. D. Chromatin domains rich in inheritance. Science 361, 33-34, doi:10.1126/science.aat7871 (2018).
4 Henikoff, S. & Greally, J. M. Epigenetics, cellular memory and gene regulation. Curr Biol 26, R644-648, doi:10.1016/j.cub.2016.06.011 (2016).
5 Schwartzentruber, J. et al. Driver mutations in histone H3.3 and chromatin remodelling genes in paediatric glioblastoma. Nature 482, 226-231, doi:10.1038/nature10833 (2012).
6 Hu, D. & Shilatifard, A. Epigenetics of hematopoiesis and hematological malignancies. Genes Dev 30, 2021-2041, doi:10.1101/gad.284109.116 (2016).
7 Mackay, A. et al. Integrated Molecular Meta-Analysis of 1,000 Pediatric High-Grade and Diffuse Intrinsic Pontine Glioma. Cancer Cell 32, 520-537 e525, doi:10.1016/j.ccell.2017.08.017 (2017).
8 Cotney, J. et al. The autism-associated chromatin modifier CHD8 regulates other autism risk genes during human neurodevelopment. Nat Commun 6, 6404, doi:10.1038/ncomms7404 (2015).
9 Lambert, S. A. et al. The Human Transcription Factors. Cell 172, 650-665, doi:10.1016/j.cell.2018.01.029 (2018).
10 Regev, A. et al. The Human Cell Atlas. Elife 6, doi:10.7554/eLife.27041 (2017).
11 Rozenblatt-Rosen, O., Stubbington, M. J. T., Regev, A. & Teichmann, S. A. The Human Cell Atlas: from vision to reality. Nature 550, 451-453, doi:10.1038/550451a (2017).
12 Feinberg, A. P. The Key Role of Epigenetics in Human Disease Prevention and Mitigation. N Engl J Med 378, 1323-1334, doi:10.1056/NEJMra1402513 (2018).
13 Teytelman, L., Thurtle, D. M., Rine, J. & van Oudenaarden, A. Highly expressed loci are vulnerable to misleading ChIP localization of multiple unrelated proteins. Proc Natl Acad Sci USA 110, 18602-18607, doi:10.1073/pnas.1316064110 (2013).
14 Skene, P. J., Henikoff, J. G. & Henikoff, S. Targeted in situ genome-wide profiling with high efficiency for low cell numbers. Nat Protoc 13, 1006-1019, doi:10.1038/nprot.2018.015 (2018).
15 Skene, P. J. & Henikoff, S. An efficient targeted nuclease strategy for high-resolution mapping of DNA binding sites. Elife 6, doi:10.7554/eLife.21856 (2017).
16 Hainer, S. J., Boskovic, A., Rando, O. J. & Fazzio, T. G. Profiling of pluripotency factors in individual stem cells and early embryos. bioRxiv, doi:doi.org/10.1101/286351 (2018).
17 Zhao, J. et al. NPAT links cyclin E-Cdk2 to the regulation of replication-dependent histone gene transcription. Genes Dev 14, 2283-2297 (2000).
18 Narendra, V. et al. CTCF establishes discrete functional chromatin domains at the Hox clusters during differentiation. Science 347, 1017-1021, doi:10.1126/science.1262088 (2015).
19 Hawkins, R. D. et al. Distinct epigenomic landscapes of pluripotent and lineage-committed human cells. Cell Stem Cell 6, 479-491, doi:10.1016/j.stem.2010.03.018 (2010).
20 Gaspar-Maia, A., Alajem, A., Meshorer, E. & Ramalho-Santos, M. Open chromatin in pluripotency and reprogramming. Nat Rev Mol Cell Biol 12, 36-47, doi:10.1038/nrm3036 (2011).
21 Bernstein, B. E. et al. A bivalent chromatin structure marks key developmental genes in embryonic stem cells. Cell 125, 315-326, doi:10.1016/j.cell.2006.02.041 (2006).
22 Rada-Iglesias, A. et al. A unique chromatin signature uncovers early developmental enhancers in humans. Nature 470, 279-283, doi:10.1038/nature09692 (2011).
23 Consortium, E. P. An integrated encyclopedia of DNA elements in the human genome. Nature 489, 57-74, doi:10.1038/nature11247 (2012).
24 Karlic, R., Chung, H. R., Lasserre, J., Vlahovicek, K. & Vingron, M. Histone modification levels are predictive for gene expression. Proc Natl Acad Sci USA 107, 2926-2931, doi:10.1073/pnas.0909344107 (2010).
25 Martello, G. & Smith, A. The nature of embryonic stem cells. Annu Rev Cell Dev Biol 30, 647-675, doi:10.1146/annurev-cellbio-100913-013116 (2014).
26 Gottgens, B. Regulatory network control of blood stem cells. Blood 125, 2614-2620, doi:10.1182/blood-2014-08-570226 (2015).

27 Nagaraja, S. et al. Transcriptional Dependencies in Diffuse Intrinsic Pontine Glioma. Cancer Cell 31, 635-652 e636, doi:10.1016/j.ccell.2017.03.011 (2017).
28 Massague, J. & Chen, Y. G. Controlling TGF-beta signaling. Genes Dev 14, 627-644 (2000).
29 Heintzman, N. D. et al. Distinct and predictive chromatin signatures of transcriptional promoters and enhancers in the human genome. Nat Genet 39, 311-318, doi:10.1038/ng1966 (2007).
30 Creyghton, M. P. et al. Histone H3K27ac separates active from poised enhancers and predicts developmental state. Proc Natl Acad Sci USA 107, 21931-21936, doi:10.1073/pnas.1016071107 (2010).
31 Heintzman, N. D. et al. Histone modifications at human enhancers reflect global cell-type-specific gene expression. Nature 459, 108-112, doi:10.1038/nature07829 (2009).
32 Liu, Q. et al. Genome-Wide Temporal Profiling of Transcriptome and Open Chromatin of Early Cardiomyocyte Differentiation Derived From hiPSCs and hESCs. Circ Res 121, 376-391, doi:10.1161/CIRCRESAHA.116.310456 (2017).
33 Andersson, R. et al. An atlas of active enhancers across human cell types and tissues. Nature 507, 455-461, doi:10.1038/nature12787 (2014).
34 Calo, E. & Wysocka, J. Modification of enhancer chromatin: what, how, and why? Mol Cell 49, 825-837, doi:10.1016/j.molcel.2013.01.038 (2013).
35 Filbin, M. G. et al. Developmental and oncogenic programs in H3K27M gliomas dissected by single-cell RNA-seq. Science 360, 331-335, doi:10.1126/science.aao4750 (2018).
36 Liu, N. et al. Direct Promoter Repression by BCL11A Controls the Fetal to Adult Hemoglobin Switch. Cell 173, 430-442 e417, doi:10.1016/j.cell.2018.03.016 (2018).
37 Neiman, M. et al. Library preparation and multiplex capture for massive parallel sequencing applications made efficient and easy. PLoS One 7, e48616, doi:10.1371/journal.pone.0048616 (2012).

Example 8

Epigenomic Profiling of Complex Tissues with Single-Cell CUT&RUN

Single-cell analysis is becoming the dominant approach for molecular characterization of development, and the recent advances in single-cell barcoding technologies have been applied to gene expression and DNA accessibility profiling of complex tissues. However, RNA-seq cannot characterize or map regulatory elements, ATAC-seq is limited to sites of DNA hyper-accessibility, and ChIP-seq is too inefficient for a single-cell strategy to be seriously pursued. But CUT&RUN antibody-tethered nuclease method has surpassed ChIP-seq in efficiency and resolution by orders of magnitude. This also applies to ITIS. As disclosed herein the original CUT&RUN method is extendable to whole tissues and sorted cells, achieving high data quality with only 100 cells, and we have developed a high-throughput automated pipeline.

To take advantage of recent advances in single-cell technologies, two distinct single-cell CUT&RUN (scCUT&RUN) strategies are developed. First, a commercial automated nanowell plate system is adapted for arraying, barcoding and amplifying thousands of intact cells for scCUT&RUN. To apply this strategy, fragments generated by tethered MNase are ligated to sequencing adapters in intact cells, followed by arraying on the nanowell plate for single-cell indexing. Second, we will adapt split-pooling of bulk cell populations to obtain combinatorial barcoding of cells in 96-well plate pools. Pooling of the cells from the plate and rearraying them into a new 96-well plate will be followed by one or more rounds of barcode ligation, repooling and rearraying. By adapting CUT&RUN for both popular single-cell barcoding strategies we can compare their distinct advantages for single-cell profiling in the context of chromatin profiling. For evaluation, human K562 cells and Drosophila S2 cells are used as are antibodies to selected histone modifications, to RNA Polymerase II modifications, and to constitutive transcription factors. In preliminary studies, both strategies have been shown to work by native in situ ligation of Illumina adapters following CUT&RUN, while retaining DNA fragments within individual nuclei. Maintaining nuclear integrity allows us to index fragments from individual cells, and the unique series of barcodes constructs single-cell landscapes from pooled sequencing.

Moving from homogeneous cell lines to heterogeneous cell populations and complex tissues, scCUT&RUN is applied to human CD34+ primary hematopoietic cells and Drosophila testes. It is found that a modification of our basic CUT&RUN protocol sufficiently permeabilizes intact Drosophila imaginal discs and brains, thus avoiding damage from tissue processing that can potentially reduce data quality. FACS isolation can be followed by CUT&RUN with high data quality. FACS-isolated subpopulatons of CD34+ lymphoid cells, and both intact and flow-sorted Drosophila germline tissues are used for CUT&RUN and adapter ligation followed by either nanodispensation or split-pooling or both for indexing. Developmental changes in regulatory elements and gene expression can be assessed in these two systems.

Computational tools are developed for CUT&RUN data that take advantage of the base-pair precision of cleavages. One will be optimization and evaluation of a novel peak-calling algorithm that uses fragment lengths to call peak summits and an empirical procedure to determine enrichment without smoothing to maintain base-pair resolution of cleavages. A second tool will be development of an algorithm that uses fragment length information to predict enhancer and promoter activity based on our recent description of a general chromatin signature of nucleosome disruption identifiable by CUT&RUN profiling. These methods allow the exploitation the structural information inherent in DNA fragment length. We will use single-cell dimensional reduction tools used widely for RNA-seq to distinguish cell types, and we will develop custom analysis software to identify enhancer-promoter-gene combinations.

Human genetic regulatory elements remain poorly defined. About 10% of the proteins encoded by the human genome are transcription factors (TFs), which regulate genes by sequence-specific binding to their sites of action. The binding of transcription factors to regulatory elements stands at the apex of the gene regulatory hierarchy, controlling development and important physiological processes. Aberrant regulation of TF binding is a key driver of many human diseases, and current efforts to edit TF binding sites (TFBSs) are promising avenues for disease intervention. However, current limitations in mapping TFBSs can compromise clinical application of these tools. For example, a powerful strategy to treat patients with sickle-cell anemia and D-thalassemia would be to "reawaken" the fetal gamma globin gene to alleviate the symptoms caused by defective adult beta globin expression. Editing the binding site of the repressive transcription factor responsible for the developmental switch between gamma and beta globin genes could accomplish this. Until very recently identification of the binding site of the repressor TF BCL11A failed because of limitations in popular methods for mapping TFs. The key binding site was readily identified by CUT&RUN mapping of BCL11A [1]; this immediately enables an editing strategy for alleviating the symptoms of one of the most common human genetic diseases, and in fact sickle-cell disease patients with mutations in this binding site show attenuated sickling of erythrocytes.

Limitations of ChIP-seq mapping of regulatory elements. Chromatin immunoprecipitation (ChIP) has been one of the most widely used techniques in chromatin biology. However, very little has changed in the way ChIP is performed since it was first described more than 30 years ago [3]. Rather, the huge successes using ChIP have come from phenomenal improvements in readout technologies. Readout platforms have progressed from southern blotting, to quantitative PCR, to microarrays, and over the past decade to high-throughput sequencing (ChIP-seq) [4-7]. ChIP-seq has become a fundamental strategy for understanding genomic sequence, with over 2000 ChIP-seq experiments forming the ENCODE project alone.

Despite this large investment, the chromatin crosslinking and shearing strategy used for ChIP has three major limitations [8-12]. 1) Crosslinking leads to epitope masking, which decreases immunoprecipitation efficiency and reduces signal-to-noise ratios. For example, the NIH Protein Capture Reagents Program (PCRP) has generated a collection of 1406 highly validated, immunoprecipitation and/or immunoblotting grade, mouse monoclonal antibodies (mAbs) to 736 human transcription factors [13]. The consortium used HuProt human protein microarrays as a primary validation tool to identify mAbs with high specificity for their cognate targets.

Nevertheless, only 50 of a sample of 305 mAbs (16%) were judged to be satisfactory for ChIP-seq based on ENCODE standards. 2) Crosslinking renders chromatin insoluble, so ChIP typically uses sonication to shear chromatin. Sonication produces chromatin fragments of 200-300 bp, whereas the footprint of a typical chromatin-associated protein is ~20 bp, and so actual binding sites must be computationally inferred from ChIP mapping. Thus the most widely used protocol for ChIP falls far short of taking advantage of the base-pair resolution possible with a sequencing readout. 3) Solubilizing crosslinked chromatin by sonication is dramatically biased. When ChIP has been carefully assessed, many "hyper-ChIPable" regions [8], "phantom" peaks [10], and other false positive artifacts are commonly found [9, 12]. In short, ChIP-seq is hampered by low reliability, poor yields, low resolution, and low accuracy. Recent versions of ChIP have improved resolution with exonuclease treatment (ChIP-exo [4] and ChIP-nexus [7]), but these methods are cumbersome and inefficient. These problems with ChIP emphasize the need for alternative epigenomic mapping metholologies.

CUT&RUN. The limitations of ChIP-seq by developing new epigenomic profiling strategies [5, 14-16]. With CUT&RUN, a factor-specific antibody is used to tether Micrococcal Nuclease (MNase) to chromatin. MNase is then activated to cleave DNA around TFBSs, releasing DNA into the supernatant for paired-end DNA sequencing (FIG. 1A). CUT&RUN eliminates solubilization and immunoprecipitation steps, and thus has inherent advantages over ChIP. As all the steps for binding to a chromatin factor and DNA cleavage occur in intact nuclei, followed by simple DNA purification, the yields and specificity of CUT&RUN are much higher than for ChIP-seq. CUT&RUN is simple, efficient, and cost-effective, with the potential to completely replace ChIP-seq.

Expanding the scope of CUT&RUN. We first used CUT&RUN to identify the binding sites of yeast and human chromatin proteins and TFs, to determine the histone composition of the insoluble budding yeast centromere, and to precisely map CTCF-bridged sites without cross-linking or ligation [16]. We have since expanded the scope of CUT&RUN to investigate other topics. These include centromeres of higher eukaryotes, chromatin structure and transcriptional regulation: 1) With CUT&RUN followed by salt-fractionation, we have discovered that human centromeres show unexpected structural and conformational variations of inner kinetochore complexes on different α-satellite dimeric units within highly homogenous arrays [18]. 2) We also used CUT&RUN to identify functional centromeres in α-satellite monomers of old-world monkeys, which lack binding sites for CENP-B (the "CENP-B paradox" [19]). 3) In describing asymmetric unwrapping of nucleosomes produced by transcription, we used fragments produced by CUT&RUN at regulatory elements to show that the same signature of nucleosome unwrapping in cells and even cell-free human plasma DNA could be produced by nucleosome remodeling [20]. Our identification of regulatory elements based on fragment position and length is a key feature of CUT&RUN.

Figure 54:
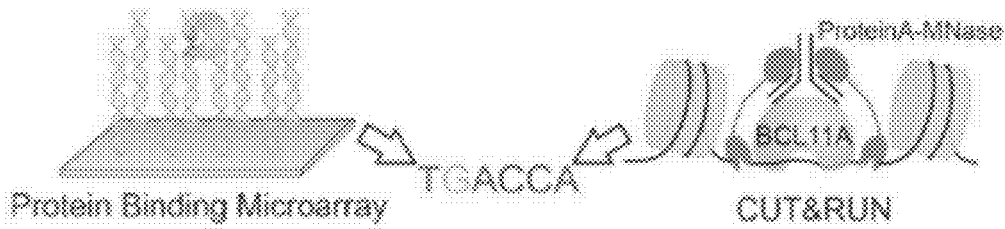
FIG. 54 shows that CUT&RUN identifies the fetal gamma to adult beta globin switch.
Figure 54:
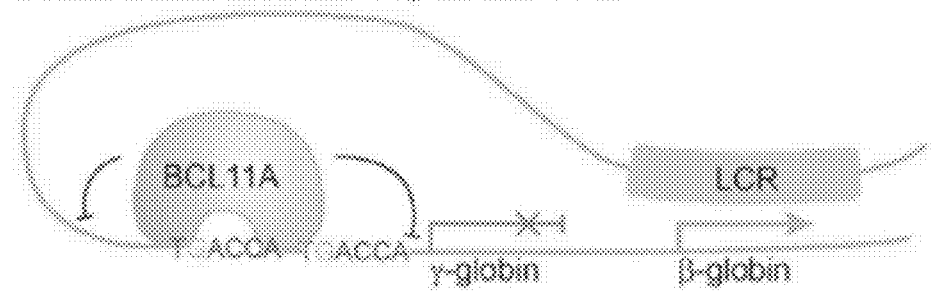
Figure 54:
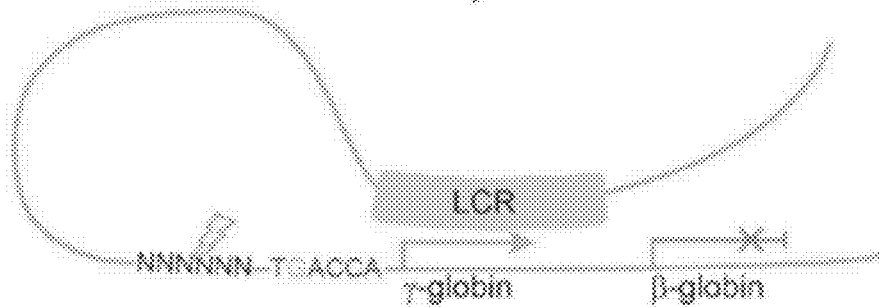

Many BCL11A antibodies have failed for ChIP-seq over the years, leading to the model that the fetal-to-adult switch resides in the locus control region (LCR) far upstream. The authors used CUT&RUN with antibodies that had failed for ChIP-seq to show that the repressor bound preferentially to the same TGACCA motif that they had identified by protein-binding microarrays (FIG. 54, top), and that it bound to one motif of two in the fetal gamma globin promoter only 21 bp apart (FIG. 54, middle). This motif is mutated in individuals with the benign condition of hereditary persistence of fetal hemoglobin, and the authors went on to prove that this site controls repression by editing it and showing that BCL11A no longer bound (FIG. 54, bottom).

To identify regulatory elements in single cells, two distinct barcoding strategies may be used: single-cell nanowell indexing and split-pool combinatorial indexing, both of which have been used with great success for single-cell RNA-seq (scRNA-seq) [28, 29].

Comparison of CUT&RUN to ChIP-seq. We compare performance of epigenomic mapping methods by 1) their resolution of factor binding sites, and 2) their signal-to-noise ratios. Signal-to-noise ratios are especially important in determining the precision and recall of binding sites, and determining what coverage of deep sequencing is required, and therefore the cost of an experiment. ChIP methods have two main limitations: First, generating a soluble chromatin preparation requires breaking the entire genome into chromatin fragments, which contributes to a genome-wide background noise. Second, by definition all ChIP methods rely on immunoprecipitation, where the solubility of chromatin particles and their recovery must be optimized. By contrast, the disclosed CUT&RUN technology is orthogonal to ChIP as it is based on targeting DNA cleavage only to factor binding sites in intact nuclei [16]. This strategy obviates the need for a soluble chromatin preparation, and gives specific signals at binding sites simply by sequencing cut DNA.

We have optimized handling of cells using Concanavalin A (ConA) coated magnetic beads for rapid and efficient solution changes. We bind antibodies and Protein A-MNase to native unfixed nuclei, where epitopes are preserved and accessible. As only chromatin fragments with cleavages on both sides of a particle enter the supernatant, we simply remove the rest of the insoluble bulk chromatin. Because the vast majority of non-specific DNA is left behind, CUT&RUN has very low background levels, dramatically reducing costs relative to ChIP, where the entire solubilized content of a cell is exposed to the antibody. As spike-in controls are now the preferred method of normalization [30], we have implemented a simple strategy for normalizing CUT&RUN data: we add a small fixed amount of fragmented yeast DNA to bead-bound intact cell samples after the cleavage reaction. The DNAs are then extracted together, and libraries are prepared and sequenced. Reads mapping to the yeast genome assembly are used to normalize sample read counts between experiments.

We find that CUT&RUN outperforms ChIP-seq with respect to simplicity, resolution, robustness, efficiency, data quality, and applicability to insoluble complexes [16]. CUT&RUN requires only ~1/10th of the sequencing depth of ChIP-seq due to the intrinsically low background achieved by performing the reaction in situ.

To test the performance of CUT&RUN in mammalian genomes, we mapped CTCF in human K562 cells [2]. The cleavage footprint is consistent over a ~300-fold digestion range, with a predominant single base-pair cut site on either side (FIG. 6C), highlighting that CUT&RUN reaches a limit digestion that reveals the minimal footprint of bound factors. FIG. 6A, lower panel compares results for 10 million fragments sampled from ENCODE ChIP-seq, ChIP-exo and CUT&RUN datasets. Profiling shows that CUT&RUN defines sharp peaks that coincide with peaks detected in ENCODE ChIP-seq. ChIP-exo detects some of these peaks, but many sites have broad distributions of read ends that are usually refined computationally. CUT&RUN required less sequencing depth than other methodologies, due mainly to the intrinsic low background of limited DNA cleavages. This greatly reduces the cost of experiments, with better data quality. Nucleosomes flanking CTCF sites are also specifically released, and appear as a distinctive size of DNA fragments.

Figure 55:
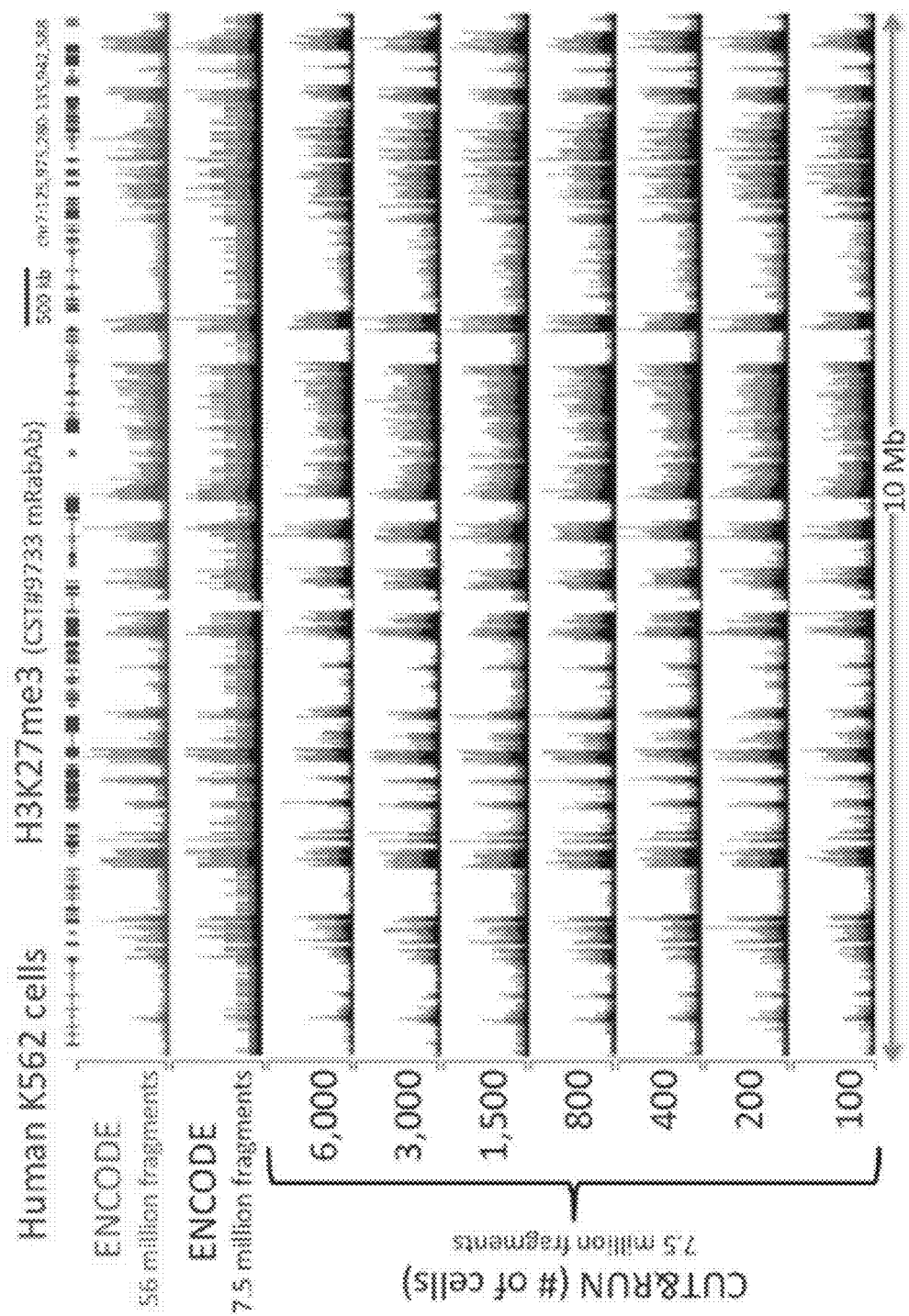
FIG. 55 shows high CUT&RUN data quality with 100 cells. Varying numbers of K562 cells were used as the starting material for profiling H3K27me3 by CUT&RUN. Following paired-end 25×25 bp Illumina sequencing and removal of duplicates, 7.5 million fragments were randomly selected and used to generate tracks representing raw counts. ENCODE X-ChIP-seq data are shown for the full profile (top track) and for a 7.5 million randomly selected subset for comparison to CUT&RUN.

Performance of CUT&RUN with low cell numbers. Standard ChIP-seq protocols are not suitable for low cell numbers that are often obtained after FACS or dissection, or in clinical settings. ATAC-seq has been used to profile samples with as few as 5000 cells, but ATAC-seq is limited to non-specific identification of TFs that are in accessible regions of chromatin. We recently showed that CUT&RUN provides high data quality for low cell numbers ([2], FIG. 55). Very little if any loss of data quality occurred with reduction in cell number from 6,000 down to 100 cells for H3K27me3. In contrast, the ENCODE profile sampled at the same depth is blurry owing to the high background inherent to ChIP. Much lower cell numbers were achieved by Hainer et al. by making minor modifications to reagent volumes and library preparation steps [23]. Therefore, CUT&RUN makes possible targeted genome-wide maps of protein-DNA interactions for low cell number applications.

Figure 56:
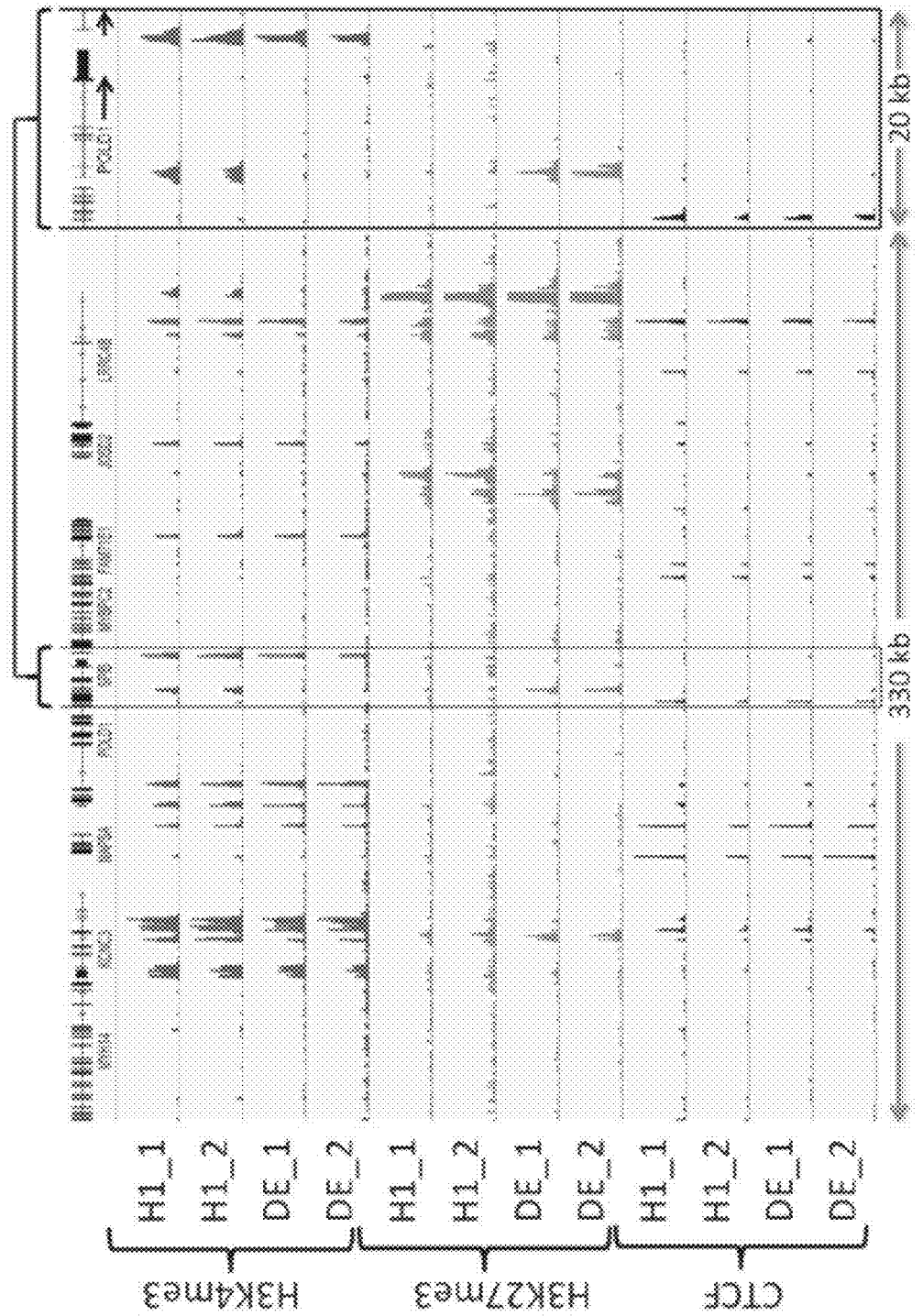
FIG. 56 shows automated CUT&RUN profiling of human ES cells differentiated to endoderm. Screenshot showing replicate CUT&RUN profiles for an "active" (H3K4me3) and "repressive" (H3K27me3) histone modification and for CTCF for H1 embryonic stem cells and differentiated endoderm cells (DE) derived from an H1 cell culture. The POLD1 transcription unit is expanded (boxed region) on the right showing a switch over the promoter from an active to a repressive modification during differentiation. POLD1 encodes the catalytic subunit of the lagging strand DNA Polymerase (Pol-delta), suggesting that the switch from a promoter-active to -repressive chromatin state of the replication machinery corresponds to exit from the cell cycle.

Automated CUT&RUN for low-cost profiling of bulk cells and tissues. We have modified the CUT&RUN protocol for what we call 'direct ligation', where protein-DNA particles in the supernatant are used for end-polishing and ligation, which made it possible to perform all steps from cells to libraries on a robot. For automated CUT&RUN we mix cells with ConA-coated magnetic beads and add permeabilizing detergent (digitonin) and antibody together with 2 mM EDTA to stop active processes. After overnight incubation at 4° C. we transfer the bead/cell slurries to wells of a 96-well plate. CUT&RUN is performed on the robot through ligation of adapters and Ampure bead clean-up, whereupon the plate is transferred to a PCR cycler for amplification, then returned to the robot for clean-up of the final barcoded libraries. An example of datasets that were prepared for the NIH 4D Nucleome project shows that differentiation of human embryonic stem cells (H1) to definitive endoderm involves the switch from H3K4me3 modification of promoter nucleosomes to H3K27me3 over a key DNA replication gene, POLD1 (FIG. 56).

Figure 57:
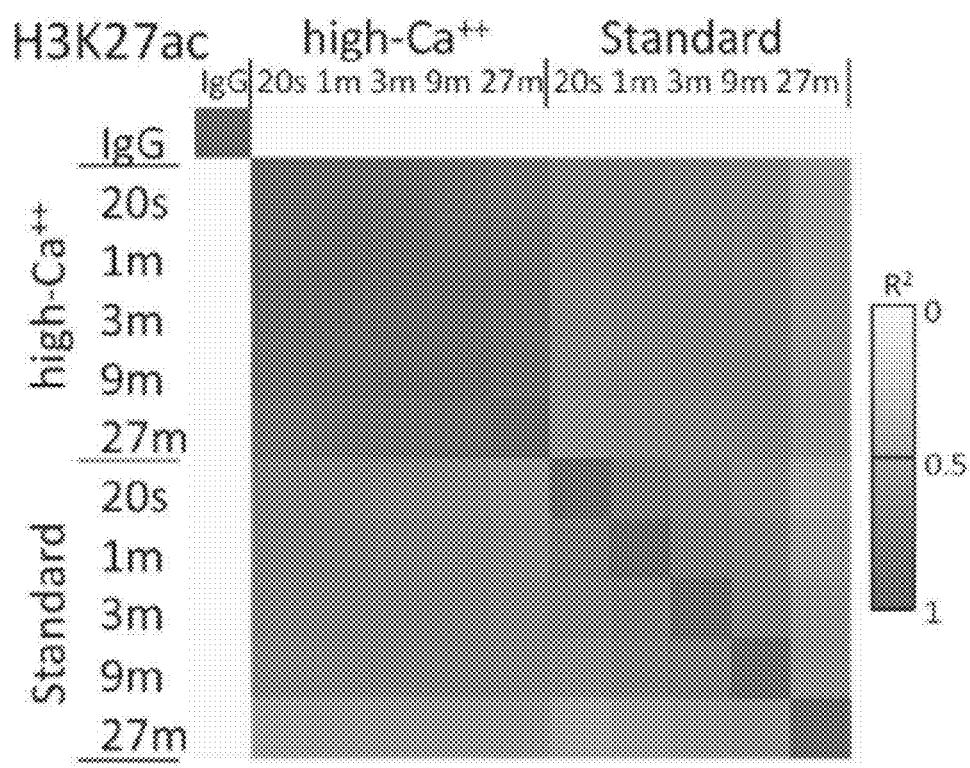
FIG. 57 shows improved consistency with high-Ca++/low salt digestion. CUT&RUN was performed with two different antibodies with digestions over a 20s to 27 min range as indicated using either high-Ca++/low salt or the standard protocol. Seventeen H3K27ac datasets from four time-course series experiments were pooled, and 74,906 peaks were called using MACS2. Peak positions were scored for each dataset and correlations ($R^2$) calculated between peak vectors.

CUT&RUN with in situ ligation. sciRNA-seq (single-cell combinatorial indexing RNA sequencing) [31] and Split-seq (split-pool ligation-based transcriptome sequencing) [28] are strategies in which RNA is converted to cDNA in bulk cells or nuclei in situ followed by ligation of barcoded adapters to cDNA ends. Cells are fixed to prevent leakage of the RNA during the cDNA synthesis and ligation. However, we have developed a simple native procedure that prevents DNA leakage without fixation. Based on the observation that nucleosome core particles aggregate in low-salt/high-divalent-cation conditions [32], we perform digestions in 10 mM $CaCl_2$) and 3.5 mM HEPES pH 7.5. Under these conditions, fragments are cleaved at a 3-fold higher rate with no detectable release of fragments into the supernatant (data not shown). Reactions are halted by removing the supernatant on a magnet and adding elution buffer containing 150 mM NaCl and 20 mM EGTA, which releases the small DNA fragments into the supernatant and is compatible with direct end-polishing and adapter ligation used for automated CUT&RUN. Libraries produced from digestions using this modified protocol showed improved consistency of H3K27ac peaks for time-course data (FIG. 57), presumably because preventing release of particles during digestion obviated their diffusion within the nucleus where they may artifactually digest accessible DNA. Thus, our simple modification of CUT&RUN both improves data quality and sets the stage for nanowell dispensing and split-pool barcoding without fixation.

Figures 58A, 58B:
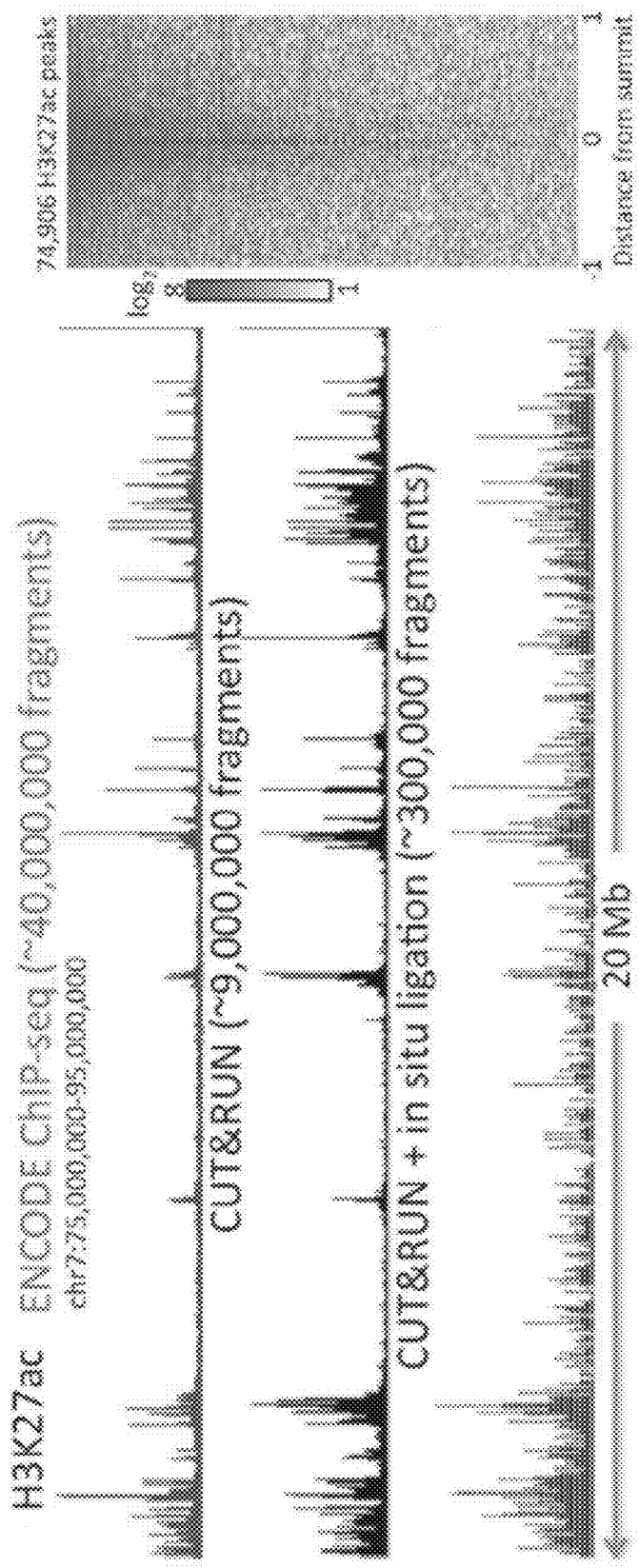
FIGS. 58A and 58B show H3K27ac CUT&RUN with in situ ligation of adapters.

To adapt this modified CUT&RUN protocol for in situ ligation, we stopped the reaction by addition of a buffer containing 20 mM EGTA, 10 mM MgCl2 and 3.5 mM HEPES to the bead/cells. Under these conditions, the low-salt and high $Mg^{++}$ conditions maintain the aggregated chromatin state, while EGTA preferentially chelates the calcium over magnesium, stopping cleavage. Addition of end-polishing and ligation reagents with barcoded Illumina adapters was followed by extraction of total DNA, PCR amplification using Illumina primers, and sequencing. Although most of the fragments were adapter dimers, we nevertheless found that there were sufficient mapped reads for an H3K27ac CUT&RUN experiment to confirm the genome-wide pattern (FIG. 58A). With only ~300,000 fragments in this experiment, the profile is similar to those of CUT&RUN with 30-fold (~9 million) and ENCODE ChIP-seq with 130-fold (~40 million) more fragments using the same Abcam ab4729 antibody, confirmed by the close correspondence to rank-ordered H3K27ac CUT&RUN peaks (FIG. 58B). These results demonstrate that in situ adapter ligation works, setting the stage for applying scCUT&RUN indexing strategies.

Optimizing in situ ligation. Although our preliminary proof-of-concept result from this first in situ ligation experiment is promising, the efficiency of blunt-end ligation was very low, and library preparations are dominated by adapter-dimers. One possible solution is to include additional Ampure bead selection steps, however, this will reduce the overall yield. Another solution is to add an A-tailing step and use adapters with a protruding 3' T base. We can also prevent formation of adapter dimers by synthesizing hairpin adapters with a deoxy-uracil in the loop. After ligation treatment, digestion with uracil-N-deglycosylase forms an appropriate protruding end for barcoded amplification in nanowells or for the first round of split-pooling. Another solution is to include a restriction enzyme during ligation that will regenerate blunt end adapters whenever they ligate.

Nanowell barcoding. Originally designed for RNA-seq with embedded oligos, the Takara SMARTer ICELL8 Single-Cell System has very recently been adapted for ATAC-seq [33], and we will follow a similar indexing strategy for chromatin profiling. CUT&RUN will be performed in bulk through the adapter ligation step, omitting the use of magnetic beads. We will follow our original protocol using digitonin-permeabilized cells with gentle centrifugation between washes [26], where loose cell pellets are dispersed into single cells by gentle pipetting and/or vortexing. Single cells will be dispensed into individual nanowells of an ICELL8 chip and imaged, and each nanowell will be indexed by dispensing 72 different barcoded Illumina i5 primers into the rows and 72 different i7 primers into the columns, which distinguishes by barcode all 5184 nanowells on the plate. The ICELL8 system imaging station will automatically identify wells with single cells, and classify cellular morphology for post-sequencing analysis. Typically about ⅓ of the 5184 nanowells on a ICELL8 chip receive a single cell, thus imaging the plate allows us to use only seeded nanowells for an overall cost of ~$1 per cell for materials. The nanowell plates will be sealed, and the plate subjected to 14 cycles of PCR as is done for standard CUT&RUN. The barcoded and amplified fragments will then be pooled for manual DNA extraction, Ampure bead clean-up and paired-end DNA sequencing sufficient for reading through the single-cell barcodes. We expect 150 million paired-end fragment sequences of the pooled sample, or on the order of ~100,000 reads per cell. Based on the yields we obtained in our low cell number experiments for abundant histone modifications (e.g., FIG. 55).

Split-pool ligation. Array-based combinatorial barcoding is especially well-suited for deep profiling of thousands of cells. However, split-pooling does not require special equipment and can be performed using simple manual methods, so that this rapidly improving class of single-cell strategies remains highly competitive with various direct single-cell strategies. We will follow a similar split-pooling strategy as described [28]. Briefly, we will perform CUT&RUN in bulk under low-salt high divalent cation conditions. We will perform in situ ligation using a universal linker that is blunt at the 5' end and has a sticky overhang at the 3' end. The 5' end of the linker will be ligated to the polished DNA fragment ends generated by CUT&RUN, while the 3' sticky end will be complementary to the 5' ends of 96 unique tags, referred to as odd-tags. The other end of these odd-tags will be complementary to the 5' ends of a different set of 96 unique tags, referred to as even-tags. Cells will be pooled and repeatedly split across a 96-well plate. In each round, unique tags distributed to each of the 96 wells will be ligated to the DNA ends. Sticky-end ligations are more efficient than the blunt-end ligation performed in the first step, so most or all captured CUT&RUN ends should be effectively barcoded. To make sure that each cell will have a unique series of tags (barcodes), we will run multiple split-pooling cycles, re-using the same set of odd and even tags. Finally, all cells will be pooled and terminal tags that contain the Illumina adapters will be ligated. Total DNA extraction of the pooled cells will be followed by library preparation and Ampure bead clean-up. There is no need to use different index primers as each cell already has its own barcode at this point. Read-pairs will be generated with at least 100×100 bp depending on the length of the added barcodes.

Applying scCUT&RUN to cell lines. As a prelude to applying scCUT&RUN to complex tissue, we will apply both single-cell strategies to ENCODE Tier 1 human K562 cells and modENCODE Drosophila S2 cells. We will use antibodies to selected histone modifications (H3K4me1, H3K27ac, H3K27me3 and H3K36me3) and to RNA Polymerase II (CTD-Ser5P and CTD-Ser2P) for both human and Drosophila cells, and also abundant constitutive TFs such as CTCF for human and GAGA factor for Drosophila. K562 and S2 are uniform cell lines, and are extensively characterized for gene expression, chromatin landscapes, and functional mapping of active enhancers. Each antibody has been validated in our bulk CUT&RUN experiments. We anticipate that the efficiency of in situ ligation will determine coverage of features in individual cells, and we will compare single-cell profiles to bulk profiles to determine our cell-by-cell coverage, the optimal sequencing depth required per cell, and the effectiveness of arrayed profiling versus split-pooling strategies. We will take advantage of profiling combinations of epitopes in the single-cell platforms to identify promoter-enhancer-gene combinations. This will involve performing CUT&RUN with single factor antibodies and in pairs, and defining interacting regulatory elements by simultaneity of two epitopes in individual cells.

Although nuclear and chromatin integrity is maintained under the low-salt/high divalent cation concentrations used in our preliminary studies, it is possible that subsequent manipulations will cause damage, but new ends will not be compatible with indexing adapters. The low efficiency of in situ ligation in our preliminary study is attributable to the predominance of primer dimers during blunt-end ligation, and we expect that using modified adapters as proposed will vastly improve efficiency. If efficiency is high, then we will prefer the nanowell strategy, because even with only ~1000 cells, there will be sufficient coverage to identify tens of thousands of regulatory elements in individual cells, and to efficiently cluster cell types. With high coverage, fewer cells will be required, and we anticipate that we could then assay as many as 8 different antibodies or tissue samples on a single chip. However, if ligation efficiency is low, then clustering cell types will require more individual cells, and split-pool barcoding becomes more attractive, as each split-pool round multiplies the number of unique barcodes by 96. For the 20-fold smaller size of the Drosophila genome, the proportionally fewer DNA fragments in each cell will allow us to profile more cells with the same amount of sequencing, favoring split-pool barcoding for Drosophila.

CUT&RUN on intact fly imaginal discs. The efficiency of CUT&RUN allows chromatin profiling in tissues and isolated cell types. With minor modifications, we adapted our cell line protocols to process intact tissues from Drosophila larvae or to process FACS-sorted cells. We dissected larval brains and wing imaginal discs from late 3rd instar larvae (FIG. 59A), permeabilized the unfixed tissue with digitonin, and then lightly coated the intact tissues with ConA beads. These steps enable reagents to be taken up into tissues simply by changing buffers, and all tissue handling is performed in tubes using a magnet for buffer exchanges. We included 2 mM EDTA and 5 mM spermidine to protect chromatin from degradation in blocking, antibody, and pA-MNase tethering steps, and found that tissues and DNA remain intact through the two-day procedure. We estimate that wing imaginal discs from ten larvae provide 4600,000 wing disc cells (more from brains), which yields sufficient material to profile histone modifications and chromatin factors with high data quality. We first profiled H3K27me3 in larval brains and in wing discs to compare Polycomb-repressed regions. A representative region is shown (FIG. 59C). The ANTP-Complex contains many of the segment identity homeobox genes of Drosophila, and these genes are regulated in part by Polycomb repression. The Antennapedia (Antp) gene is silenced in most cells of the larval brain, and is expressed in all cells of the wing imaginal disc. A corresponding change in H3K27me3 patterns is apparent across the Antp gene, which is H3K27-trimethylated in brain samples but mostly unmethylated in wing tissue. The low background outside of the ANTP-Complex and high signals in H3K27-trimethylated regions makes it straightforward to identify regions that differ in chromatin state between tissues. Similarly, we have profiled multiple histone modifications and chromatin factors in tissue samples, including H3K27Ac, H3K27me2, and Polycomb, with similar data quality as in cell culture samples, demonstrating that we can fully characterize chromatin states from small amounts of intact material. This is especially useful for profiling of mutant animals where tissue is limiting.

Intact tissues contain a variety of cell types. We combined FACS isolation with CUT&RUN to profile a subset of cells from wing imaginal discs. We used a characterized enhancer of the vestigial gene to produce GFP in the proliferating pouch of the wing imaginal disc (FIG. 59B), and then dissociated cells using Accutase (Innovative Cell Technologies, Inc), which we found does not degrade glycoproteins on the cell surface. This allowed us to bind cells after FACS sorting to ConA beads, and process cells by our standard bulk CUT&RUN protocol. We recover ~10,000 GFP-positive cells representing 9% of the input material after 20 minutes of FACS, which is sufficient for H3K27me3 profiling, with results similar to intact wing imaginal discs across the genome. The vestigial gene itself is included in an H3K27me3 domain in cell culture and in larval brain samples (FIG. 59D). While H3K27me3 appears reduced in wing imaginal disc samples, this tissue is a mixture of cells with and without vestigial expression. In contrast, FACS-isolated vestigial-expressing cells show low H3K27me3 methylation across the vestigial gene. These results confirm that, with minor modifications to our standard protocol, we can accurately profile cells from intact tissues or from FACS-isolated unfixed cells. As tissues are manipulated magnetically, whole tissue CUT&RUN can be readily performed robotically through adapter ligation and clean-up, followed directly by dissociation and rounds of split-pool barcode-ligation.

scCUT&RUN on primary cells and intact tissues with split-pooling. To develop an scCUT&RUN protocol, we will apply CUT&RUN to two model systems that are extensively characterized at the single-cell level. First, we will profile histone modifications and chromatin factors in human hematopoietic cells, and compare single-cell chromatin profiling to the transcriptional diversity of these cells. Second, we will profile chromatin in the Drosophila testes, where the entire developmental sequence from germline stem cells to post-meiotic sperm is present. The 20-fold smaller genome size of Drosophila compared to human also reduces sequencing costs for this technology development project. These two systems will be used to assess the accuracy of chromatin profiling for cell states, and to develop computational frameworks for clustering single-cell chromatin profiling.

scCUT&RUN on human hematopoietic cells. Pluripotent CD34+ cells from bone marrow differentiates into 10 categories of blood cells, distinguished by surface markers). The transcriptional diversity of these cell types has been extensively characterized in bulk, in FACS-isolated, and in single-cell ensembles. We will use this system to assess how scCUT&RUN profiling of histone modifications accurately recapitulates the diversity in CD34+ cell populations. We obtain FACS-isolated human CD34+ primary hematopoietic cells from bone marrow of healthy individuals. We will perform CUT&RUN and adapter ligation steps in bulk for dispensing into nanowells and for sequential split-pooling steps to index individual cells.

We will profile two modifications of RNAPII (CTD-S5P and CTD-S2P), three histone modifications (H3K27Ac, H3K27me3, and H3K4me1) and two chromatin factors (CTCF and the hematopoietic TF PU.1) in CD34+ cells. Profiles of RNAPII will identify poised and active gene promoters, H3K27Ac and H3K4me1 will report on active promoters and enhancers, and H3K27me3 on Polycomb-repressed chromatin. These profiles will be used to identify the transcriptional status of 1000-2000 cells. Combining all data, 100 million paired-end reads should recapitulate the bulk chromatin landscape in CD34+ cells, and we will compare the depth of these profiles with standard CUT&RUN profiling to assess efficiency. We will then examine fragment coverage at gene promoters in individual barcoded cells. With efficient recovery, 10,000-100,000 independent fragments should cover the features in one cell run. We can process many more cells to exhaustively capture fragments from each CD34+ subtype. Even sparse coverage across many genes is sufficient to cluster and distinguish cell types. We will compare profiles to benchmark the necessary cell numbers and sequencing depth to stringently distinguish between cell types, comparing clusters derived from scCUT&RUN datasets to clusters derived from single-cell ATAC-seq and RNA-seq datasets for the same 10 cell types [33]. H3K27Ac is also abundant at enhancers, and so fragments distant from promoters putatively identify sites.

scCUT&RUN on fly testes. We will use the Drosophila testis as a model system of single-cell CUT&RUN with a solid tissue. Drosophila ovaries and testes are the largest adult organs, and are easily dissected from abdomens. However, ovaries are dominated by hyper-polyploid nurse cells, whereas testes are composed of somatic epithelial cells, somatic cyst cells, and germline cells. This germline population includes all the developmental stages of spermatogenesis, with 6-10 germline stem cells, mitotically proliferating gonial cells, growing primary spermatocytes, meiotic cells, and differentiating spermatids. Thus, single-cell profiling of the testes will allow us to cluster and order the chromatin sequence of germline development. All of these stages are readily distinguished by microscopy of unstained nuclei, and this is one situation where we prefer array-based indexing, because imaging of nanowells will be useful to assign profiles to distinct cell types. We will track both the activation of germline-specific gene expression programs and chromosome-wide changes in regulation. Drosophila spermatogenesis uses testis-specific TBP-associated factors (tTAFs) to broadly activate and regulate alternative gene promoters starting in spermatocyte stages. We will use available antibodies to profile TAF5 (a somatic and early germline TFIID component [36]), its primary spermatocyte variant Cannonball (Can) [37], and H3K27Ac and H3K27me3 histone modifications. TAF5 and Cannonball profiling will be used to inform single-cell clustering from histone modification profiling, since binding sites of these tTAFs at alternative promoters will be unique between somatic and early germline cells compared to late germline cells. Finally, a small collection of genes are known to be expressed only in post-meiotic cells [38], and reads at these genes will be used to cluster barcodes from these cells.

There are two major chromosome-wide remodeling events during spermatogenesis. First, in growing primary sprmatocytes the megabase-sized Y chromosome genes are activated, and there is some evidence that the entire X chromosome is precociously inactivated. Second, most core histones are stripped from chromatin in differentiating spermatids, and replaced with protamines and sperm-specific non-histone proteins. In mammalian spermatogenesis, both X chromosome inactivation and histone/protamine replacement involves chromatin remodeling by the H3.3 and H2A.Z histone variants, so we will profile these conserved variants in Drosophila testes. Our preliminary cytological characterization shows that the Drosophila H2A.Z homolog is moderately enriched on the X chromosome in primary spermatocytes, consistent with the idea that precocious X-inactivation may involve this variant in Drosophila as well (data not shown). It is not known in any system whether histone variants become enriched throughout the X chromosome or at specific sites or genes during germline chromosomal inactivation; single-cell chromatin profiling will address this.

Figures 60A, 60B:
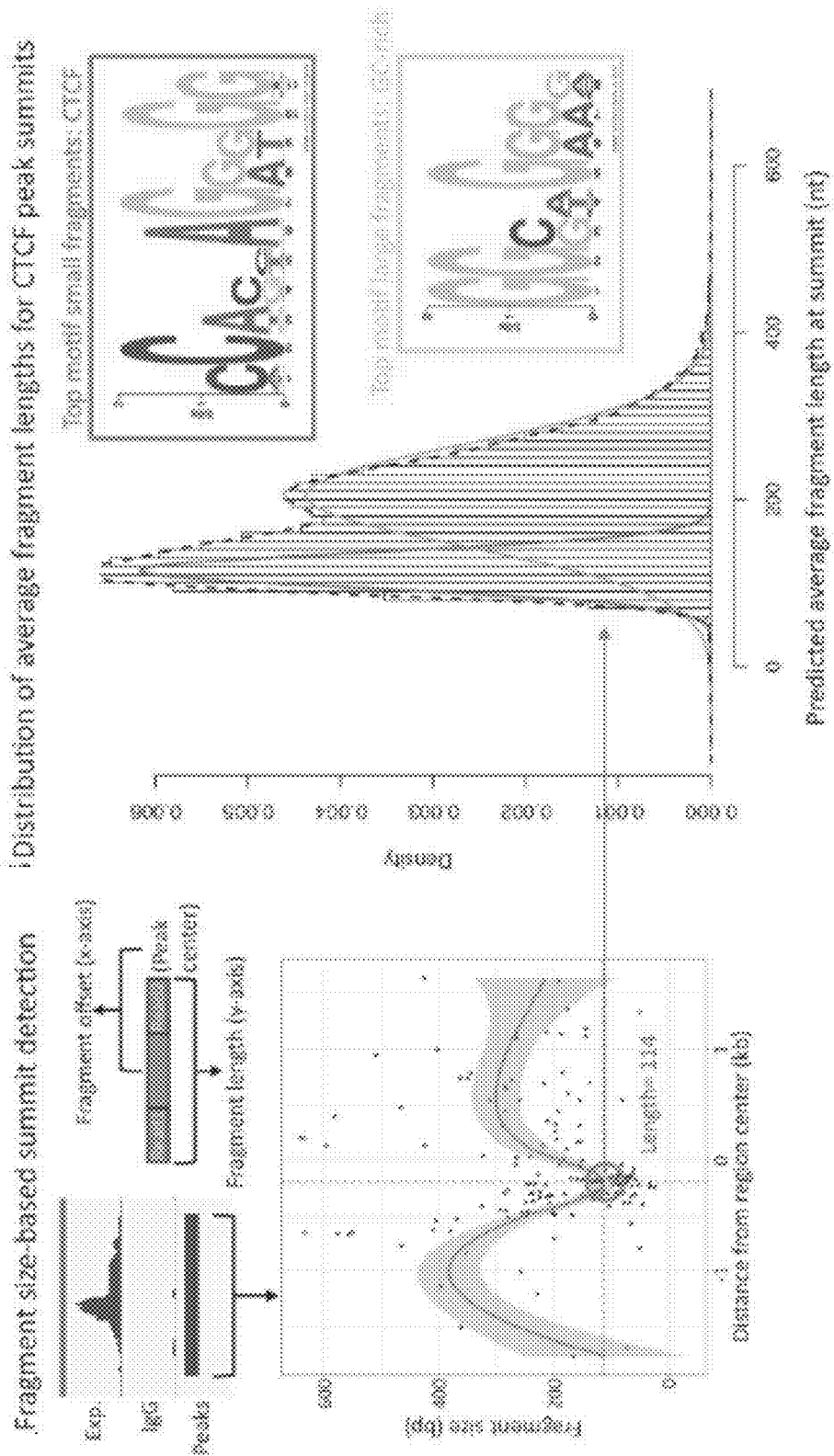
FIGS. 60A and 60B show size-based peak summit detection in CUT&RUN data.

CUT&RUN fragment length as the basis for peak-calling. Currently, analysis of enrichment of epigenome data at specific loci typically involves inference based on reported roles for specific targets (e.g., H3K27me3 in silencing or H3K4me3 in active gene expression), or an analysis of overlap of multiple profiles at regions of interest. This approach, which has changed very little in more than a decade of epigenome data analysis, requires complex methods for target refinement and parameter optimization (e.g., [14]) that are difficult to implement even on bulk populations. Therefore, we sought to leverage the unique information yielded from CUT&RUN to improve upon the standard analysis paradigm. In addition to generating genome-wide epigenome profiles in the style of ChIP-seq, CUT&RUN preserves information on sequenced fragment lengths at base-pair resolution, similar to MNase-seq, but for specific target epitopes. Fragment length can elucidate the nature of protein binding on a single molecule level; for instance, TFs protect small footprints and often leave behind short fragments of fewer than 80 bp, whereas nucleosomes protect roughly 150 bp of DNA in its two wraps. Our lab has used fragment length information from MNase-seq data in the past to infer TF binding at distal regulatory elements, and the presence of partially disrupted nucleosomes at sites of active transcription [20, 39]. Inspired by this, we developed a computational method that uses fragment size to predict sites of regulatory activity within CUT&RUN peaks at base-pair resolution. We used LOESS regression of the distribution of fragment offsets from the peak center vs. fragment lengths to identify single base-pairs within the peak at which the predicted fragment size is minimized, similar to our V-plot method [39], indicating the highest likelihood of binding or regulatory activity (FIG. 60A). When we applied our method to CUT&RUN data from an experiment targeting CTCF in K562 cells, we detected summits that corresponded to two major populations: a small fragment population that was highly enriched for overlap with the CTCF binding motif, and a larger fragment population that overlapped with a GC-rich sequences that typically favor nucleosomes [40] (FIG. 60B). These results show that the summits of small DNA fragments more precisely define CTCF binding sites, distinguishing them from flanking nucleosomes within cleaved regions. Thus, stratifying fragment sizes is an effective way to identify factor-bound sites with high resolution.

Using CUT&RUN Fragment Length to Identify Regulatory Elements.

Comparison of peak calling algorithms on CUT&RUN data. Existing analysis software packages for processing epigenome data were written specifically with ChIP-seq in mind, and therefore are designed to extract signal from high noise data. These methods typically estimate background read counts across the genome and then use higher signal as the sole indicator of direct binding. Because CUT&RUN has extremely low background, these approaches are not well-suited for peak-calling. But CUT&RUN data contain DNA fragment size information that ChIP-seq lacks, because TF-bound sites typically appear as short DNA fragments and flanking nucleosomes that are also released in CUT&RUN [16] appear as ~150 bp fragments. We will directly compare common peak-calling algorithms and our fragment-size-based algorithm to determine performance and develop an effective algorithm that uses fragment size information. We will test the MACS2 and SPP algorithms, the two major peak-calling packages used as standards for the ENCODE project. We will first use CUT&RUN data for CTCF from bulk experiments. CTCF has a well-defined DNA binding motif, and this provides a "gold standard" to test the recall and resolution of each algorithm. To determine the sensitivity of each algorithm, we will compare the number of peaks detected that overlap CTCF motifs by each algorithm. To determine resolution, we will construct Cumulative Distribution Function (CDF) curves for the distance to a CTCF motif to each peak summit. Our preliminary studies described above with fragment size-based binding site detection make us confident that our method could outperform current peak-callers on CUT&RUN data.

Fragment length-based peak-calling with scCUT&RUN data. Single-cell sequencing technologies can convey important information about intra-sample heterogeneity. This is achieved via dimensionality reduction strategies such as t-Distributed Stochastic Neighbor Embedding (tSNE) [31] and Uniform Manifold Approximation and Projection (UMAP) [41]. These clustering methods use many digital dimensions (e.g. gene expression values from single cells) to distinguish cell conditions. Developmental trajectories or transition states between cell types can be inferred by pseudotemporal organization of clusters. Such methods are robust using scRNA-seq data, which provides thousands of dimensions, so that even sparse sampling of dimensions from hundreds of individual cells is sufficient to drive clustering. However, while scRNA-seq uses read counts as a quantitative measure of expression, datasets are dominated by abundant transcripts and limited by high noise, which requires elaborate methods to eliminate PCR amplification artifacts. More recently, DNA accessibility measured in single cells by scATAC-seq, has been used to classify CD34+ lymphoid cells [42]. In this method putative regulatory elements can be identified, but what chromatin factor binds at each specific site is unknown, and scATAC-seq uses DNA motifs to guess factors at sites. Direct interrogation of factor binding at regulatory elements would create trajectories of cell types based on changes in regulatory elements and in binding of determinative TFs, to understand how cell types are controlled. However, ChIP-based profiling has lacked the sensitivity for single cells. Moreover, because of the low copy number of DNA molecules in the cell (2 copies in a G1-phase diploid cell), any single-cell epigenome profiling technique is constrained by a binary value for each dimension.

We propose two improvements to single-cell epigenome profiling analysis. We will use 1) the sensitivity of CUT&RUN, and 2) fragment size information to maximize the number of sites called as informative dimensions for single cell analysis. Hainer et al. [23] recently showed that scCUT&RUN sensitivity is an order of magnitude higher than that of scATAC-seq, implying that CUT&RUN will provide superior input for dimensionality reduction strategies. As DNA fragment size in CUT&RUN profiling is informative of direct TF binding, fragment size presents an ideal metric to reduce noise in single-cell chromatin profiling. We will first define binding sites from bulk cell populations, and then represent each site in individual cells as the DNA fragment size at that site. These values will be used as input for dimensional reduction strategies. Principal component analysis (PCA) has been implemented for scATAC-seq data, and we will first use PCA with scCUT&RUN datasets generated from lymphoid cells for H3K27Ac and H3K27me3 modifications, and the PU.1 TF to define key sites that capture the most variation in single cell data. We will then use tSNE or UMAP algorithms with scCUT&RUN data or with PCA-defined subsets. This will test the optimal number of dimensions to use for the detection of known lymphoid subpopulations. We will then compare how considering DNA fragment sizes compares to pooling all fragments. We will conduct similar analyses of single cells from Drosophila testes, where the developmental trajectory of germline cells from stem cells to differentiating sperm is well-defined, including the determinative transcription factors. We expect to be able to order the activation of stage-specific enhancers and changes in gene expression. These studies are releant because they will allow us to evaluate how factor-specific mapping performs compares to the more general mapping of histone modifications (by scCUT&RUN), DNA accessibility (by scATAC-seq), and gene expression (by scRNA-seq).

Defining enhancers and gene expression in single cells from scCUT&RUN. Binding and progression of RNA polymerases through chromatin generates dynamic nucleosome intermediates in vivo. We previously showed that DNA fragments of characteristic subnucleosomal lengths are found at the promoters of active genes [20]. Subnucleosomal fragments appear after MNase cleavage and after CUT&RUN to H3K27Ac modifications. These subnucleosomal fragments can be used to report on gene expression, even in cell-free DNA found in patient blood serum, and is thus useful for defining cell type-of-origin in situations where mRNA is difficult or impossible to obtain [20]. Importantly, subnucleosomal fragments are not limited to transcriptionally active promoters, but are characteristic of CTCF binding sites where TF binding competes with nucleosomes. This provides a unique strategy to identify enhancers, where we expect that binding of any TF will compete with nucleosomes, generating a distinctive subnucleosomal fragment. We will first use CUT&RUN data for H3K27Ac in human K562 and fly S2 cells generated for; CUT&RUN for H3K27Ac effectively enriches data for active regulatory elements in a genome. In training experiments, we will derive nucleosome positions in a population of cells, and examine the frequency of subnucleosomal fragments using our fragment-length peak-caller algorithm to define potential factor binding sites. We will test the performance of these calls using the known repertoire of gene expression and enhancers in these cell lines, defined by RNA-seq and STARR-seq, respectively.

The advantage of this strategy is that a single read of subnucleosomal length should be uniquely diagnostic of an active regulatory element, and thus provides a way to interrogate enhancers in individual cells. We will annotate lymphoid cell types with subnucleosomal fragments at gene promoters, and for fragments more distant from promoters, providing a cell-type-specific map of promoters and regulatory elements. Finally, we aim to link promoters with enhancers in individual cells to begin to infer regulatory element usage. We will do this by annotating subnucleosomal fragments throughout the genome of individual cells after scCUT&RUN. We will also evaluate increasing the coverage of enhancers and promoters by using antibodies to histone modifications in the same experiment. For example, tethering pA-MNase with both an antibody to H3K27Ac and to H3K4me1 histone modifications can capture enhancers withboth and with either histone modification (we can deconvolve which sites are likely due to which modification from single-antibody experiments). The goal of these experiments is to ask what pairs of sites are engaged at the same time in individual cells, an inference that is currently impossible by any technology. If this approach is promising, a particularly interesting pair will be to simultaneously map active enhancers with an antibody to H3K4me1 and engaged promoters with an antibody to RNAPII-CTD-S5P. With sufficient coverage, this combination allows assessment if multiple active enhancers for a gene are bound when a target promoter is engaged with RNAPII, or if enhancer-promoter interactions are more dynamic.

References for Example 8 (Each of which is Incorporated by Reference in its Entirety)

1. Liu, N., Hargreaves, V. V., Zhu, Q., Kurland, J. V., Hong, J., Kim, W., Sher, F., Macias-Trevino, C., Rogers, J. M., Kurita, R., et al. (2018). Direct Promoter Repression by BCL11A Controls the Fetal to Adult Hemoglobin Switch. Cell 173, 430-442 e417.
2. Skene, P. J., Henikoff, J. G., and Henikoff, S. (2018). Targeted in situ genome-wide profiling with high efficiency for low cell numbers. Nat Protoc 13, 1006-1019.
3. Solomon, M. J., and Varshavsky, A. (1985). Formaldehyde-mediated DNA-protein crosslinking: a probe for in vivo chromatin structures. Proc. Natl. Acad. Sci. U.S.A 82, 6470-6474.
4. Rhee, H. S., and Pugh, B. F. (2011). Comprehensive genome-wide protein-DNA interactions detected at single-nucleotide resolution. Cell 147, 1408-1419.
5. Skene, P. J., and Henikoff, S. (2015). A simple method for generating high-resolution maps of genome wide protein binding. eLife 4, e09225.
6. Zentner, G. E., and Henikoff, S. (2014). High-resolution digital profiling of the epigenome. Nat. Rev. Genet. 15, 814-827.
7. He, Q., Johnston, J., and Zeitlinger, J. (2015). ChIP-nexus enables improved detection of in vivo transcription factor binding footprints. Nature biotechnology 33, 395-401.
8. Teytelman, L., Thurtle, D. M., Rine, J., and van Oudenaarden, A. (2013). Highly expressed loci are vulnerable to misleading ChIP localization of multiple unrelated proteins. Proc. Natl. Acad. Sci. U.S.A 110, 18602-18607.
9. Park, D., Lee, Y., Bhupindersingh, G., and Iyer, V. R. (2013). Widespread misinterpretable ChIP-seg bias in yeast. PLoS One 8, e83506.

10. Jain, D., Baldi, S., Zabel, A., Straub, T., and Becker, P. B. (2015). Active promoters give rise to false positive 'Phantom Peaks' in ChIP-seq experiments. Nucleic Acids Res 43, 6959-6968.
11. Baranello, L., Kouzine, F., Sanford, S., and Levens, D. (2016). ChIP bias as a function of cross-linking time. Chromosome Res 24, 175-181.
12. Meyer, C. A., and Liu, X. S. (2014). Identifying and mitigating bias in next-generation sequencing methods for chromatin biology. Nat Rev Genet 15, 709-721.
13. Venkataraman, A., Yang, K., Irizarry, J., Mackiewicz, M., Mita, P., Kuang, Z., Xue, L., Ghosh, D., Liu, S., Ramos, P., et al. (2018). A toolbox of immunoprecipitation-grade monoclonal antibodies to human transcription factors. Nat Methods.
14. Kasinathan, S., Orsi, G. A., Zentner, G. E., Ahmad, K., and Henikoff, S. (2014). High-resolution mapping of transcription factor binding sites on native chromatin. Nature Methods 11, 203-209.
15. Zentner, G. E., Kasinathan, S., Xin, B., Rohs, R., and Henikoff, S. (2015). ChEC-seq kinetics discriminate transcription factor binding sites by DNA sequence and shape in vivo. Nat Commun 6, 8733.
16. Skene, P. J., and Henikoff, S. (2017). An efficient targeted nuclease strategy for high-resolution mapping of DNA binding sites. eLife 6, e21856.
17. Schmid, M., Durussel, T., and Laemmli, U.K. (2004). ChIC and ChEC; genomic mapping of chromatin proteins. Mol. Cell 16, 147-157.
18. Thakur, J., and Henikoff, S. (2018). Unexpected conformational variations of the human centromeric chromatin complex. Genes Dev. 32, 20-25.
19. Kasinathan, S., and Henikoff, S. (2018). Non-B-Form DNA Is Enriched at Centromeres. Mol. Biol. Evol.
20. 35, 949-962.
21. Ramachandran, S., Ahmad, K., and Henikoff, S. (2017). Transcription and Remodeling Produce Asymmetrically Unwrapped Nucleosomal Intermediates. Mol. Cell 68, 1038-1053 e1034.
22. Chereji, R. V., Ocampo, J., and Clark, D. J. (2017). MNase-Sensitive Complexes in Yeast: Nucleosomes and Non-histone Barriers. Mol. Cell 65, 565-577 e563.
23. Kubik, S., Bruzzone, M. J., Albert, B., and Shore, D. (2017). A Reply to "MNase-Sensitive Complexes in Yeast: Nucleosomes and Non-histone Barriers," by Chereji et al. Mol. Cell 65, 578-580.
24. Hainer, S. J., Boskovic, A., Rando, O. J., and Fazzio, T. G. (2018). Profiling of pluripotency factors in individual stem cells and early embryos. bioRxiv.
25. van Steensel, B., and Henikoff, S. (2000). Identification of in vivo DNA targets of chromatin proteins using tethered Dam methyltransferase. Nat. Biotechnol. 18, 424-428.
26. van Steensel, B., Delrow, J., and Henikoff, S. (2001). Chromatin profiling using targeted DNA adenine methyltransferase. Nat. Genet. 27, 304-308.
27. Skene, P. J., and Henikoff, S. (2017). CUT&RUN: Targeted in situ genome-wide profiling with high efficiency for low cell numbers. biorxiv biorxiv.org/content/early/2017/09/24/193219.
28. Roth, T. L., Puig-Saus, C., Yu, R., Shifrut, E., Carnevale, J., Hiatt, J., Saco, J., Li, H., Li, J., Tobin, V., et al. (2017). Reprogramming human T cell function and specificity with non-viral genome targeting. bioRxiv.
29. Rosenberg, A. B., Roco, C. M., Muscat, R. A., Kuchina, A., Sample, P., Yao, Z., Graybuck, L. T., Peeler, D. J., Mukherjee, S., Chen, W., et al. (2018). Single-cell profiling of the developing mouse brain and spinal cord with split-pool barcoding. Science 360, 176-182.
30. Goldstein, L. D., Chen, Y. J., Dunne, J., Mir, A., Hubschle, H., Guillory, J., Yuan, W., Zhang, J., Stinson, J., Jaiswal, B., et al. (2017). Massively parallel nanowell-based single-cell gene expression profiling. BMC Genomics 18, 519.
31. Chen, K., Hu, Z., Xia, Z., Zhao, D., Li, W., and Tyler, J. K. (2015). The Overlooked Fact: Fundamental Need for Spike-In Control for Virtually All Genome-Wide Analyses. Mol. Cell. Biol. 36, 662-667.
32. Cao, J., Packer, J. S., Ramani, V., Cusanovich, D. A., Huynh, C., Daza, R., Qiu, X., Lee, C., Furlan, S. N., Steemers, F. J., et al. (2017). Comprehensive single-cell transcriptional profiling of a multicellular organism. Science 357, 661-667.
33. de Frutos, M., Raspaud, E., Leforestier, A., and Livolant, F. (2001). Aggregation of nucleosomes by divalent cations. Biophys. J. 81, 1127-1132.
34. Mezger, A., Klemm, S., Mann, I., Brower, K., Mir, A., Bostick, M., Farmer, A., Fordyce, P., Linnarsson, S., and Greenleaf, W. (2018). High-throughput chromatin accessibility profiling at single-cell resolution. bioRxiv, doi: 10.1101/310284.
35. Svensson, V., Vento-Tormo, R., and Teichmann, S.A. (2018). Exponential scaling of single-cell RNA-seq in the past decade. Nat Protoc 13, 599-604.
36. Zheng, G. X., Terry, J. M., Belgrader, P., Ryvkin, P., Bent, Z. W., Wilson, R., Ziraldo, S. B., Wheeler, T. D., McDermott, G. P., Zhu, J., et al. (2017). Massively parallel digital transcriptional profiling of single cells. Nat Commun 8, 14049.
37. Wright, K. J., Marr, M. T., 2nd, and Tjian, R. (2006). TAF4 nucleates a core subcomplex of TFIID and mediates activated transcription from a TATA-less promoter. Proc. Natl. Acad. Sci. U.S.A 103, 12347-12352.
38. Chen, X., Hiller, M., Sancak, Y., and Fuller, M. T. (2005). Tissue-specific TAFs counteract Polycomb to turn on terminal differentiation. Science 310, 869-872.
39. Barreau, C., Benson, E., Gudmannsdottir, E., Newton, F., and White-Cooper, H. (2008). Post-meiotic transcription in Drosophila testes. Development 135, 1897-1902.
40. Henikoff, J. G., Belsky, J. A., Krassovsky, K., Macalpine, D. M., and Henikoff, S. (2011). Epigenome characterization at single base-pair resolution. Proc. Natl. Acad. Sci. U.S.A 108, 18318-18323.
41. Kaplan, N., Moore, I. K., Fondufe-Mittendorf, Y., Gossett, A. J., Tillo, D., Field, Y., LeProust, E. M., Hughes, T. R., Lieb, J. D., Widom, J., et al. (2009). The DNA-encoded nucleosome organization of a eukaryotic genome. Nature 458, 362-366.
42. Becht, E., Dutertre, C.-A., Kwok, I. W. H., Ng, L. G., Ginhoux, F., and Newell, E. W. (2018). Evaluation of UMAP as an alternative to t-SNE for single-cell data. biorxiv, doi.org/10.1101/298430.
43. Buenrostro, J.D., Corces, M. R., Lareau, C.A., Wu, B., Schep, A. N., Aryee, M. J., Majeti, R., Chang, H. Y., and Greenleaf, W. J. (2018). Integrated Single-Cell Analysis Maps the Continuous Regulatory Landscape of Human Hematopoietic Differentiation. Cell.
44. Regev, A., Teichmann, S. A., Lander, E. S., Amit, I., Benoist, C., Birney, E., Bodenmiller, B., Campbell, P., Carninci, P., Clatworthy, M., et al. (2017). The Human Cell Atlas. eLife 6.
45. Buenrostro, J. D., Giresi, P. G., Zaba, L. C., Chang, H. Y., and Greenleaf, W. J. (2013). Transposition of native chromatin for fast and sensitive epigenomic profiling of open chromatin, DNA-binding proteins and nucleosome position. Nat Methods 10, 1213-1218.
46. Corces, M. R., Buenrostro, J. D., Wu, B., Greenside, P. G., Chan, S. M., Koenig, J. L., Snyder, M. P., Pritchard, J. K., Kundaje, A., Greenleaf, W. J., et al. (2016). Lineage-specific and single-cell chromatin accessibility charts human hematopoiesis and leukemia evolution. Nat. Genet. 48, 1193-1203.
47. Cusanovich, D. A., Daza, R., Adey, A., Pliner, H. A., Christiansen, L., Gunderson, K. L., Steemers, F. J., Trapnell, C., and Shendure, J. (2015). Epigenetics. Multiplex single-cell profiling of chromatin accessibility by combinatorial cellular indexing. Science 348, 910-914.
48. Kester, L., and van Oudenaarden, A. (2018). Single-Cell Transcriptomics Meets Lineage Tracing. Cell Stem Cell.
49. Henikoff, S., Ahmad, K., and Malik, H. S. (2001). The centromere paradox: Stable inheritance with rapidly evolving DNA. Science 293, 1098-1102.

Example 9

An Improved CUT&RUN Vector

Figure 61:
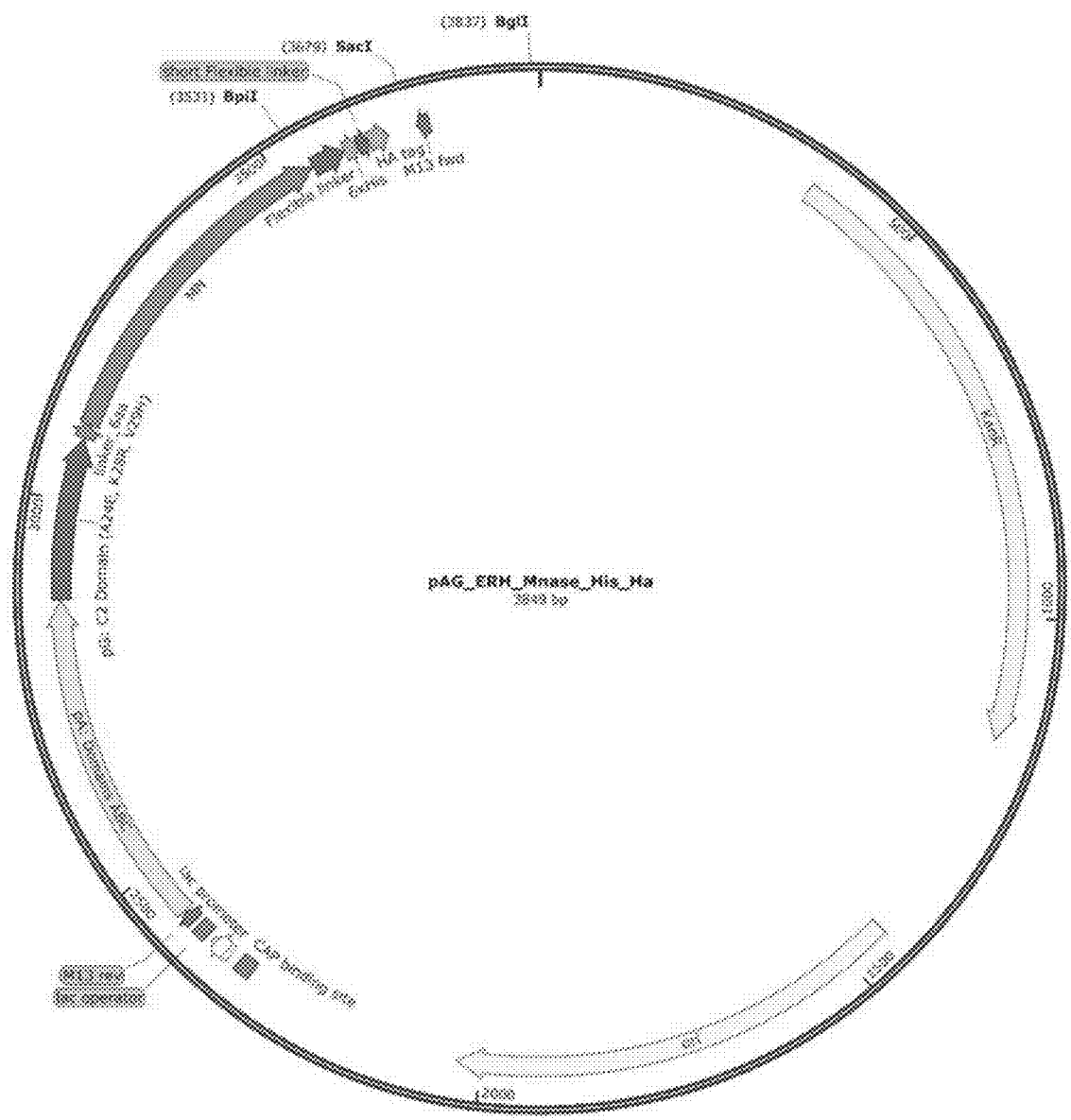
FIG. 61 is the plasmid map for an improved vector for CUT&RUN.

Until recently, all pA-MNase that we used for CUT&RUN as disclosed herein was derived from the original pK19-pA-MN vector (Schmid et al., 2004). However, the fusion protein produced by this construct requires purification from lysates of E. coli overexpressing cells using an IgG column, and elution with low pH followed by neutralization has resulted in variations between batches. To improve the purification protocol, we added a 6-His Tag in pK19-pA-MN (Bornhorst and Falke, 2000). This allows for simple and gentle purification on a nickel resin column (see FIG. 61). In addition, we found that the commercial 6-His-cobalt resin kit also provides very clean and highly active enzyme (Pierce™ Pull-Down PolyHis Protein:Protein Interaction Kit, cat #21277).

While the 6-His tag can in principle be used for chromatin pull-down from a CUT&RUN supernatant, in practice this is complicated by the requirement for a chelating agent to release the 6-His Tag from the resin. Therefore, we also added an HA (hemagglutinin) tag that can be applied to CUT&RUN.ChIP (Brahma and Henikoff, 2018), whereby the CUT&RUN supernatant is treated with excess Tag-specific peptide to release the antibody, allowing for binding by a second antibody for Chromatin Immunoprecipitation. With an HA tag on the MNase fusion construct, we increase the versatility of the method by allowing CUT&RUN.ChIP to be performed with any antibody, and not just antibodies against an epitope tag such as HA or 3×FLAG.

Protein A binds only weakly to mouse IgG, and so for mouse antibodies, Protein G is generally used. To further improve the versatility of the MNase fusion protein, we added a single Protein G domain adjacent to the Protein A domain in pK19-pA-MN. This has resulted in a fusion protein that binds strongly to most all commercial antibodies without requiring a secondary antibody (Eliasson et al., 1988). In addition, we mutated 3 residues in the Protein G coding sequence to further increase binding for rabbit antibodies (Jha et al., 2014).

The map of the resulting pA/G-MNase construct is shown in the Figure. We have found that for ordinary CUT&RUN applications it behaves very similarly to pA-MNase, but is more easily purified and is more versatile, for example allowing us to perform CUT&RUN without requiring a secondary antibody for mouse primary monoclonal antibodies.

References for Example 9 (Each of which is Incorporated by Reference in its Entirety)

Bornhorst, J. A., and Falke, J. J. (2000). Purification of proteins using polyhistidine affinity tags. Methods Enzymol 326, 245-254.
Brahma, S., and Henikoff, S. (2018). RSC-associated Subnucleosomes Define MNase-sensitive Promoters in Yeast. In revision.
Eliasson, M., Olsson, A., Palmcrantz, E., Wiberg, K., Inganas, M., Guss, B., Lindberg, M., and Uhlen, M. (1988). Chimeric IgG-binding receptors engineered from staphylococcal protein A and streptococcal protein G. J Biol Chem 263, 4323-4327.
Jha, R. K., Gaiotto, T., Bradbury, A. R., and Strauss, C. E. (2014). An improved Protein G with higher affinity for human/rabbit IgG Fc domains exploiting a computationally designed polar network. Protein engineering, design & selection: PEDS 27, 127-134.
Schmid, M., Durussel, T., and Laemmli, U. K. (2004). ChIC and ChEC; genomic mapping of chromatin proteins. Mol Cell 16, 147-157.

Example 10

Rapid Targeted Epigenome Profiling by ImmunoTethered Insertion Sequencing

Introduction

The advent of massively parallel sequencing and the dramatic reduction in cost per base quickly fueled a genomics revolution, however, the full promise of epigenomic profiling has lagged owing to limitations in methodologies used for mapping chromatin fragments to the genome[1]. Chromatin immunoprecipitation with sequencing (ChIP-seq) is currently the most widely used method for chromatin profiling[2]. However ChIP-seq is limited in resolution by the few hundred base-pair size of sonicated fragments, although variations such as ChIP-exo[3], MNase-X-ChIP-seq[4] and ORGANIC[5] provide base-pair resolution to take full advantage of the sequencing platform. Nevertheless, issues remain with cross-linking, epitope masking and artifacts for cross-linking methods and low yields require large numbers of cells[2,6-9]. Alternatives to ChIP have also advanced, especially enzyme-tethering methods including DamID[10], ChEC-seq[7] and CUT&RUN[11,12], where a specific protein of interest is targeted in situ then profiled genome-wide. For example, CUT&RUN, which is based on Laemmli's Chromatin ImmunoCleavage (ChIC) strategy[13], targets a chromatin protein or modification of interest by successive addition of a specific antibody and a Protein A/Micrococcal Nuclease (pA-MNase) fusion protein to permeabilized cells without cross-linking[11]. MNase is activated by addition of calcium, and fragments are released into the supernatant for extraction of DNA, library preparation and paired-end sequencing. CUT&RUN provides base-pair resolution of specific chromatin components with background levels much lower than ChIP-seq, dramatically reducing the cost of genome-wide profiling. Although CUT&RUN can be applied to 100-1000 cells without significant loss of data quality[12,14], high-throughput single-cell applications are complicated by the need to separate the supernatant containing the targeted fragments from the cells containing the rest of the genome. Furthermore, the easy workflow afforded by immobilizing cells on paramagnetic beads must be followed by DNA sequencing library preparation, greatly increasing the time, cost and effort of the overall procedure.

Here we overcome the limitations of ChIP-seq and CUT&RUN by fusing the hyperactive Tn5 transposase[15] to Protein A and substituting addition of pA-MN by Protein A/Tn5 complex loaded with Illumina-compatible Mosaic End oligonucleotides. Activation of Tn5 with $Mg^{++}$ results in antibody-targeted tagmentation, ready for PCR amplification for both bulk and single-cell applications. Beginning with live cells, our single-tube ImmunoTethered Insertion sequencing (ITIS) protocol provides amplified sequence-ready libraries in a single day.

Methods

Materials

Reagents

Cell suspension. We have used human K562 cells.

Concanavalin-coated magnetic beads (Bangs Laboratories, ca. no. BP531)

Antibody to an epitope of interest. For example, rabbit α-CTCF polyclonal antibody (Millipore 07-729) for mapping 1D and 3D interactions by CUT&RUN Positive control antibody to an abundant epitope, e.g. α-H3K27me3 rabbit monoclonal antibody (Cell Signaling Technology, cat. no. 9733)

Secondary antibody, e.g. guinea pig α-rabbit antibody

5% Digitonin (EMD Millipore, cat. no. 300410)

Protein A-Tn5 (pA-Tn5) fusion protein Store at −20° C.

Mosaic End double-stranded oligonucleotides with Illumina-compatible overhangs (Sequence information was derived from ref. [16], ordered through Eurofins, 100 μM in TE buffer)

```
Mosaic end_reverse
                                  (SEQ ID NO: 2)
[PHO]CTGTCTCTTATACACATCT Mosaic end_Adapter A
                                  ((SEQ ID NO: 3)
TCGTCGGCAGCGTCAGATGTGTATAAGAGACAG Mosaic end_Adapter B
                                  (SEQ ID NO: 4)
GTCTCGTGGGCTCGGAGATGTGTATAAGAGACAG
```

Distilled, deionized or RNAse-free $H_2O$ ($dH_2O$ e.g., Promega, cat. no. P1197)

1 M Manganese Chloride ($MnCl_2$; Sigma-Aldrich, cat. no. 203734)

1 M Calcium Chloride ($CaCl_2$; Fisher, cat. no. BP510)

1 M Potassium Chloride (KCl; Sigma-Aldrich, cat. no. P3911)

1 M Magnesium Chloride ($MgCl_2$)

1 M Hydroxyethyl piperazineethanesulfonic acid pH 7.5 (HEPES ($Na^+$); Sigma-Aldrich, cat. no. H3375)

1 M Hydroxyethyl piperazineethanesulfonic acid pH 7.9 (HEPES ($K^+$); Sigma-Aldrich, cat. no. H3375)

5 M Sodium chloride (NaCl; Sigma-Aldrich, cat. no. 55150-1L)

0.5 M Ethylenediaminetetraacetic acid (EDTA; Research Organics, cat. no. 3002E)

2 M Spermidine (Sigma-Aldrich, cat. no. S2501)

Roche Complete Protease Inhibitor EDTA-Free tablets (Sigma-Aldrich, cat. no. 5056489001)

2 mg/ml Glycogen (1:10 dilution of Sigma-Aldrich, cat. no. 10930193001)

RNase A, DNase and protease-free (10 mg/ml; Thermo Fisher Scientific, cat. no. EN0531)

10% Sodium dodecyl sulfate (SDS; Sigma-Aldrich, cat. no. L4509)

Proteinase K (Thermo Fisher Scientific, cat. no. E00492)

Agencourt AMPure XP paramagnetic beads (Beckman Coulter, cat. no. A63880)

1 M Tris-HCl pH 8.0

Ethanol (DeconLabs, cat. no. 2716)

NEBNext HiFi 2×PCR Master mix

PCR primers (Sequences of custom PCR primers with unique indexes were derived from refs. [17] and [18])

Equipment

Centrifuge Eppendorf 5810, swinging bucket

Centrifuge Eppendorf 5424, fixed angle rotor

Centrifuge Eppendorf 5415R, refrigerated fixed angle rotor

Macsimag magnetic separator (Miltenyi, cat. no. 130-092-168), which allows clean withdrawal of the liquid from the bottom of 1.7 and 2 ml microfuge tubes.

Vortex mixer (e.g., VWR Vortex Genie)

Micro-centrifuge (e.g., VWR Model V)

1.5-ml microcentrifuge tubes (Genesee, cat. no. 22-282)

2-ml microcentrifuge tubes (Axygen, cat. no. MCT-200-C)

Tube rotator (Labquake, Thermo Fisher)

Heater block with wells for 1.5-ml microcentrifuge tubes

Water baths (set to 37° C., 55° C. and 70° C.)

MaXtract phase-lock microcentrifuge tubes (Qiagen, cat. no. 139046)

Capillary electrophoresis instrument (e.g. Agilent Tapestation 4200)

Qubit Fluorometer (Life Technologies, cat. no. Q33216)

Reagent Setup

5% Digitonin Dissolve Digitonin powder (Calbiochem) in DMSO to 5% (w/v).

Binding buffer Mix 400 μL 1M HEPES-KOH pH 7.9, 200 μL 1M KCl, 20 μL 1M $CaCl_2$ and 20 μL 1M $MnCl_2$, and bring the final volume to 20 ml with $dH_2O$. Store the buffer at 4° C. for 6 months.

Concanavalin A-coated beads Gently resuspend and withdraw enough of the slurry such that there will be 10 μL for each final sample and/or digestion time point. Transfer into 1.5 ml Binding buffer in a 2 ml tube. Place the tube on a magnet stand to clear (30 s to 2 min). Withdraw the liquid, and remove from the magnet stand. Add 1.5 ml Binding buffer, mix by inversion or gentle pipetting, remove liquid from the cap and side with a quick pulse on a microcentrifuge. Resuspend in a volume of Binding buffer equal to the volume of ConA bead slurry (10 μL per sample).

Tn5-adapter complex: Anneal each of Mosaic end-adapter A (ME-A) and Mosaic end-adapter B (ME-B) oligonucleotides with Mosaic end-reverse oligonucleotides. Mix 16 ul of 100 uM equimolar mixture of preannealed ME-A and ME-B oligonucleotides with 100 ul of 5.5 uM protein A-Tn5 fusion protein. Incubate the mixture on a rotating platform for 1 hour at room temperature and then store at −20° C.

Wash buffer Mix 1 ml 1 M HEPES pH 7.5, 1.5 ml 5 M NaCl, 12.5 μL 2 M Spermidine, bring the final volume to 50 ml with $dH_2O$, and add 1 Roche Complete Protease Inhibitor EDTA-Free tablet. Store the buffer at 4° C. for up to 1 week.

Dig-wash buffer Mix 400 μL 5% Digitonin with 40 ml Wash buffer. Store the buffer at 4° C. for up to 1 day.

Antibody buffer Mix 8 μL 0.5 M EDTA with 2 ml Dig-wash buffer and place on ice until use.

Dig-med buffer Mix 20 ml Dig-wash buffer with 600 μL 5 M NaCl. Store the buffer at 4° C. for up to 1 day.

Tagmentation buffer Mix 20 µL 1 M MgCl$_2$ with 2 ml Dig-med buffer and place on ice until use.

Procedure

Cell Permeabilization and Primary Antibody Incubation

TIMING 1.5 hr-several days

1) Harvest fresh culture(s) at room temperature and count cells. The same protocol can be used for up to 500,000 mammalian cells per sample.

PAUSE POINT: If necessary, cells can be cryopreserved in 10% DMSO using a Mr. Frosty isopropyl alcohol chamber. We do not recommend flash freezing, as this can cause background DNA breakage that may impact final data quality.

2) Centrifuge 3 min 600×g at room temperature and withdraw liquid.
3) Resuspend in 1.5 ml room temperature Wash buffer by gently pipetting and transfer if necessary to a 2 ml tube.
4) Centrifuge 3 min 600×g at room temperature and withdraw liquid.
5) Repeat steps 3 and 4.
6) Place on vortex set to low (~1100 rpm) and resuspend in 1 ml cold antibody buffer.
7) Divide cell slurry into 100 µL aliquots in 1.5-ml tubes, one for each antibody to be used.
8) Add 1-2 µL antibody.
9) Rotate 1-2 hr at room temperature or up to several days at 4° C.

Bind Secondary Antibody

TIMING 1 hr

10) Place each tube on the vortex mixer set to low (~1100 rpm) and slowly add 10 µL of the activated ConA bead slurry.
11) Nutate or rotate at room temperature to allow binding (5-10 min).
12) Mix 1-2 µL of the secondary antibody (e.g. guinea pig anti-rabbit for a rabbit primary) per 100 µL Dig-wash.
13) Remove liquid from the cap and side with a quick pulse on a micro-centrifuge and place tubes on the magnet stand to clear.
14) Pull off all the liquid and place each tube at a low angle on the vortex mixer set to low (~1100 rpm) and squirt 100 µL of the secondary antibody mix while gently vortexing to allow the solution to dislodge most or all of the beads. Tap to dislodge the remaining beads.
15) Nutate or rotate at room temperature for ~30 min.
16) Quick spin, place on the magnet stand to clear, and pull off all of the liquid.
17) Add 1 ml Dig-Wash buffer, mix by inversion, or by gentle pipetting if clumps persist.
18) Repeat steps 16-17 twice.

Bind Protein A-Tn5 Fusion Protein

TIMING 1.5 hr

19) Mix pA-Tn5 complex in Dig-med buffer to a final concentration of 1:200 for 100 µL per sample.
20) Place on the magnet stand to clear and pull off all of the liquid.
21) Place each tube at a low angle on the vortex mixer set to low (~1100 rpm) and squirt 100 µL of the pA-Tn5 mix while gently vortexing to allow the solution to dislodge most or all of the beads. Tap to dislodge the remaining beads.
22) Place on the tube mutator rotator at room temperature for 1 hr.
23) Quick spin, place on the magnet stand to clear, and pull off all of the liquid.
24) Add 1 ml Dig-med buffer, mix by inversion, or by gentle pipetting if clumps persist.
25) Repeat steps 23-24 twice.

Tagmentation

TIMING 1.2 hr

26) Quick spin, place on the magnet stand to clear and pull off all of the liquid.
27) Place each tube at a low angle on the vortex mixer set to low (~1100 rpm) and add 100 µL of the Tagmentation buffer per sample along the side while gently vortexing to allow the solution to dislodge most or all of the beads. Tap to dislodge the remaining beads.
28) Incubate at 37° C. for 1 hr.

STOP Tagmentation & DNA Extraction

TIMING 1.5 hr

29) To each sample at room temperature add 4.5 µL 0.5M EDTA, 5.5 µL 10% SDS and 1 µL 20 mg/ml Proteinase K.
30) Incubate 30 min 55° C. to digest.
31) Incubate 20 min 70° C. to inactivate Proteinase K.
32) Add 1.1 volume (122 µL) AMPure XP paramagnetic beads and vortex briefly on full.
33) Quick spin and let sit at room temperature for 10-15 min.
34) Place on magnet and allow to clear before carefully withdrawing liquid.
35) On magnet and without disturbing the beads, add 1 ml 80% ethanol.
36) Withdraw liquid with a 1 ml pipette to the bottom of the tube and add 1 ml 80% ethanol.
37) Withdraw liquid with a 1 ml pipette.
38) Remove the remaining liquid with a 20 µL pipette and allow to dry for 4-5 min.
39) Remove from magnet stand, add 30 µL 10 mM Tris-HCl pH 8 and vortex on full.
40) After 5 min place on magnet stand and allow to clear.
41) Remove liquid to a fresh tube with a pipette.

PCR

TIMING 1 hr

42) Mix 21 µL DNA+2 µL custom Ad1_noMX i5+2 µL v2_Ad2.? Barcoded i7 primers, using a different barcode for each sample.
43) Add 25 µL NEBNext HiFi 2×PCR Master mix.
44) Mix, quick spin and place in Thermocycler and begin cycling program with heated lid.
45) Cycle 1: 72° C. for 5 min (gap filling)
46) Cycle 2: 98° C. for 30 sec
47) Cycle 3: 98° C. for 10 sec
48) Cycle 4: 63° C. for 30 sec
49) Repeat Cycles 3-4 13 times
50) 72° C. for 1 min and hold at 8° C.

To minimize the contribution of large DNA fragments and excess primers, PCR cycles should be at least 12-14 cycles, preferably with a 10 s 60-63° C. combined annealing/extension step.

Post-PCR Clean-Up

51) After tubes have cooled, remove from cycler and add 1.1 volume (55 µL) Ampure XP beads, and vortex briefly on full.
52) Quick spin and let sit at room temperature 10-15 min.
53) Place on magnet and allow to clear before carefully withdrawing liquid. On magnet and without disturbing the beads, add 200 µL 80% ethanol.
54) Withdraw liquid with a pipette to the bottom of the tube and add 200 µL 80% ethanol.
55) Withdraw liquid and remove the remaining liquid with a 20 µL pipette and allow to dry for 4-5 min.
56) Remove from magnet stand, add 30 µL 10 mM Tris-HCl pH 8 and vortex on full.

57) After 5 min place on magnet stand and allow to clear.
58) Remove liquid to a fresh tube with a pipette.

DNA Sequencing and Data Processing

59) Determine the size distribution of libraries by Agilent 4200 TapeStation analysis.
60) Mix libraries to achieve equal representation as desired aiming for a final concentration as recommended by the manufacturer.
61) Perform paired-end Illumina sequencing on the barcoded libraries following the manufacturer's instructions.
62) We align paired-end reads using Bowtie2 version 2.2.5 with options: -local -very -sensitive-local -no-unal -no-mixed -no-discordant -phred33 -I 10 -X 700. For mapping fragments for calibration, we also use the -no-overlap -no-dovetail options to avoid cross-mapping of the experimental genome to that of the spike-in DNA.

Results and Discussion

Figure 62:
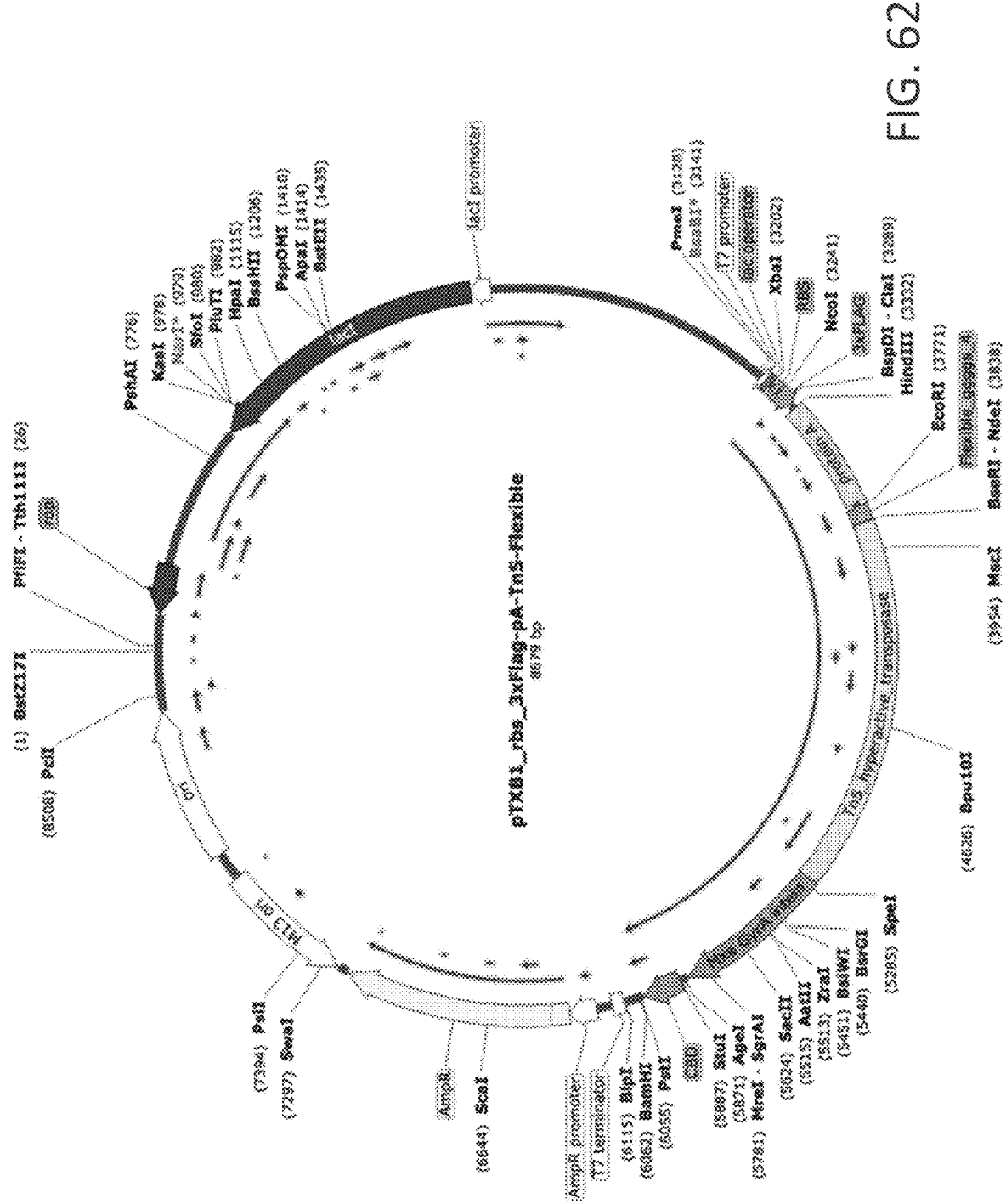
FIG. 62 shows a ProteinA-Tn5 expression vector. A version of hyperactive Tn5 transposase was constructed in which the C-terminus of Protein A was separated from the transposase by a 26 residue flexible linker peptide (pA-Tn5). Two IgG binding domains of staphylococcal protein A were PCR amplified from pK19 pA-MN vector (Schmid et al. 2004) and C-terminally fused to a hyperactive Tn5 allele (E54K, L372P) in the expression vector pTXB1-Tn5 (Picelli et al, 2014). A flexible linker composed of DDDKEF (GGGGS)$_4$ (SEQ ID NO: 1) was included between protein A and Tn5. A 3×FLAG-tagged version (pAf-Tn5) was also constructed by inserting three tandem FLAG epitope tags at the N-terminal end of protein A. Sequences downstream of lac operator was replaced with an efficient ribosome binding site.
Figures 63A, 63B:
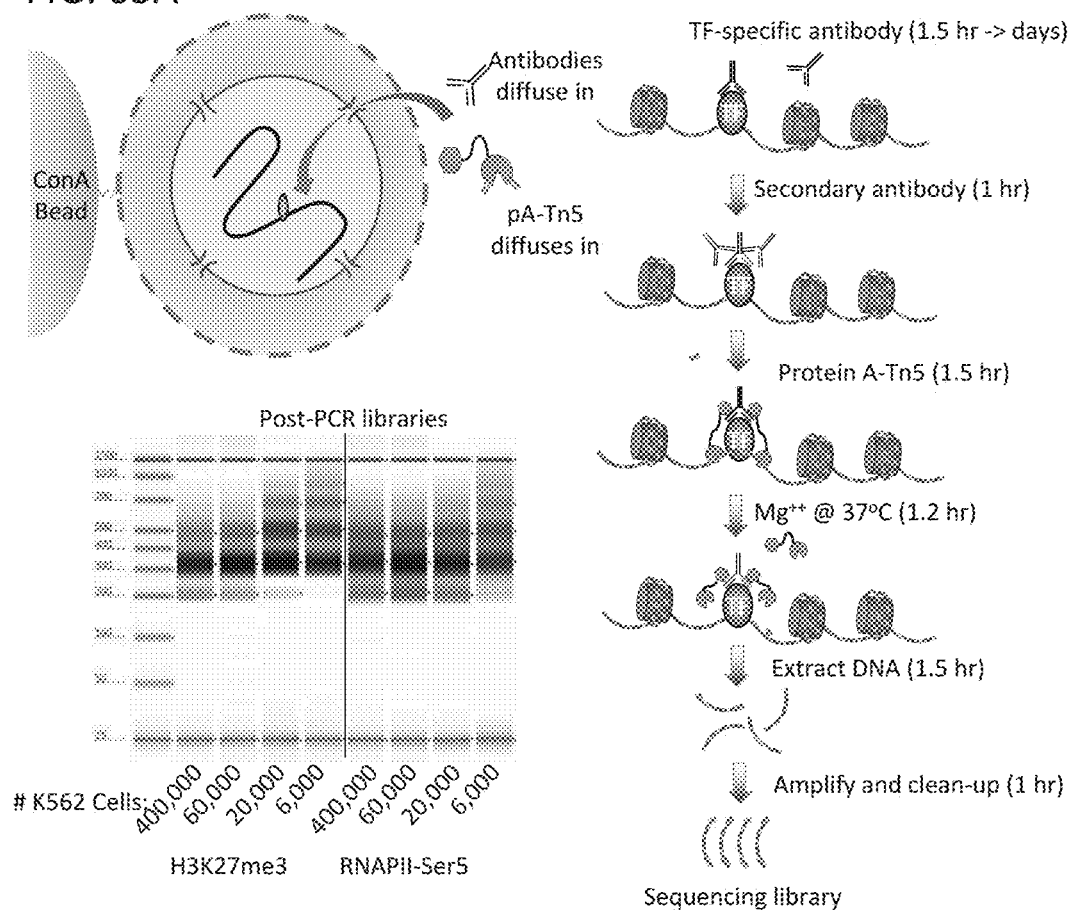
FIGS. 63A and 63B show the ITIS strategy and application to low cell numbers.
Figure 64:
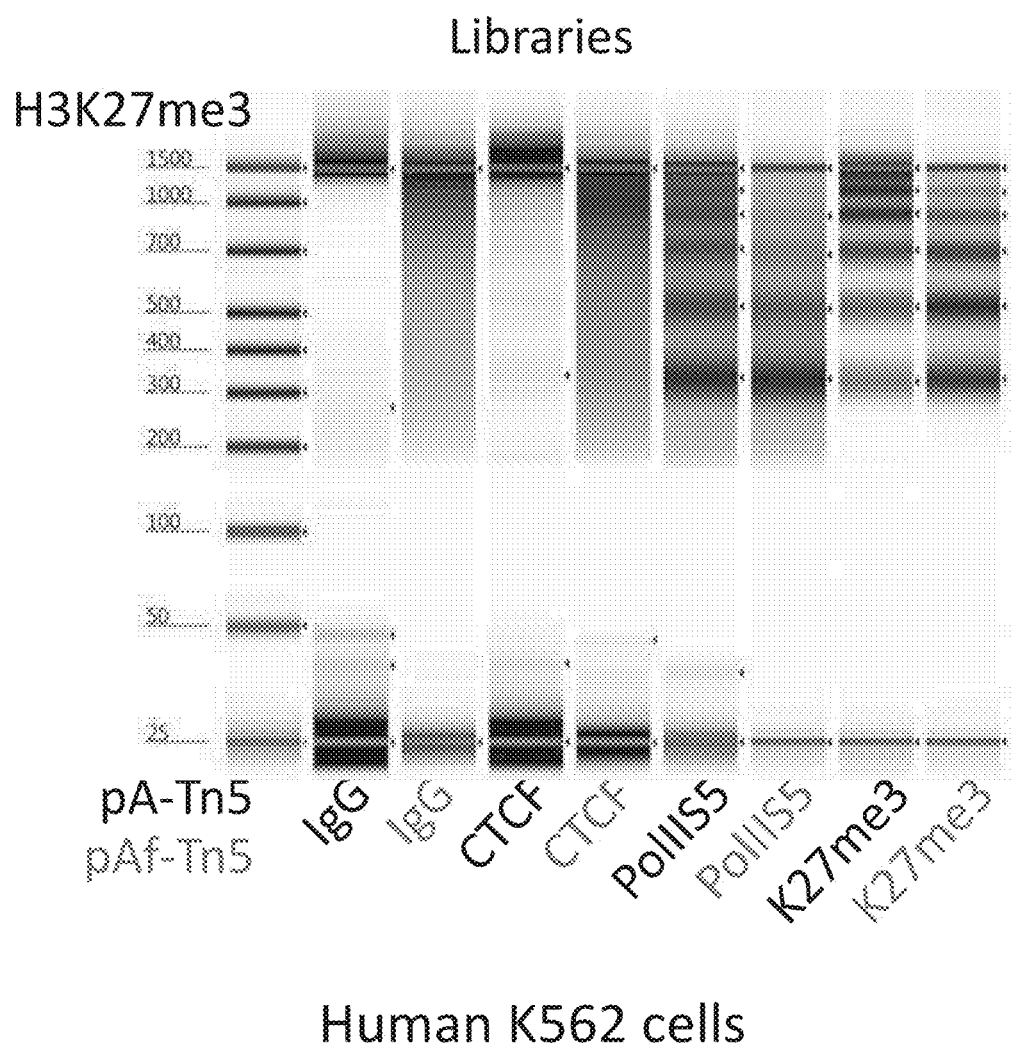
FIG. 64 shows ITIS libraries from different pA-Tn5 constructs. When used with various antibodies, including to a negative control (IgG, guinea pig anti-rabbit IgG), to the CTCF DNA-binding protein (rabbit monoclonal), to RNA Polymerase C-terminal domain serine-5 phosphate (PolIIS5, mouse monoclonal), and to Histone H3 lysine 27 trimethyl (H3K27me3, rabbit monoclonal), libraries showed the characteristic size distribution following 12 cycles of PCR. Similar results were seen with both pA-Tn5 and 3×FLAG-pA-Tn5 (pAf-Tn5), although the presence of more *E. coli* DNA in the pAf-Tn5 preparation caused a smeary background of library fragments.

Our basic ITIS protocol involves (1) permeabilizing cells, (2) adding the primary antibody and incubating, (3) immobilizing on Concanavalin A-coated paramagnetic beads, (4) adding a secondary antibody, incubating and washing, (5) adding pA-Tn5 (FIG. 62) and washing, (6) incubating with $Mg^{++}$, (7) stopping the reaction and digesting with Proteinase K and (8) adding Ampure XP beads for paramagnetic cleanup (FIG. 63A). All operations are performed in a single tube or a well of a microtiter plate, and aqueous elution from the magnetic beads yields PCR-ready DNA libraries. Tapestation display of 10% aliquots after 14 cycles of PCR shows ladders of fragment-adapters for RNAPII-Ser5 and H3K27me3, but not for an IgG control using two different pA-Tn5 constructs (FIG. 64). Ladders are seen for cell numbers ranging from 6,000 to 400,000 (FIG. 63B). Profiles are nearly identical for cell numbers down to 60,000 for H3K27me3 and 20,000 for RNA Polymerase II Serine-5 (RNAPII-Ser5), showing small fragments (<100 bp+61-bp adapters on both ends), mononucleosomes (~170 bp+adapters) and oligonucleosomes. Similar nucleosome ladders for both nucleosomal and non-nucleosomal epitopes were seen for CUT&RUN and interpreted as release of neighboring nucleosomes by cleavage within linker regions on both side. At lower cell numbers, there is a conspicuous increase in the average length of fragments, with a reduction in small fragments and mononucleosomes and an increase in oligonucleosomes. We interpret these differences in size distribution with number of cells as resulting from a limiting amount of primary antibody, such that at higher cell numbers there is not enough antibody to bind all available epitopes, a limitation that we previously reported for CUT&RUN[12]. With decreasing cell numbers, nearly all of the sites become saturated with antibody, and so there is a higher probability of releasing fragments between particles for H3K27me3, which is abundant in domains, and for RNAPII-Ser5, which is abundant over transcriptional start sites and genes. Assuming equal concentrations of antibody, depletion will occur with more cells for H3K27me3 than for RNAPII-Ser5 because there are at most two copies of H3K27me3 per nucleosome but as many as 52 copies of the C-terminal domain (CTD) heptamer per RNAPII complex[19]. We have found that incubation of the primary antibody for several days does not affect ITIS yield.

Figure 65:
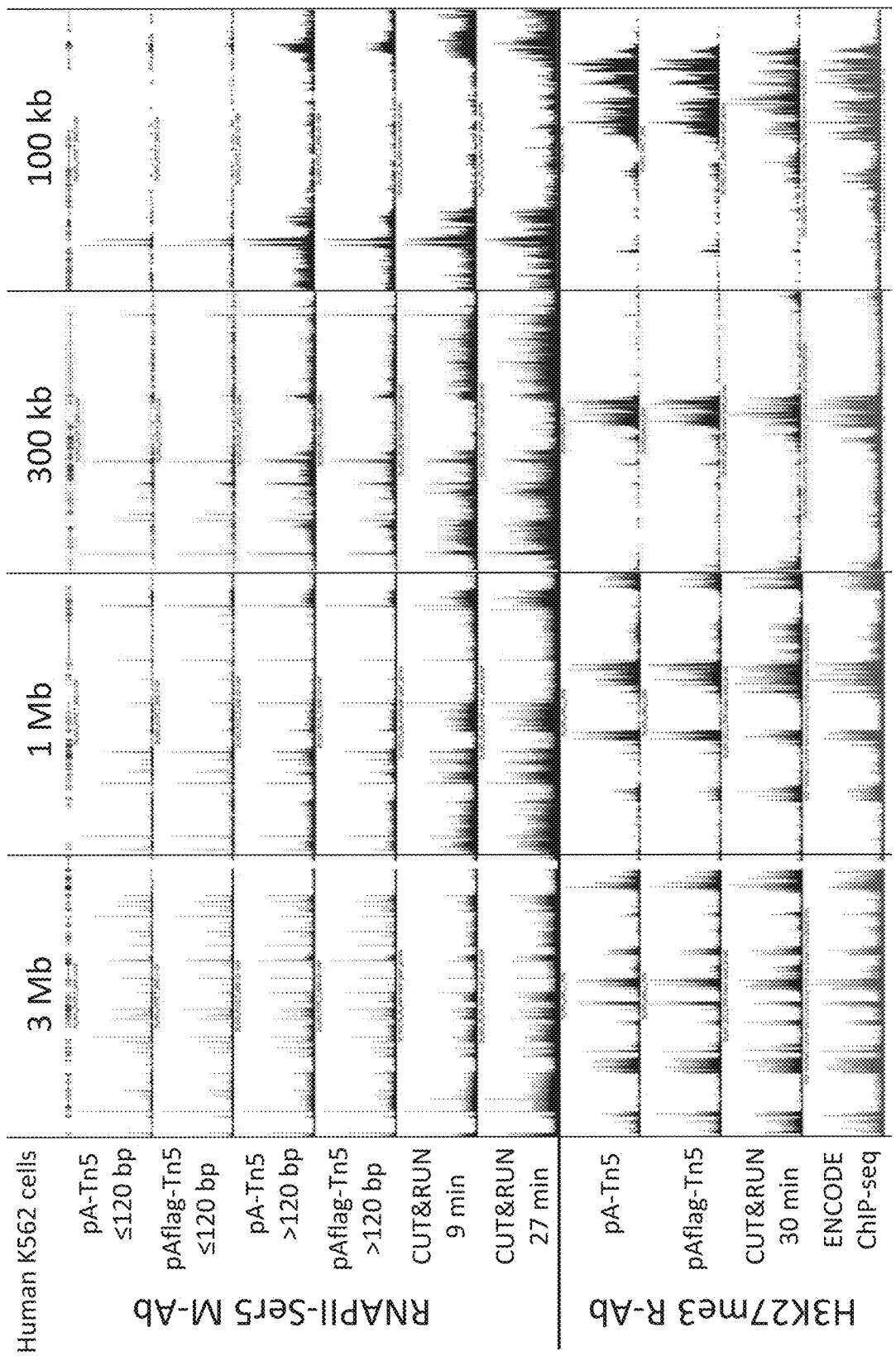
FIG. 65 shows ITIS profiles compare favorably with CUT&RUN profiles. Top: Mapping of fragments produced by ITIS shows that data quality is improved relative to CUT&RUN using the same RNA Polymerase II (RNAPII) Ser5 mouse monoclonal antibody, where the ≤120-bp fragments show sharp spikes representing the transcriptional initiation form of RNAPII. Unlike CUT&RUN, where over digestion can result in cleavages over accessible regions (compare 27 min to 9 min tracks), each molecule of pA-Tn5 can only cut-and-paste to a single end, so that once it has delivered its load, it is unable to react further. As a result, backgrounds are reduced even further than is possible with CUT&RUN. Bottom: For H3K27me3, the correspondence between ITIS and CUT&RUN is very close despite the far fewer mapped reads for ITIS samples, 6.5-6.9 million compared to 25 million for CUT&RUN. For both ITIS and CUT&RUN, profiles are noticeably cleaner than for ENCODE ChIP-seq, which required 56 million reads to produce the profiles shown. From left to right the panels show successive 3-fold magnifications of the same region.
Figure 66A:
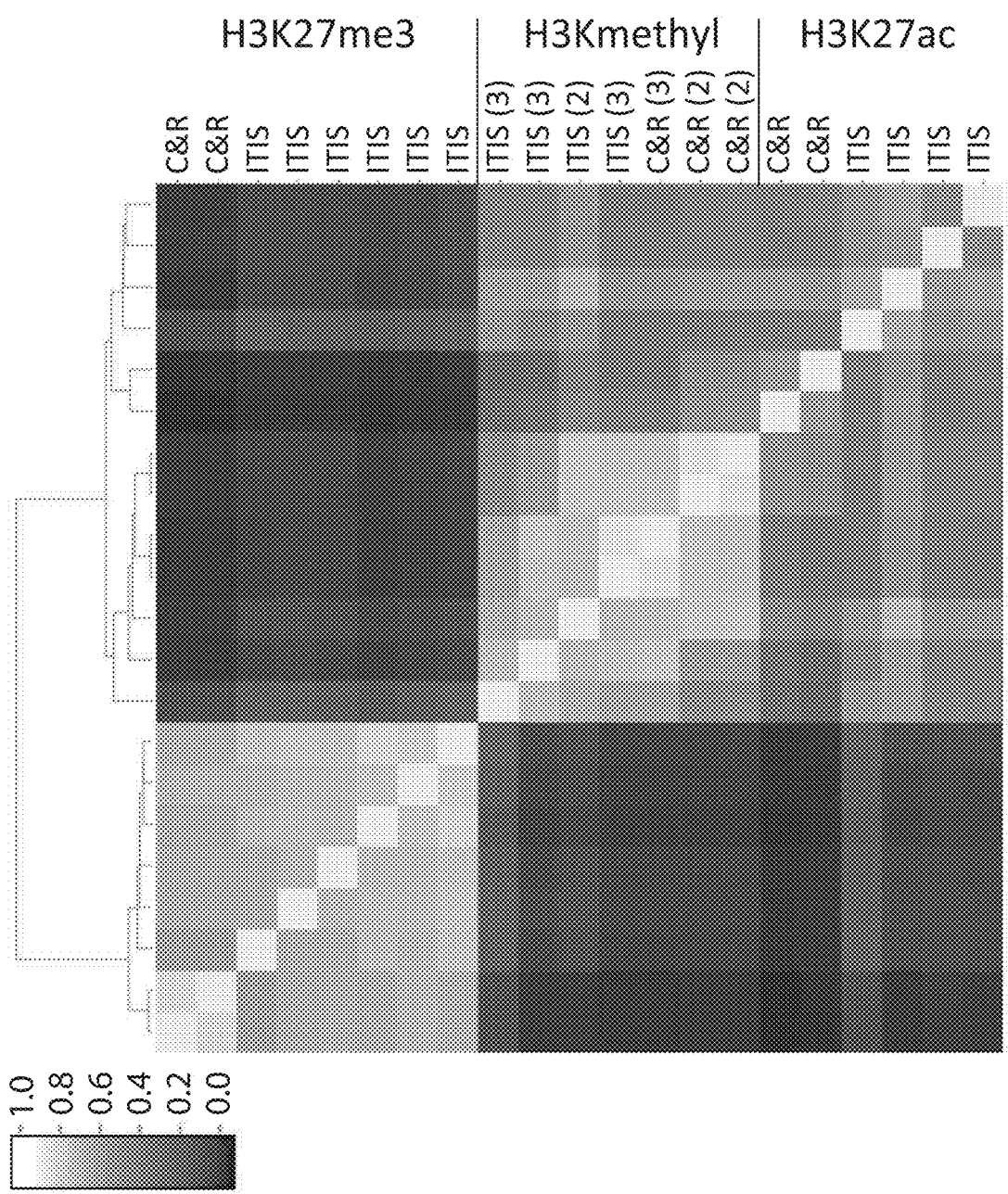
FIG. 66A shows close correspondence between ITIS and CUT&RUN for histone modifications. Correlation plots were constructed from ITIS and CUT&RUN datasets as described in Janssens et al. (2018). The same antibodies were used for both ITIS and CUT&RUN: H3K27me3 (Cell Signaling Technology cat. no. 9733), H3K4 di-methyl ("2", Millipore cat. no. 07-030), H3K4 tri-methyl ("3", Active Motif cat. no. 39159), and H3K27ac (Millipore cat. no. MABE647).
Figure 66B:
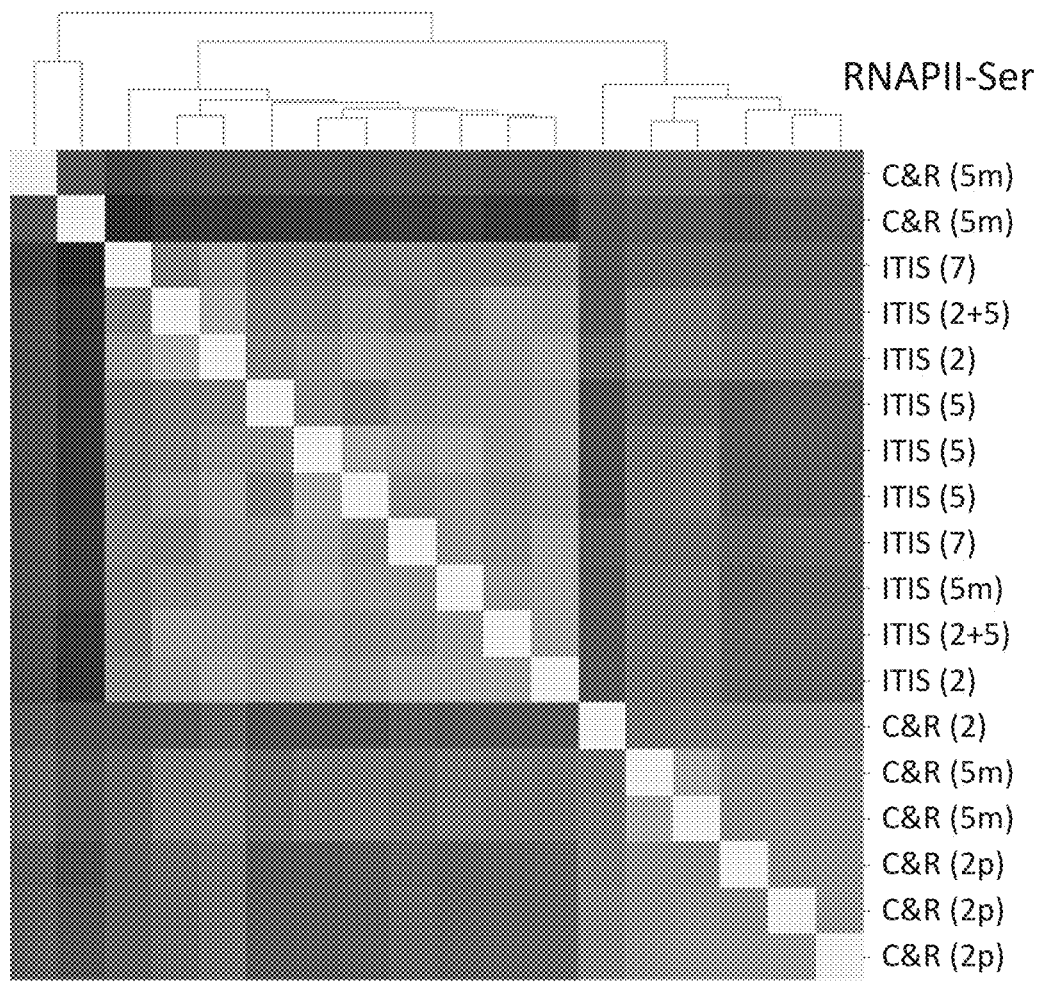
FIG. 66B shows close correspondence between ITIS and CUT&RUN for CTD-serine-phosphorylated RNAPII. Correlation plots were constructed from ITIS and CUT&RUN datasets as described in Janssens et al. (2018). Numbers in parentheses indicate the CTD heptamer residue, where "m" indicates a mouse monoclonal antibody (Abcam cat. no. ab5408 followed by the Abcam cat. no. ab46540 rabbit anti-mouse antibody), and "p" indicates Abcam cat. no. 5095 rabbit polyclonal antibody. The same antibodies were used for both ITIS and CUT&RUN.

We first compared ITIS to CUT&RUN for profiling of RNAPII. With CUT&RUN, the length of digestion determines the yield of fragments. Under digestion results in low signal with only a fraction of sites within the population of cells undergoing cleavages on both sides of the targeted particle to release fragments into the supernatant. Over digestion releases pA-MN-bound fragments that can result in untargeted digestion, a problem that becomes serious for highly abundant epitopes such as RNAPII and H3K27ac. To reduce untargeted digestion with CUT&RUN, we modified the protocol such that digestion is performed using low-salt and high-divalent cation concentrations that were previously shown to result in precipitation of nucleosome core particles. Indeed, using 3.5 mM HEPES pH 7.5 and 10 mM $CaCl_2$ for CUT&RUN digestion we detected no release of H3K27ac-targeted chromatin during digestion, but quantitative release upon addition of 150 mM NaCl. This procedure greatly reduced variation between time points by correlation matrix analysis (FIG. 57), and we have since adopted this improved CUT&RUN protocol for all applications. Nevertheless, when our improved CUT&RUN protocol was applied to the initiation form of RNAPII using an anti-RNAPII-Ser5 antibody, we observed both underdigestion and overdigestion over a time course from 1 min to 27 min at 0° C. (FIG. 65). In contrast, ITIS using the same antibody and two different pA-Tn5 constructs at different concentrations showed sharp peaks over promoters with low broad domains over gene bodies and lower background than the best CUT&RUN time point (9 min). We confirmed this consistency of RNAPII CUT&RUN using 4 additional antibodies to RNAPII epitopes (Ser-2, Ser5, Ser2+Ser5 and Ser7). Correlation matrix analysis shows that all 5 antibodies give highly concordant profiles genome-wide, with no clustering of biological replicates to the exclusion of different antibodies in the same experiment, whereas CUT&RUN profiles for our best experiment show lower overall concordance despite the fact that the time points were taken in succession from the same incubation mixture (FIG. 66B). We conclude that ITIS provides robust profiling of RNAPII with lower backgrounds than are seen using our improved CUT&RUN protocol. We observed similarly high robustness and concordance for ITIS profiling of silencing (H3K27me3) and active (H3K4me2 and H3K27me3) histone modifications using different (FIG. 66A).

Figure 67:
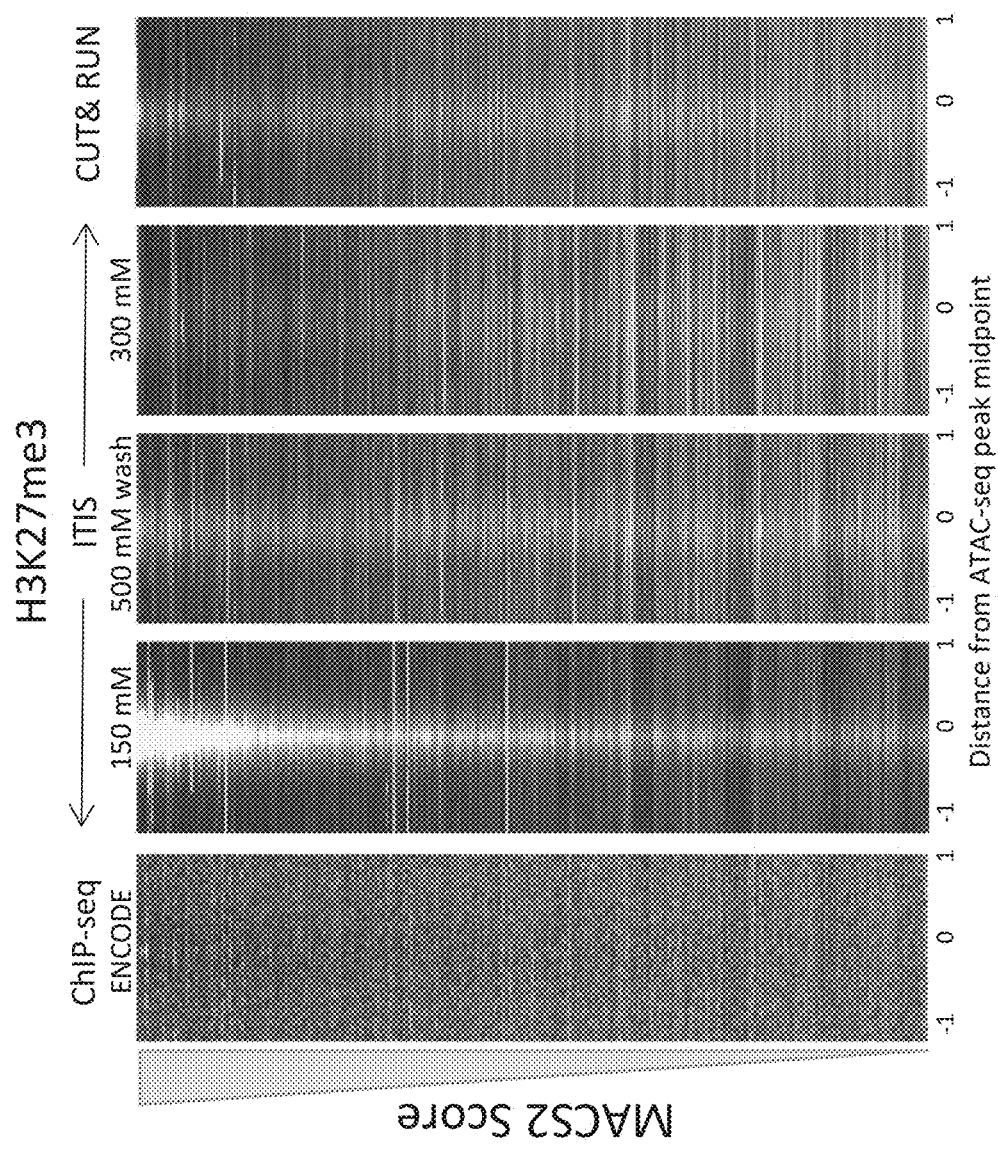
FIG. 67 shows genome-wide hypersensitivity to pA-Tn5 binding and tagmentation is essentially eliminated by raising the salt concentration. Heat map displays of selected datasets ordered by ATAC-seq MACS2 peak score show that ITIS under 150 mM NaCl conditions strongly correlates with ATAC-seq peak score. In contrast, ITIS under 150 mM conditions shows a slight anti-correlation with ATAC-seq peak calls, similar to what is seen with CUT&RUN, and the hypersensitivity signal is essentially eliminated by performing pA-Tn5 addition and tagmentation at 300 mM NaCl. This confirms that hypersensitivity results from untethered Tn5, and that salt treatment is effective in removing it. ATAC-seq peak calls (61,153) are from GSE31755 (K562 cells). Heat maps were plotted using Java TreeView on an arbitrary linear scale.
Figures 69A, 69B:
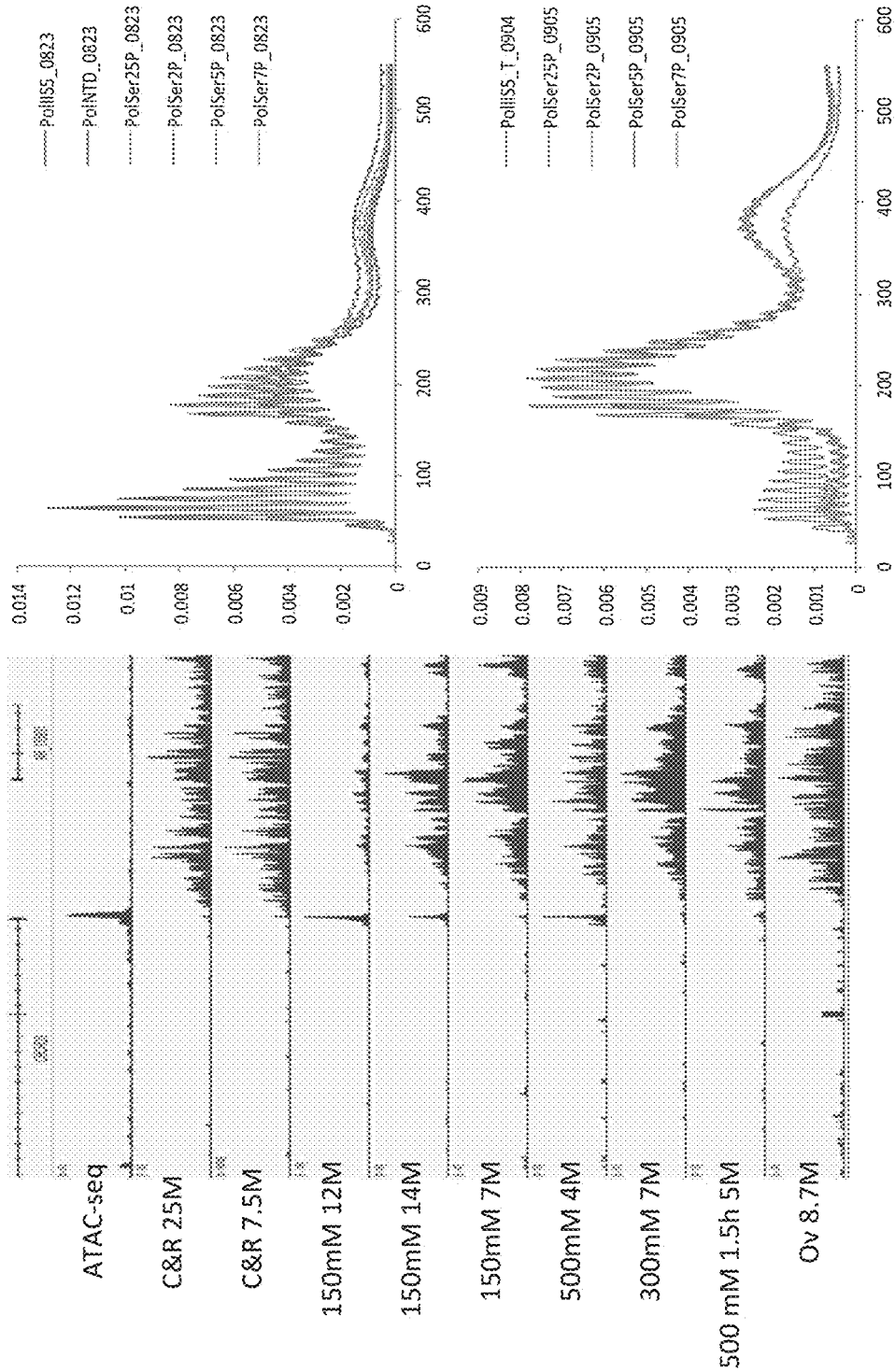
FIGS. 69A-69B show high salt reduces untargeted tagmentation and small fragment recovery.

Tagmentation using Tn5 has previously been applied in an untargeted fashion following the popular ATAC-seq method for hypersensitive site detection[17], and a challenge for ITIS is to avoid untargeted tagmentation, which will be confounded with antibody-targeted profiling. To assay the degree of untargeted tagmentation, we used a rabbit monoclonal antibody against H3K27me3 that we have used as a CUT&RUN positive control, because this epitope is found exclusively in silenced regions of the genome that essentially lack hypersensitive sites. To identify hypersensitive sites in human K562 cells, we downloaded a set of 61,153 peak calls for a recently released ATAC-seq dataset (GSM2695561). Using the midpoint of each peak as the location of a hypersensitive site, we aligned fragments produced by H3K27me3 ITIS following various treatments of the cells during and/or after pA-Tn5 complex addition. We found a high occupancy of hypersensitive sites for ITIS using physiological (~150 mM) NaCl, slightly reduced using brief 500 mM salt washes after pA-Tn5 binding, but eliminated using 300 mM NaCl for binding, washing and tagmentation (FIG. 69A). When all 61,153 ATAC-seq sites were ordered by score, CUT&RUN showed a weak negative correlation with ATAC-seq score, whereas ITIS using 150 mM NaCl and only brief 500 mM NaCl washes resulted in a strongly correlated heat map (FIG. 67), confirming that pA-Tn5 binds to hypersensitive sites genome-wide during incubation and a substantial amount of active enzyme complex remains during washes and tagmentation. Strikingly, prolonged washes with 500 mM NaCl reduced occupancy over ATAC-seq sites down to the level seen for CUT&RUN. Further reduction in hypersensitive site occupancy was obtained by using an NaCl concentration of 300 mM during pA-Tn5 binding, washes and tagmentation results. We attribute this weak anti-correlation to the high concentration of epitope within H3K27me3 domains that the hypersensitive sites are embedded in, resulting in preferential release of background fragments by pA-Tn5 bound to H3K27me3 nucleosomes that flank these sites relative to sites that are embedded in H3K27me3-free domains. These results also suggest that by incubating with untethered Tn5 complexed with one set of adapters followed by pA-Tn5 complexed with a different set of adapters, and omitting high-salt treatments, both ITIS and ATAC-seq can be performed on the same sample.

Figure 68:
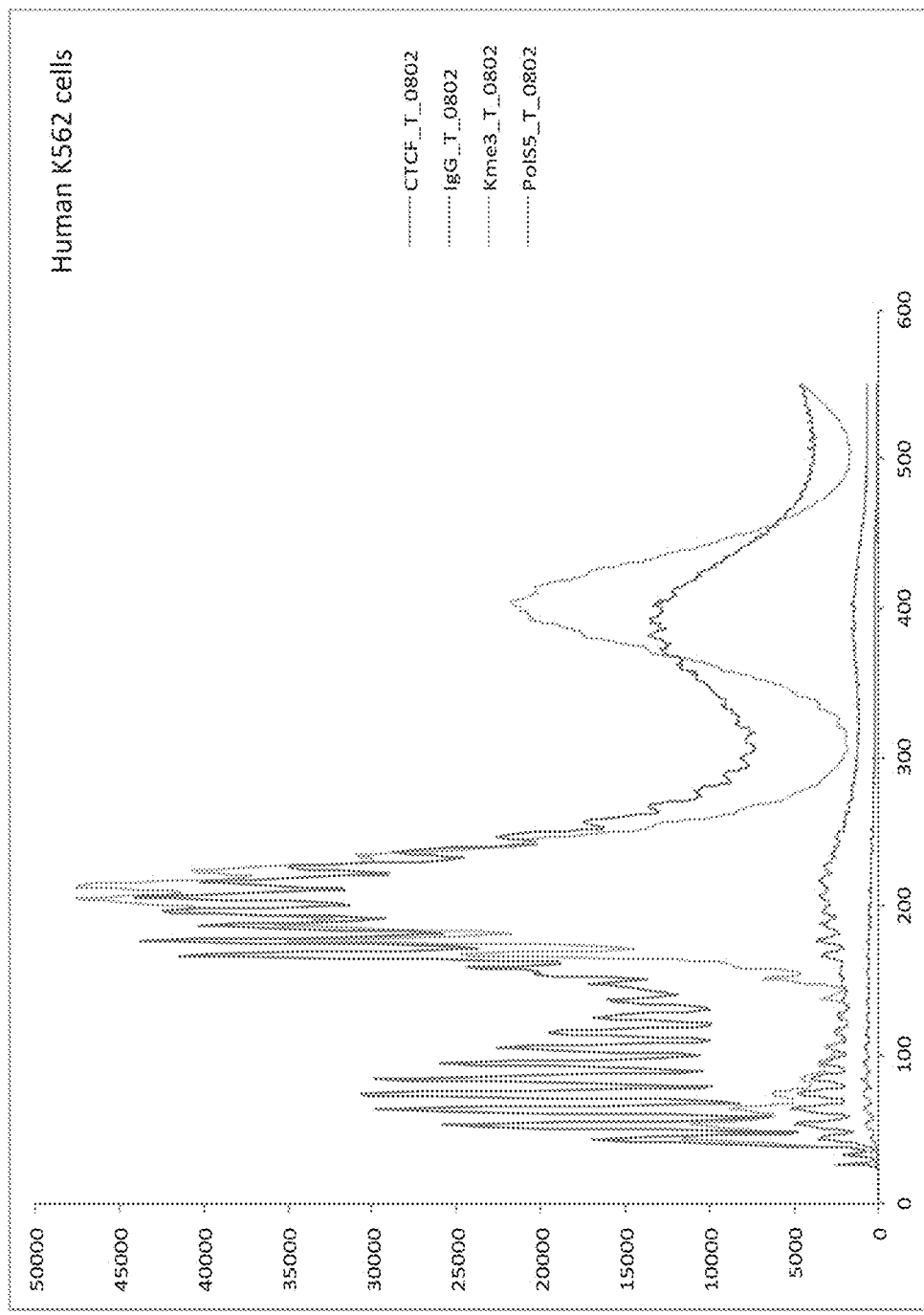
FIG. 68 shows ITIS fragments fall into multiple size classes. When ITIS libraries were subjected to paired-end sequencing, the expected profiles were obtained, with small fragments representing transcription factors and the large fragments representing mononucleosomes and lower levels of dinucleosomes. The ~10-bp periodicity likely reflects the tight constraints of tethered cleavage.

We find that the ionic concentration can affect the size distribution of ITIS fragments. ITIS produces small fragments (≤120 bp) that represent transcription factors and large fragments (≥150 bp) that represent mostly mononucleosomes with lower levels of dinucleosomes (FIG. 68). The ~10-bp periodicity likely reflects the tight constraints of tethered cleavage, similar to the less striking periodicity seen for CUT&RUN of yeast transcription factors, which we interpreted as reflecting access of the enzyme to one face of the DNA double-helix[11]. By raising the salt concentration to eliminate untargeted pA-Tn5, we also observed a reduction in the small fragment size population (FIG. 69B). Additionally, we observed a reduction in the number of fragments mapping the *E. coli* genome in the below Table.

Tn5 Binding and Tagmentation in 300 mM NaCl Reduces *E. coli* DNA Contamination in Human K562 Cells.

| Sample | Raw reads | Human | E. coli | % E. coli |
|---|---|---|---|---|
| RNAPII S2 150 mM | 10467975 | 10066096 | 61428 | 0.61 |
| RNAPII S2 + 5 150 mM | 10109833 | 9675912 | 79073 | 0.82 |
| RNAPII S5 150 mM | 9244781 | 8782462 | 107458 | 1.22 |
| RNAPII S7 150 mM | 8945071 | 7886741 | 468969 | 5.95 |
| RNAPII S2m 150 mM | 9806040 | 8729801 | 527111 | 6.04 |
| Average | | | 248808 | 2.93 |
| K27me3 300 mM | 7496975 | 7072486 | 335 | 0 |
| K4me3 300 mM | 7632792 | 7217728 | 2095 | 0.03 |
| CTCF 300 mM | 5767872 | 5319692 | 35763 | 0.67 |
| RNAPII S2 300 mM | 8286376 | 7813084 | 3787 | 0.05 |
| RNAPII S2 + 5 300 mM | 6465402 | 6082502 | 2817 | 0.05 |
| RNAPII S5 300 mM | 6984022 | 6561247 | 2884 | 0.04 |
| RNAPII S7 300 mM | 4013530 | 3680956 | 38347 | 1.04 |
| Average | | | 12731 | 0.23 |

Mapped paired-end read counts from two different ITIS experiments. In the first experiment 150 mM NaCl was used for pA-Tn5 binding, followed by two brief 500 mM washes, then tagmentation in 150 mM NaCl. In the second experiment, 300 mM NaCl was used for pA-Tn5 binding, followed by three brief washes and tagmentation. During purification, Tn5 transposase binds to available fragments of *E. coli* DNA and some of it remains bound through the purification process. For any batch of transposase, the percentage of *E. coli* DNA contamination brought into the reaction serves as a "non-invasive" spike-in proxy that can be used to calibrate samples so that they can be quantitatively compared.

Figure 70:
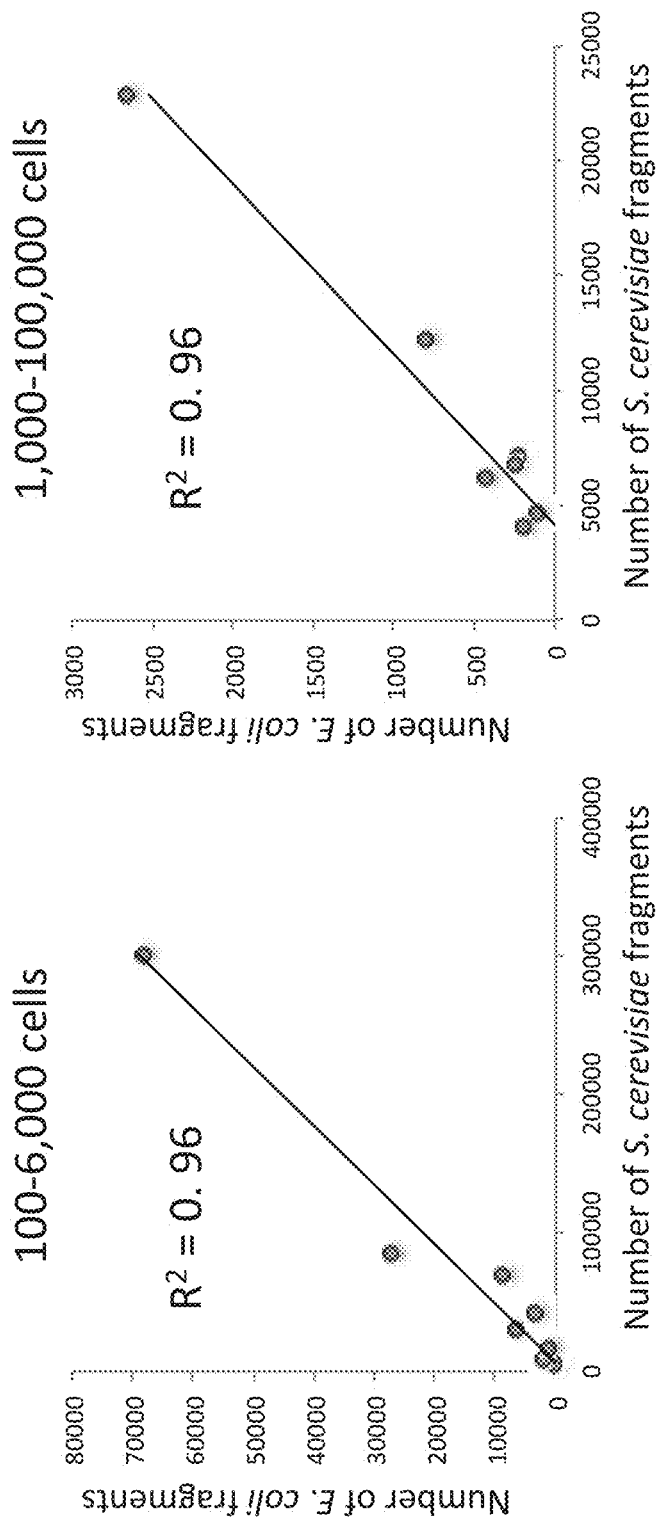
FIG. 70 shows *E. coli* DNA contamination of pA-MNase can proxy for spike-in calibration. Fragments from K562 cell CUT&RUN datasets (GSE104550) for H3K27me3 (100-6,000 cells) and CTCF (1,000-100,000 cells) were mapped to the repeat-masked genome of *S. cerevisiae* and the full genome *E. coli*.

This contaminant occurs because the Tn5-encoding gene is induced to high levels of expression in *E. coli*, producing high concentrations of enzyme that binds to *E. coli* genomic DNA, and some of it survives the purification process and are simultaneously tagmented together with the cellular DNA. Although there is a protocol for removal of this contaminant during purification, we found that our 300 mM NaCl protocol reduced *E. coli* DNA to insignificant levels. We noticed that relatively rare epitopes, such as CTCF, showed higher levels of contamination than more abundant epitopes, such as histone modifications, and IgG, which gives only a low uniform background, showed very high contamination. This indicated that we can use the *E. coli* contamination as a "non-invasive" proxy for a spike-in for calibration. Spike-in calibration is essential for comparing samples[20], and this is especially the case for methods such as CUT&RUN and ITIS where background levels are too low to be used for calibration. To test whether or not contaminating *E. coli* DNA can be used as a proxy for a spike-in, we mapped fragments to the *E. coli* genome using K562 cell datasets from serially diluted cells profiled for H3K27me3 (100-6,000 cells) and CTCF (1,000-100,000 cells) including *S. cerevisiae* yeast DNA spike-ins. Indeed, for both cell number ranges the correlations between yeast spike-in and *E. coli* contamination were so close as to be the same within likely measurement error ($R^2$=0.96, FIG. 70). Therefore, *E. coli* DNA that contaminates pA-MNase can be used to calibrate CUT&RUN, obviating the need for a spike-in, confirming our evidence that *E. coli* DNA that contaminates pA-Tn5 serves as a suitable spike-in proxy for ITIS. Using *E. coli* contamination as a spike-in proxy is advantageous to using a heterologous spike-in, because addition of pA-MNase to CUT&RUN samples is performed earlier than the addition of heterologous spike-in DNA to the stop buffer and so controls for sample-to-sample variation at an earlier stage in the CUT&RUN process, and this advantage extends to ITIS. The *E. coli* genome is simpler than yeast or *Drosophila* genomes used for CUT&RUN spike-ins and does not require repeat masking, and as it is heterologous to all eukaryotes it should suffice for virtually all ITIS applications.

Figure 71:
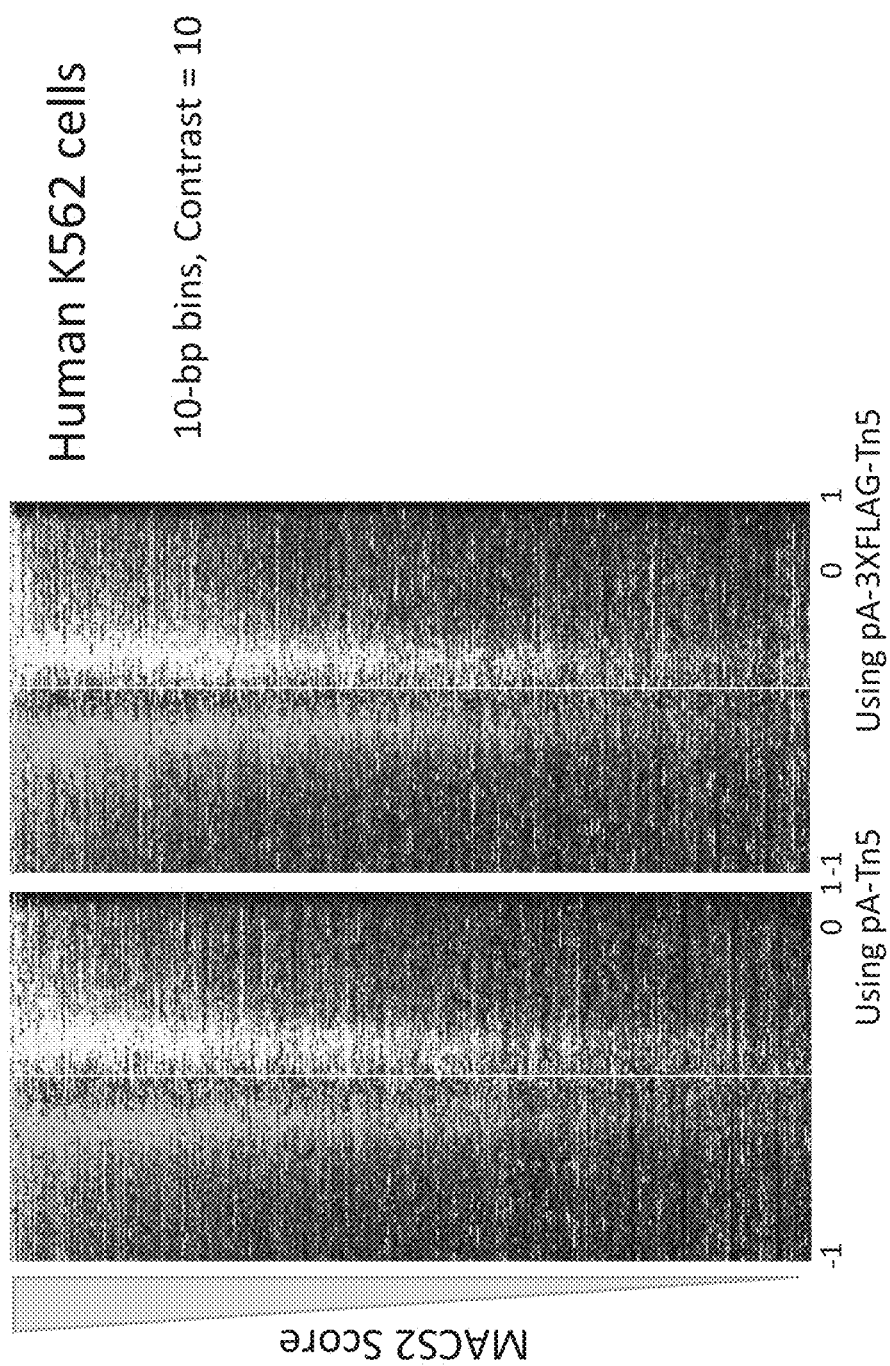
FIG. 71 shows ITIS peak calls for RNAPII-Ser5P correspond to transcription initiation sites. To validate ITIS, peaks were called for both pA-Tn5 and pA-3×FLAG-Tn5 RNA-PII-Ser5P datasets using MACS2 with default parameters, yielding ~17,500 peaks each. Processed datasets from PRO-seq run-on for human K562 cells (SRA GSM1480327) were aligned to the peak calls. When ordered by ITIS MACS2 score, a close correspondence between PRO-seq occupancy and PolII-Ser5 ITIS score is seen, where the blue heat map values represent PRO-seq occupancies to the 3' side of each peak call and the yellow values represent PRO-seq occupancies to the 5' side.

We used RNAPII-Ser5 datasets to validate ITIS. RNAPII has been profiled in K562 cells using PRO-seq, which is a transcriptional run-on method that maps the nascent chain in the active site of RNAPII, and so is orthogonal to chromatin-based methods such as ChIP-seq, CUT&RUN and ITIS. Peaks were called for both pA-Tn5 and pA-3×FLAG-Tn5 datasets (FIG. 64, PolIIIS5) using MACS2 with default parameters, yielding ~17,500 peaks each. Processed PRO-seq datasets for human K562 cells (SRA GSM1480327) were aligned to the peak calls. When ordered by ITIS MACS2 score, a close correspondence between PRO-seq occupancy and PolII-Ser5 ITIS score is seen, where the blue heat map values represent PRO-seq occupancies to the 3' side of each peak call and the yellow values represent PRO-seq occupancies to the 5' side (FIG. 71). This provides direct validation that PolII-Ser5 ITIS maps the initiation form of RNAPII without requiring reference to any external annotation. Very similar PRO-seq heatmaps are produced from peak calls for both forms of pA-Tn5. We conclude that ITIS provides accurate maps of RNAPII.

Figure 72:
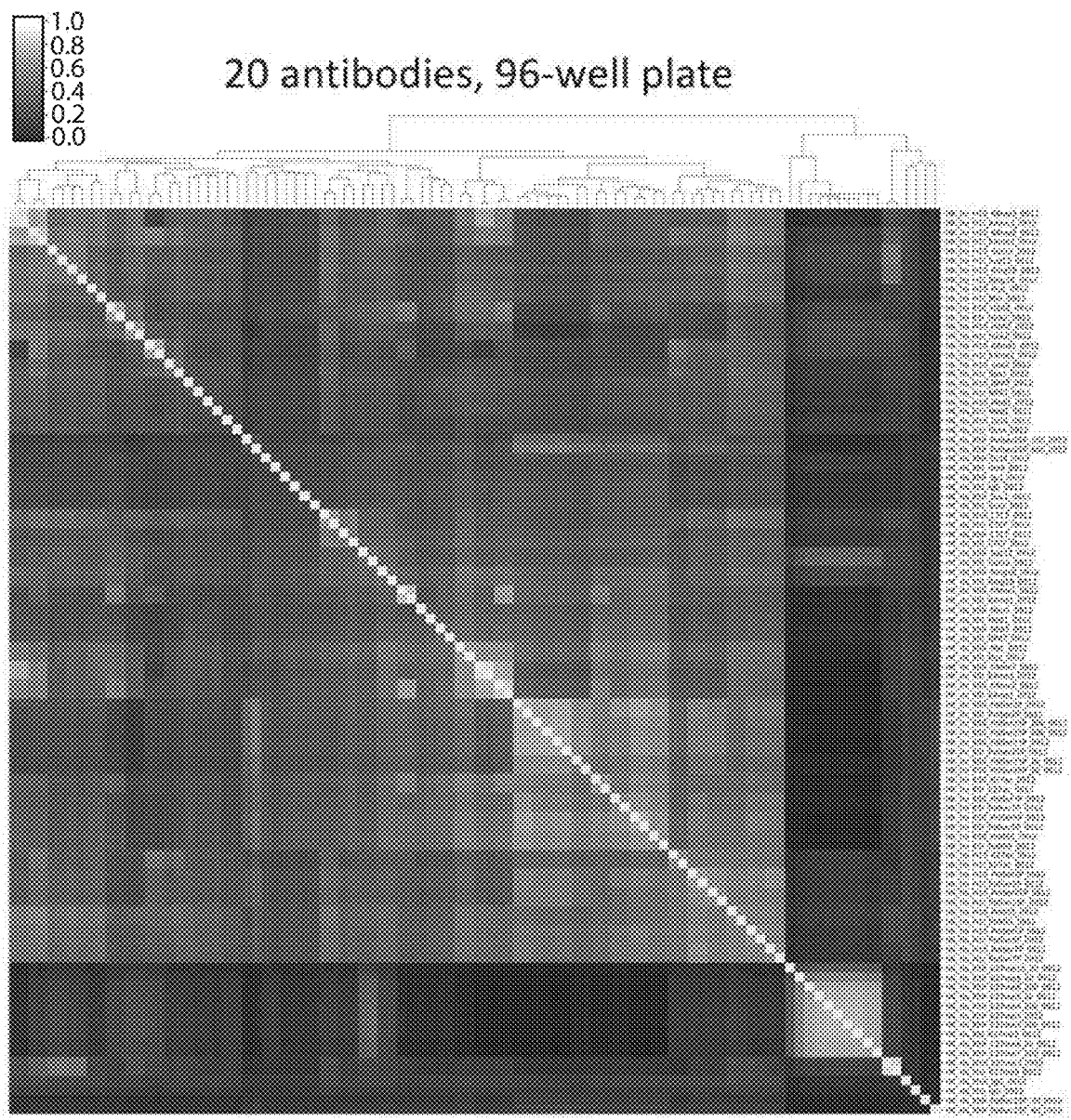
FIG. 72 is a correlation matrix showing hierarchical clustering for 96 ITIS samples run together on a single 96-well plate for 20 different antibodies and two cell types from two different batches of cells each. After permeabilization for 1 or 4.5 hr, antibody was added (1:50) and incubated at 4° C. overnight. The plate was then subjected to ITIS using an 8-channel pipettor and 96-well plate handler, and approximately equimolar samples from every well were pooled and sequenced on a single Illumina 2500 Rapid flow cell, averaging 3 million paired-end reads per sample. Except for the 5 different RNA PolII antibodies, all biological replicates clustered together to the exclusion of all samples bound by other antibodies, demonstrating a remarkable degree of reproducibility for high-throughput ITIS.

To determine whether ITIS can be used more generally for epigenomic components, and to adapt the protocol for high throughput, we reduced the volume of reactions by half, dispensed into individual wells of a 96-well microtiter plate from two batches each of both K562 and H1 human embryonic stem cells that had been harvested and permeabilized. To each sample we added one from a set of 20 antibodies at 1:50 concentration for a total of 96 samples. After overnight incubation at 4° C., ITIS was performed on the plate, Ampure beads were added and the eluate was amplified with 14 cycles using 96 different barcodes, then pooled. The size distributions based on Tapestation analysis and the concentrations based on Qubit readings were used to mix approximately equimolar amounts of all 96 samples, which were sequenced on a single 2-lane flow cell. We mapped on average ~3 million paired-end reads to the human genome. Using hierarchical clustering for correlation matrix analysis, we found that all biological replicates for both K562 and H1 cells clustered together without exception (FIG. 72). Such remarkable reproducibility confirms the robustness of ITIS, while demonstrating that ITIS is suitable for a wide variety of epitopes, including those for histone modifications (H3K4me1-me3, K27ac and me3) and variants (H2A.Z), transcription factors (CTCF, Myc Sox2, Oct4 and NPAT) and chromatin-associated complexes (PolII, Med1, Suz12 and Ring1B).

In conclusion, we have described a novel method that combines antibody-targeting of a tethered enzyme with tagmentation that requires only one day from live cells to sequencing-ready libraries. ITIS outperforms our CUT&RUN method in profiling RNAPII and achieves similar results in profiling histones and the CTCF transcription factor. As the workflow for ITIS is similar to CUT&RUN, but simpler, it can be easily adapted for high-throughput and application to tissues and tumor samples[21]. Furthermore, ITIS is easily adaptable for single-cell applications following the same protocols that have been applied to single-cell ATAC-seq[18,22-25], including single-cell ChIT/ATAC-seq. ITIS has the potential of replacing ChIP-seq as the premier method for profiling specific components of the chromatin landscape for the bench-top, the high-throughput pipeline, and eventually the clinic.

References for Example 10 (Each of which is Incorporated by Reference in its Entirety)

1. Zentner, G. E. & Henikoff, S. High-resolution digital profiling of the epigenome. Nat Rev Genet 15, 814-27 (2014).
2. Policastro, R.A. & Zentner, G. E. Enzymatic methods for genome-wide profiling of protein binding sites. Brief Funct Genomics 17, 138-145 (2018).
3. Rhee, H. S. & Pugh, B. F. Comprehensive genome-wide protein-DNA interactions detected at single-nucleotide resolution. Cell 147, 1408-19 (2011).
4. Skene, P. J. & Henikoff, S. A simple method for generating high-resolution maps of genome wide protein binding. eLife 4, e09225 (2015).
5. Kasinathan, S., Orsi, G. A., Zentner, G. E., Ahmad, K. & Henikoff, S. High-resolution mapping of transcription factorbinding sites on native chromatin. Nature Methods 11, 203-9 (2014).
6. Teytelman, L., Thurtle, D. M., Rine, J. & van Oudenaarden, A. Highly expressed loci are vulnerable to misleading ChIP localization of multiple unrelated proteins. Proc Natl Acad Sci USA 110, 18602-7 (2013).
7. Zentner, G. E., Kasinathan, S., Xin, B., Rohs, R. & Henikoff, S. ChEC-seq kinetics discriminate transcription factor binding sites by DNA sequence and shape in vivo. Nature Communications 6, 8733 (2015).
8. Park, D., Lee, Y., Bhupindersingh, G. & Iyer, V. R. Widespread misinterpretable ChIP-seq bias in yeast. PLoS One 8, e83506 (2013).
9. Venkataraman, A. et al. A toolbox of immunoprecipitation-grade monoclonal antibodies to human transcription factors. Nat Methods (2018).
10. van Steensel, B., Delrow, J. & Henikoff, S. Chromatin profiling using targeted DNA adenine methyltransferase. Nature Genetics 27, 304-308 (2001).
11. Skene, P. J. & Henikoff, S. An efficient targeted nuclease strategy for high-resolution mapping of DNA binding sites. Elife 6, e21856 (2017).
12. Skene, P. J., Henikoff, J. G. & Henikoff, S. Targeted in situ genome-wide profiling with high efficiency for low cell numbers. Nat Protoc 13, 1006-1019 (2018).
13. Schmid, M., Durussel, T. & Laemmli, U.K. ChIC and ChEC; genomic mapping of chromatin proteins. Mol Cell 16, 147-57 (2004).
14. Hainer, S. J., Boškovic, A., Rando, O. J. & Fazzio, T. G. Profiling of pluripotency factors in individual stem cells and early embryos. bioRxiv (2018).
15. Reznikoff, W. S. Tn5 as a model for understanding DNA transposition. Mol Microbiol 47, 1199-206 (2003).
16. Picelli, S. et al. Tn5 transposase and tagmentation procedures for massively scaled sequencing projects. Genome Res 24, 2033-40 (2014).
17. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nat Methods 10, 1213-8 (2013).
18. Buenrostro, J. D. et al. Single-cell chromatin accessibility reveals principles of regulatory variation. Nature 523, 486-90 (2015).
19. Zaborowska, J., Egloff, S. & Murphy, S. The pol II CTD: new twists in the tail. Nat Struct Mol Biol 23, 771-7 (2016).
20. Chen, K. et al. The Overlooked Fact: Fundamental Need for Spike-In Control for Virtually All Genome-Wide Analyses. Mol Cell Biol 36, 662-7 (2015).
21. Janssens, D. H. et al. Automated in situ profiling of chromatin modifications resolves cell types and gene regulatory programs. biorxiv doi.org/10.1101/41868 (2018).
22. Corces, M. R. et al. Lineage-specific and single-cell chromatin accessibility charts human hematopoiesis and leukemia evolution. Nat Genet 48, 1193-203 (2016).
23. Buenrostro, J. D. et al. Integrated Single-Cell Analysis Maps the Continuous Regulatory Landscape of Human Hematopoietic Differentiation. Cell 173, 1535-1548 e16 (2018).
24. Mezger, A. et al. High-throughput chromatin accessibility profiling at single-cell resolution. Nat Commun 9, 3647 (2018).
25. Cusanovich, D. A. et al. The cis-regulatory dynamics of embryonic development at single-cell resolution. Nature 555, 538-542 (2018).

Figure 73:
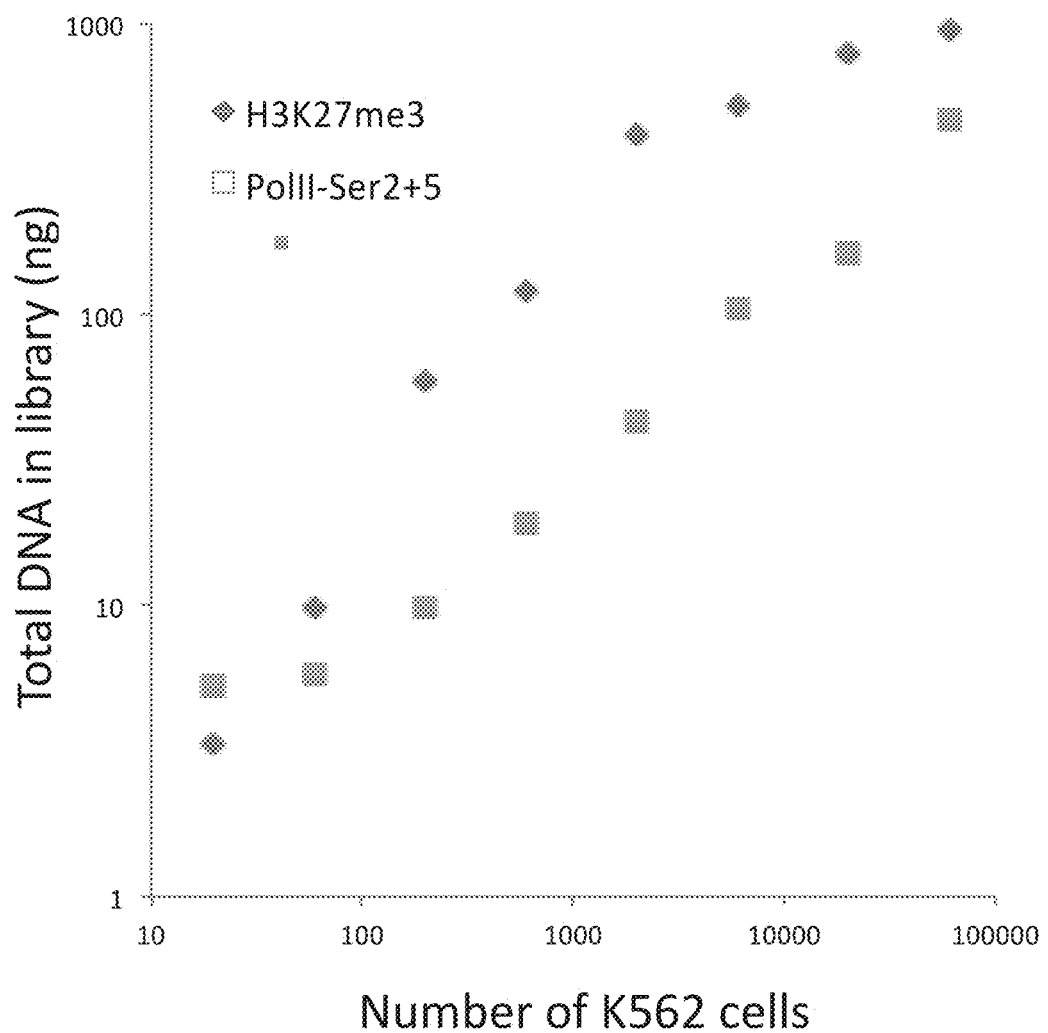
FIG. 73 shows the recovery of fragments for low cell numbers using ITIS. K562 cells were serially diluted from 60,000 cells down to 20 cells and ITIS was performed for H3K27me3 and RNAPII-Ser2+5. Approximately linear recovery of fragments (on a log scale) is seen down to 20 cells for H3K27me3 and 60 cells for RNAPII.

Example 11 Low-Cell and Single-Cell Epigenomic Profiling with ImmunoTargeted Insertion Sequencing A major limitation of ChIP-seq is that it is too inefficient for applications that require fewer than thousands of cells (Brind'Amour et al., 2015). We have shown that CUT&RUN is suitable for as few as 100 cells without loss of data quality (Skene et al., 2018). In most of our experiments with ITIS we have used 50,000-500,000 human K562 or H1 ES cells. To determine whether ITIS can also be applied to low cell numbers, we serially diluted K562 cells down to 20 cells and performed ITIS for H3K27me3 and RNAPII-Ser2+5 following our standard protocol using 14 cycles. Based on Tapestation analysis, we observed linear recovery (on a log scale down to 20 cells for H3K27me3 and 60 cells for RNAPII (FIG. 73). Thus, ITIS can be used for applications that require low cell numbers.

Figure 74:
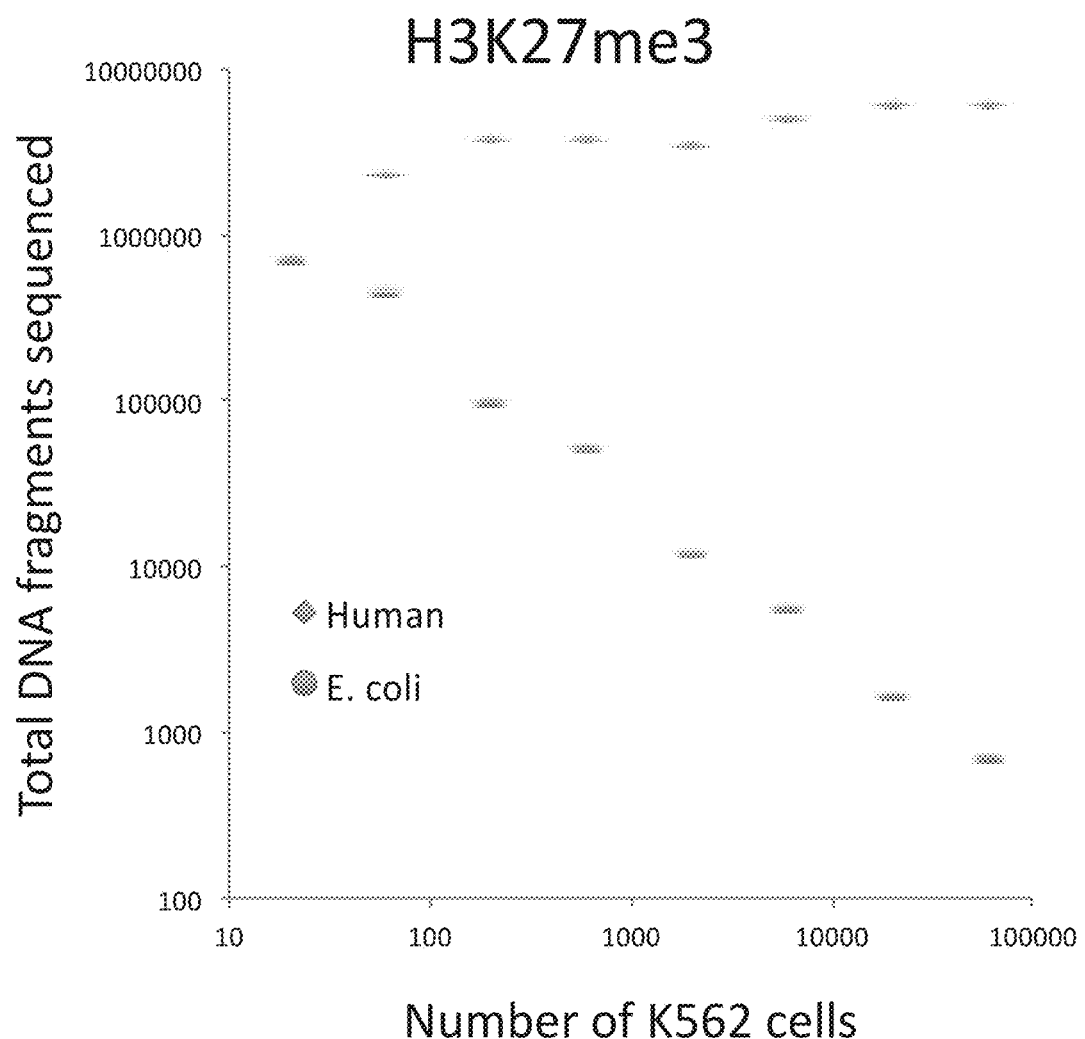
FIG. 74 shows that there is an inverse relationship between the number of human and number of *E. coli* fragments, confirming the use of *E. coli* contamination in the pA-Tn5 preparation as a spike-in proxy for ITIS, similar to what was observed for CUT&RUN.

We sequenced the samples and plotted the number of human and number of *E. coli* fragments (FIG. 74). We observe a monotonic relationship between the number of cells and the number of fragments released ($R^2$=0.46), approximately linear for the lowest cell numbers (20-200 cells). We also observe an inverse relationship between the number of human and number of *E. coli* fragments. This confirms that *E. coli* contamination can serve as a spike-in proxy for ITIS down to low cell numbers, similar to what we observed for CUT&RUN.

Figure 75:
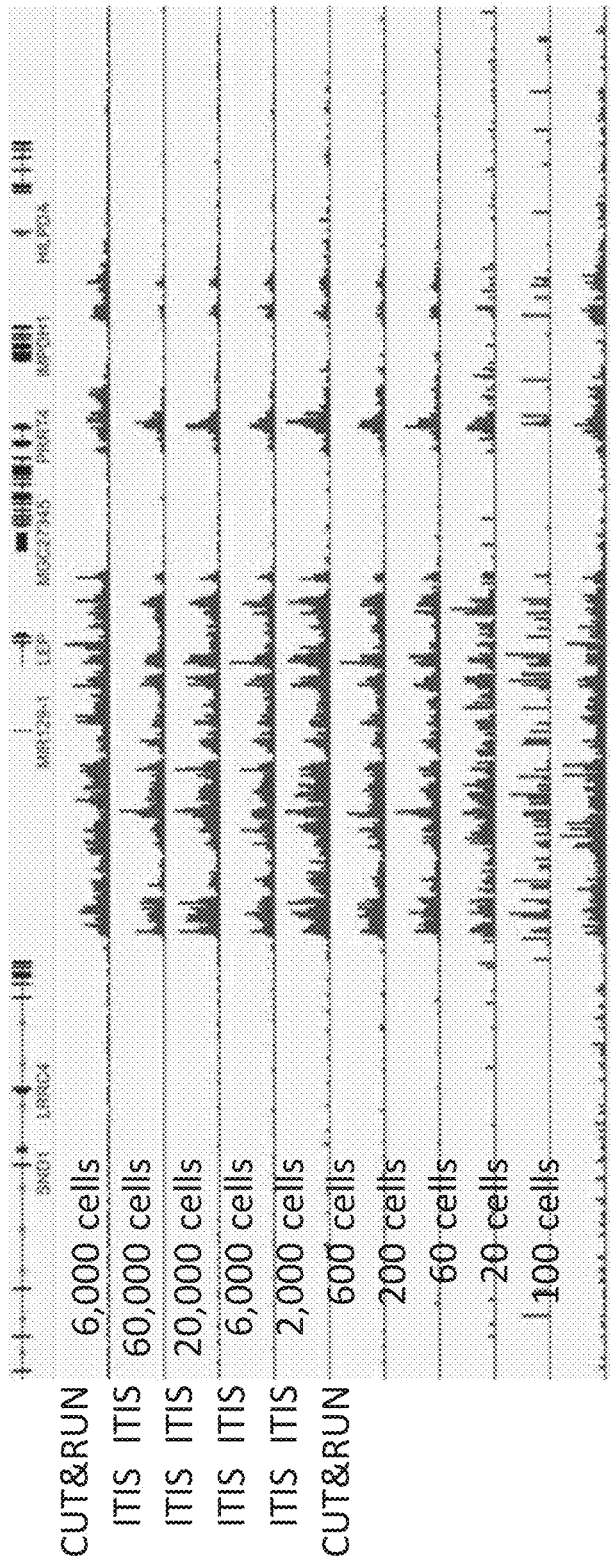
FIG. 75 shows high CUT&RUN data quality with low backgrounds down to 20 cells.

When low cell number H27me3 ITIS profiles were examined and compared to CUT&RUN profiles, we observed no loss of data quality down to 200 cells, and only slight reduction in signal to noise for 60 cells, but nevertheless better than obtained for CUT&RUN with 100 cells (FIG. 75). We conclude that ITIS is suitable for low cell numbers.

Several applications, such as distinguishing cell types, require single cells, where the sparseness of fragments requires from hundreds to thousands of individual single-cell libraries to provide enough information for deconvolution (Buenrostro et al., 2015; Cusanovich et al., 2018; Rosenberg et al., 2018). For single-cell applications, we have evaluated ITIS on the Takara ICELL8 system, recently applied to ATAC-seq (Mezger et al., 2018). The ICELL8 uses nanowells in a 72×72 array, including a dispenser that sorts individual cells into single wells. The nanodispenser deposits single cells in only a subset of the wells, with others getting either no cells or multiple cells. Accordingly, the ICELL8 images the array using a fluorescence microscope, recognizes wells with single cells, and dispenses reagents and primers only into wells with single cells. The ICELL8 is compatible with ITIS, in that the cells remain intact through the tagmentation step, and so can be dispensed after the adapters are inserted by in situ tagmentation. This is followed by amplification with 72 i7 and 72 i5 barcoded primers arrayed respectively horizontally and vertically to distinguish DNA fragments derived from single nanowells after their contents are combined for sequencing using the multiplexed i7 and i5 inline barcodes read from each end during paired-end sequencing.

As single-cell ITIS requires only PCR amplification after tagmentation, it is readily adapted to other platforms. ATAC-seq has been implemented using dispensing by cell sorting (Buenrostro et al., 2015) and ICELL8 nanodispensing (Mezger et al., 2018), and is in principle directly adaptable to droplet encapsulation (Zheng et al., 2017). We anticipate that ITIS will be similarly adaptable to these and other single-cell platforms including combinatorial barcoding using the same steps as outlined for the ICELL8.

To calibrate each cell, we omit the salt treatment, so that we obtain hypersensitive sites superimposed over the sites specifically bound by antibody. Absence of salt treatment also results in high levels of tagmentation of contaminating *E. coli* DNA. By taking the ratio of the total number of hypersensitive site fragments to the total number of *E. coli* fragments, we can infer ploidy, as the hypersensitive sites scale with ploidy while the *E. coli* fragments scale with cellular components. This ploidy calibration informs on cell cycle stage and S-phase progression, as G2 will have twice the ratio as G1, with S-phase in between depending on how much of the genome is replicated in that particular cell at the time the cells were harvested. The hypersensitive site fragment count also calibrates the antibody-targeted ITIS sites, as both scale with cell ploidy. Thus, by not removing otherwise undesirable tagmented fragments we can obtain useful cell-specific information that can improve the power of single-cell profiling.

Adaptation of ITIS for single cells makes possible multiplexing of antibodies, also applicable to bulk populations. For example, multiplexing with antibodies for RNAPII and H3K27 acetylation would provide information on promoters and enhancers in single cells analogous to what has been achieved using RNA-seq and ATAC-seq (Cusanovich et al., 2018). The combinatorial possibilities for multi-ITIS are limited only by the availability of antibodies for different epigenomic features, whereas each multi-OMIC method is dedicated to a single pair of features. Moreover, multi-ITIS has the advantage that the same genomic readout is obtained without the inherent complexity caused by the heterogeneity of using two completely different substrates required for "multi-OMIC" strategies. An example of a multiplexing strategy would be successive addition of 1) a primary rabbit antibody; 2) a guinea pig anti-rabbit secondary antibody and washes; 3) pA-Tn5 complexed with one adapter set and washes; 4) a primary mouse antibody; 5) a rabbit anti-mouse secondary antibody and washes; 6) pA-Tn5 complexed with a second adapter set and washes, where saturation with the first pA-Tn5 occludes the rabbit primary and guinea pig secondary IgG epitopes, leaving only the rabbit anti-mouse secondary IgG available for pA-Tn5 to bind. Tagmentation is performed as usual by addition of $Mg^{++}$ and cells are nanodispensed or prepared for another platform. Steps 1-3 are identical to those in our current protocol, and steps 4-6 are identical to steps 1-3 except for using different IgG molecules. Therefore, it can be performed with materials that have already been used for ITIS and CUT&RUN (guinea pig anti-rabbit and rabbit anti-mouse secondary antibodies). In principle this procedure can be adapted for other affinity systems, such as streptavidin/biotin, which would allow for additional multiplexing.

An example of a multiplexing strategy would be preparing antibody+pA-Tn5+indexed adaptor complexes and performing successive rounds of binding these complexes to targets and tagmentation with target-specific indexes so that each target will be labelled by a unique barcode. Insertion of a barcode sequence between the Mosaic end and the sequencer adapter will suffice to distinguish the first primary antibody from the second. After desired numbers of different epitopes are targeted, cells are nanodispensed or prepared for another platform.

Another unique application of ITIS is that we can detect interacting or close proximity of two different proteins or histone modifications on the same DNA. As described above, antibody+pA-Tn5+indexed adapter complexes or more simply antibody A +pA-Tn5+P5 adaptor or antibody B+pA-Tn5+P7 adaptor complexes can be made in vitro and these complexes can be sequentially introduced to permeabilized intact cells. To avoid adaptor exchange, the second complex will be introduced after first tagmentation is completed. Only fragments with both P5 and P7 adaptors at each end can be amplified during library preparations so DNA molecules which have both proteins will be enriched in the libraries. This approach will also provide information on relative orientations of the two target proteins on DNA. Possible applications of this approach include bivalent nucleosomes which have both H3K27me3 and H3K4me3 histone marks, pioneering transcription factors and co-operating transcription factors and the like.

Also, Tn5 has the ability to not only tagment DNA but also insert a wide size range of DNA inserts. Therefore, it can be used in applications when preserving the integrity of chromatin is desired and fragmentation of DNA needs to be prevented.

References for Example 11 (Each of which is Incorporated by Reference in its Entirety)

Brind'Amour, J., Liu, S., Hudson, M., Chen, C., Karimi, M. M., and Lorincz, M. C. (2015). An ultra-low-input native ChIP-seq protocol for genome-wide profiling of rare cell populations. Nat Commun 6, 6033.

Buenrostro, J. D., Wu, B., Litzenburger, U. M., Ruff, D., Gonzales, M. L., Snyder, M. P., Chang, H. Y., and Greenleaf, W. J. (2015). Single-cell chromatin accessibility reveals principles of regulatory variation. Nature 523, 486-490.

Cusanovich, D. A., Reddington, J. P., Garfield, D. A., Daza, R. M., Aghamirzaie, D., Marco-Ferreres, R., Pliner, H. A., Christiansen, L., Qiu, X., Steemers, F. J., et al. (2018). The cis-regulatory dynamics of embryonic development at single-cell resolution. Nature 555, 538-542.

Mezger, A., Klemm, S., Mann, I., Brower, K., Mir, A., Bostick, M., Farmer, A., Fordyce, P., Linnarsson, S., and Greenleaf, W. (2018). High-throughput chromatin accessibility profiling at single-cell resolution. Nat Commun 9, 3647.

Rosenberg, A. B., Roco, C. M., Muscat, R. A., Kuchina, A., Sample, P., Yao, Z., Graybuck, L. T., Peeler, D. J., Mukherjee, S., Chen, W., et al. (2018). Single-cell profiling of the developing mouse brain and spinal cord with split-pool barcoding. Science 360, 176-182.

Skene, P. J., Henikoff, J. G., and Henikoff, S. (2018). Targeted in situ genome-wide profiling with high efficiency for low cell numbers. Nat Protoc 13, 1006-1019.

Zheng, G. X., Terry, J. M., Belgrader, P., Ryvkin, P., Bent, Z. W., Wilson, R., Ziraldo, S. B., Wheeler, T. D., McDermott, G. P., Zhu, J., et al. (2017). Massively parallel digital transcriptional profiling of single cells. Nat Commun 8, 14049.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A method for detecting the binding of a chromatin-associated factor of interest to a sequence of chromatin DNA in a cell or nucleus, comprising:
   contacting a permeabilized cell or nucleus immobilized on a solid surface with a first specific binding agent that specifically recognizes the chromatin-associated factor of interest, wherein the first specific binding agent is coupled to a nuclease in an inactive state;
   activating the nuclease and cleaving DNA bound to the chromatin-associated factor of interest to thereby excise the DNA bound to the chromatin-associated factor of interest and release it to a supernatant;
   isolating the excised DNA in the supernatant; and
   determining the sequence of the excised DNA, thereby mapping binding of a chromatin-associated factor of interest to a sequence of DNA in the cell or nucleus.

2. The method of claim 1, wherein the first specific binding agent is directly coupled to the nuclease.

3. The method of claim 1, wherein the first specific binding agent is indirectly coupled to the nuclease.

4. The method of claim 1, wherein the nuclease is linked to a second specific binding agent that specifically binds the first specific binding agent.

5. The method of claim 4, wherein the specific binding agent linked to the nuclease comprises protein A or a fragment thereof, protein G or a fragment thereof, or a fusion of protein A or a fragment thereof and protein G or a fragment thereof.

6. The method of claim 1, further comprising:
   contacting the cell or nucleus with a second specific binding agent that specifically binds the first specific binding agent, and wherein the nuclease is linked to a third specific binding agent that specifically binds the second specific binding agent.

7. The method of claim 1, further comprising:
   contacting the cell or nucleus with a second specific binding agent that specifically binds the first specific binding agent;
   contacting the cell or nucleus with a third specific binding agent that specifically binds the second specific binding agent, and wherein the nuclease is linked to a fourth specific binding agent that specifically binds the third specific binding agent.

8. The method of claim 1, wherein the binding of the chromatin-associated factor of interest to the sequence of chromatin DNA is indirect.

9. The method of claim 1, wherein the binding of the chromatin-associated factor of interest to the sequence of chromatin DNA is direct.

10. The method of claim 1, wherein the chromatin-associated factor of interest is a transcription factor.

11. The method of claim 1, wherein the solid surface—comprises—a bead or wall of a microtiter plate.

12. The method of claim 1, further comprising tagging the excised chromatin DNA with a nucleic acid tag wherein the nucleic acid tag comprises a sequencing adaptor, a barcode, and/or a universal priming site.

13. The method of claim 1, wherein the nuclease is activatable by addition of a divalent cation.

14. The method of claim 1, wherein the nuclease is an endonuclease, optionally wherein the endonuclease is micrococcal nuclease (MNase).

15. The method of claim 1, wherein the nuclease is activated by $Ca^{2+}$ ions.

16. The method of claim 1, wherein the nuclease activity is quenched by addition of a chelating agent.

17. The method of claim 1, wherein the first specific binding agent is an antibody or an antigen-binding fragment thereof.

18. The method of claim 1, wherein the nuclease is part of a fusion protein, optionally wherein the nuclease is fused to protein A or a fragment thereof, protein G or a fragment thereof, or a fusion of protein A or a fragment thereof and protein G or a fragment thereof, optionally wherein the fusion protein is protein A-MNase, protein G-MNase, or protein A/G-MNase.

19. The method of claim 1, wherein the cell and/or the nucleus of the cell is permeabilized by contacting the cell with digitonin.

20. The method of claim 1, further comprising subjecting the excised DNA to ChIP-seq.

21. The method of claim 1, further comprising determining an identity of one or more proteins associated with of the chromatin-associated factor of interest, optionally wherein determining the identity of the protein comprises the use of an antibody or an antigen-binding fragment thereof or mass spectrometry.

22. The method of claim 1, wherein the method is carried out on a sample comprising about one to about 1000 cells or nuclei, optionally about one to about 100 cells or nuclei.

23. The method of claim 1, wherein the method is carried out on a sample comprising one cell or nucleus, optionally wherein the method comprises cell sorting, nanodispensing, or droplet encapsulation of the cell or nucleus.

24. The method of claim 1, wherein the nuclease is activated in a buffer to prevent the cleaved fragments from being released from the nucleus wherein the buffer comprises 10 mM $CaCl_2$ and 3.5 mM HEPES pH 7.5.

25. The method of claim 24, further comprising performing an adaptor ligation reaction in situ.

26. The method of claim 1, comprising single cell nanowell indexing or split pool combinatorial indexing.

27. The method of claim 1, further comprising measuring three-dimensional interactions, optionally further comprising a step of proximity-based ligation.

28. The method of claim 1, further comprising contacting the permeabilized cell or nucleus with one or more additional specific binding agents that each specifically recognize a different chromatin-associated factor of interest, wherein the one or more additional specific binding agents are linked to a nuclease in an inactive state.

29. A method for preparing a library of excised chromatin DNA comprising carrying out the method of claim 1.

30. The method of claim 1, wherein mapping the chromatin-associated factor is performed at a resolution of less than 5 base pairs.

31. The method of claim 1, further comprising preparing a sequencing library comprising the excised DNA by tagging the excised DNA at both ends with a nucleic acid tag comprising a barcode and performing paired-end sequencing of the sequencing library.

32. A method for detecting the binding of a chromatin-associated factor of interest to a sequence of chromatin DNA in a cell or nucleus, comprising:
- contacting an unfixed permeabilized cell or nucleus with a first specific binding agent that specifically recognizes the chromatin-associated factor of interest, wherein the first specific binding agent is coupled to a nuclease in an inactive state;
- activating the nuclease, thereby excising the DNA bound to the chromatin-associated factor of interest;
- releasing the DNA to a supernatant;
- isolating the excised DNA in the supernatant; and
- determining the sequence of the excised DNA, thereby mapping binding of a chromatin-associated factor of interest to a sequence of DNA in the cell or nucleus.

* * * * *

UNITED STATES PATENT AND TRADEMARK OFFICE
CERTIFICATE OF CORRECTION

| | | |
|---|---|---|
| PATENT NO. | : 11,885,814 B2 | Page 1 of 2 |
| APPLICATION NO. | : 17/585465 | |
| DATED | : January 30, 2024 | |
| INVENTOR(S) | : Henikoff et al. | |

It is certified that error appears in the above-identified patent and that said Letters Patent is hereby corrected as shown below:

In the Specification

Column 4, Line 24: Please correct "log 2 (Insoluble)=log 2 (Total)-log 2 (Soluble)=log 2" to read --$\log_2$ (Insoluble)=$\log_2$ (Total)-$\log_2$ (Soluble)=$\log_2$--

Column 19, Line 64: Please correct "(it RT-PCR)" to read --(rt RT-PCR)--

Column 20, Line 40: Please correct "(A;" to read --(A)--

Column 24, Line 66: Please correct "Art" to read --Arnt--

Column 25, Line 21: Please correct "Eff-1" to read --EIf-1--

Column 25, Line 22: Please correct "Elk-1" to read --EIk-1--

Column 25, Line 39: Please correct "HITF1, HITF2" to read --H1TF1, H1TF2--

Column 38, Line 39: Please correct "Art" to read --Arnt--

Column 38, Line 62: Please correct "Elf-1, Elk-1" to read --EIf-1, EIk-1--

Column 39, Line 45: Please correct "M1B67, M1BF1" to read --MB67, MBF1--

Column 39, Lines 48-49: Please correct "MEF-2D0B" to read --MEF-2D0B--

Column 40, Line 58: Please correct "bllO" to read --bcllO--

Column 40, Line 59: Please correct "BRGI, CARMI" to read --BRG1, CARM1--

Signed and Sealed this
Fourth Day of March, 2025

Coke Morgan Stewart
*Acting Director of the United States Patent and Trademark Office*

Column 40, Line 63: Please correct "JHDMID" to read --JHDM1D--

Column 47, Line 55: Please correct "~-1%" to read --~1%--

Column 53, Line 51: Please correct "~×10$^8$ cells" to read --~5×10$^8$ cells--

Column 54, Line 64: Please correct "CaCl$_2$)" to read --CaCl$_2$--

Column 55, Line 36: Please correct "%2 volume" to read --½ volume--

Column 60, Line 27: Please correct "~-0.7" to read --~0.7--

Column 70, Line 46: Please correct "55150-1L" to read --S5150-1L--

Column 70, Line 65: Please correct "E00492" to read --EO0492--

Column 71, Line 26: Please correct "CaCl$_2$)" to read --CaCl$_2$--

Column 74, Line 2: Please correct "CaCl$_2$)" to read --CaCl$_2$--

Column 77, Line 50: Please correct "Bert" to read --Bernt--

Column 106, Line 30: Please correct "($C_i$+αi)" to read --($C_i$+$a_i$)--

Column 106, Line 34: Please correct "(FPKM$_i$+α$_{y,i}$)" to read --(FPKM$_i$+$a_{y,i}$)--

Column 106, Lines 44-45: Please correct "=0.858 ln(CH$_{3K27ac}$+0.058)–0.615 ln(CH$_{3K27me3}$+0.0816)+1.609 ln(CH$_{3K4me2}$+0.054)" to read --=0.858 ln(C$_{H3K27ac}$+0.058)–0.615 ln(C$_{H3K27me3}$+0.0816)+1.609 ln(C$_{H3K4me2}$+0.054)--

Column 110, Lines 62-63: Please correct "D-thalassemia" to read --β-thalassemia--

Column 114, Line 22: Please correct "CaCl$_2$)" to read --CaCl$_2$--

Column 117, Line 1: Please correct "4600,000" to read --~600,000--

Column 127, Line 56: Please correct "55150-1L" to read --S5150-1L--

Column 128, Line 1: Please correct "E00492" to read --EO0492--

Column 133, Line 21: Please correct "$\geq$150 bp" to read --$\gtrsim$150 bp--

In the Claims

Column 142, Line 36, Claim 21: Please correct "with of the" to read --with the--